US012760021B2

(12) United States Patent
Hu et al.

(10) Patent No.: US 12,760,021 B2
(45) Date of Patent: Oct. 13, 2026

(54) CARBONYL SUBSTITUTED DIAZASPIRO COMPOUNDS AND ITS USE

(71) Applicant: BIONOVA PHARMACEUTICALS LTD., Grand Cayman (KY)

(72) Inventors: Taishan Hu, Shanghai (CN); Bryan Huang, Shanghai (CN); Quanrong Shen, Shanghai (CN); Honghai Li, Shanghai (CN); Xiaochu Ma, Shanghai (CN)

(73) Assignee: SERVIER PHARMACEUTICALS LLC, Boston, MA (US)

(*) Notice: Subject to any disclaimer, the term of this patent is extended or adjusted under 35 U.S.C. 154(b) by 116 days.

(21) Appl. No.: 18/263,592

(22) PCT Filed: Dec. 2, 2022

(86) PCT No.: PCT/CN2022/136203
§ 371 (c)(1),
(2) Date: Jul. 31, 2023

(87) PCT Pub. No.: WO2023/098876
PCT Pub. Date: Jun. 8, 2023

(65) Prior Publication Data

US 2024/0317748 A1 Sep. 26, 2024

(30) Foreign Application Priority Data

Dec. 3, 2021 (WO) ................ PCT/CN2021/135427
Aug. 26, 2022 (WO) ................ PCT/CN2022/115162

(51) Int. Cl.
*C07D 471/10* (2006.01)
*A61K 31/506* (2006.01)
*A61K 31/53* (2006.01)
*A61K 31/5377* (2006.01)
*C07D 487/10* (2006.01)
*C07D 519/00* (2006.01)

(52) U.S. Cl.
CPC .......... *C07D 471/10* (2013.01); *A61K 31/506* (2013.01); *A61K 31/53* (2013.01); *A61K 31/5377* (2013.01); *C07D 487/10* (2013.01); *C07D 519/00* (2013.01)

(58) Field of Classification Search
None
See application file for complete search history.

(56) References Cited

U.S. PATENT DOCUMENTS

2019/0010167 A1 1/2019 Claremon et al.
2019/0144459 A1 5/2019 Cacatian et al.
2020/0157114 A1* 5/2020 Kamioka ............ C07D 487/10
2020/0216471 A1 7/2020 Wu et al.
2021/0338668 A1 11/2021 Kamioka et al.

FOREIGN PATENT DOCUMENTS

| | | | |
|---|---|---|---|
| CL | 2022001583 | A1 | 2/2023 |
| CN | 108779116 | | 11/2018 |
| CN | 109743875 | A | 5/2019 |
| CN | 112585140 | A | 3/2021 |
| CN | 117069721 | A | 11/2023 |
| JP | 2018-538330 | A | 12/2018 |
| JP | 2019-517548 | A | 6/2019 |
| JP | 2020-514388 | A | 5/2020 |
| JP | 2021/134218 | | 9/2021 |
| WO | 2017112768 | A1 | 6/2017 |
| WO | 2017214367 | A1 | 12/2017 |
| WO | 2019060365 | A1 | 3/2019 |
| WO | 2020032105 | A1 | 2/2020 |
| WO | 2020/045334 | A1 | 3/2020 |
| WO | WO 2021/121327 | | 6/2021 |

(Continued)

OTHER PUBLICATIONS

Issa et al., "Therapeutic Implications of Menin Inhibition in Acute Leukemias," Leukemia, vol. 35, No. 9, p. 2482-2495, (2021); Abstract only.
Krivtsov et al., "A Menin-MLL Inhibitor Induces Specific Chromatin Changes and Eradicates Disease in Models of MLL-Rearranged Leukemia," Cancer Cell, vol. 36, No. 6, p. 660-673, (2019).
Kuehn et al., "Targeting Chromatin Regulators Inhibits Leukemogenic Gene Expression in NPM1 Mutant Leukemia," Cancer Discov, vol. 6, No. 10, p. 1166-1181, (2016).

(Continued)

*Primary Examiner* — Adam C Milligan
*Assistant Examiner* — Jason M. Nolan

(57) ABSTRACT

A compound of formula I, in which the variables are as defined in the specification; pharmaceutical compositions containing them, methods for preparing them, and their use.

(I)

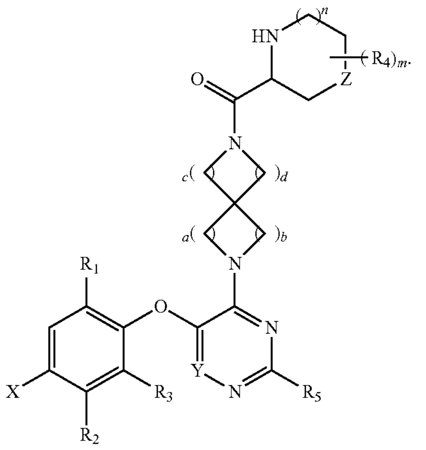

32 Claims, No Drawings

(56) References Cited

FOREIGN PATENT DOCUMENTS

WO 2022086986 A1 4/2022

OTHER PUBLICATIONS

Marschalek, R., "Mechanisms of Leukemogenesis by MLL Fusion Proteins," Br J Haematol, vol. 152, No. 2, p. 141-154, (2011).

Meyer et al., "The MLL Recombinome of Acute Leukemias in 2017," Leukemia, vol. 32, No. 2, p. 273-284, (2018).

* cited by examiner

CARBONYL SUBSTITUTED DIAZASPIRO COMPOUNDS AND ITS USE

CROSS-REFERENCE TO RELATED APPLICATION

This application is a United States Application under 35 U.S.C. § 371 of International Application No. PCT/CN2022/136203, filed on Dec. 2, 2022, which claims the priority benefit of the International Application No. PCT/CN2021/135427 filed on Dec. 3, 2021, and the International Application No. PCT/CN2022/115162 filed on Aug. 26, 2022, each of which are herein incorporated by reference in their entirety.

TECHNICAL FIELD

The present disclosure provides carbonyl substituted diazaspiro compounds that inhibit the interaction of menin with MLL and MLL fusion proteins. The present disclosure also provides processes for preparing these compounds, pharmaceutical compositions comprising these compounds, and use thereof for the prevention or treatment of cancer and other diseases mediated by the interaction of menin with MLL and/or MLL fusion proteins.

BACKGROUND

Rearrangement of the mixed lineage leukemia (MLL, also known as MLL1 or KMT2A) gene occurs in about 10% of acute leukemias, and is particularly prevalent in infant acute leukemias, accounting for up to ~70% of infant acute lymphocytic leukemia (ALL) cases (Issa, G. C. et al., *Leukemia,* 2021, 35, 2482). MLLr (MLL rearrangement) is also found in 85% of secondary acute myeloid (myelogenous) leukemia (AML) cases that occur in patients treated with topoisomerase II inhibitors. More than 80 partner genes are implicated in MLL fusions, and six main partner genes make up about 80% of cases, which include AF4 (ALL-1 fused gene from chromosome 4), AF6, AF9, AF10, ENL (eleven-nineteen leukemia) and ELL (eleven-nineteen lysine-rich leukemia) (Meyer, C. et al., 2018, *Leukemia,* 32, 273). MLL translocations lead to the expression of MLL fusion proteins that enhance proliferation and block hematopoietic differentiation, ultimately driving the development of leukemia. MLLr leukemia is one of the high-risk types of leukemia with aggressive nature, resistance to therapy, and high frequency of early relapse, and with a 5-year survival rate of only approximately 35% (Marschalek, R. Br J Haematol. 2011, 152, 141). Therefore, there is huge unmet medical needs for MLLr leukemias.

The protein protein interaction (PPI) between menin and MLLr is critical to the pathogenesis of MLLr-driven leukemias by desregulation of the HOXA and MEIS1 genes. On the other hand, recent studies revealed the importance of the menin-MLL1 wild-type (wt) interaction in AML with mutations in the nucleophosmin 1 (NPM1) gene. NPM1 mutation (NMP1c) is found in over 30% of AML patients with poor 5-year overall survival rate, and also associated with the upregulated expression of HOXA, and MEIS1 genes (Kuhn, M. W. et al. Cancer Discov. 2016, 6, 1166). Menin inhibitors were reported to be able to block the interaction of menin with MLLr and MLL wt, and demonstrated potential use in the treatment of MLLr associated acute leukemias and NPM-mutated AML (Klossowski, S. et al. J Clin Invest. 2020, 130, 981).

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The present disclosure provides a compound of formula I:

I

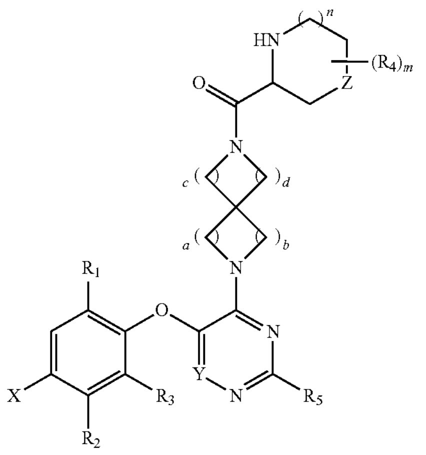

or pharmaceutically acceptable salt, or a stereoisomer, a racemate, a tautomer, a hydrate or a solvate thereof, wherein:

X is halo or CN;

Y is N or CH;

Z is selected from the group consisting of $CH_2$, O, S and NH;

$R_1$ is selected from the group consisting of:

1) —(C═O)—NRaRb, wherein:

Ra and Rb are each independently selected from the group consisting of $C_{1-6}$alkyl, 3-6 membered cycloalkyl ring and 5-9 membered heterocyclyl ring, which is optionally substituted with 1, 2 or 3 substituents selected from the group consisting of deuterium, halo, OH, CN and $C_{1-6}$alkoxyl;

or Ra and Rb, together with the nitrogen atom to which they are attached, form a 5-9 membered heterocyclyl ring, which is optionally substituted with 1, 2 or 3 substituents selected from the group consisting of $C_{1-6}$alkyl, halo, OH and CN;

2) a 5-10 membered heteroaryl ring or $C_{6-10}$aryl ring, optionally substituted with 1, 2 or 3 substituents selected from the group consisting of halo, CN, $C_{1-6}$alkyl optionally substituted with 1, 2 or 3 substituents selected from the group consisting of halo, CN and OH, 3-5 membered cycloalkyl ring, oxo and $C_{1-6}$alkoxyl;

$R_2$ and $R_3$ are each independently H or D;

each $R_4$ is independently selected from the group consisting of halo, CN, OH, oxo, $C_{1-6}$alkylsulfonyl-, $C_{1-6}$alkylsulfonylamino-, $C_{1-6}$alkylcarbonylamino-, $C_{6-10}$aryl ring, $C_{1-6}$alkyl, $C_{2-6}$alkenyl, $C_{2-6}$alkynyl, $C_{1-6}$alkoxyl, 3-9 membered cycloalkyl ring, 5-10 membered heteroaryl ring and 4-9 membered heterocyclyl ring, wherein the alkyl, alkenyl, alkynyl, alkoxyl, cycloalkyl ring, heteroaryl ring or heterocyclyl ring is optionally substituted with 1, 2 or 3 substituents selected from the group consisting of halo, CN and OH;

wherein two adjacent $R_4$, together with the carbon atoms to which they are attached, optionally form a 3-9 membered cycloalkyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl-, halo, CN and OH;

or, two $R_4$ attached to the same carbon atom together with said carbon atom optionally form a 3-6 membered cycloalkyl ring or 4-6 membered heterocyclyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl-, halo, CN and OH;

or, two adjacent $R_4$, together with the carbon atoms to which they are attached, optionally form a 5-10 membered heteroaryl ring, $C_{6-10}$aryl ring or 5-9 membered heterocyclyl ring, wherein said heteroaryl ring or aryl ring is optionally substituted with 1, 2 or 3 substituents selected from the group consisting of $C_{1-6}$alkyl, $C_{1-6}$haloalkyl, —$C_{1-6}$alkyl-OH, $C_{1-6}$alkoxyl-$C_{1-6}$alkyl-, halo, CN and OH, wherein the alkyl is optionally substituted with one 3-6 membered cycloalkyl ring or phenyl; said heterocyclyl ring is optionally substituted with 1, 2 or 3 substituents selected from the group consisting of $C_{1-6}$alkyl, $C_{1-6}$haloalkyl, —$C_{1-6}$alkyl-OH, $C_{1-6}$alkoxyl-$C_{1-6}$alkyl-, oxo, halo, CN and OH;

$R_5$ is selected from the group consisting of H, halo, methyl optionally substituted by 1, 2 or 3 deuterium or halo, methoxyl optionally substituted by 1, 2 or 3 deuterium or halo, $NH_2$, $CH_3NH$ or $(CH_3)_2N$;

a, b, c and d are each independently 1 or 2;

n is 0, 1 or 2; and m is 0, 1, 2, 3 or 4;

provided that $R_4$, if present, substituted at any chemically permissible position(s) on the heterocyclyl except for the N atom adjacent to the attachment point of the heterocyclyl to the remaining structure of the compound.

The compound of formula I or a stereoisomer, a racemate, a tautomer, a hydrate or a solvate, or pharmaceutically acceptable salt thereof as well as the specific compounds disclosed in the context of the present invention and covered by the scope of the compounds above are collectively called "the compound of the present disclosure".

The present disclosure also provides the compound of the present disclosure for use as a medicament.

The present disclosure also provides the compound of the present disclosure for use in the treatment or prevention of cancer or diabetes.

The present disclosure also provides a pharmaceutical composition, comprising the compound of the present disclosure, and optionally a pharmaceutically acceptable carrier.

The present disclosure also provides a kit for treating or preventing a cancer or diabetes, comprising a pharmaceutical composition of the present disclosure and an instruction for use.

The present disclosure also provides the use of the compound of the present disclosure for treatment or prevention of cancer or diabetes.

The present disclosure also provides the use of the compound of the present disclosure in the manufacture of a medicament for treatment or prevention of cancer or diabetes.

The present disclosure also provides a method of in vivo or in vitro inhibiting the interaction of menin with MLL and/or MLL fusion proteins, comprising contacting an effective amount of the compound of the present disclosure with menin.

The present disclosure also provides a method of treating or preventing cancer or diabetes, comprising administering to the subject in need thereof an effective amount of the compound of the present disclosure.

The present disclosure also provides a combination, comprising the compound of the present disclosure and at least one additional therapeutic agent.

The present disclosure also provides a process for the preparation of the compound of the present disclosure, and intermediates for preparing the compound of the present disclosure.

DETAILED DESCRIPTION OF THE DISCLOSURE

Embodiments of the Disclosure—Part A

Embodiment 1. A compound of formula I:

I

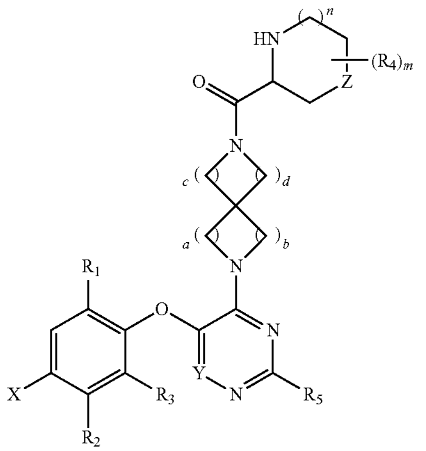

or a stereoisomer, a racemate, a tautomer, a hydrate or a solvate, or pharmaceutically acceptable salt thereof, wherein:

X is halo or CN;

Y is N or CH;

Z is selected from the group consisting of $CH_2$, O, S and NH;

$R_1$ is selected from the group consisting of:

1) —(C═O)—NRaRb, wherein:

Ra and Rb are each independently selected from the group consisting of $C_{1-6}$alkyl, 3-6 membered cycloalkyl ring and 5-9 membered heterocyclyl ring, which is optionally substituted with 1, 2 or 3 substituents selected from the group consisting of deuterium, halo, OH, CN and $C_{1-6}$alkoxyl;

or Ra and Rb, together with the nitrogen atom to which they are attached, form a 5-9 membered heterocyclyl ring, which is optionally substituted with 1, 2 or 3 substituents selected from the group consisting of $C_{1-6}$alkyl, halo, OH and CN;

2) a 5-10 membered heteroaryl ring or $C_{6-10}$aryl ring, optionally substituted with 1, 2 or 3 substituents selected from the group consisting of halo, CN, $C_{1-6}$alkyl optionally substituted with 1, 2 or 3 substituents selected from the group consisting of halo, CN and OH, 3-5 membered cycloalkyl ring, oxo and $C_{1-6}$alkoxyl;

$R_2$ and $R_3$ are each independently H or D;

each $R_4$ is independently selected from the group consisting of halo, CN, OH, oxo, $C_{1-6}$alkylsulfonyl-, $C_{1-6}$alkylsulfonylamino-, $C_{1-6}$alkylcarbonylamino-, $C_{6-10}$aryl ring, $C_{1-6}$alkyl, $C_{2-6}$alkenyl, $C_{2-6}$alkynyl, $C_{1-6}$alkoxyl, 3-9 membered cycloalkyl ring, 5-10 membered heteroaryl ring and 4-9 membered heterocyclyl ring, wherein the alkyl, alkenyl, alkynyl, alkoxyl, cycloalkyl ring, heteroaryl ring or heterocyclyl ring is optionally substituted with 1, 2 or 3 substituents selected from the group consisting of halo, CN and OH;

wherein two adjacent $R_4$, together with the carbon atoms to which they are attached, optionally form a 3-9 membered cycloalkyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl-, halo, CN and OH;

or, two $R_4$ attached to the same carbon atom together with said carbon atom optionally form a 3-6 membered cycloalkyl ring or 4-6 membered heterocyclyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl-, halo, CN and OH;

or, two adjacent $R_4$, together with the carbon atoms to which they are attached, optionally form a 5-10 membered heteroaryl ring, $C_{6-10}$aryl ring or 5-9 membered heterocyclyl ring, wherein said heteroaryl ring or aryl ring is optionally substituted with 1, 2 or 3 substituents selected from the group consisting of $C_{1-6}$alkyl, $C_{1-6}$haloalkyl, —$C_{1-6}$alkyl-OH, $C_{1-6}$alkoxyl-$C_{1-6}$alkyl-, halo, CN and OH, wherein the alkyl is optionally substituted with one 3-6 membered cycloalkyl ring or phenyl; said heterocyclyl ring is optionally substituted with 1, 2 or 3 substituents selected from the group consisting of $C_{1-6}$alkyl, $C_{1-6}$haloalkyl, —$C_{1-6}$alkyl-OH, $C_{1-6}$alkoxyl-$C_{1-6}$alkyl-, oxo, halo, CN and OH;

$R_5$ is selected from the group consisting of H, halo, methyl optionally substituted by 1, 2 or 3 deuterium or halo, methoxyl optionally substituted by 1, 2 or 3 deuterium or halo, $NH_2$, $CH_3NH$ or $(CH_3)_2N$;

a, b, c and d are each independently 1 or 2;

n is 0, 1 or 2; and m is 0, 1, 2, 3 or 4;

provided that $R_4$, if present, substituted at any chemically permissible position(s) on the heterocyclyl except for the N atom adjacent to the attachment point of the heterocyclyl to the remaining structure of the compound.

Embodiment 2. The compound according to Embodiment 1 or a stereoisomer, a racemate, a tautomer, a hydrate or a solvate, or pharmaceutically acceptable salt thereof, wherein:

X is F, $C_1$ or CN;

Y is N or CH;

Z is selected from the group consisting of $CH_2$, O, S and NH;

$R_1$ is selected from the group consisting of:

1) —(C═O)—NRaRb, wherein:

Ra and Rb are each independently selected from the group consisting of $C_{1-6}$alkyl and 3-5 membered cycloalkyl ring, wherein the $C_{1-6}$alkyl is optionally substituted with 1, 2 or 3 substituents selected from the group consisting of deuterium, halo, OH and $C_{1-6}$alkoxyl;

or Ra and Rb, together with the nitrogen atom to which they are attached, form a 5-6 membered monocyclic or 7-9 membered bicyclic heterocyclyl ring, which is optionally substituted with 1, 2 or 3 substituents selected from the group consisting of $C_{1-6}$alkyl and halo;

2) a 5-6 membered heteroaryl ring, optionally substituted with 1, 2 or 3 substituents selected from the group consisting of halo, CN, $C_{1-6}$alkyl optionally substituted with 1, 2 or 3 substituents selected from the group consisting of halo and CN, 3-5 membered cycloalkyl ring, oxo and $C_{1-6}$alkoxyl;

3) $C_{6-10}$aryl ring substituted with 1, 2 or 3 substituents selected from the group consisting of halo, CN, $C_{1-6}$alkyl optionally substituted with 1, 2 or 3 substituents selected from the group consisting of halo and CN, 3-5 membered cycloalkyl ring and $C_{1-6}$alkoxyl;

$R_2$ and $R_3$ are each independently H or D;

each $R_4$ is independently selected from the group consisting of halo, CN, OH, $C_{1-6}$alkylsulfonyl-, $C_{1-6}$alkylsulfonylamino-, $C_{1-6}$alkylcarbonylamino-, phenyl, $C_{1-6}$alkyl, $C_{1-6}$alkoxyl, 3-6 membered cycloalkyl ring, 5-10 membered heteroaryl ring and 5-9 membered heterocyclyl ring, wherein the alkyl, alkoxyl, cycloalkyl ring, heteroaryl ring or heterocyclyl ring is optionally substituted with 1, 2 or 3 substituents selected from the group consisting of halo, CN and OH;

wherein two adjacent $R_4$, together with the carbon atoms to which they are attached, optionally form a 3-6 membered cycloalkyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl- and halo;

or, two $R_4$ attached to the same carbon atom together with said carbon atom optionally form a 3-6 membered cycloalkyl ring, which is optionally substituted with 1, 2 or 3 substituents selected from the group consisting of halo, CN and OH;

or, two adjacent $R_4$, together with the carbon atoms to which they are attached, optionally form a 5-10 membered heteroaryl ring, phenyl or 5-9 membered heterocyclyl ring, which is optionally substituted with 1, 2 or 3 substituents selected from the group consisting of halo, $C_{1-6}$alkyl and $C_{1-6}$haloalkyl, wherein the alkyl is optionally substituted with one 3-6 membered cycloalkyl ring or phenyl;

$R_5$ is H or halo;

a, b, c and d are each independently 1 or 2;

n is 0 or 1; and m is 0, 1, 2 or 3;

provided that $R_4$, if present, substituted at any chemically permissible position(s) on the heterocyclyl except for the N atom adjacent to the attachment point of the heterocyclyl to the remaining structure of the compound.

Embodiment 3. The compound according to any one of the preceding Embodiments or a stereoisomer, a racemate, a tautomer, a hydrate or a solvate, or pharmaceutically acceptable salt thereof, wherein:

each $R_4$ is independently selected from the group consisting of halo, CN, OH, $C_{1-6}$alkylsulfonyl-, $C_{1-6}$alkylsulfonylamino-, phenyl, $C_{1-6}$alkyl, $C_{1-6}$alkoxyl and 3-6 membered cycloalkyl ring, wherein the alkyl or alkoxyl is optionally substituted with 1, 2 or 3 substituents selected from the group consisting of halo, CN and OH;

wherein two adjacent $R_4$, together with the carbon atoms to which they are attached, optionally form a 3-6 membered cycloalkyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl- and halo;

or, two $R_4$ attached to the same carbon atom together with said carbon atom optionally form a 3-6 membered cycloalkyl ring, which is optionally substituted with 1, 2 or 3 substituents selected from the group consisting of halo, CN and OH;

or, two adjacent $R_4$, together with the carbon atoms to which they are attached, optionally form a 5-10 membered heteroaryl ring or phenyl, which is optionally substituted with 1, 2 or 3 substituents selected from the group consisting of $C_{1-6}$alkyl, wherein the alkyl is optionally substituted with one 3-6 membered cycloalkyl ring or phenyl.

Embodiment 4. The compound according to any one of the preceding Embodiments or a stereoisomer, a racemate, a tautomer, a hydrate or a solvate, or pharmaceutically acceptable salt thereof, wherein $R_5$ is H.

Embodiment 5. The compound according to any one of the preceding Embodiments or a stereoisomer, a racemate, a tautomer, a hydrate or a solvate, or pharmaceutically acceptable salt thereof, wherein the compound is of formula II:

II

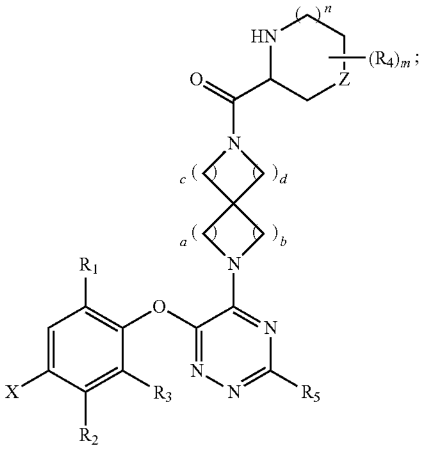

Preferably, the compound is of formula IIa:

IIa

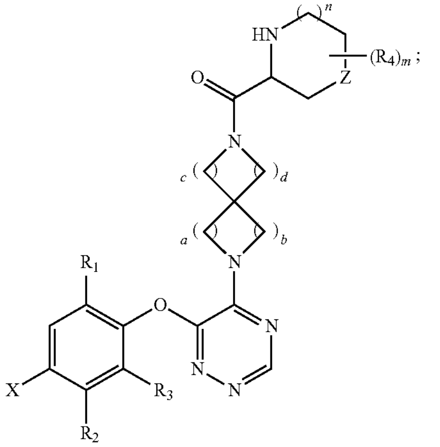

which preferably is

IIa

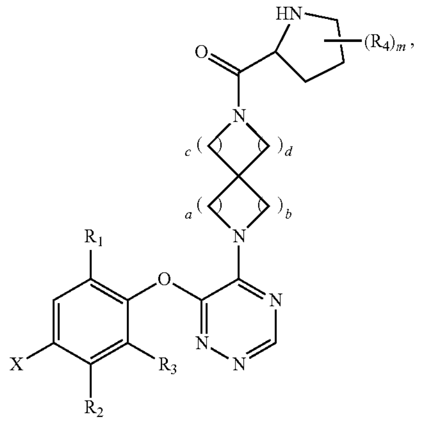

more preferably is:

IIc

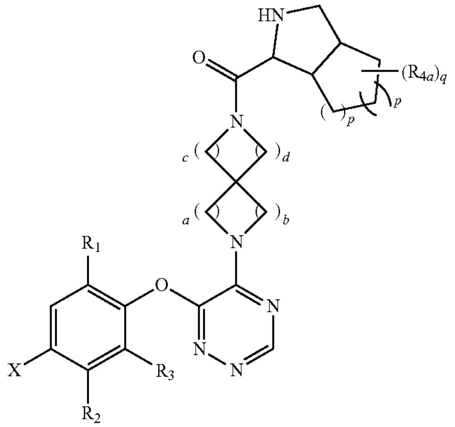

wherein each p is dependently 0 or 1; q is 0, 1 or 2; $R_4^a$ is $C_{1-3}$alkyl or halo;

most preferably is:

IId

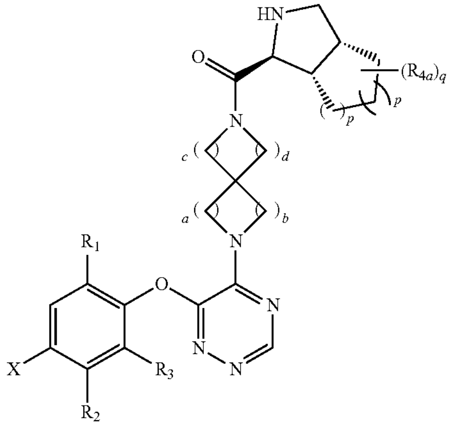

wherein each p is dependently 0 or 1; q is 0, 1 or 2; $R_4^a$ is $C_{1-3}$alkyl or halo.

Embodiment 6. The compound according to any of the Embodiments 1 to 4 or a stereoisomer, a racemate, a tautomer, a hydrate or a solvate, or pharmaceutically acceptable salt thereof, wherein the compound is of formula III:

III

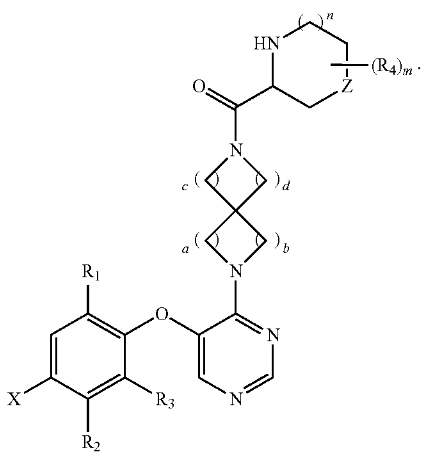

Embodiment 7. The compound according to any one of the preceding Embodiments or a stereoisomer, a racemate, a tautomer, a hydrate or a solvate, or pharmaceutically acceptable salt thereof, wherein X is F.

Embodiment 8. The compound according to any one of the preceding Embodiments or a stereoisomer, a racemate, a tautomer, a hydrate or a solvate, or pharmaceutically acceptable salt thereof, wherein Z is selected from the group consisting of $CH_2$, O and S, preferably $CH_2$.

Embodiment 9. The compound according to any one of the preceding Embodiments or a stereoisomer, a racemate, a tautomer, a hydrate or a solvate, or pharmaceutically acceptable salt thereof, wherein $R_2$ and $R_3$ are each independently H.

Embodiment 10. The compound according to any one of the preceding Embodiments or a stereoisomer, a racemate, a tautomer, a hydrate or a solvate, or pharmaceutically acceptable salt thereof, wherein:

$R_1$ is —(C═O)—NRaRb, wherein:

Ra and Rb are each independently selected from the group consisting of $C_{1-6}$alkyl and 3-5 membered cycloalkyl ring, wherein the $C_{1-6}$alkyl is optionally substituted with 1, 2 or 3 substituents selected from the group consisting of deuterium, halo, OH and $C_{1-6}$alkoxyl; or Ra and Rb, together with the nitrogen atom to which they are attached, form a 5-6 membered monocyclic or 7-9 membered bicyclic heterocyclyl ring with another ring heteroatoms selected from N, O and S, which is optionally substituted with 1, 2 or 3 substituents selected from the group consisting of $C_{1-6}$alkyl and halo.

Embodiment 11. The compound according to any one of Embodiments 1-9 or a stereoisomer, a racemate, a tautomer, a hydrate or a solvate, or pharmaceutically acceptable salt thereof, wherein:

$R_1$ is —(C═O)—NRaRb, wherein $R^a$ and Rb are each $C_{1-3}$alkyl optionally substituted with one OH; preferably Ra is ethyl and Rb is iso-propyl; or $R_1$ is a 5-6 membered heteroaryl ring substituted with 1, 2 or 3 substituents selected from the group consisting of halo, CN, $C_{1-3}$alkyl and cyclopropyl; or phenyl substituted with 1, 2 or 3 substituents selected from the group consisting of halo, CN and cyclopropyl.

Embodiment 12. The compound according to Embodiment 11 or a stereoisomer, a racemate, a tautomer, a hydrate or a solvate, or pharmaceutically acceptable salt thereof, wherein:

$R_1$ is —(C═O)—NRaRb, wherein $R^a$ and Rb are each $C_{1-3}$alkyl optionally substituted with one OH; preferably Ra is ethyl and Rb is iso-propyl; or $R_1$ is pyridyl, pyrimidinyl or pyrazolyl, substituted with 1, 2 or 3 substituents selected from the group consisting of halo, CN, $C_{1-3}$alkyl and cyclopropyl; or phenyl substituted with 1, 2 or 3 substituents selected from the group consisting of halo, CN and cyclopropyl.

Embodiment 13. The compound according to any one of Embodiments 1-9 or a stereoisomer, a racemate, a tautomer, a hydrate or a solvate, or pharmaceutically acceptable salt thereof, wherein:

$R_1$ is —(C═O)—NRaRb, wherein $R^a$ and Rb are each $C_{1-3}$alkyl, preferably Ra is ethyl and Rb is iso-propyl; or $R_1$ is a 6 membered heteroaryl or phenyl ring, substituted with 1, 2 or 3 substituents selected from the group consisting of halo, CN and cyclopropyl.

Embodiment 14. The compound according to any one of Embodiments 1-9 or a stereoisomer, a racemate, a tautomer, a hydrate or a solvate, or pharmaceutically acceptable salt thereof, wherein:

$R_1$ is —(C═O)—NRaRb, wherein Ra is ethyl and Rb is iso-propyl.

Embodiment 15. The compound according to any one of Embodiments 1-9 or a stereoisomer, a racemate, a tautomer, a hydrate or a solvate, or pharmaceutically acceptable salt thereof, wherein:

$R_1$ is pyridyl, pyrimidinyl or phenyl, substituted with 1, 2 or 3 substituents selected from the group consisting of halo, CN and cyclopropyl.

Embodiment 16. The compound according to any one of Embodiments 1-9 or a stereoisomer, a racemate, a tautomer, a hydrate or a solvate, or pharmaceutically acceptable salt thereof, wherein:

$R_1$ is

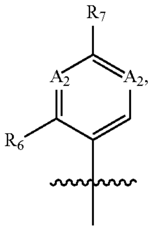

wherein $A_1$ or $A_2$ is N or CH; $R_6$ is selected from the group consisting of halo, CN and cyclopropyl; and $R_7$ is selected from the group consisting of H, halo, CN and cyclopropyl;

preferably, $R_1$ is

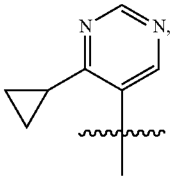

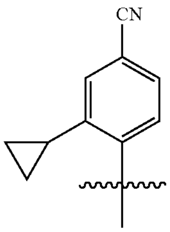

, or

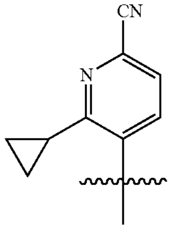

;

or $R_1$ is

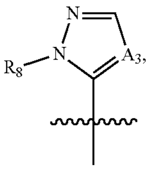

wherein $A_3$ is N or C substituted by halo, and $R_8$ is $C_{1-3}$alkyl; preferably, $R_1$ is

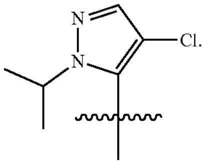 [SMILES: *c1c(Cl)cnn1C(C)C]

Embodiment 17. The compound according to Embodiment 16 or a stereoisomer, a racemate, a tautomer, a hydrate or a solvate, or pharmaceutically acceptable salt thereof, wherein the compound is of formula IIb:

IIb'

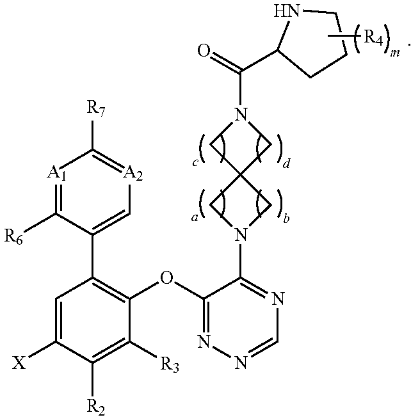

Embodiment 18. The compound according to any one of Embodiments 1-9 or a stereoisomer, a racemate, a tautomer, a hydrate or a solvate, or pharmaceutically acceptable salt thereof, wherein:

$R_1$ is —(C═O)—NRaRb, wherein Ra and Rb are each $C_{1-3}$alkyl; preferably Ra is ethyl and Rb is iso-propyl; or $R_1$ is a 6 membered heteroaryl ring, substituted with 1, 2 or 3 substituents selected from the group consisting of halo, CN and cyclopropyl.

Embodiment 19. The compound according to Embodiment 19 or a stereoisomer, a racemate, a tautomer, a hydrate or a solvate, or pharmaceutically acceptable salt thereof, wherein:

$R_1$ is —(C═O)—NRaRb, wherein Ra and Rb are each $C_{1-3}$alkyl; preferably Ra is ethyl and Rb is iso-propyl; or $R_1$ is pyridyl or pyrimidinyl, substituted with 1, 2 or 3 substituents selected from the group consisting of halo, CN and cyclopropyl.

Embodiment 20. The compound according to any one of the preceding Embodiments 1-9 or a stereoisomer, a racemate, a tautomer, a hydrate or a solvate, or pharmaceutically acceptable salt thereof, wherein:

$R_1$ is selected from the group consisting of:

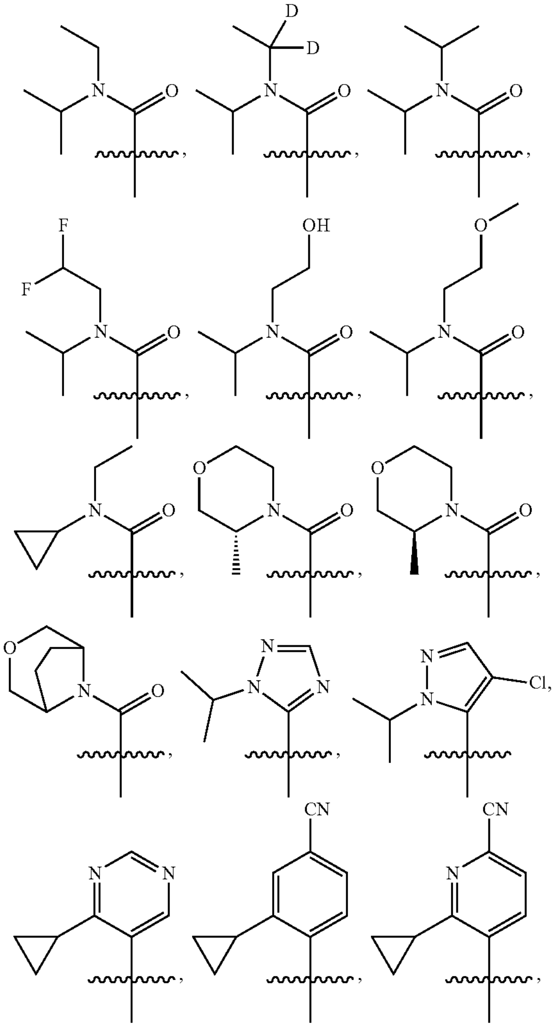

-continued

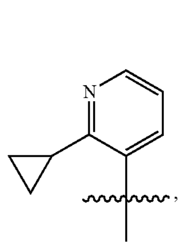,
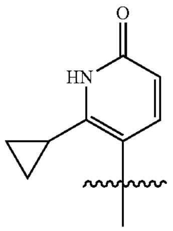
and
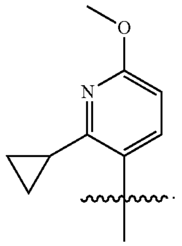.

Embodiment 21. The compound according to any one of the preceding Embodiments or a stereoisomer, a racemate, a tautomer, a hydrate or a solvate, or pharmaceutically acceptable salt thereof, wherein:

each of a and b is 1; and each of c and d is 1 or 2;

Embodiment 22. The compound according to any one of the preceding Embodiments or a stereoisomer, a racemate, a tautomer, a hydrate or a solvate, or pharmaceutically acceptable salt thereof, wherein:

n is 0 or 1, preferably 0.

Embodiment 23. The compound according to any one of Embodiments 1-15 or a stereoisomer, a racemate, a tautomer, a hydrate or a solvate, or pharmaceutically acceptable salt thereof, wherein n is 0.

Embodiment 24. The compound according to any one of Embodiments 1-15 or a stereoisomer, a racemate, a tautomer, a hydrate or a solvate, or pharmaceutically acceptable salt thereof, wherein n is 1.

Embodiment 25. The compound according to any one of the preceding Embodiments or a stereoisomer, a racemate, a tautomer, a hydrate or a solvate, or pharmaceutically acceptable salt thereof, wherein m is 0, 1 or 2.

Embodiment 26. The compound according to any one of the preceding Embodiments or a stereoisomer, a racemate, a tautomer, a hydrate or a solvate, or pharmaceutically acceptable salt thereof, wherein:

each of a and b is 1.

Embodiment 27. The compound according to any one of the preceding Embodiments or a stereoisomer, a racemate, a tautomer, a hydrate or a solvate, or pharmaceutically acceptable salt thereof, wherein:

each of c and d is 2.

Embodiment 28. The compound according to any one of the preceding Embodiments or a stereoisomer, a racemate, a tautomer, a hydrate or a solvate, or pharmaceutically acceptable salt thereof, wherein:

m is 1 or 2.

Embodiment 29. The compound according to any one of Embodiments 1-16 or a stereoisomer, a racemate, a tautomer, a hydrate or a solvate, or pharmaceutically acceptable salt thereof, wherein:

each of a and b is 1;

each of c and dis 2;

n is 0 or 1, preferably 0; and m is 0, 1 or 2.

Embodiment 30. The compound according to any one of the preceding Embodiments or a stereoisomer, a racemate, a tautomer, a hydrate or a solvate, or pharmaceutically acceptable salt thereof, wherein:

each $R_4$ is independently selected from the group consisting of halo; CN; OH; $C_{1-6}$alkylsulfonyl-; $C_{1-6}$alkylsulfonylamino-; phenyl; $C_{1-6}$alkyl optionally substituted with 1, 2 or 3 substituents selected from the group consisting of halo, CN and OH; $C_{1-6}$alkoxyl optionally substituted with 1, 2 or 3 halo; and cyclopropyl, wherein two adjacent $R_4$, together with the carbon atoms to which they are attached, optionally form a 3-6 membered cycloalkyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl- and halo;

or, two $R_4$ attached to the same carbon atom together with said carbon atom optionally form a 3-6 membered cycloalkyl ring, which is optionally substituted with 1, 2 or 3 halo;

or, two adjacent $R_4$, together with the carbon atoms to which they are attached, optionally form a 5-6 membered heteroaryl ring, which is optionally substituted with 1, 2 or 3 $C_{1-6}$alkyl, wherein the alkyl is optionally substituted with one 3-6 membered cycloalkyl ring or phenyl;

or, two adjacent $R_4$, together with the carbon atoms to which they are attached, optionally form a phenyl.

Embodiment 31. The compound according to any one of the preceding Embodiments or a stereoisomer, a racemate, a tautomer, a hydrate or a solvate, or pharmaceutically acceptable salt thereof, wherein:

each $R_4$ is independently selected from the group consisting of halo; CN; OH; $C_{1-3}$alkylsulfonyl-; $C_{1-3}$alkylsulfonylamino-; phenyl; $C_{1-3}$alkyl optionally substituted with 1, 2 or 3 substituents selected from the group consisting of halo, CN and OH; $C_{1-3}$alkoxyl optionally substituted with 1, 2 or 3 halo; and cyclopropyl, wherein two adjacent $R_4$, together with the carbon atoms to which they are attached, optionally form a 3-6 membered cycloalkyl ring, which is optionally substituted with 1, 2 or 3 substituents selected from the group consisting of $C_{1-3}$alkyl, —$C_{1-3}$alkyl-OH, $C_{1-3}$alkoxyl-$C_{1-3}$alkyl- and halo;

or, two $R_4$ attached to the same carbon atom together with said carbon atom optionally form a 3-6 membered cycloalkyl ring, which is optionally substituted with 1, 2 or 3 halo;

or, two adjacent $R_4$, together with the carbon atoms to which they are attached, optionally form a 5-6 membered heteroaryl ring, which is optionally substituted with 1, 2 or 3 $C_{1-3}$alkyl, wherein the alkyl is optionally substituted with one 3-6 membered cycloalkyl ring or phenyl;

or, two adjacent $R_4$, together with the carbon atoms to which they are attached, optionally form a phenyl.

Embodiment 32. The compound according to any one of the preceding Embodiments or a stereoisomer, a racemate, a tautomer, a hydrate or a solvate, or pharmaceutically acceptable salt thereof, wherein:

the moiety

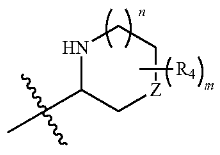
or
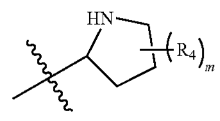

is selected from the group consisting of:
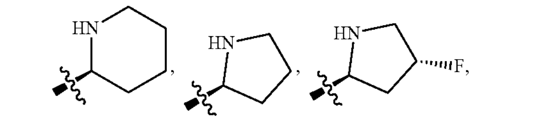
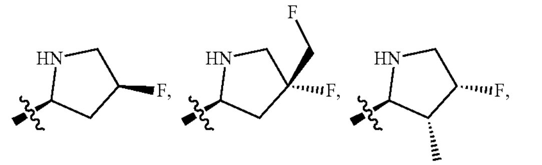
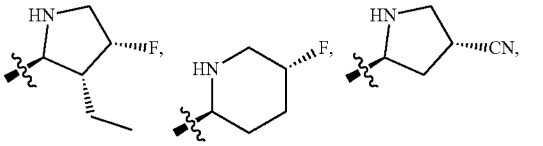
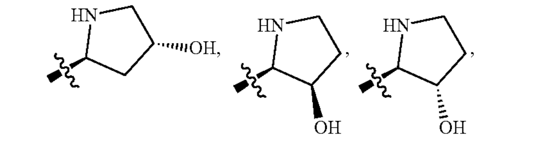
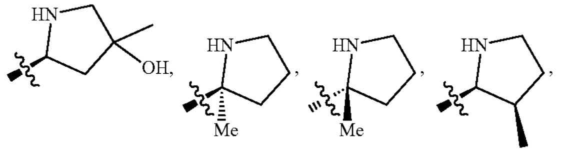
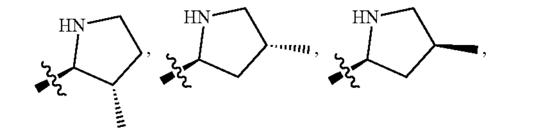
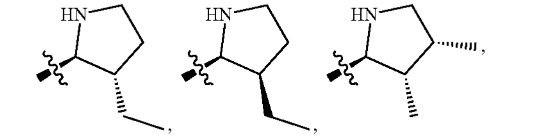
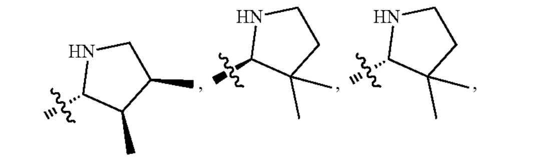
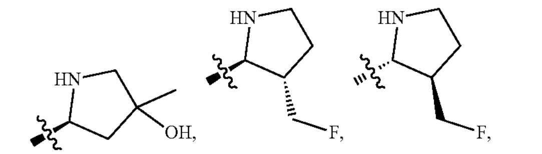
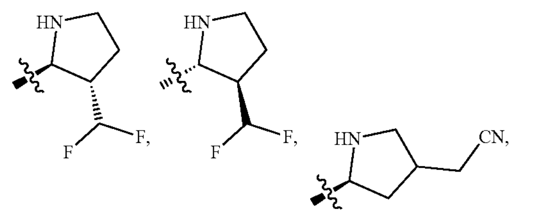
-continued
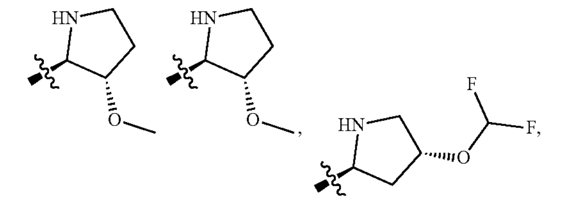
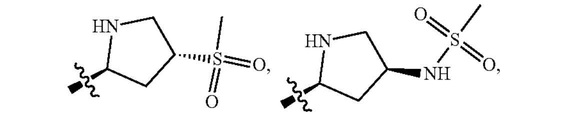
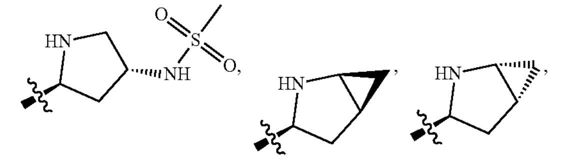
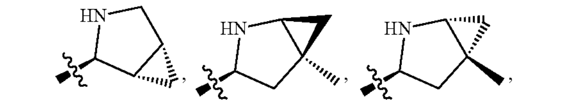
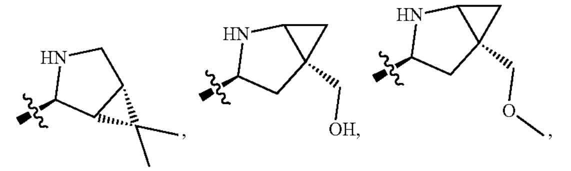
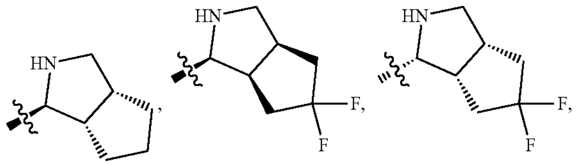
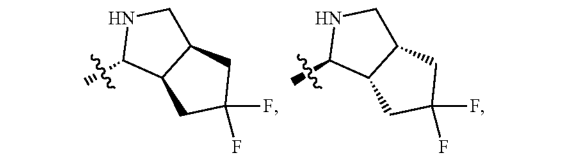
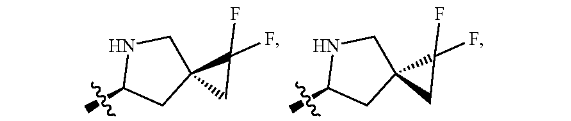
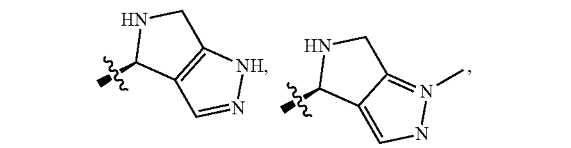
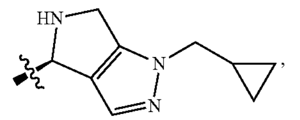
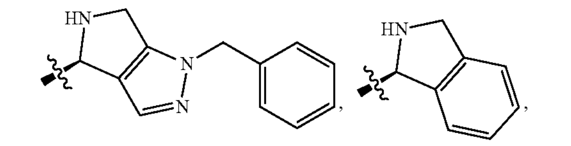

-continued

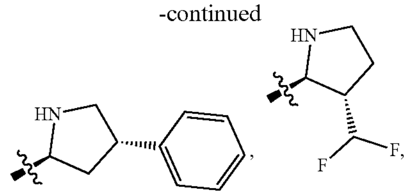

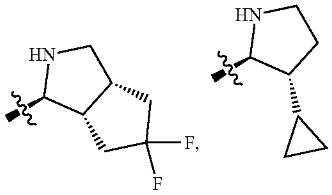

and

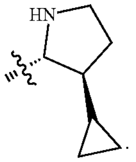

Embodiment 33. The compound according to any one of Embodiments 1-5 or a stereoisomer, a racemate, a tautomer, a hydrate or a solvate, or pharmaceutically acceptable salt thereof, wherein:

X is F;

Z is $CH_2$;

$R_1$ is selected from the group consisting of:

1) —(C═O)—NRaRb, wherein:

Ra and Rb are each independently selected from the group consisting of $C_{1-6}$alkyl optionally substituted by 1, 2 or 3 deuterium;

or Ra and Rb, together with the nitrogen atom to which they are attached, form a 5-6 membered monocyclic or 7-9 membered bicyclic heterocyclyl ring, which is optionally substituted with 1, 2 or 3 $C_{1-6}$alkyl;

2) a 5-6 membered heteroaryl ring substituted with 1, 2 or 3 substituents selected from the group consisting of halo, CN, $C_{1-6}$alkyl, $CF_3$, 3-5 membered cycloalkyl ring, oxo and $C_{1-6}$alkoxyl;

3) $C_{6-10}$aryl ring substituted with 1, 2 or 3 substituents selected from the group consisting of halo, CN, $C_{1-6}$alkyl, $CF_3$, 3-5 membered cycloalkyl ring and $C_{1-6}$alkoxyl;

$R_2$ and $R_3$ are each independently H;

each $R_4$ is independently selected from the group consisting of halo; CN; OH; $C_{1-6}$alkylsulfonyl-; $C_{1-6}$alkylsulfonylamino-; phenyl; $C_{1-6}$alkyl optionally substituted with 1, 2 or 3 substituents selected from the group consisting of halo, CN and OH; $C_{1-6}$alkoxyl optionally substituted with 1, 2 or 3 halo; and 3-6 membered cycloalkyl ring, wherein two adjacent $R_4$, together with the carbon atoms to which they are attached, optionally form a 3-6 membered cycloalkyl ring, which is optionally substituted with 1, 2 or 3 substituents selected from the group consisting of $C_{1-6}$alkyl and halo;

or, two adjacent $R_4$, together with the carbon atoms to which they are attached, optionally form a phenyl;

$R_5$ is H or halo;

each of a and b is 1;

each of c and d is 2;

n is 0; and m is 0, 1 or 2;

provided that $R_4$, if present, substituted at any chemically permissible position(s) the heterocyclyl except for the N atom adjacent to the attachment point of the heterocyclyl to the remaining structure of the compound.

Embodiment 34. The compound according to Embodiment 33 or a stereoisomer, a racemate, a tautomer, a hydrate or a solvate, or pharmaceutically acceptable salt thereof, wherein $R_5$ is H.

Embodiment 35. The compound according to any one of Embodiments 33-34 or a stereoisomer, a racemate, a tautomer, a hydrate or a solvate, or pharmaceutically acceptable salt thereof, wherein $R_1$ is —(C═O)—NRaRb, and Ra and Rb are each independently selected from the group consisting of ethyl or isopropyl.

Embodiment 36. The compound according to any one of Embodiments 33-34 or a stereoisomer, a racemate, a tautomer, a hydrate or a solvate, or pharmaceutically acceptable salt thereof, wherein $R_1$ is a 5 or 6 membered heteroaryl ring or phenyl ring, which is substituted with 1 or 2 substituents selected from the group consisting of halo, CN, $C_{1-3}$alkyl, $CF_3$, cyclopropyl, oxo and $C_{1-3}$alkoxyl.

Embodiment 37. The compound according to any one of Embodiments 33-34 or a stereoisomer, a racemate, a tautomer, a hydrate or a solvate, or pharmaceutically acceptable salt thereof, wherein:

$R_1$ is selected from the group consisting of:

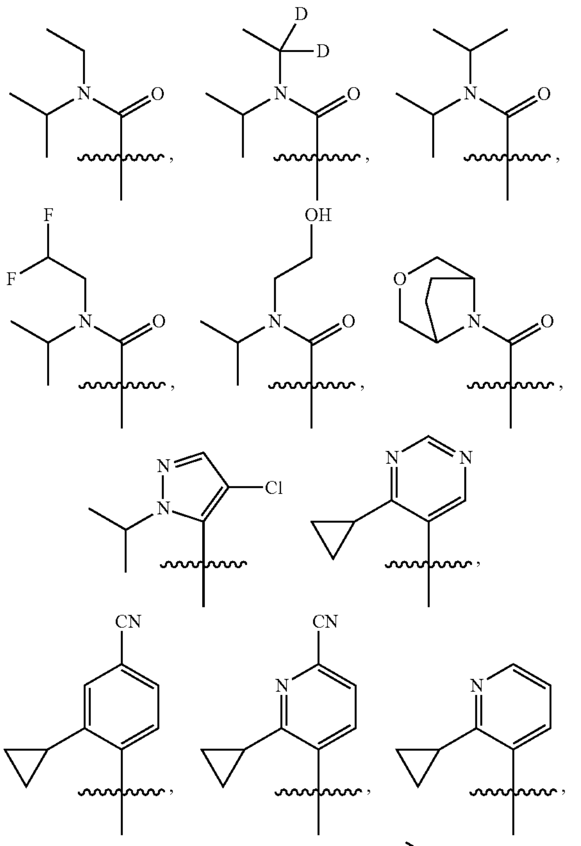

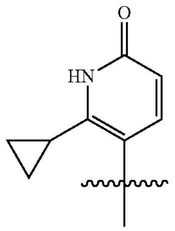

and

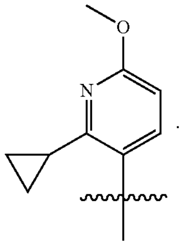

Embodiment 38. The compound according to any one of Embodiments 33-37 or a stereoisomer, a racemate, a tautomer, a hydrate or a solvate, or pharmaceutically acceptable salt thereof, wherein each $R_4$ is independently selected from the group consisting of halo; CN; OH; $C_{1-3}$alkylsulfonyl-; $C_{1-3}$alkylsulfonylamino-; phenyl; $C_{1-3}$alkyl optionally substituted with 1, 2 or 3 substituents selected from the group consisting of halo, CN and OH; $C_{1-3}$alkoxyl optionally substituted with 1, 2 or 3 halo; and cyclopropyl;

wherein two adjacent $R_4$, together with the carbon atoms to which they are attached, optionally form a 3-6 membered cycloalkyl ring, which is optionally substituted with 1, 2 or 3 substituents selected from the group consisting of $C_{1-3}$alkyl and halo;

or, two adjacent $R_4$, together with the carbon atoms to which they are attached, optionally form a phenyl.

Embodiment 39. The compound according to any one of Embodiments 33-38 or a stereoisomer, a racemate, a tautomer, a hydrate or a solvate, or pharmaceutically acceptable salt thereof, wherein:

the moiety

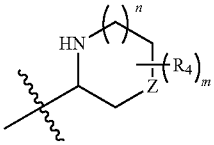
or
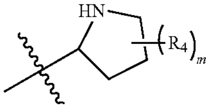

is selected from the group consisting of:

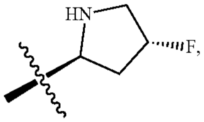
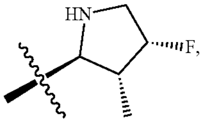
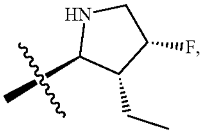
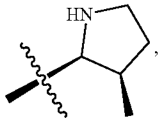,
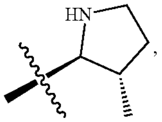,
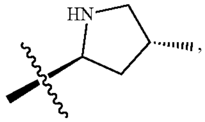,
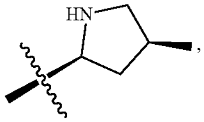,
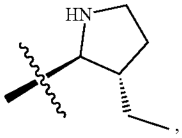,
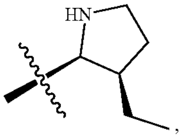,
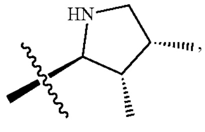,
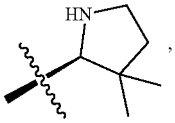,
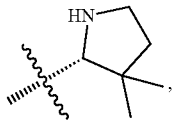,
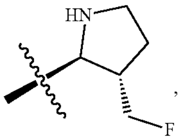,
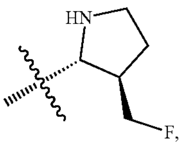
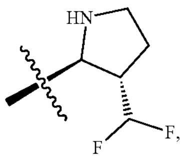
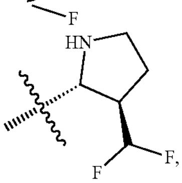

-continued

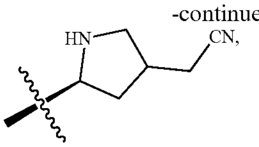
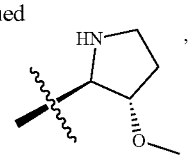,
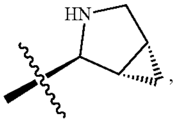,
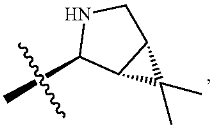,
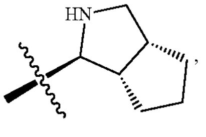,
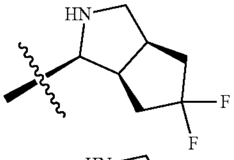,
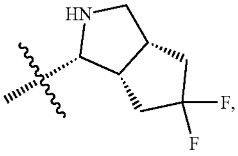
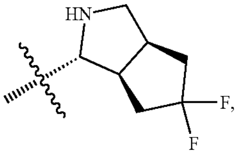
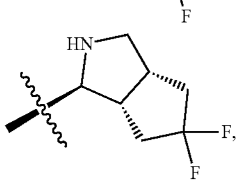
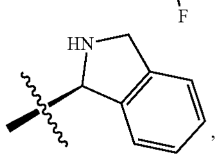,
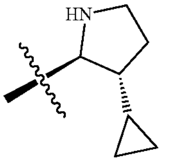
and
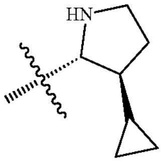.

Embodiment 40. The compound according to any one of Embodiments 1-30 and 34-38 or a stereoisomer, a racemate, a tautomer, a hydrate or a solvate, or pharmaceutically acceptable salt thereof, wherein:

each $R_4$ is independently selected from the group consisting of halo, CN, $C_{1-3}$alkoxyl and cyclopropyl, or two adjacent $R_4$, together with the carbon atoms to which they are attached, form cyclopropyl; and m is 1 or 2.

Embodiment 41. The compound according to any one of Embodiments 1-29 and 33-38 or a stereoisomer, a racemate, a tautomer, a hydrate or a solvate, or pharmaceutically acceptable salt thereof, wherein the moiety

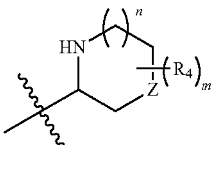
or
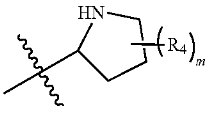

is

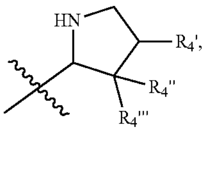

wherein $R_4'$, $R_4''$ and $R_4'''$ are independently selected from the group consisting of H; halo; CN; OH; $C_{1-6}$alkyl optionally substituted with 1, 2 or 3 substituents selected from the group consisting of halo and CN; $C_{1-6}$alkoxyl; and cyclopropyl; or $R_4'$ and $R_4''$, together with the carbon atoms to which they are attached, optionally form a 3-6 membered cycloalkyl ring, which is optionally substituted with 1, 2 or 3 substituents selected from the group consisting of $C_{1-6}$alkyl and halo; and $R_4'''$ is H.

Embodiment 42. The compound according to any one of Embodiments 1-29 and 33-38 or a stereoisomer, a racemate, a tautomer, a hydrate or a solvate, or pharmaceutically acceptable salt thereof, wherein the moiety

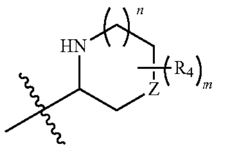

or

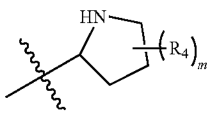

is

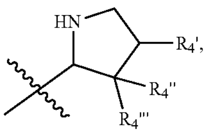

wherein $R_4'$, $R_4''$ and $R_4'''$ are independently selected from the group consisting of H; halo; CN; OH; $C_{1-6}$alkyl optionally substituted with one halo; and $C_{1-6}$alkoxyl; or $R_4'$ and $R_4''$, together with the carbon atoms to which they are attached, optionally form a 3-6 membered cycloalkyl ring, which is optionally substituted with 1 or 2 $C_{1-6}$alkyl; and $R_4'''$ is H.

Embodiment 43. The compound according to any one of Embodiments 1-29 and 33-38 or a stereoisomer, a racemate, a tautomer, a hydrate or a solvate, or pharmaceutically acceptable salt thereof, wherein the moiety

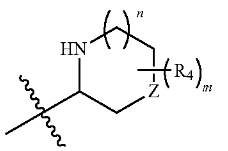

or

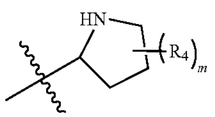

is

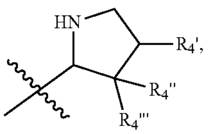

wherein $R_4'$, $R_4''$ and $R_4'''$ are independently selected from the group consisting of H; halo; CN; $C_{1-3}$alkyl optionally substituted with one halo; and $C_{1-3}$alkoxyl; or $R_4'$ and $R_4''$, together with the carbon atoms to which they are attached, optionally form a 3-5 membered cycloalkyl ring, which is optionally substituted with 1 or 2 $C_{1-3}$alkyl; and $R_4'''$ is H.

Embodiment 44. The compound according to any one of Embodiments 1-29 and 33-38 or a stereoisomer, a racemate, a tautomer, a hydrate or a solvate, or pharmaceutically acceptable salt thereof, wherein:

the moiety

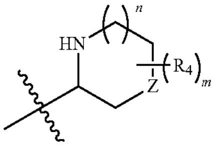

or

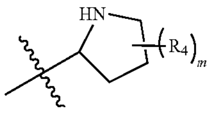

is

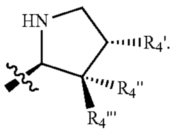

Embodiment 45. The compound according to any one of the Embodiments 41-44 or a stereoisomer, a racemate, a tautomer, a hydrate or a solvate, or pharmaceutically acceptable salt thereof, wherein:

wherein $R_4'$, $R_4''$ and $R_4'''$ are independently selected from the group consisting of H; halo; CN; OH; $C_{1-3}$alkyl optionally substituted with one halo; and $C_{1-3}$alkoxyl.

Embodiment 46. The compound according to any one of Embodiments 41-44 or a stereoisomer, a racemate, a tautomer, a hydrate or a solvate, or pharmaceutically acceptable salt thereof, wherein:

$R_4'$ and $R_4''$, together with the carbon atoms to which they are attached, optionally form a 3-5 membered cycloalkyl ring, which is optionally substituted with 1 or 2 $C_{1-3}$alkyl; and $R_4'''$ is H.

Embodiment 47. The compound according to any one of Embodiments 41-44 or a stereoisomer, a racemate, a tautomer, a hydrate or a solvate, or pharmaceutically acceptable salt thereof, wherein:

wherein each of $R_4'$ and $R_4'''$ are H; and $R_4''$ is $C_{1-3}$alkyl substituted with one halo.

Embodiment 48. The compound according to any one of Embodiments 41-44 or a stereoisomer, a racemate, a tautomer, a hydrate or a solvate, or pharmaceutically acceptable salt thereof, wherein:

$R_4'$ and $R_4''$, together with the carbon atoms to which they are attached, optionally form a 3 or 5 membered cycloalkyl ring, which is optionally substituted with 1 or 2 methyl; and $R_4'''$ is H.

Embodiment 49. The compound according to any one of 1-29 and 33-38 or a stereoisomer, a racemate, a tautomer, a hydrate or a solvate, or pharmaceutically acceptable salt thereof, wherein:

the moiety

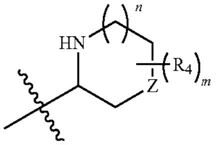

or

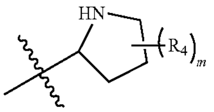

is

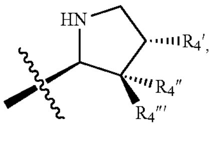

wherein $R_4'''$ is H; and $R_4'$ and $R_4''$ are independently selected from the group consisting of H; halo; $C_{1-6}$alkyl optionally substituted with one halo; and $C_{1-6}$alkoxyl; provided that one of $R_4'$ and $R_4''$ is not H; or, $R_4'$ and $R_4''$, together with the carbon atoms to which they are attached, form a 3 or 5 membered cycloalkyl ring optionally substituted with 1 or 2 $C_{1-3}$alkyl, or form a phenyl ring.

Embodiment 50. The compound according to 1-29 and 33-38 or a stereoisomer, a racemate, a tautomer, a hydrate or a solvate, or pharmaceutically acceptable salt thereof, wherein:

the moiety

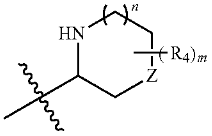

or

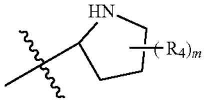

is

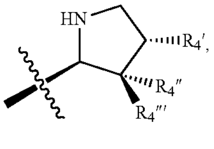

wherein $R_4'''$ is H; and $R_4'$ and $R_4''$ are independently selected from the group consisting of H; halo; $C_{1-6}$alkyl optionally substituted with one halo; and $C_{1-6}$alkoxyl; provided that one of $R_4'$ and $R_4''$ is not H; or, $R_4'$ and $R_4''$, together with the carbon atoms to which they are attached, form a 3 or 5 membered cycloalkyl ring optionally substituted with 1 or 2 $C_{1-3}$alkyl.

Embodiment 51. The compound according to any one of Embodiments 1-29 and 33-38 or a stereoisomer, a racemate, a tautomer, a hydrate or a solvate, or pharmaceutically acceptable salt thereof, wherein:

the moiety

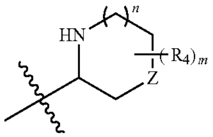

or

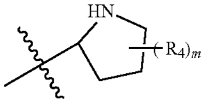

is

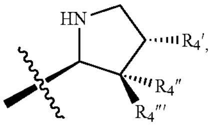

wherein $R_4'$ is H; and $R_4''$ and $R_4'''$ are independently $C_{1-3}$alkyl.

Embodiment 52. The compound according to any one of Embodiments 1-29 and 33-38 or a stereoisomer, a racemate, a tautomer, a hydrate or a solvate, or pharmaceutically acceptable salt thereof, wherein the moiety

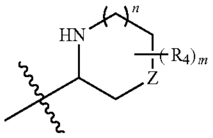

or

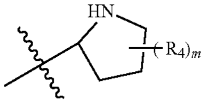

is

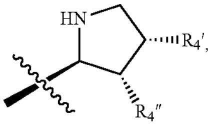

wherein one of $R_4'$ and $R_4''$ is H; and the other is $C_{1-6}$alkyl; or $R_4'$ and $R_4''$, together with the carbon atoms to which they are attached, optionally form a 3 or 5 membered cycloalkyl ring, which is optionally substituted with 1 or 2 $C_{1-3}$alkyl.

Embodiment 53. The compound according to any one of Embodiments 1-29 and 33-38 or a stereoisomer, a racemate, a tautomer, a hydrate or a solvate, or pharmaceutically acceptable salt thereof, wherein the moiety

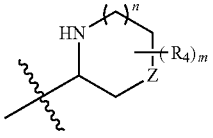

or

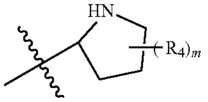

is

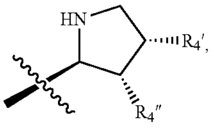

wherein $R_4$' is H; and $R_4$" is $C_{1-6}$alkyl substituted with one halo; or $R_4$' and $R_4$", together with the carbon atoms to which they are attached, optionally form a 3 or 5 membered cycloalkyl ring.

Embodiment 54. The compound according to any one of Embodiments 1-29 and 33-38 or a stereoisomer, a racemate, a tautomer, a hydrate or a solvate, or pharmaceutically acceptable salt thereof, wherein the moiety

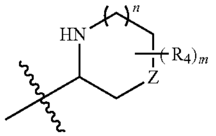
or
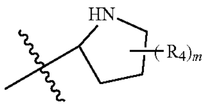

is

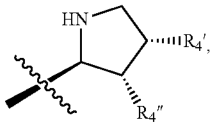

wherein $R_4$' is H; and $R_4$" is $C_{1-3}$alkyl substituted with one F; or $R_4$' and $R_4$", together with the carbon atoms to which they are attached, optionally form a 3 or 5 membered cycloalkyl ring.

Embodiment 55. The compound according to any one of Embodiments 1-29 and 33-38 or a stereoisomer, a racemate, a tautomer, a hydrate or a solvate, or pharmaceutically acceptable salt thereof, wherein the moiety

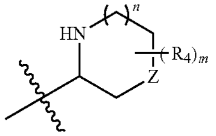
or
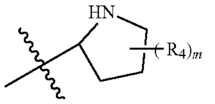

is

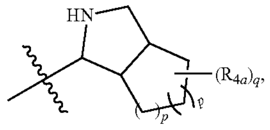

wherein each p is dependently 0 or 1; preferably both p are 0, or both p are 1;

q is 0, 1 or 2; preferably q is 0 or 2;

$R_{4a}$ is $C_{1-3}$alkyl, preferably methyl.

Embodiment 56. The compound according to Embodiment 55 or a stereoisomer, a racemate, a tautomer, a hydrate or a solvate, or pharmaceutically acceptable salt thereof, wherein the moiety

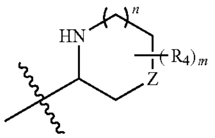
or
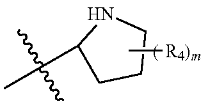

is

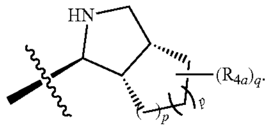

Embodiment 57. The compound according to any one of the Embodiments 1 to 2 or a stereoisomer, a racemate, a tautomer, a hydrate or a solvate, or pharmaceutically acceptable salt thereof, wherein the compound is selected from the group consisting of:

| Compound Nos. | Structures |
| --- | --- |
| Example 2 | 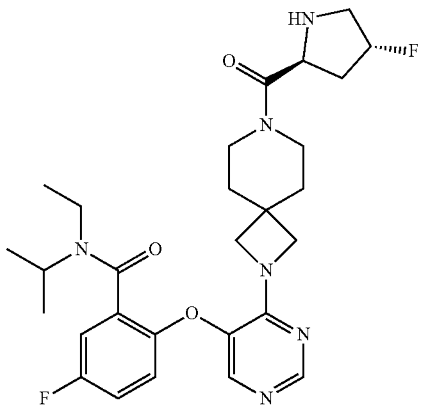 [SMILES: CCN(C(=O)c1cc(F)ccc1Oc1cncnc1N1CC2(CCN(C(=O)[C@@H]3C[C@@H](F)CN3)CC2)C1)C(C)C] |

-continued
| Compound Nos. | Structures |
|---|---|
| Example 3 | 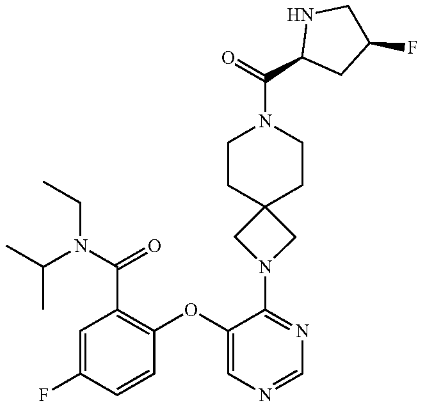 [SMILES: CCN(C(=O)c1cc(F)ccc1Oc1cncnc1N1CC2(CCN(C(=O)[C@@H]3C[C@H](F)CN3)CC2)C1)C(C)C] |
| Example 4 | 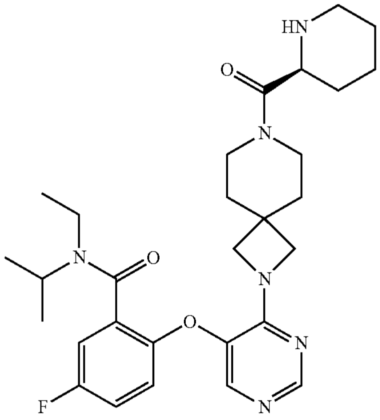 [SMILES: CCN(C(=O)c1cc(F)ccc1Oc1cncnc1N1CC2(CCN(C(=O)[C@@H]3CCCCN3)CC2)C1)C(C)C] |
| Example 5 | 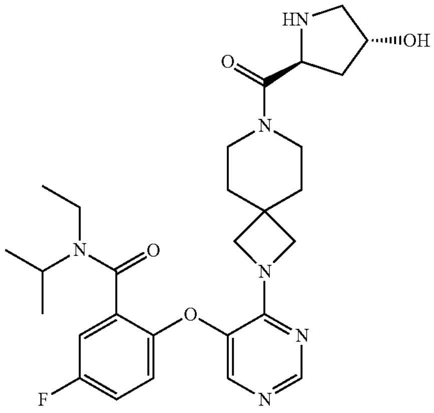 [SMILES: CCN(C(=O)c1cc(F)ccc1Oc1cncnc1N1CC2(CCN(C(=O)[C@@H]3C[C@@H](O)CN3)CC2)C1)C(C)C] |

-continued
| Compound Nos. | Structures |
| --- | --- |
| Example 6 | 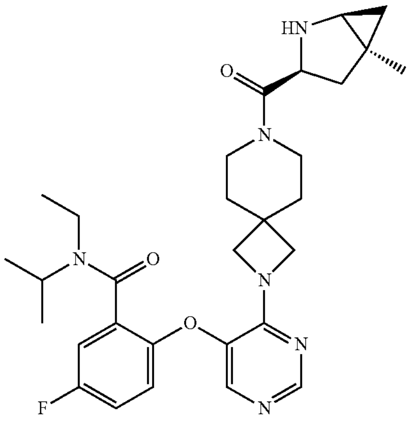 [SMILES: CCN(C(=O)c1cc(F)ccc1Oc1cncnc1N1CC2(CCN(C(=O)[C@@H]3C[C@]4(C)C[C@@H]4N3)CC2)C1)C(C)C] |
| Example 7 | 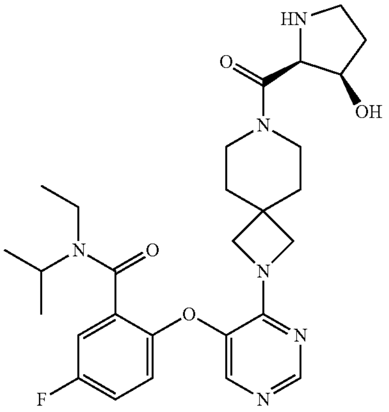 [SMILES: CCN(C(=O)c1cc(F)ccc1Oc1cncnc1N1CC2(CCN(C(=O)[C@H]3NCC[C@H]3O)CC2)C1)C(C)C] |
| Example 8 | 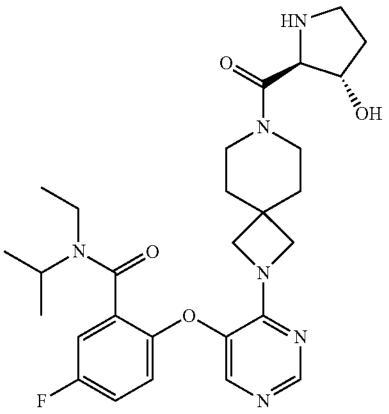 [SMILES: CCN(C(=O)c1cc(F)ccc1Oc1cncnc1N1CC2(CCN(C(=O)[C@H]3NCC[C@@H]3O)CC2)C1)C(C)C] |

-continued
| Compound Nos. | Structures |
|---|---|
| Example 9 | 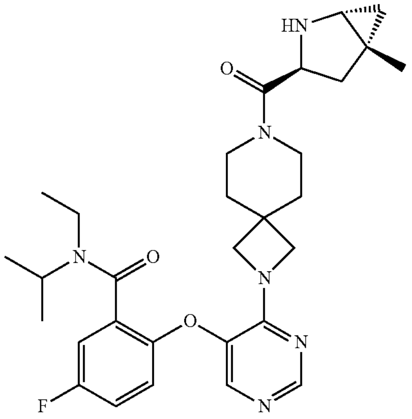 [SMILES: CCN(C(=O)c1cc(F)ccc1Oc1cncnc1N1CC2(CCN(C(=O)[C@@H]3C[C@@]4(C)C[C@H]4N3)CC2)C1)C(C)C] |
| Example 10 | 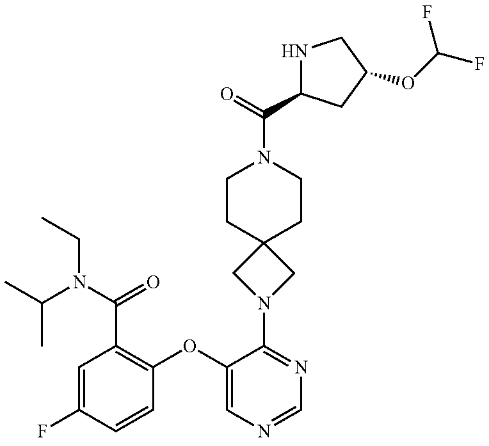 [SMILES: CCN(C(=O)c1cc(F)ccc1Oc1cncnc1N1CC2(CCN(C(=O)[C@@H]3C[C@@H](OC(F)F)CN3)CC2)C1)C(C)C] |
| Example 11 | 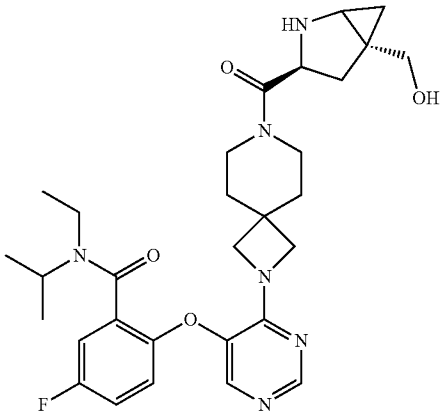 [SMILES: CCN(C(=O)c1cc(F)ccc1Oc1cncnc1N1CC2(CCN(C(=O)[C@@H]3C[C@]4(CO)CC4N3)CC2)C1)C(C)C] |

-continued
| Compound Nos. | Structures |
| --- | --- |
| Example 12 | 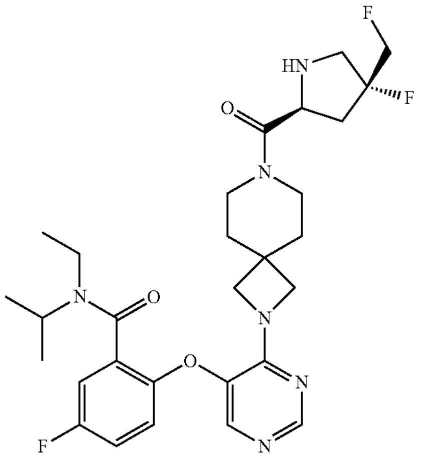 [SMILES: CCN(C(=O)c1cc(F)ccc1Oc1cncnc1N1CC2(CCN(C(=O)[C@@H]3C[C@](F)(CF)CN3)CC2)C1)C(C)C] |
| Example 13 | 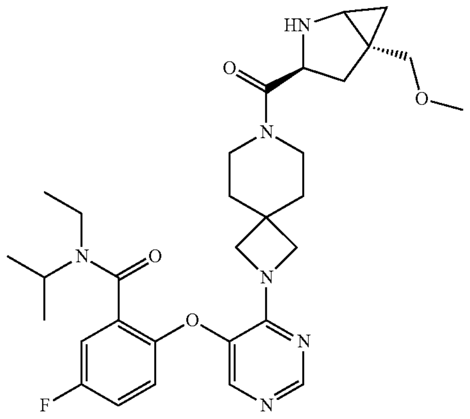 [SMILES: CCN(C(=O)c1cc(F)ccc1Oc1cncnc1N1CC2(CCN(C(=O)[C@@H]3C[C@]4(COC)CC4N3)CC2)C1)C(C)C] |
| Example 14 | 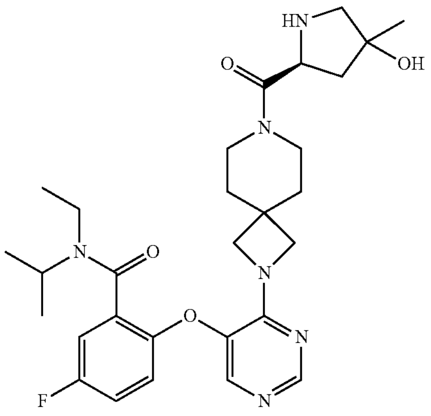 [SMILES: CCN(C(=O)c1cc(F)ccc1Oc1cncnc1N1CC2(CCN(C(=O)[C@@H]3CC(C)(O)CN3)CC2)C1)C(C)C] |

-continued
| Compound Nos. | Structures |
|---|---|
| Example 15 | 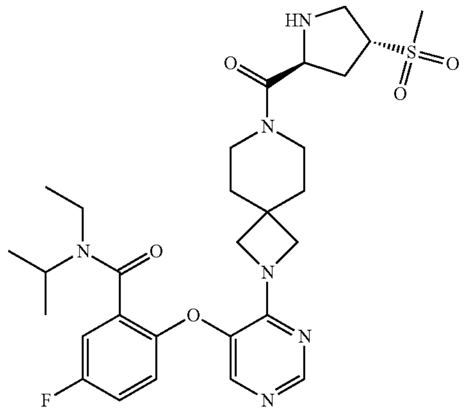 [SMILES: CCN(C(=O)c1cc(F)ccc1Oc1cncnc1N1CC2(CCN(C(=O)[C@@H]3C[C@@H](S(C)(=O)=O)CN3)CC2)C1)C(C)C] |
| Example 16 | 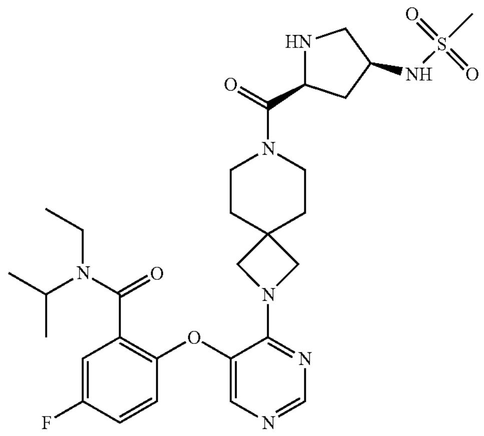 [SMILES: CCN(C(=O)c1cc(F)ccc1Oc1cncnc1N1CC2(CCN(C(=O)[C@@H]3C[C@H](NS(C)(=O)=O)CN3)CC2)C1)C(C)C] |
| Example 17 | 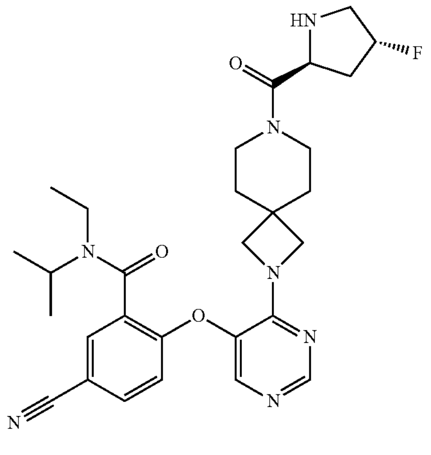 [SMILES: CCN(C(=O)c1cc(C#N)ccc1Oc1cncnc1N1CC2(CCN(C(=O)[C@@H]3C[C@@H](F)CN3)CC2)C1)C(C)C] |

-continued
| Compound Nos. | Structures |
|---|---|
| Example 18 | 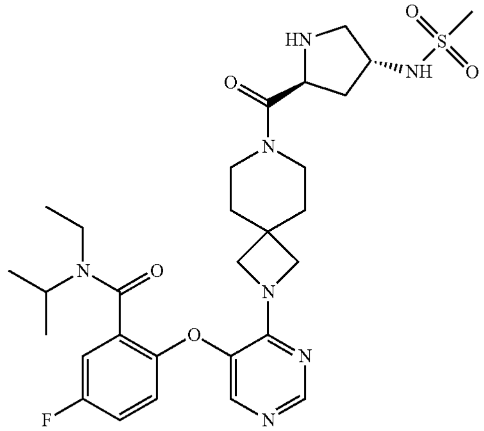 [SMILES: CCN(C(=O)c1cc(F)ccc1Oc1cncnc1N1CC2(CCN(C(=O)[C@@H]3C[C@@H](NS(C)(=O)=O)CN3)CC2)C1)C(C)C] |
| Example 19 | 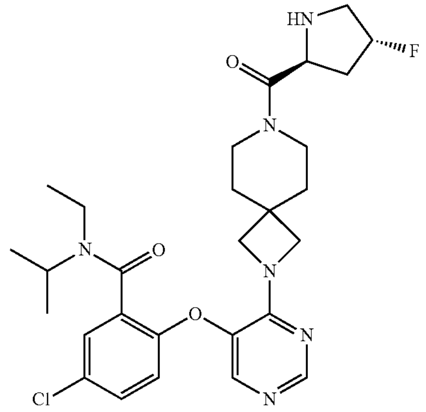 [SMILES: CCN(C(=O)c1cc(Cl)ccc1Oc1cncnc1N1CC2(CCN(C(=O)[C@@H]3C[C@@H](F)CN3)CC2)C1)C(C)C] |
| Example 20 | 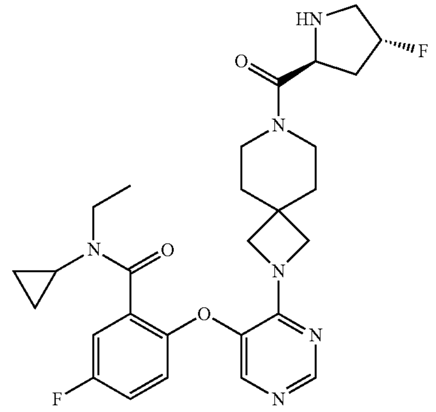 [SMILES: CCN(C(=O)c1cc(F)ccc1Oc1cncnc1N1CC2(CCN(C(=O)[C@@H]3C[C@@H](F)CN3)CC2)C1)C1CC1] |

-continued
| Compound Nos. | Structures |
| --- | --- |
| Example 21 | 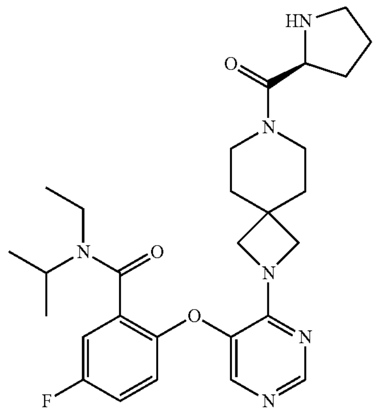 [SMILES: CCN(C(=O)c1cc(F)ccc1Oc1cncnc1N1CC2(CCN(C(=O)[C@@H]3CCCN3)CC2)C1)C(C)C] |
| Example 22 | 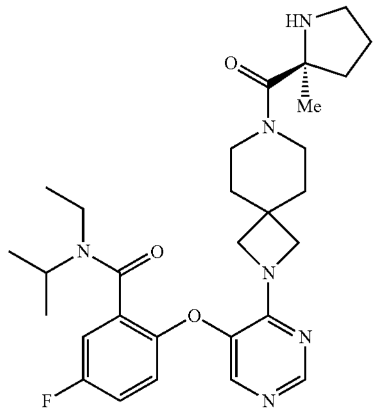 [SMILES: CCN(C(=O)c1cc(F)ccc1Oc1cncnc1N1CC2(CCN(C(=O)[C@]3(C)CCCN3)CC2)C1)C(C)C] |
| Example 23 | 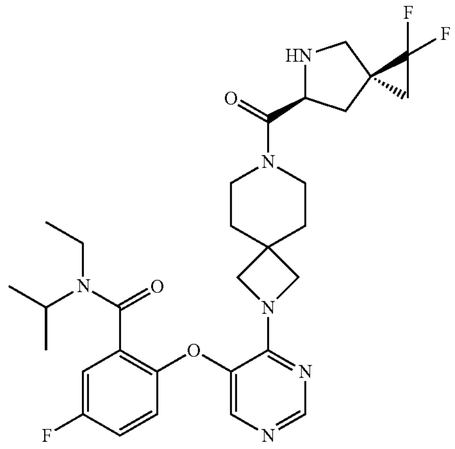 [SMILES: CCN(C(=O)c1cc(F)ccc1Oc1cncnc1N1CC2(CCN(C(=O)[C@@H]3C[C@]4(CN3)CC4(F)F)CC2)C1)C(C)C] |

-continued
| Compound Nos. | Structures |
|---|---|
| Example 24 | 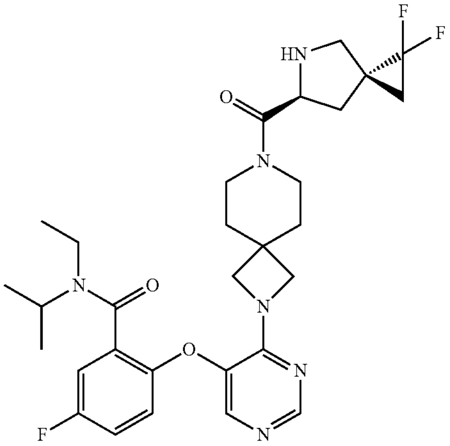 [SMILES: CCN(C(=O)c1cc(F)ccc1Oc1cncnc1N1CC2(CCN(C(=O)[C@@H]3C[C@@]4(CN3)CC4(F)F)CC2)C1)C(C)C] |
| Example 25 | 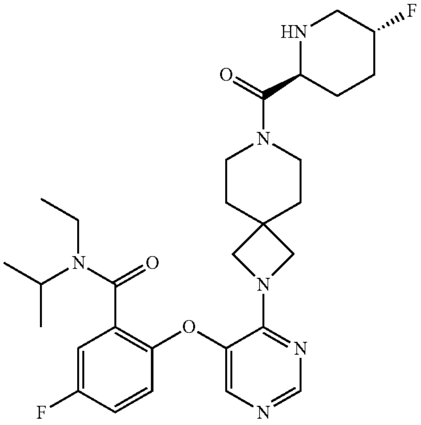 [SMILES: CCN(C(=O)c1cc(F)ccc1Oc1cncnc1N1CC2(CCN(C(=O)[C@@H]3CC[C@@H](F)CN3)CC2)C1)C(C)C] |
| Example 26 | 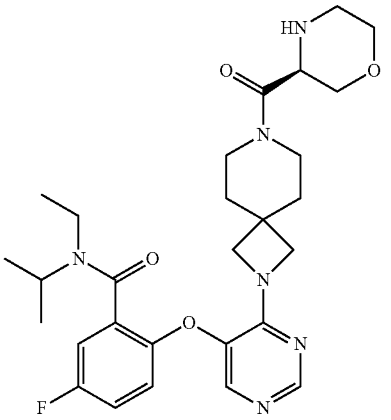 [SMILES: CCN(C(=O)c1cc(F)ccc1Oc1cncnc1N1CC2(CCN(C(=O)[C@@H]3COCCN3)CC2)C1)C(C)C] |

-continued
| Compound Nos. | Structures |
|---|---|
| Example 27 | 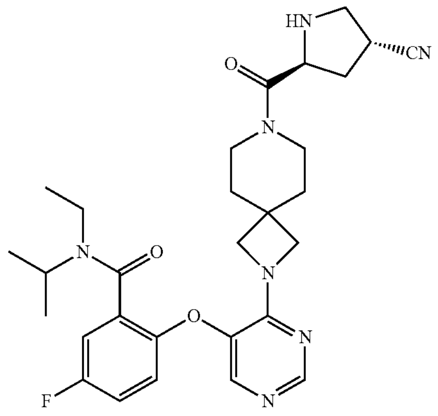 [SMILES: CCN(C(=O)c1cc(F)ccc1Oc1cncnc1N1CC2(CCN(C(=O)[C@@H]3C[C@@H](C#N)CN3)CC2)C1)C(C)C] |
| Example 28 | 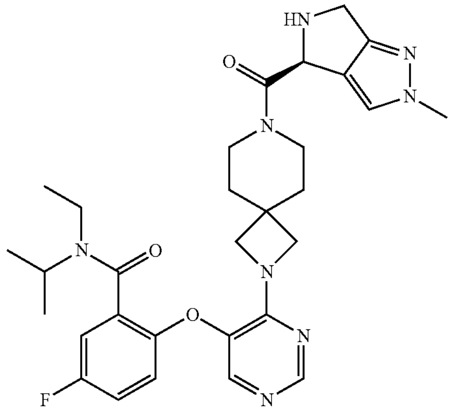 [SMILES: CCN(C(=O)c1cc(F)ccc1Oc1cncnc1N1CC2(CCN(C(=O)[C@H]3NCc4nn(C)cc43)CC2)C1)C(C)C] |
| Example 29 | 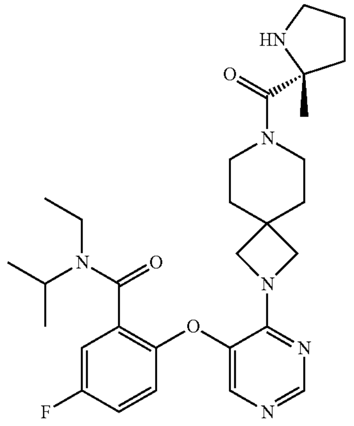 [SMILES: CCN(C(=O)c1cc(F)ccc1Oc1cncnc1N1CC2(CCN(C(=O)[C@@]3(C)CCCN3)CC2)C1)C(C)C] |

-continued
| Compound Nos. | Structures |
| --- | --- |
| Example 30 | 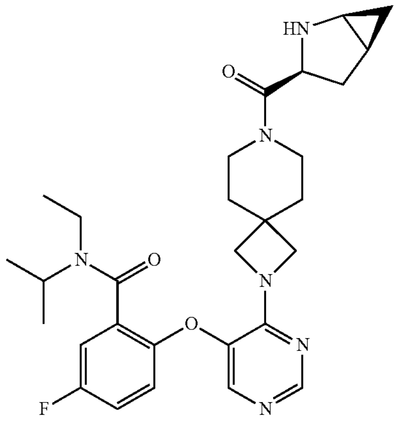 [SMILES: CCN(C(=O)c1cc(F)ccc1Oc1cncnc1N1CC2(CCN(C(=O)[C@@H]3C[C@@H]4C[C@@H]4N3)CC2)C1)C(C)C] |
| Example 31 | 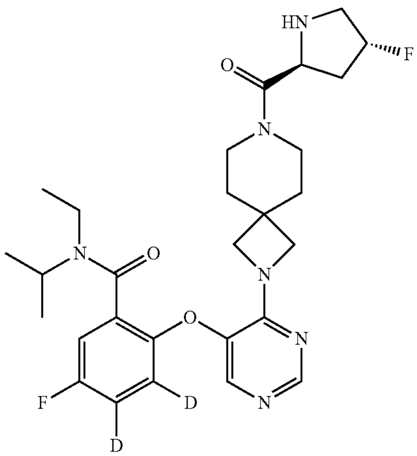 [SMILES: [2H]c1c(F)cc(C(=O)N(CC)C(C)C)c(Oc2cncnc2N2CC3(CCN(C(=O)[C@@H]4C[C@@H](F)CN4)CC3)C2)c1[2H]] |
| Example 32 | 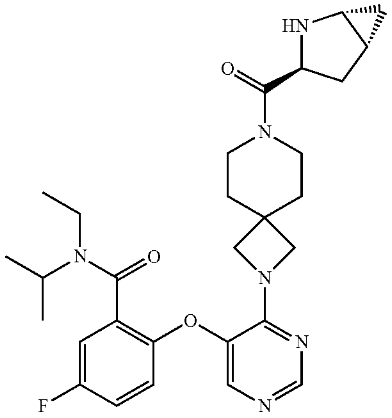 [SMILES: CCN(C(=O)c1cc(F)ccc1Oc1cncnc1N1CC2(CCN(C(=O)[C@@H]3C[C@H]4C[C@H]4N3)CC2)C1)C(C)C] |

-continued
| Compound Nos. | Structures |
|---|---|
| Example 33 | 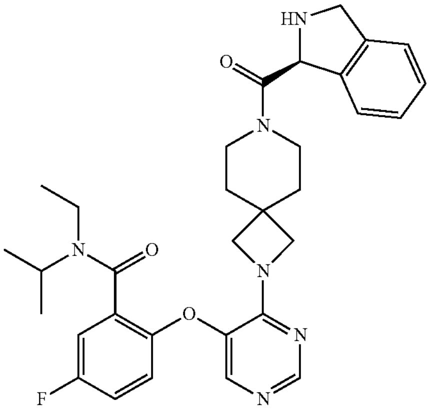 [SMILES: CCN(C(=O)c1cc(F)ccc1Oc1cncnc1N1CC2(CCN(C(=O)[C@H]3NCc4ccccc43)CC2)C1)C(C)C] |
| Example 34 | 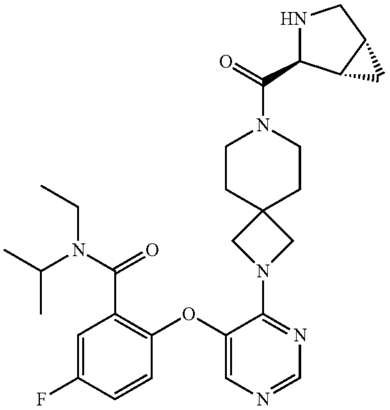 [SMILES: CCN(C(=O)c1cc(F)ccc1Oc1cncnc1N1CC2(CCN(C(=O)[C@H]3NC[C@@H]4C[C@@H]43)CC2)C1)C(C)C] |
| Example 36 | 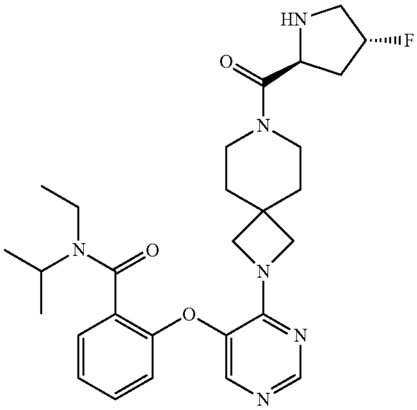 [SMILES: CCN(C(=O)c1ccccc1Oc1cncnc1N1CC2(CCN(C(=O)[C@@H]3C[C@@H](F)CN3)CC2)C1)C(C)C] |
| Example 37 | 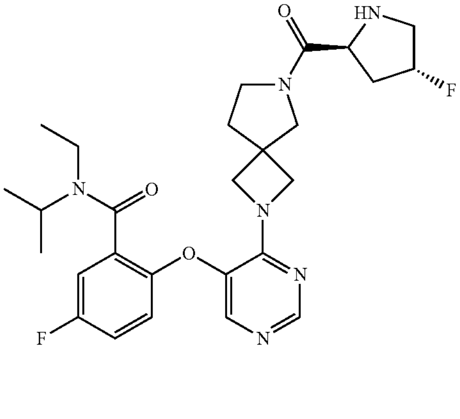 [SMILES: CCN(C(=O)c1cc(F)ccc1Oc1cncnc1N1CC2(CCN(C(=O)[C@@H]3C[C@@H](F)CN3)C2)C1)C(C)C] |

-continued
| Compound Nos. | Structures |
|---|---|
| Example 38 | 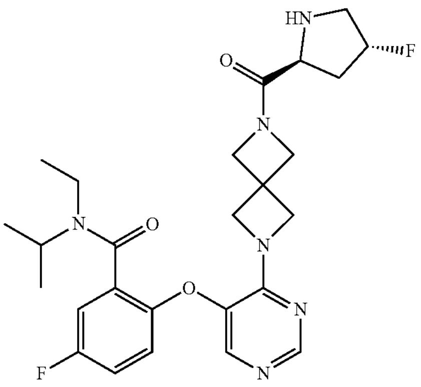 [SMILES: CCN(C(=O)c1cc(F)ccc1Oc1cncnc1N1CC2(CN(C(=O)[C@@H]3C[C@@H](F)CN3)C2)C1)C(C)C] |
| Example 39 | 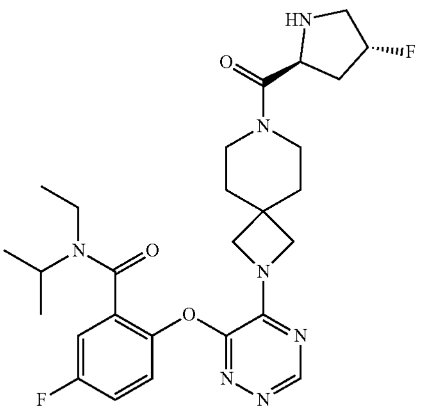 |
| Example 40 | 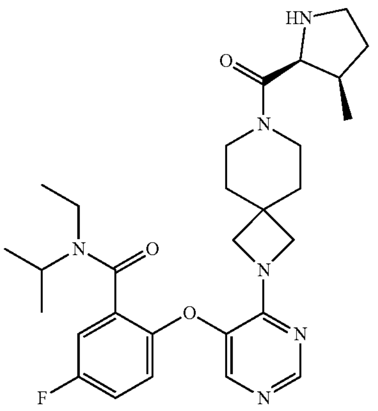 [SMILES: CCN(C(=O)c1cc(F)ccc1Oc1cncnc1N1CC2(CCN(C(=O)[C@H]3NCC[C@H]3C)CC2)C1)C(C)C] |

-continued
| Compound Nos. | Structures |
| --- | --- |
| Example 41 | 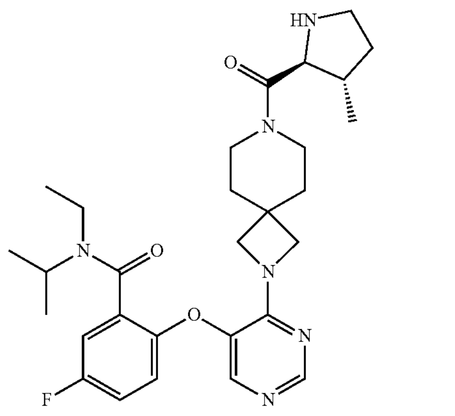 [SMILES: CCN(C(=O)c1cc(F)ccc1Oc1cncnc1N1CC2(CCN(C(=O)[C@H]3NCC[C@@H]3C)CC2)C1)C(C)C] |
| Example 42 | 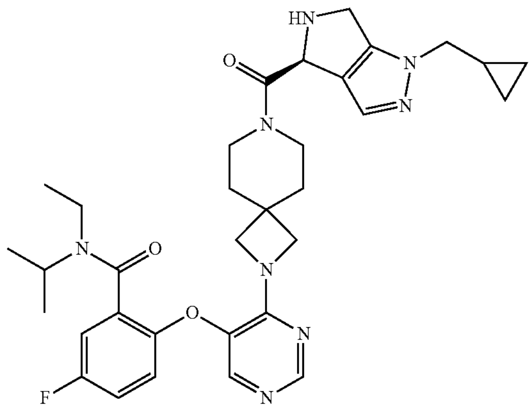 [SMILES: CCN(C(=O)c1cc(F)ccc1Oc1cncnc1N1CC2(CCN(C(=O)[C@H]3NCc4c3cnn4CC3CC3)CC2)C1)C(C)C] |
| Example 43 | 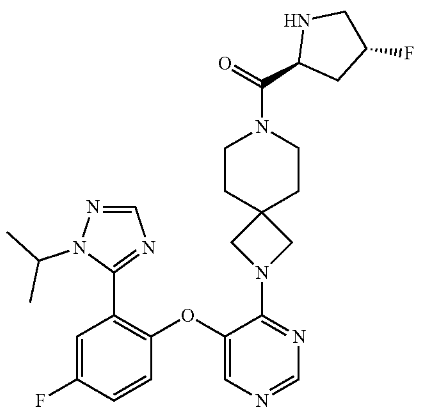 [SMILES: CC(C)n1ncnc1-c1cc(F)ccc1Oc1cncnc1N1CC2(CCN(C(=O)[C@@H]3C[C@@H](F)CN3)CC2)C1] |

-continued
| Compound Nos. | Structures |
|---|---|
| Example 44 | 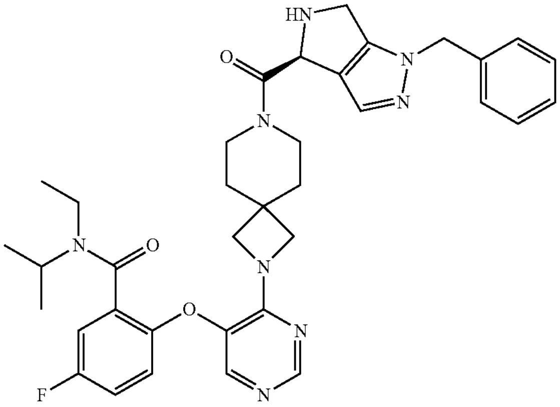 [SMILES: CCN(C(=O)c1cc(F)ccc1Oc1cncnc1N1CC2(CCN(C(=O)[C@H]3NCc4c3cnn4Cc3ccccc3)CC2)C1)C(C)C] |
| Example 45 | 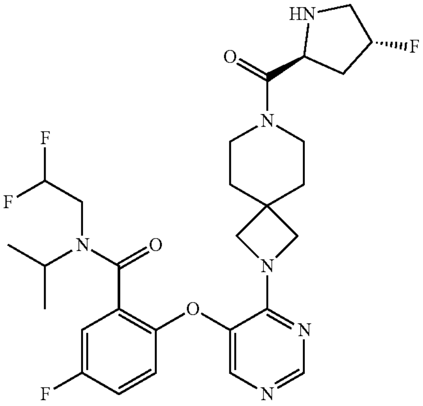 [SMILES: CC(C)N(CC(F)F)C(=O)c1cc(F)ccc1Oc1cncnc1N1CC2(CCN(C(=O)[C@@H]3C[C@@H](F)CN3)CC2)C1] |
| Example 46 | 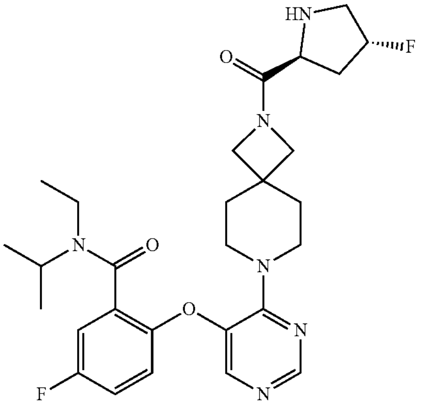 [SMILES: CCN(C(=O)c1cc(F)ccc1Oc1cncnc1N1CCC2(CC1)CN(C(=O)[C@@H]1C[C@@H](F)CN1)C2)C(C)C] |

-continued
| Compound Nos. | Structures |
| --- | --- |
| Example 47 | 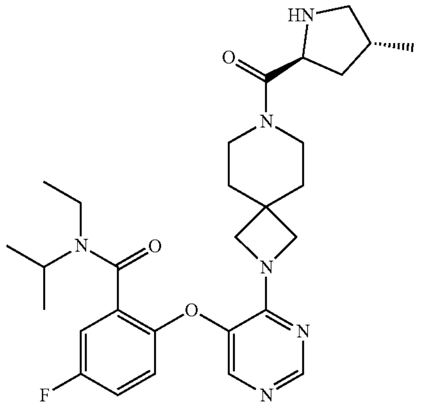 [SMILES: CCN(C(=O)c1cc(F)ccc1Oc1cncnc1N1CC2(CCN(C(=O)[C@@H]3C[C@@H](C)CN3)CC2)C1)C(C)C] |
| Example 48 | 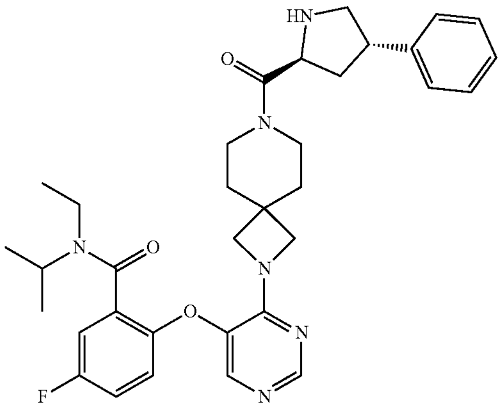 [SMILES: CCN(C(=O)c1cc(F)ccc1Oc1cncnc1N1CC2(CCN(C(=O)[C@@H]3C[C@@H](c4ccccc4)CN3)CC2)C1)C(C)C] |
| Example 49 | 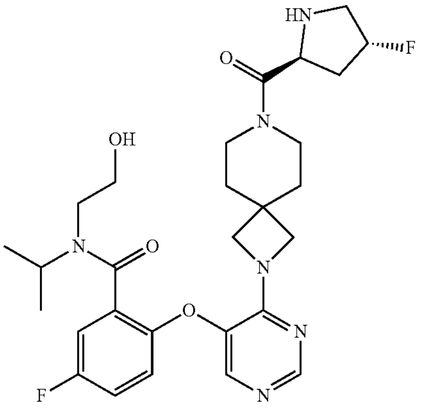 [SMILES: CC(C)N(CCO)C(=O)c1cc(F)ccc1Oc1cncnc1N1CC2(CCN(C(=O)[C@@H]3C[C@@H](F)CN3)CC2)C1] |

-continued
| Compound Nos. | Structures |
|---|---|
| Example 50 | 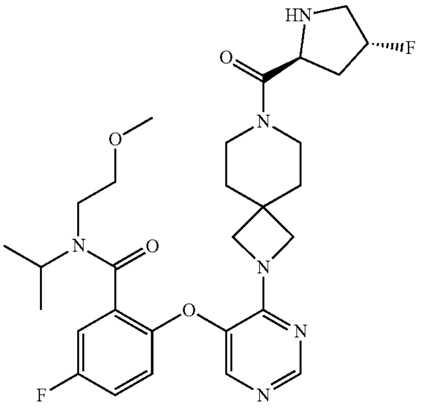 [SMILES: COCCN(C(=O)c1cc(F)ccc1Oc1cncnc1N1CC2(CCN(C(=O)[C@@H]3C[C@@H](F)CN3)CC2)C1)C(C)C] |
| Example 51 | 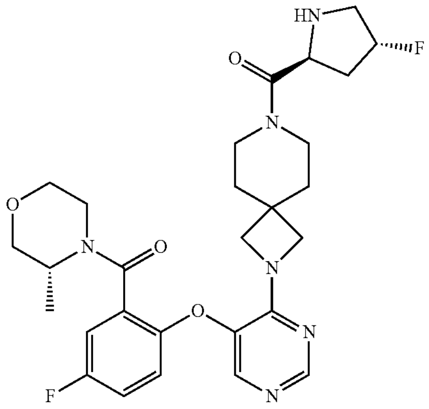 [SMILES: C[C@@H]1COCCN1C(=O)c1cc(F)ccc1Oc1cncnc1N1CC2(CCN(C(=O)[C@@H]3C[C@@H](F)CN3)CC2)C1] |
| Example 52 | 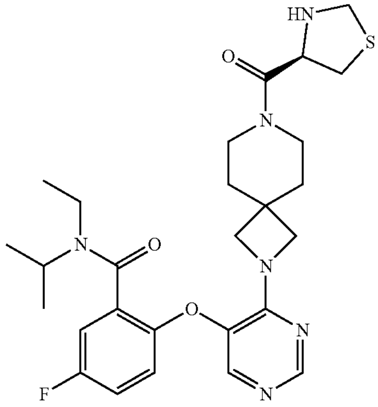 [SMILES: CCN(C(=O)c1cc(F)ccc1Oc1cncnc1N1CC2(CCN(C(=O)[C@@H]3CSCN3)CC2)C1)C(C)C] |

-continued
| Compound Nos. | Structures |
| --- | --- |
| Example 53 | 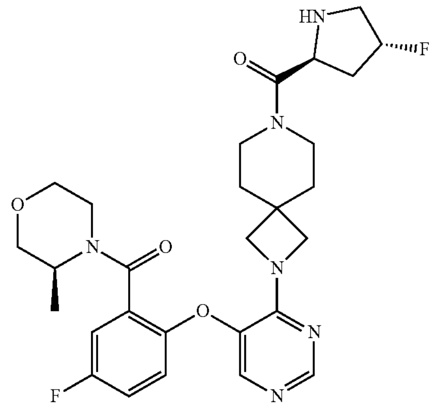 [SMILES: C[C@H]1COCCN1C(=O)c1cc(F)ccc1Oc1cncnc1N1CC2(CCN(C(=O)[C@@H]3C[C@@H](F)CN3)CC2)C1] |
| Example 54 | 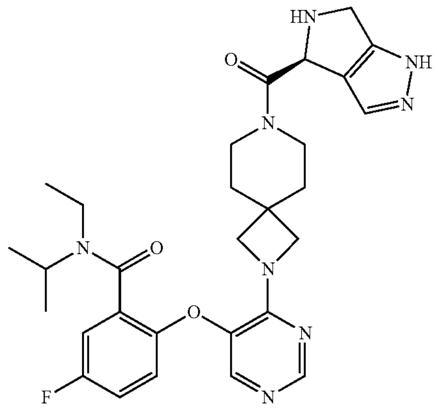 [SMILES: CCN(C(=O)c1cc(F)ccc1Oc1cncnc1N1CC2(CCN(C(=O)[C@H]3NCc4[nH]ncc43)CC2)C1)C(C)C] |
| Example 55 | 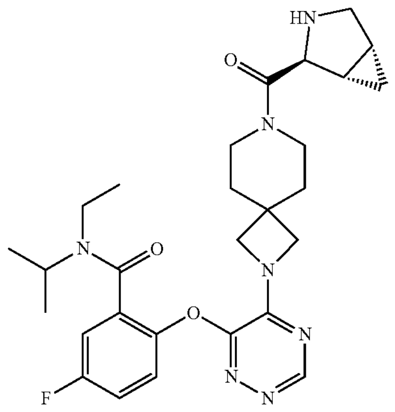 [SMILES: CCN(C(=O)c1cc(F)ccc1Oc1nncnc1N1CC2(CCN(C(=O)[C@H]3NC[C@@H]4C[C@@H]43)CC2)C1)C(C)C] |

-continued
| Compound Nos. | Structures |
| --- | --- |
| Example 56 | 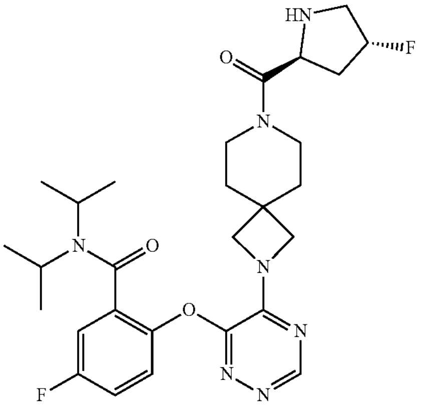 [SMILES: CC(C)N(C(=O)c1cc(F)ccc1Oc1nncnc1N1CC2(CCN(C(=O)[C@@H]3C[C@@H](F)CN3)CC2)C1)C(C)C] |
| Example 57 | 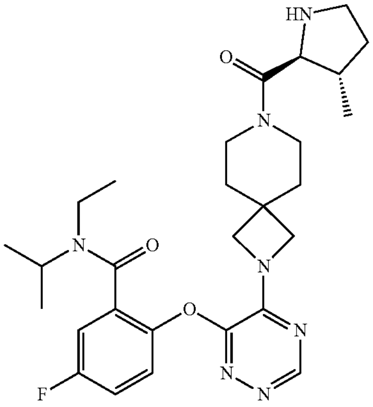 [SMILES: CCN(C(=O)c1cc(F)ccc1Oc1nncnc1N1CC2(CCN(C(=O)[C@H]3NCC[C@@H]3C)CC2)C1)C(C)C] |
| Example 58 | 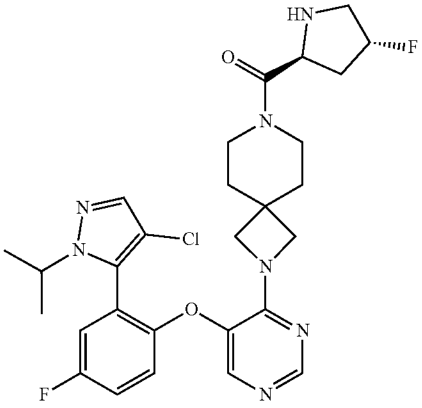 [SMILES: CC(C)n1ncc(Cl)c1-c1cc(F)ccc1Oc1cncnc1N1CC2(CCN(C(=O)[C@@H]3C[C@@H](F)CN3)CC2)C1] |

-continued
| Compound Nos. | Structures |
| --- | --- |
| Example 59 | 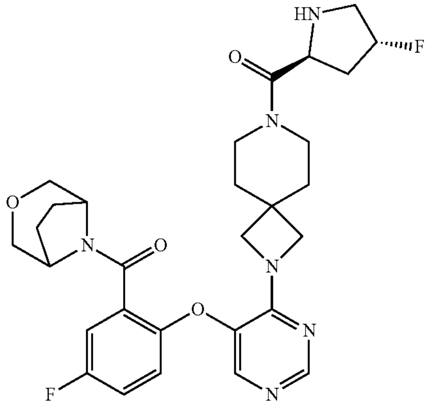 [SMILES: O=C([C@@H]1C[C@@H](F)CN1)N1CCC2(CC1)CN(c1ncncc1Oc1ccc(F)cc1C(=O)N1C3CCC1COC3)C2] |
| Example 60 | 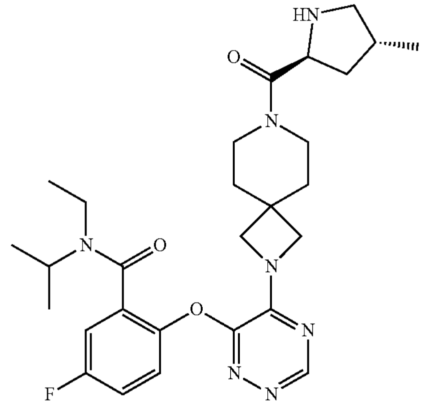 [SMILES: CCN(C(=O)c1cc(F)ccc1Oc1nncnc1N1CC2(CCN(C(=O)[C@@H]3C[C@@H](C)CN3)CC2)C1)C(C)C] |
| Example 61 | 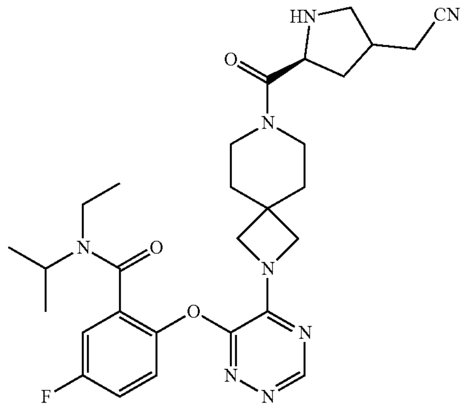 [SMILES: CCN(C(=O)c1cc(F)ccc1Oc1nncnc1N1CC2(CCN(C(=O)[C@@H]3CC(CC#N)CN3)CC2)C1)C(C)C] |

-continued
| Compound Nos. | Structures |
| --- | --- |
| Example 62 | 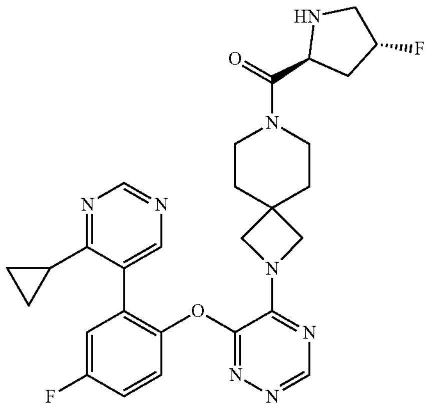 [SMILES: O=C([C@@H]1C[C@@H](F)CN1)N1CCC2(CC1)CN(c1ncnnc1Oc1ccc(F)cc1-c1cncnc1C1CC1)C2] |
| Example 63 | 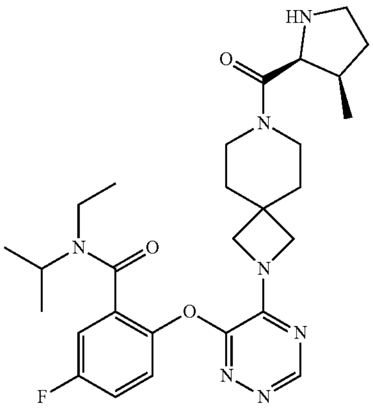 [SMILES: CCN(C(=O)c1cc(F)ccc1Oc1nncnc1N1CC2(CCN(C(=O)[C@H]3NCC[C@H]3C)CC2)C1)C(C)C] |
| Example 64 | 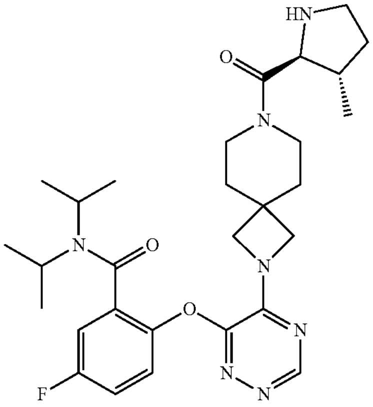 [SMILES: CC(C)N(C(=O)c1cc(F)ccc1Oc1nncnc1N1CC2(CCN(C(=O)[C@H]3NCC[C@@H]3C)CC2)C1)C(C)C] |

-continued
| Compound Nos. | Structures |
| --- | --- |
| Example 65 | 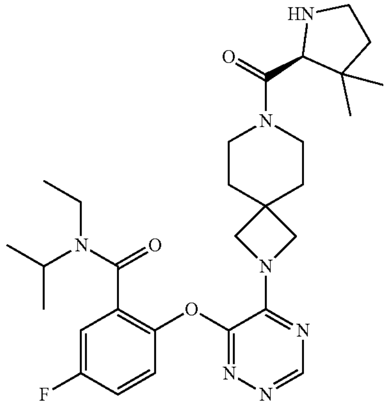 [SMILES: CCN(C(=O)c1cc(F)ccc1Oc1nncnc1N1CC2(CCN(C(=O)[C@H]3NCCC3(C)C)CC2)C1)C(C)C] |
| Example 66 | 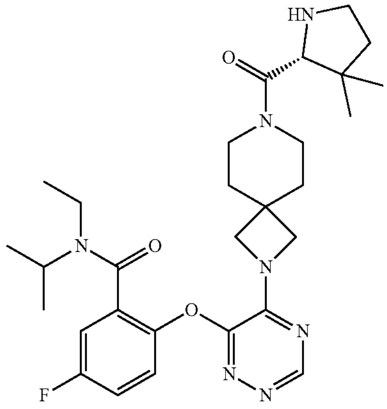 [SMILES: CCN(C(=O)c1cc(F)ccc1Oc1nncnc1N1CC2(CCN(C(=O)[C@@H]3NCCC3(C)C)CC2)C1)C(C)C] |
| Example 67 | 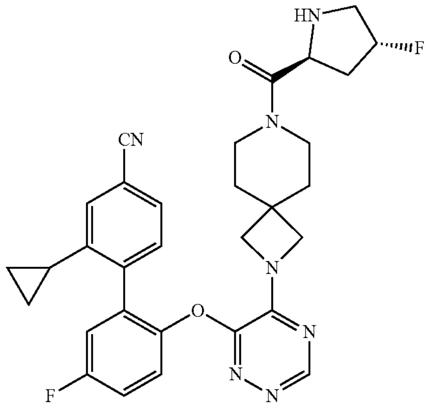 [SMILES: N#Cc1ccc(-c2cc(F)ccc2Oc2nncnc2N2CC3(CCN(C(=O)[C@@H]4C[C@@H](F)CN4)CC3)C2)c(C2CC2)c1] |

-continued
| Compound Nos. | Structures |
|---|---|
| Example 68 | 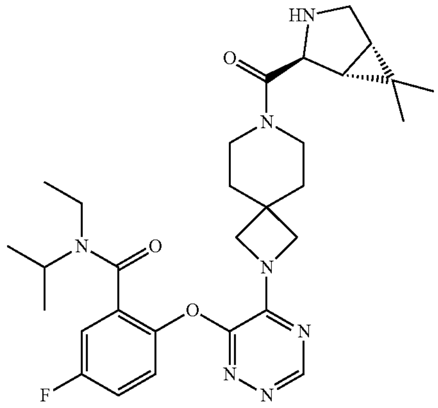 [SMILES: CCN(C(=O)c1cc(F)ccc1Oc1nncnc1N1CC2(CCN(C(=O)[C@H]3NC[C@H]4[C@@H]3C4(C)C)CC2)C1)C(C)C] |
| Example 69 | 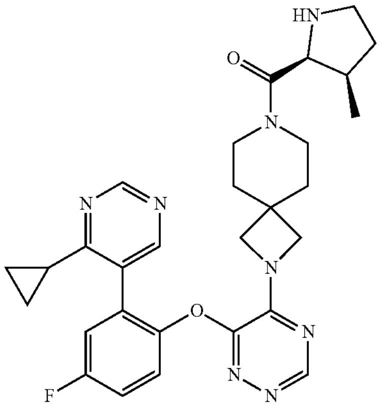 [SMILES: C[C@@H]1CCN[C@@H]1C(=O)N1CCC2(CC1)CN(c1ncnnc1Oc1ccc(F)cc1-c1cncnc1C1CC1)C2] |
| Example 70 | 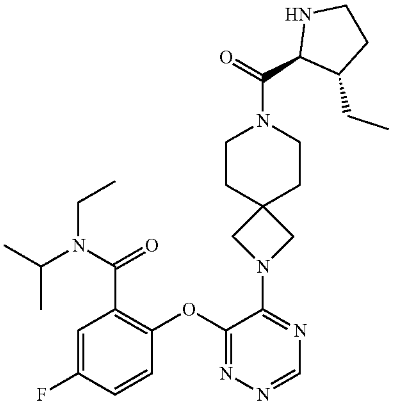 [SMILES: CC[C@H]1CCN[C@@H]1C(=O)N1CCC2(CC1)CN(c1ncnnc1Oc1ccc(F)cc1C(=O)N(CC)C(C)C)C2] |

-continued
| Compound Nos. | Structures |
| --- | --- |
| Example 71 | 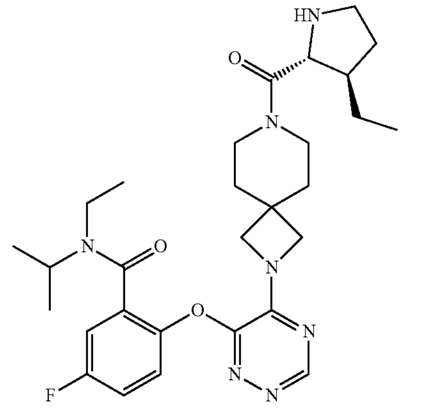 [SMILES: CC[C@@H]1CCN[C@H]1C(=O)N1CCC2(CC1)CN(c1ncnnc1Oc1ccc(F)cc1C(=O)N(CC)C(C)C)C2] |
| Example 72 | 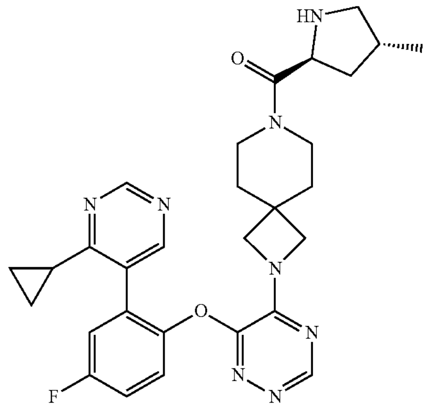 [SMILES: C[C@H]1CN[C@H](C(=O)N2CCC3(CC2)CN(c2ncnnc2Oc2ccc(F)cc2-c2cncnc2C2CC2)C3)C1] |
| Example 73 | 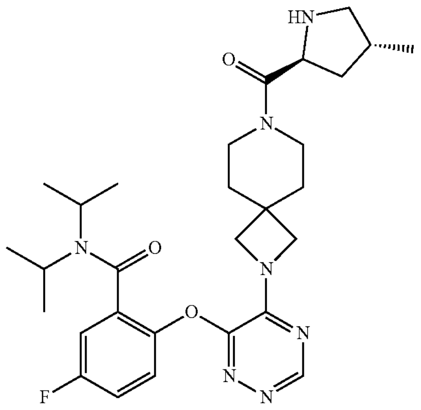 [SMILES: CC(C)N(C(=O)c1cc(F)ccc1Oc1nncnc1N1CC2(CCN(C(=O)[C@@H]3C[C@@H](C)CN3)CC2)C1)C(C)C] |

-continued
| Compound Nos. | Structures |
| --- | --- |
| Example 74 | 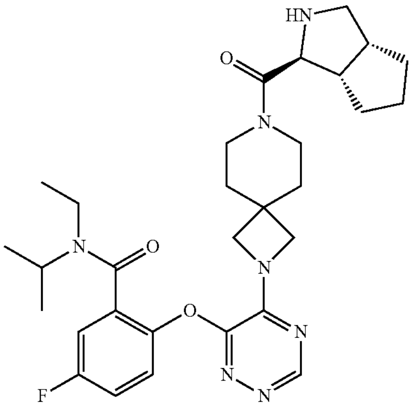 [SMILES: CCN(C(=O)c1cc(F)ccc1Oc1nncnc1N1CC2(CCN(C(=O)[C@H]3NC[C@@H]4CCC[C@@H]43)CC2)C1)C(C)C] |
| Example 75 | 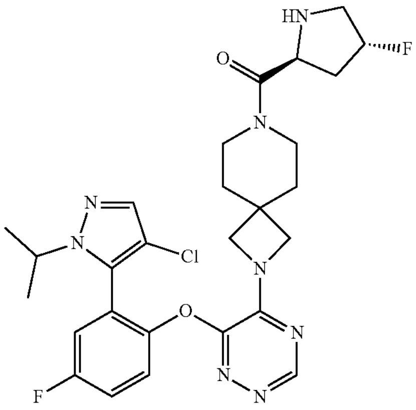 [SMILES: CC(C)n1ncc(Cl)c1-c1cc(F)ccc1Oc1nncnc1N1CC2(CCN(C(=O)[C@@H]3C[C@@H](F)CN3)CC2)C1] |
| Example 76 | 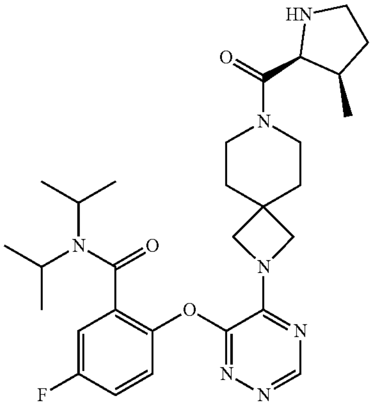 [SMILES: CC(C)N(C(=O)c1cc(F)ccc1Oc1nncnc1N1CC2(CCN(C(=O)[C@H]3NCC[C@H]3C)CC2)C1)C(C)C] |

-continued
| Compound Nos. | Structures |
|---|---|
| Example 77 | 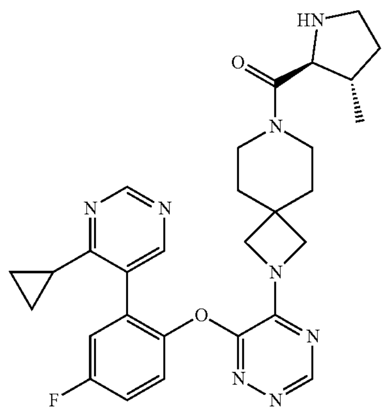 [SMILES: C[C@H]1CCN[C@@H]1C(=O)N1CCC2(CC1)CN(c1ncnnc1Oc1ccc(F)cc1-c1cncnc1C1CC1)C2] |
| Example 78 | 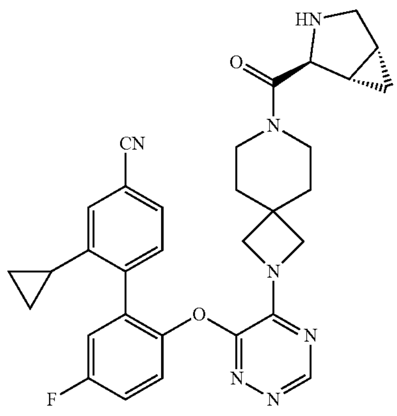 [SMILES: N#Cc1ccc(-c2cc(F)ccc2Oc2nncnc2N2CC3(CCN(C(=O)[C@H]4NC[C@@H]5C[C@@H]54)CC3)C2)c(C2CC2)c1] |
| Example 79 | 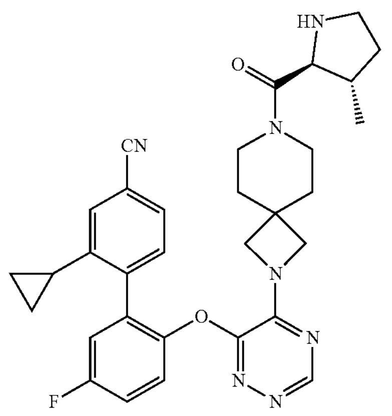 [SMILES: C[C@H]1CCN[C@@H]1C(=O)N1CCC2(CC1)CN(c1ncnnc1Oc1ccc(F)cc1-c1ccc(C#N)cc1C1CC1)C2] |

-continued
| Compound Nos. | Structures |
| --- | --- |
| Example 80 | 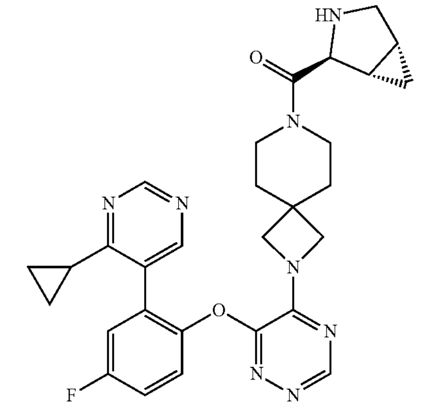 [SMILES: O=C([C@H]1NC[C@@H]2C[C@@H]21)N1CCC2(CC1)CN(c1ncnnc1Oc1ccc(F)cc1-c1cncnc1C1CC1)C2] |
| Example 81 | 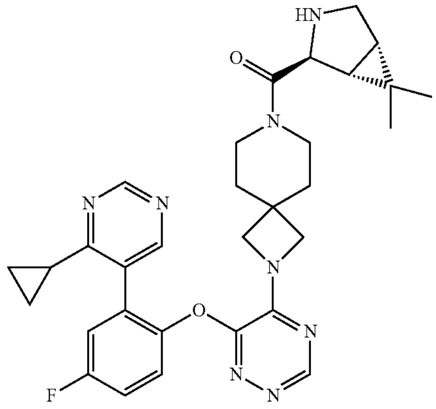 [SMILES: CC1(C)[C@@H]2[C@@H](C(=O)N3CCC4(CC3)CN(c3ncnnc3Oc3ccc(F)cc3-c3cncnc3C3CC3)C4)NC[C@@H]21] |
| Example 82 | 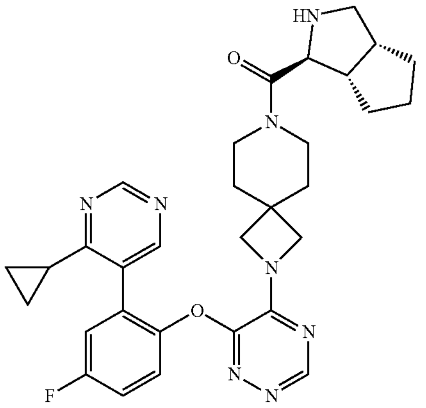 |

-continued
| Compound Nos. | Structures |
|---|---|
| Example 83 | 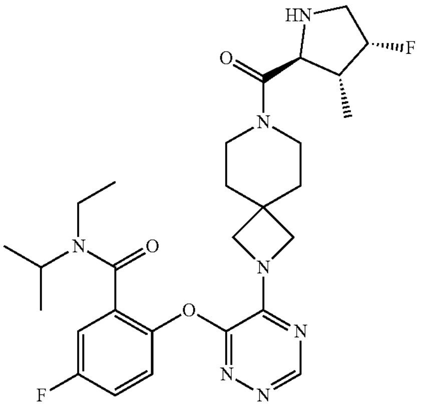 [SMILES: CCN(C(=O)c1cc(F)ccc1Oc1nncnc1N1CC2(CCN(C(=O)[C@H]3NC[C@H](F)[C@@H]3C)CC2)C1)C(C)C] |
| Example 84 | 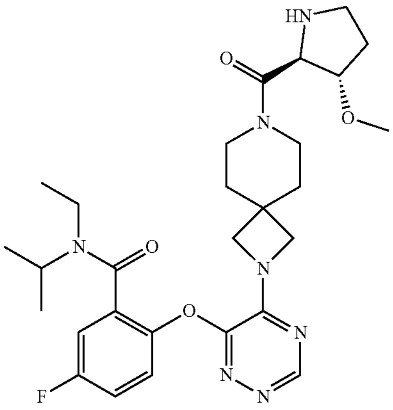 [SMILES: CCN(C(=O)c1cc(F)ccc1Oc1nncnc1N1CC2(CCN(C(=O)[C@H]3NCC[C@@H]3OC)CC2)C1)C(C)C] |
| Example 85 | 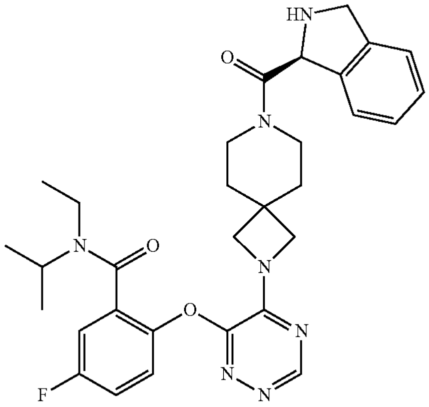 |

-continued
| Compound Nos. | Structures |
| --- | --- |
| Example 86 | 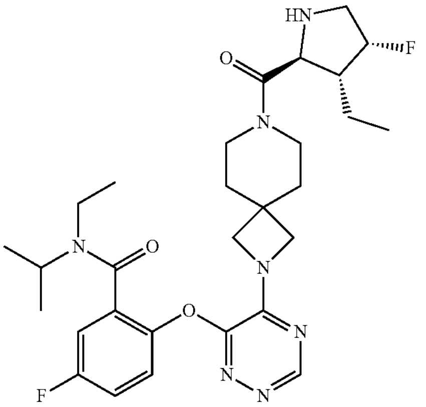 [SMILES: CC[C@@H]1[C@@H](C(=O)N2CCC3(CC2)CN(c2ncnnc2Oc2ccc(F)cc2C(=O)N(CC)C(C)C)C3)NC[C@@H]1F] |
| Example 87 | 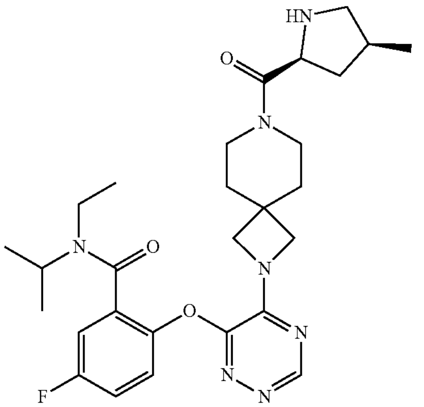 [SMILES: CCN(C(=O)c1cc(F)ccc1Oc1nncnc1N1CC2(CCN(C(=O)[C@@H]3C[C@H](C)CN3)CC2)C1)C(C)C] |
| Example 88 | 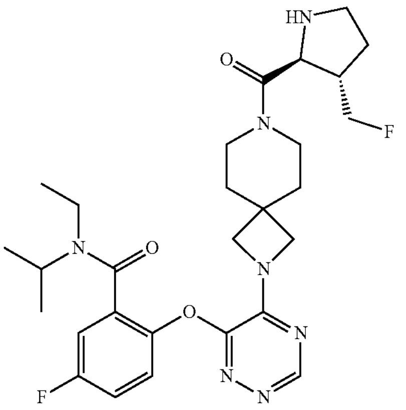 [SMILES: CCN(C(=O)c1cc(F)ccc1Oc1nncnc1N1CC2(CCN(C(=O)[C@H]3NCC[C@@H]3CF)CC2)C1)C(C)C] |

-continued
| Compound Nos. | Structures |
|---|---|
| Example 89 | 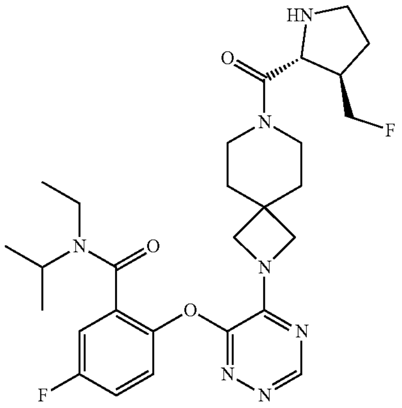 [SMILES: CCN(C(=O)c1cc(F)ccc1Oc1nncnc1N1CC2(CCN(C(=O)[C@@H]3NCC[C@H]3CF)CC2)C1)C(C)C] |
| Example 90 | 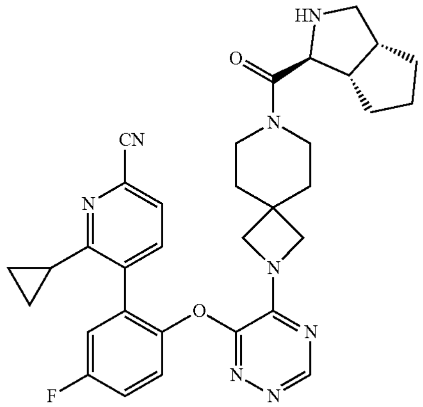 [SMILES: N#Cc1ccc(-c2cc(F)ccc2Oc2nncnc2N2CC3(CCN(C(=O)[C@H]4NC[C@@H]5CCC[C@@H]54)CC3)C2)c(C2CC2)n1] |
| Example 91 | 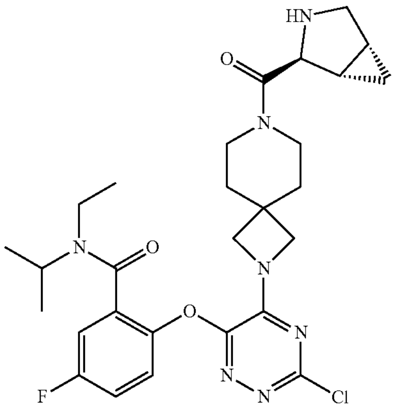 [SMILES: CCN(C(=O)c1cc(F)ccc1Oc1nnc(Cl)nc1N1CC2(CCN(C(=O)[C@H]3NC[C@@H]4C[C@@H]43)CC2)C1)C(C)C] |

-continued
| Compound Nos. | Structures |
| --- | --- |
| Example 92 | 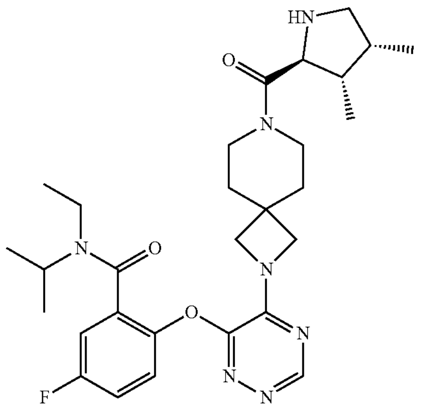 [SMILES: CCN(C(=O)c1cc(F)ccc1Oc1nncnc1N1CC2(CCN(C(=O)[C@H]3NC[C@H](C)[C@@H]3C)CC2)C1)C(C)C] |
| Example 93 | 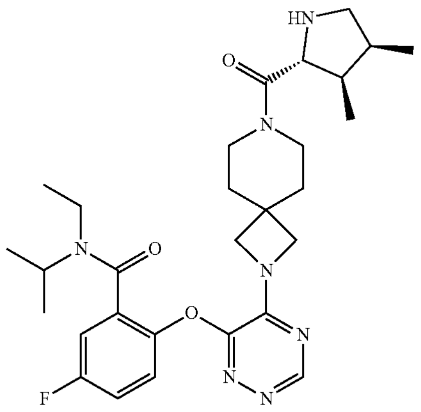 [SMILES: CCN(C(=O)c1cc(F)ccc1Oc1nncnc1N1CC2(CCN(C(=O)[C@@H]3NC[C@@H](C)[C@H]3C)CC2)C1)C(C)C] |
| Example 94 | 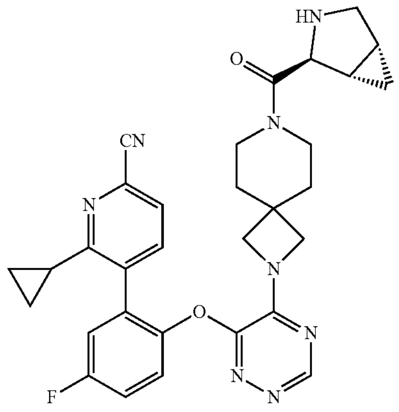 [SMILES: N#Cc1ccc(-c2cc(F)ccc2Oc2nncnc2N2CC3(CCN(C(=O)[C@H]4NC[C@@H]5C[C@@H]54)CC3)C2)c(C2CC2)n1] |

-continued
| Compound Nos. | Structures |
|---|---|
| Example 95 | 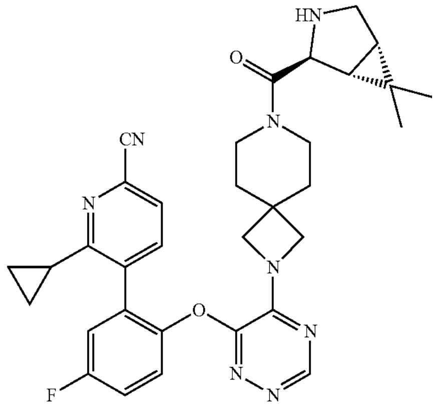 [SMILES: CC1(C)[C@@H]2[C@@H](C(=O)N3CCC4(CC3)CN(c3ncnnc3Oc3ccc(F)cc3-c3ccc(C#N)nc3C3CC3)C4)NC[C@@H]21] |
| Example 96 | 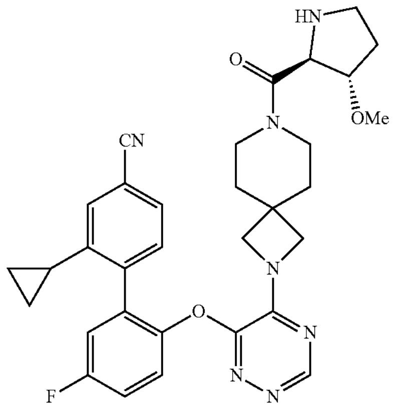 [SMILES: CO[C@H]1CCN[C@@H]1C(=O)N1CCC2(CC1)CN(c1ncnnc1Oc1ccc(F)cc1-c1ccc(C#N)cc1C1CC1)C2] |
| Example 97 | 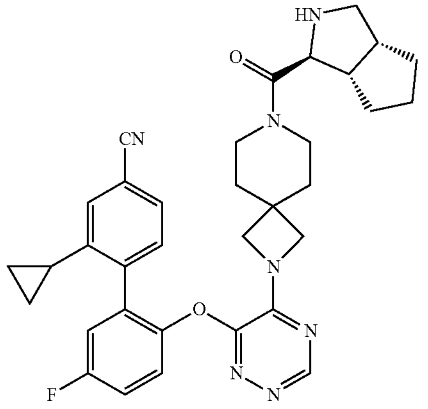 |

-continued
| Compound Nos. | Structures |
| --- | --- |
| Example 98a | 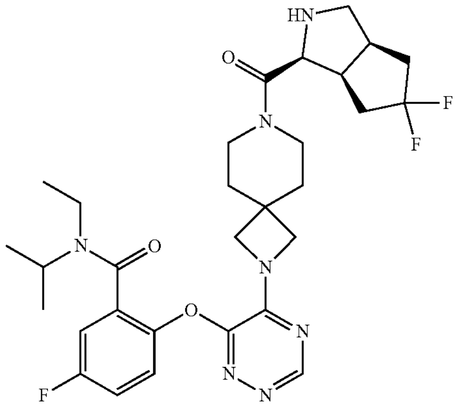 [SMILES: CCN(C(=O)c1cc(F)ccc1Oc1nncnc1N1CC2(CCN(C(=O)[C@H]3NC[C@H]4CC(F)(F)C[C@H]43)CC2)C1)C(C)C] |
| Example 98b | 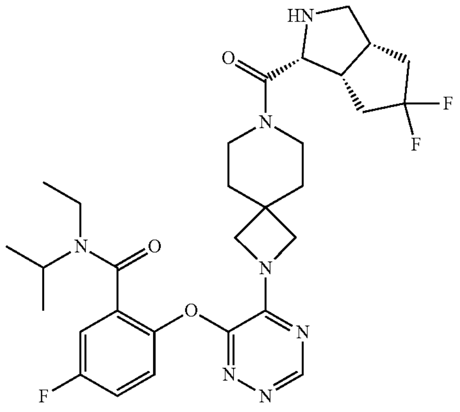 [SMILES: CCN(C(=O)c1cc(F)ccc1Oc1nncnc1N1CC2(CCN(C(=O)[C@@H]3NC[C@@H]4CC(F)(F)C[C@@H]43)CC2)C1)C(C)C] |
| Example 98c | 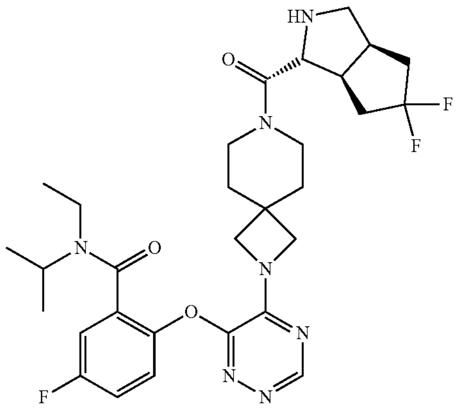 |

-continued
| Compound Nos. | Structures |
|---|---|
| Example 98d | 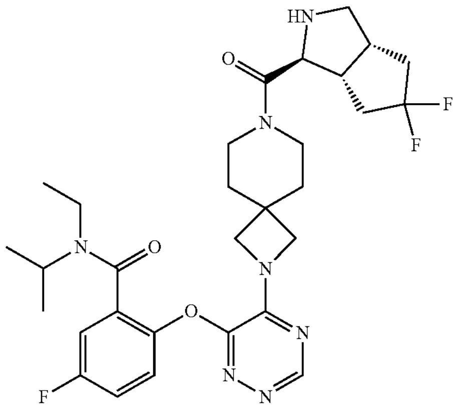 [SMILES: CCN(C(=O)c1cc(F)ccc1Oc1nncnc1N1CC2(CCN(C(=O)[C@H]3NC[C@@H]4CC(F)(F)C[C@@H]43)CC2)C1)C(C)C] |
| Example 99a | 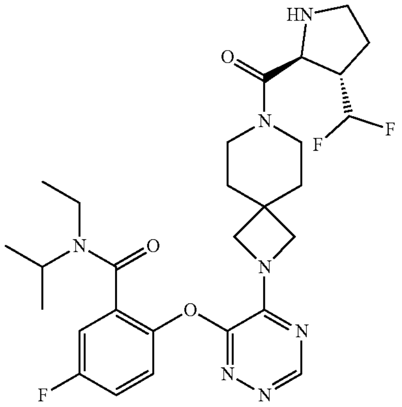 [SMILES: CCN(C(=O)c1cc(F)ccc1Oc1nncnc1N1CC2(CCN(C(=O)[C@H]3NCC[C@@H]3C(F)F)CC2)C1)C(C)C] |
| Example 99b | 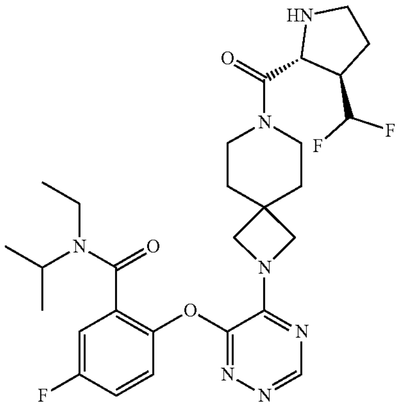 [SMILES: CCN(C(=O)c1cc(F)ccc1Oc1nncnc1N1CC2(CCN(C(=O)[C@@H]3NCC[C@H]3C(F)F)CC2)C1)C(C)C] |

-continued
| Compound Nos. | Structures |
|---|---|
| Example 100a | 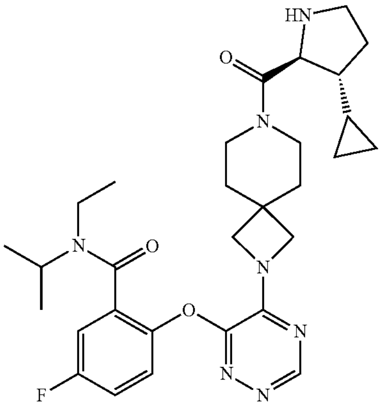 [SMILES: CCN(C(=O)c1cc(F)ccc1Oc1nncnc1N1CC2(CCN(C(=O)[C@H]3NCC[C@@H]3C3CC3)CC2)C1)C(C)C] |
| Example 100b | 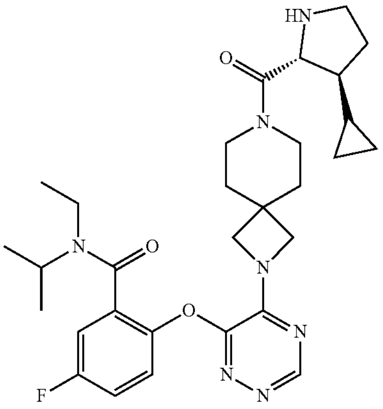 [SMILES: CCN(C(=O)c1cc(F)ccc1Oc1nncnc1N1CC2(CCN(C(=O)[C@@H]3NCC[C@H]3C3CC3)CC2)C1)C(C)C] |
| Example 101 | 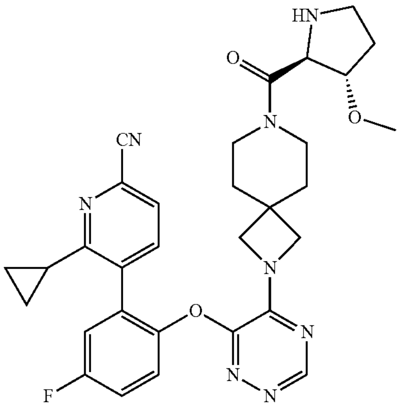 [SMILES: CO[C@H]1CCN[C@@H]1C(=O)N1CCC2(CC1)CN(c1ncnnc1Oc1ccc(F)cc1-c1ccc(C#N)nc1C1CC1)C2] |

-continued
| Compound Nos. | Structures |
|---|---|
| Example 102 | 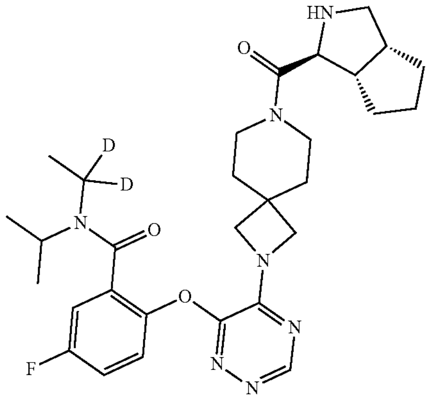 [SMILES: [2H]C([2H])(C)N(C(=O)c1cc(F)ccc1Oc1nncnc1N1CC2(CCN(C(=O)[C@H]3NC[C@@H]4CCC[C@@H]43)CC2)C1)C(C)C] |
| Example 103 | 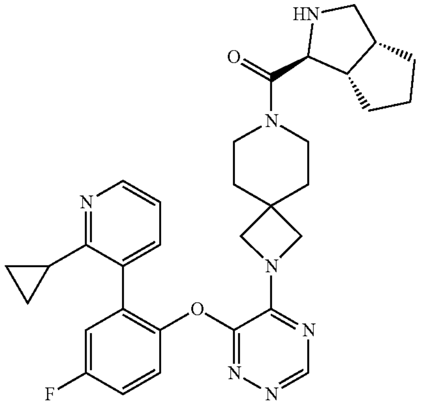 [SMILES: O=C([C@H]1NC[C@@H]2CCC[C@@H]21)N1CCC2(CC1)CN(c1ncnnc1Oc1ccc(F)cc1-c1cccnc1C1CC1)C2] |
| Example 104 | 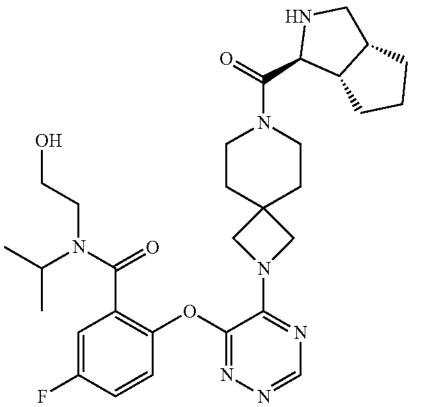 [SMILES: CC(C)N(CCO)C(=O)c1cc(F)ccc1Oc1nncnc1N1CC2(CCN(C(=O)[C@H]3NC[C@@H]4CCC[C@@H]43)CC2)C1] |

-continued

| Compound Nos. | Structures |
|---|---|
| Example 105 | 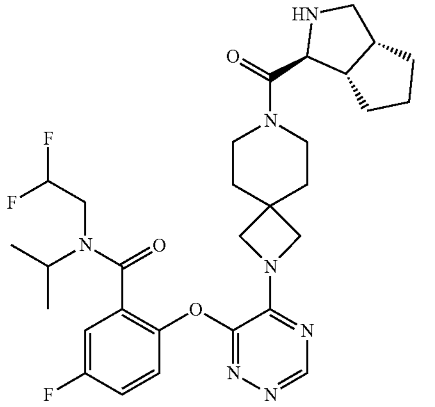 [SMILES: CC(C)N(CC(F)F)C(=O)c1cc(F)ccc1Oc1nncnc1N1CC2(CCN(C(=O)[C@H]3NC[C@@H]4CCC[C@@H]43)CC2)C1] |
| Example 106 | 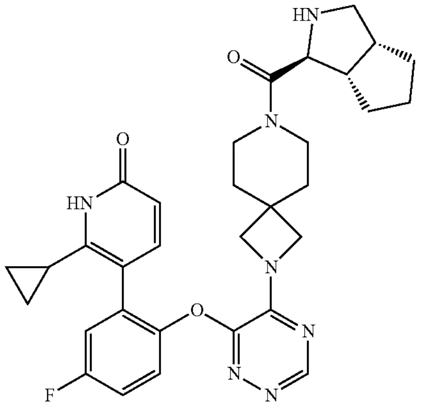 [SMILES: O=C([C@H]1NC[C@@H]2CCC[C@@H]21)N1CCC2(CC1)CN(c1ncnnc1Oc1ccc(F)cc1-c1ccc(=O)[nH]c1C1CC1)C2] |
| Example 107 | 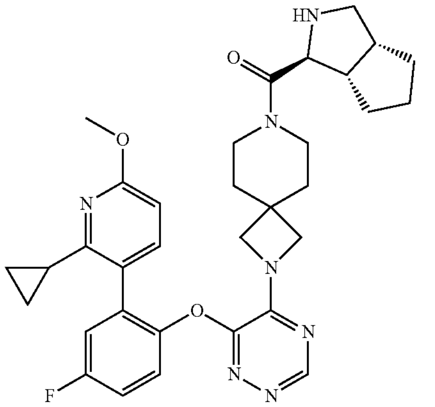 [SMILES: COc1ccc(-c2cc(F)ccc2Oc2nncnc2N2CC3(CCN(C(=O)[C@H]4NC[C@@H]5CCC[C@@H]54)CC3)C2)c(C2CC2)n1] |

Embodiment 58. The compound of any one of the Embodiments 1-57, or a stereoisomer, a racemate, a tautomer, a hydrate or a solvate, or pharmaceutically acceptable salt thereof, for use as a medicament.

Embodiment 59. The compound of any one of the Embodiments 1-57, or a stereoisomer, a racemate, a tautomer, a hydrate or a solvate, or pharmaceutically acceptable salt thereof, for use in the treatment or prevention of cancer and other diseases mediated by the interaction of menin with MLL and/or MLL fusion proteins.

Embodiment 60. The compound of any one of the Embodiments 1-57, or a stereoisomer, a racemate, a tautomer, a hydrate or a solvate, or pharmaceutically acceptable salt thereof, for use in the treatment or prevention of cancer or diabetes;

preferably, the cancer is hematological tumor, e.g., leukemia, lymphomas, myelomas (e.g., multiple myeloma), myelodysplastic syndrome (MDS), and myeloproliferative neoplasms (MPN), polycythemia vera; or solid tumor, e.g., prostate cancer, lung cancer, breast cancer, pancreatic cancer, colon cancer, liver cancer, melanoma and glioblastoma;

more preferably, the leukemia is selected from acute leukemias, chronic leukemias, myeloid leukemias, myelogenous leukemias, lymphoblastic leukemias, lymphocytic leukemias, acute myeloid leukemias (AML), chronic myeloid leukemias (CML), acute lymphoblastic leukemias (ALL), chronic lymphocytic leukemias (CLL), T cell prolymphocytic leukemias (T-PLL), large granular lymphocytic leukemia, hairy cell leukemia (HCL), mixed lineage leukemia (MLL), MLL-rearranged leukemias (MLLr leukemia), MLL-PTD leukemias, MLL amplified leukemias, MLL-positive leukemias, nucleophosmin (NPM)-mutated leukemia, MOZ acute leukemia, NUP98 acute leukemia, CALM acute leukemia, MLL-AF4 leukemia, MLL-AF6 leukemia, MLL-AF9 leukemia, MLL-AF10 leukemia, MLL-ENL leukemia and MILL-ELL leukemia.

Embodiment 61. A pharmaceutical composition, comprising the compound of any one of the Embodiments 1-57, or a stereoisomer, a racemate, a tautomer, a hydrate or a solvate, or pharmaceutically acceptable salt thereof, and optionally a pharmaceutically acceptable carrier.

Embodiment 62. Use of the compound of any one of the Embodiments 1-57, or a stereoisomer, a racemate, a tautomer, a hydrate or a solvate, or pharmaceutically acceptable salt thereof, in the manufacture of a medicament for treatment or prevention of cancer or diabetes;

preferably, the cancer is hematological tumor, e.g., leukemia, lymphomas, myelomas (e.g., multiple myeloma), myelodysplastic syndrome (MDS), and myeloproliferative neoplasms (MPN), polycythemia vera; or solid tumor, e.g., prostate cancer, lung cancer, breast cancer, pancreatic cancer, colon cancer, liver cancer, melanoma and glioblastoma;

more preferably, the leukemia is selected from acute leukemias, chronic leukemias, myeloid leukemias, myelogenous leukemias, lymphoblastic leukemias, lymphocytic leukemias, acute myeloid leukemias (AML), chronic myeloid leukemias (CML), acute lymphoblastic leukemias (ALL), chronic lymphocytic leukemias (CLL), T cell prolymphocytic leukemias (T-PLL), Large granular lymphocytic leukemia, Hairy cell leukemia (HCL), mixed lineage leukemia (MLL), MLL-rearranged leukemias (MLLr leukemia), MLL-PTD leukemias, MLL amplified leukemias, MLL-positive leukemias, nucleophosmin (NPM)-mutated leukemia, MOZ acute leukemia, NUP98 acute leukemia, CALM acute leukemia, MLL-AF4 leukemia, MLL-AF6 leukemia, MLL-AF9 leukemia, MLL-AF10 leukemia, MLL-ENL leukemia and MILL-ELL leukemia.

Embodiment 63. A method of in vivo or in vitro inhibiting the interaction of menin with MLL and/or MLL fusion proteins, comprising contacting an effective amount of the compound of any one of the Embodiments 1-57 or a pharmaceutically acceptable salt thereof with menin and MLL and/or MLL fusion proteins.

Embodiment 64. A method of treating or preventing cancer or diabetes, comprising administering to the subject in need thereof an effective amount of the compound of any one of the Embodiments 1-57 or a stereoisomer, a racemate, a tautomer, a hydrate or a solvate, or pharmaceutically acceptable salt thereof;

preferably, the cancer is hematological tumor, e.g., leukemia, lymphomas, myelomas (e.g., multiple myeloma), myelodysplastic syndrome (MDS), and myeloproliferative neoplasms (MPN), polycythemia vera; or solid tumor, e.g., prostate cancer, lung cancer, breast cancer, pancreatic cancer, colon cancer, liver cancer, melanoma and glioblastoma;

more preferably, the leukemia is selected from acute leukemias, chronic leukemias, myeloid leukemias, myelogenous leukemias, lymphoblastic leukemias, lymphocytic leukemias, acute myeloid leukemias (AML), chronic myeloid leukemias (CML), acute lymphoblastic leukemias (ALL), chronic lymphocytic leukemias (CLL), T cell prolymphocytic leukemias (T-PLL), Large granular lymphocytic leukemia, Hairy cell leukemia (HCL), mixed lineage leukemia (MLL), MLL-rearranged leukemias (MLLr leukemia), MLL-PTD leukemias, MLL amplified leukemias, MLL-positive leukemias, nucleophosmin (NPM)-mutated leukemia, MOZ acute leukemia, NUP98 acute leukemia, CALM acute leukemia, MLL-AF4 leukemia, MLL-AF6 leukemia, MLL-AF9 leukemia, MLL-AF10 leukemia, MLL-ENL leukemia and MLL-ELL leukemia.

Embodiment 65. A combination, comprising the compound of any one of the Embodiments 1-57, or a stereoisomer, a racemate, a tautomer, a hydrate or a solvate, or pharmaceutically acceptable salt thereof, and at least one additional therapeutic agent, wherein said additional therapeutic agent preferably is an anti-neoplastic agent, e.g., a radiotherapeutic agent, a chemotherapeutic agent, an immunotherapeutic agent, or a targeted therapeutic agent.

Embodiments of the Disclosure—Part B

Embodiment 1. A compound of formula I:

I

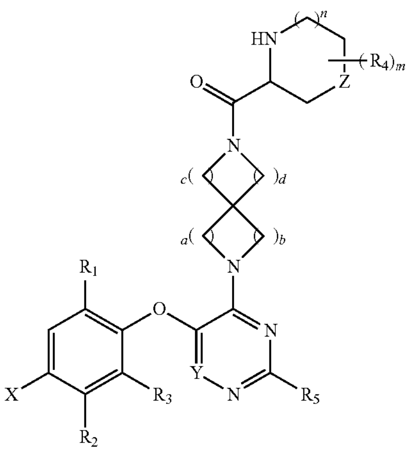

or a stereoisomer, a racemate, a tautomer, a hydrate or a solvate, or pharmaceutically acceptable salt thereof, wherein:

X is halo or CN;

Y is N or CH;

Z is selected from the group consisting of $CH_2$, O, S and NH;

$R_1$ is selected from the group consisting of:

1) —(C═O)—NRaRb, wherein:

Ra and Rb are each independently selected from the group consisting of $C_{1-6}$alkyl, 3-6 membered cycloalkyl ring and 5-9 membered heterocyclyl ring, which is optionally substituted with 1, 2 or 3 substituents selected from the group consisting of halo, OH, CN and $C_{1-6}$alkoxyl;

or Ra and Rb, together with the nitrogen atom to which they are attached, form a 5-9 membered heterocyclyl ring, which is optionally substituted with 1, 2 or 3 substituents selected from the group consisting of $C_{1-6}$alkyl, halo, OH and CN;

2) a 5-10 membered heteroaryl ring or $C_{6-10}$aryl ring, optionally substituted with 1, 2 or 3 substituents selected from the group consisting of halo, CN, $C_{1-6}$alkyl and 3-5 membered cycloalkyl ring;

$R_2$ and $R_3$ are each independently H or D;

each $R_4$ is independently selected from the group consisting of halo, CN, OH, oxo, $C_{1-6}$alkylsulfonyl-, $C_{1-6}$alkylsulfonylamino-, $C_{1-6}$alkylcarbonylamino-, $C_{6-10}$aryl ring, $C_{1-6}$alkyl, $C_{2-6}$alkenyl, $C_{2-6}$alkynyl, $C_{1-6}$alkoxyl, 3-9 membered cycloalkyl ring, 5-10 membered heteroaryl ring and 4-9 membered heterocyclyl ring, wherein the alkyl, alkenyl, alkynyl, alkoxyl, cycloalkyl ring, heteroaryl ring or heterocyclyl ring is optionally substituted with 1, 2 or 3 substituents selected from the group consisting of halo, CN and OH;

wherein two adjacent $R_4$, together with the carbon atoms to which they are attached, optionally form a 3-9 membered cycloalkyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl-, halo, CN and OH;

or, two $R_4$ attached to the same carbon atom together with said carbon atom optionally form a 3-6 membered cycloalkyl ring or 4-6 membered heterocyclyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl-, halo, CN and OH;

or, two adjacent $R_4$, together with the carbon atoms to which they are attached, optionally form a 5-10 membered heteroaryl ring, $C_{6-10}$aryl ring or 5-9 membered heterocyclyl ring, wherein said heteroaryl ring or aryl ring is optionally substituted with 1, 2 or 3 substituents selected from the group consisting of $C_{1-6}$alkyl, $C_{1-6}$haloalkyl, —$C_{1-6}$alkyl-OH, $C_{1-6}$alkoxyl-$C_{1-6}$alkyl-, halo, CN and OH, wherein the alkyl is optionally substituted with one 3-6 membered cycloalkyl ring or phenyl; said heterocyclyl ring is optionally substituted with 1, 2 or 3 substituents selected from the group consisting of $C_{1-6}$alkyl, $C_{1-6}$haloalkyl, —$C_{1-6}$alkyl-OH, $C_{1-6}$alkoxyl-$C_{1-6}$alkyl-, oxo, halo, CN and OH;

$R_5$ is selected from the group consisting of H, halo, methyl optionally substituted by 1, 2 or 3 deuterium or halo, methoxyl optionally substituted by 1, 2 or 3 deuterium or halo, $NH_2$, $CH_3NH$ or $(CH_3)_2N$;

a, b, c and d are each independently 1 or 2;

n is 0, 1 or 2; and m is 0, 1, 2, 3 or 4.

Embodiment 2. The compound according to Embodiment 1 or a stereoisomer, a racemate, a tautomer, a hydrate or a solvate, or pharmaceutically acceptable salt thereof, wherein:

X is F, $C_1$ or CN;

Y is N or CH;

Z is selected from the group consisting of $CH_2$, O, S and NH;

$R_1$ is selected from the group consisting of:

1) —(C═O)—NRaRb, wherein:

Ra and Rb are each independently selected from the group consisting of $C_{1-6}$alkyl and 3-5 membered cycloalkyl ring, wherein the $C_{1-6}$alkyl is optionally substituted with 1, 2 or 3 substituents selected from the group consisting of halo, OH and $C_{1-6}$alkoxyl;

or Ra and Rb, together with the nitrogen atom to which they are attached, form a 5-6 membered monocyclic or 7-9 membered bicyclic heterocyclyl ring, which is optionally substituted with 1, 2 or 3 substituents selected from the group consisting of $C_{1-6}$alkyl and halo;

2) a 5-6 membered heteroaryl ring, optionally substituted with 1, 2 or 3 substituents selected from the group consisting of halo, CN, $C_{1-6}$alkyl and 3-5 membered cycloalkyl ring;

3) $C_{6-10}$aryl ring substituted with 1, 2 or 3 substituents selected from the group consisting of halo, CN, $C_{1-6}$alkyl and 3-5 membered cycloalkyl ring;

$R_2$ and $R_3$ are each independently H or D;

each $R_4$ is independently selected from the group consisting of halo, CN, OH, $C_{1-6}$alkylsulfonyl-, $C_{1-6}$alkylsulfonylamino-, $C_{1-6}$alkylcarbonylamino-, phenyl, $C_{1-6}$alkyl, $C_{1-6}$alkoxyl, 3-6 membered cycloalkyl ring, 5-10 membered heteroaryl ring and 5-9 membered heterocyclyl ring, wherein the alkyl, alkoxyl, cycloalkyl ring, heteroaryl ring or heterocyclyl ring is optionally substituted with 1, 2 or 3 substituents selected from the group consisting of halo, CN and OH;

wherein two adjacent $R_4$, together with the carbon atoms to which they are attached, optionally form a 3-6 membered cycloalkyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl- and halo;

or, two $R_4$ attached to the same carbon atom together with said carbon atom optionally form a 3-6 membered cycloalkyl ring, which is optionally substituted with 1, 2 or 3 substituents selected from the group consisting of halo, CN and OH;

or, two adjacent $R_4$, together with the carbon atoms to which they are attached, optionally form a 5-10 membered heteroaryl ring, phenyl or 5-9 membered heterocyclyl ring, which is optionally substituted with 1, 2 or 3 substituents selected from the group consisting of halo, $C_{1-6}$alkyl and $C_{1-6}$haloalkyl, wherein the alkyl is optionally substituted with one 3-6 membered cycloalkyl ring or phenyl;

$R_5$ is H or halo;

a, b, c and d are each independently 1 or 2;

n is 0 or 1; and m is 0, 1, 2 or 3.

Embodiment 3. The compound according to any one of the preceding Embodiments or a stereoisomer, a racemate, a tautomer, a hydrate or a solvate, or pharmaceutically acceptable salt thereof, wherein:

each $R_4$ is independently selected from the group consisting of halo, CN, OH, $C_{1-6}$alkylsulfonyl-, $C_{1-6}$alkylsulfonylamino-, phenyl, $C_{1-6}$alkyl, $C_{1-6}$alkoxyl and 3-6 membered cycloalkyl ring, wherein the alkyl or alkoxyl is optionally substituted with 1, 2 or 3 substituents selected from the group consisting of halo, CN and OH;

wherein two adjacent $R_4$, together with the carbon atoms to which they are attached, optionally form a 3-6 membered cycloalkyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl- and halo;

or, two $R_4$ attached to the same carbon atom together with said carbon atom optionally form a 3-6 membered cycloalkyl ring, which is optionally substituted with 1, 2 or 3 substituents selected from the group consisting of halo, CN and OH;

or, two adjacent $R_4$, together with the carbon atoms to which they are attached, optionally form a 5-10 membered heteroaryl ring or phenyl, which is optionally substituted with 1, 2 or 3 substituents selected from the group consisting of $C_{1-6}$alkyl, wherein the alkyl is optionally substituted with one 3-6 membered cycloalkyl ring or phenyl.

Embodiment 4. The compound according to any one of the preceding Embodiments or a stereoisomer, a racemate, a tautomer, a hydrate or a solvate, or pharmaceutically acceptable salt thereof, wherein:

each $R_4$ is independently selected from the group consisting of halo, CN, OH, $C_{1-6}$alkylsulfonyl-, $C_{1-6}$alkylsulfonylamino-, phenyl, $C_{1-6}$alkyl and $C_{1-6}$alkoxyl, wherein the alkyl or alkoxyl is optionally substituted with 1, 2 or 3 substituents selected from the group consisting of halo, CN and OH;

wherein two adjacent $R_4$, together with the carbon atoms to which they are attached, optionally form a 3-6 membered cycloalkyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl- and halo;

or, two $R_4$ attached to the same carbon atom together with said carbon atom optionally form a 3-6 membered cycloalkyl ring, which is optionally substituted with 1, 2 or 3 substituents selected from the group consisting of halo, CN and OH;

or, two adjacent $R_4$, together with the carbon atoms to which they are attached, optionally form a 5-10 membered heteroaryl ring or phenyl, which is optionally substituted with 1, 2 or 3 substituents selected from the group consisting of $C_{1-6}$alkyl, wherein the alkyl is optionally substituted with one 3-6 membered cycloalkyl ring or phenyl.

Embodiment 5. The compound according to any one of the preceding Embodiments or a stereoisomer, a racemate, a tautomer, a hydrate or a solvate, or pharmaceutically acceptable salt thereof, wherein the compound is of formula II:

II

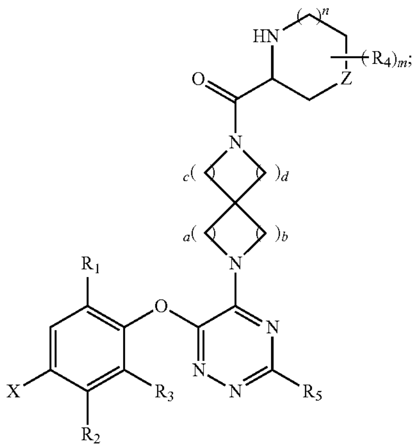

Preferably, the compound is of formula IIa:

IIa

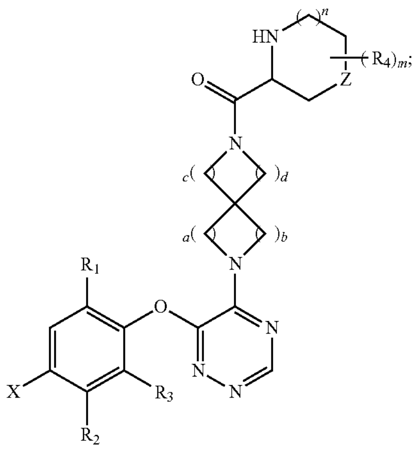

which preferably is

IIb

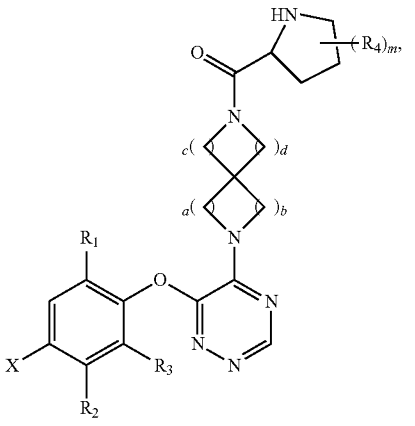

more preferably is:

IIc

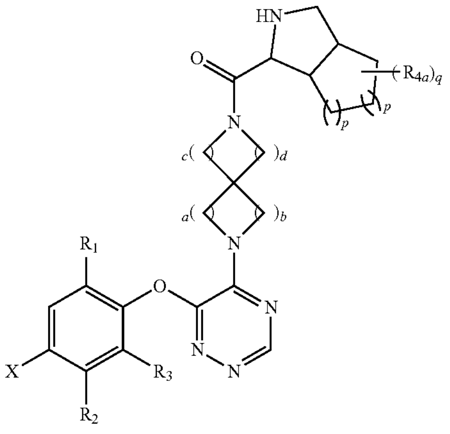

wherein each p is dependently 0 or 1; q is 0, 1 or 2; $R_{4a}$ is $C_{1-3}$alkyl or halo;

most preferably is:

IId

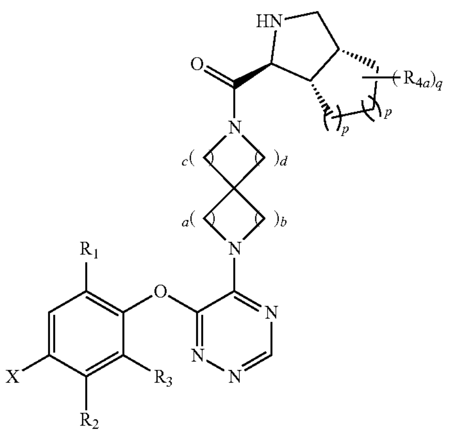

wherein each p is dependently 0 or 1; q is 0, 1 or 2; $R_{4a}$ is $C_{1-3}$alkyl or halo.

Embodiment 6. The compound according to any of the Embodiments 1 to 4 or a stereoisomer, a racemate, a tautomer, a hydrate or a solvate, or pharmaceutically acceptable salt thereof, wherein the compound is of formula III:

III

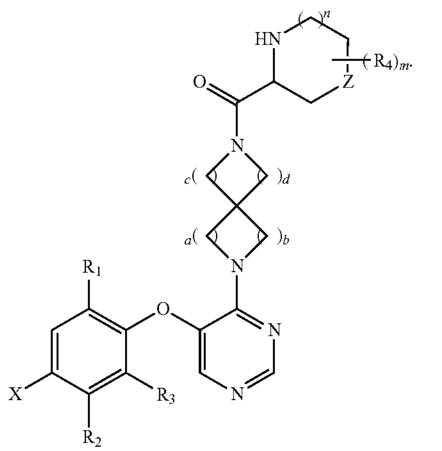

Embodiment 7. The compound according to any one of the preceding Embodiments or a stereoisomer, a racemate, a tautomer, a hydrate or a solvate, or pharmaceutically acceptable salt thereof, wherein X is F.

Embodiment 8. The compound according to any one of the preceding Embodiments or a stereoisomer, a racemate, a tautomer, a hydrate or a solvate, or pharmaceutically acceptable salt thereof, wherein Z is selected from the group consisting of $CH_2$, O and S, preferably $CH_2$.

Embodiment 9. The compound according to any one of the preceding Embodiments or a stereoisomer, a racemate, a tautomer, a hydrate or a solvate, or pharmaceutically acceptable salt thereof, wherein $R_2$ and $R_3$ are each independently H.

Embodiment 10. The compound according to any one of the preceding Embodiments or a stereoisomer, a racemate, a tautomer, a hydrate or a solvate, or pharmaceutically acceptable salt thereof, wherein:

$R_1$ is —(C═O)—NRaRb, wherein:

Ra and Rb are each independently selected from the group consisting of $C_{1-6}$alkyl and 3-5 membered cycloalkyl ring, wherein the $C_{1-6}$alkyl is optionally substituted with 1, 2 or 3 substituents selected from the group consisting of halo, OH and $C_{1-6}$alkoxyl; or Ra and Rb, together with the nitrogen atom to which they are attached, form a 5-6 membered monocyclic or 7-9 membered bicyclic heterocyclyl ring with another ring heteroatoms selected from N, O and S, which is optionally substituted with 1, 2 or 3 substituents selected from the group consisting of $C_{1-6}$alkyl and halo.

Embodiment 11. The compound according to any one of the preceding Embodiments or a stereoisomer, a racemate, a tautomer, a hydrate or a solvate, or pharmaceutically acceptable salt thereof, wherein:

$R_1$ is —(C═O)—NRaRb, wherein $R^a$ and Rb are each $C_{1-6}$alkyl, preferably Ra is ethyl and Rb is iso-propyl; or $R_1$ is a 5-6 membered heteroaryl ring, optionally substituted with 1, 2 or 3 substituents selected from the group consisting of halo, CN, $C_{1-6}$alkyl and 3-5 membered cycloalkyl ring; or phenyl substituted with 1, 2 or 3 substituents selected from the group consisting of halo, CN, $C_{1-6}$alkyl and 3-5 membered cycloalkyl ring.

Embodiment 12. The compound according to any one of the preceding Embodiments or a stereoisomer, a racemate, a tautomer, a hydrate or a solvate, or pharmaceutically acceptable salt thereof, wherein:

$R_1$ is —(C═O)—NRaRb, wherein Ra is ethyl and Rb is iso-propyl.

Embodiment 13. The compound according to any one of the preceding Embodiments or a stereoisomer, a racemate, a tautomer, a hydrate or a solvate, or pharmaceutically acceptable salt thereof, wherein:

$R_1$ is a 5-6 membered heteroaryl ring, optionally substituted with 1, 2 or 3 substituents selected from the group consisting of halo, CN, $C_{1-6}$alkyl and 3-5 membered cycloalkyl ring; or phenyl substituted with 1, 2 or 3 substituents selected from the group consisting of halo, CN, $C_{1-6}$alkyl and 3-5 membered cycloalkyl ring.

Embodiment 14. The compound according to any one of the preceding Embodiments or a stereoisomer, a racemate, a tautomer, a hydrate or a solvate, or pharmaceutically acceptable salt thereof, wherein:

$R_1$ is

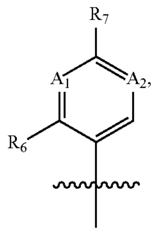

wherein $A_1$ or $A_2$ is N or CH; $R_6$ is selected from the group consisting of halo, CN, $C_{1-6}$alkyl and 3-5 membered cycloalkyl ring; and $R_7$ is selected from the group consisting of H, halo, CN, $C_{1-6}$alkyl and 3-5 membered cycloalkyl ring; preferably, $R_1$ is

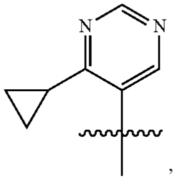,

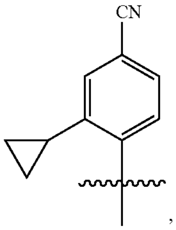, or

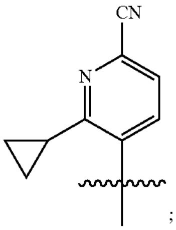;

or $R_1$ is

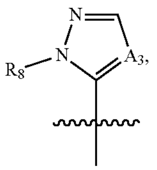

wherein $A_3$ is N or C substituted by halo, and $R_8$ is $C_{1-6}$alkyl; preferably, $R_1$ is

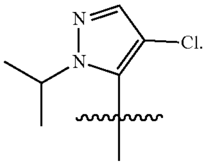 [SMILES: *c1c(Cl)cnn1C(C)C]

Embodiment 15. The compound according to Embodiment 14 or a stereoisomer, a racemate, a tautomer, a hydrate or a solvate, or pharmaceutically acceptable salt thereof, wherein the compound is of formula IIb:

IIb'

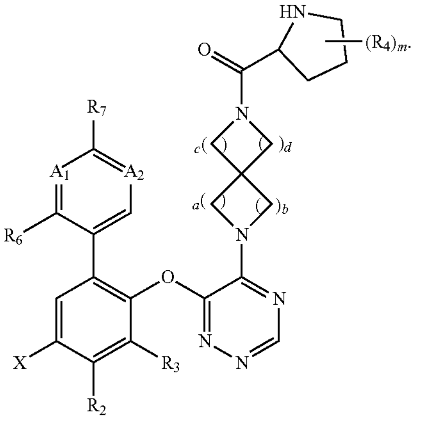

Embodiment 16. The compound according to any one of the preceding Embodiments or a stereoisomer, a racemate, a tautomer, a hydrate or a solvate, or pharmaceutically acceptable salt thereof, wherein:

each of a and b is 1; and each of c and d is 1 or 2;

Embodiment 17. The compound according to any one of the preceding Embodiments or a stereoisomer, a racemate, a tautomer, a hydrate or a solvate, or pharmaceutically acceptable salt thereof, wherein:

n is 0 or 1, preferably 0.

Embodiment 18. The compound according to any one of the preceding Embodiments or a stereoisomer, a racemate, a tautomer, a hydrate or a solvate, or pharmaceutically acceptable salt thereof, wherein n is 0.

Embodiment 19. The compound according to any one of the preceding Embodiments or a stereoisomer, a racemate, a tautomer, a hydrate or a solvate, or pharmaceutically acceptable salt thereof, wherein n is 1.

Embodiment 20. The compound according to any one of the preceding Embodiments or a stereoisomer, a racemate, a tautomer, a hydrate or a solvate, or pharmaceutically acceptable salt thereof, wherein m is 0, 1 or 2.

Embodiment 21. The compound according to any one of the preceding Embodiments or a stereoisomer, a racemate, a tautomer, a hydrate or a solvate, or pharmaceutically acceptable salt thereof, wherein:

each of a and b is 1.

Embodiment 22. The compound according to any one of the preceding Embodiments or a stereoisomer, a racemate, a tautomer, a hydrate or a solvate, or pharmaceutically acceptable salt thereof, wherein:

each of c and d is 2.

Embodiment 23. The compound according to any one of the preceding Embodiments or a stereoisomer, a racemate, a tautomer, a hydrate or a solvate, or pharmaceutically acceptable salt thereof, wherein:

m is 1 or 2.

Embodiment 24. The compound according to any one of the preceding Embodiments or a stereoisomer, a racemate, a tautomer, a hydrate or a solvate, or pharmaceutically acceptable salt thereof, wherein:

each of a and b is 1;

each of c and d is 2;

n is 0 or 1, preferably 0; and m is 0, 1 or 2.

Embodiment 25. The compound according to any one of the preceding Embodiments or a stereoisomer, a racemate, a tautomer, a hydrate or a solvate, or pharmaceutically acceptable salt thereof, wherein:

each $R_4$ is independently selected from the group consisting of halo; CN; OH; $C_{1-6}$alkylsulfonyl-; $C_{1-6}$alkylsulfonylamino-; phenyl; $C_{1-6}$alkyl optionally substituted with 1, 2 or 3 substituents selected from the group consisting of halo, CN and OH; and $C_{1-6}$alkoxyl optionally substituted with halo, wherein two adjacent $R_4$, together with the carbon atoms to which they are attached, optionally form a 3-6 membered cycloalkyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl- and halo;

or, two $R_4$ attached to the same carbon atom together with said carbon atom optionally form a 3-6 membered cycloalkyl ring, which is optionally substituted with 1, 2 or 3 halo;

or, two adjacent $R_4$, together with the carbon atoms to which they are attached, optionally form a 5-6 membered heteroaryl ring, which is optionally substituted with 1, 2 or 3 $C_{1-6}$alkyl, wherein the alkyl is optionally substituted with one 3-6 membered cycloalkyl ring or phenyl;

or, two adjacent $R_4$, together with the carbon atoms to which they are attached, optionally form a phenyl.

Embodiment 26. The compound according to any one of the preceding Embodiments or a stereoisomer, a racemate, a tautomer, a hydrate or a solvate, or pharmaceutically acceptable salt thereof, wherein:

$R_1$ is selected from the group consisting of:

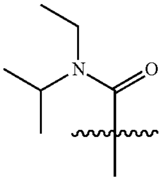 , 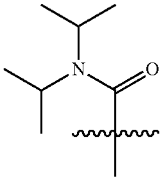 ,

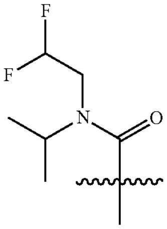 , 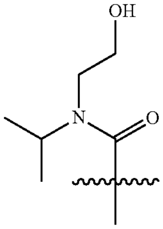 ,

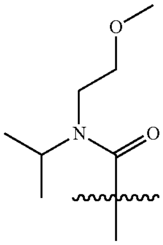 , 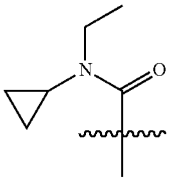 ,

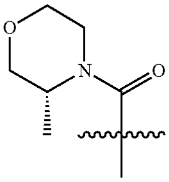 , 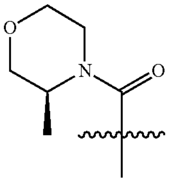 ,

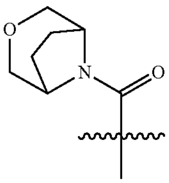 , 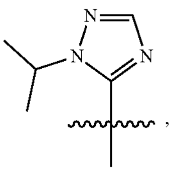 ,

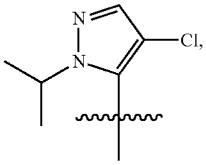

-continued

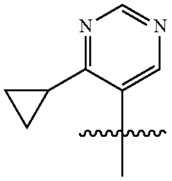 , 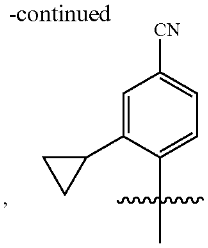 , and

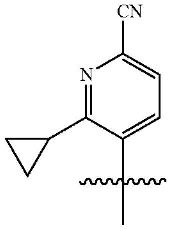 .

Embodiment 27. The compound according to any one of the preceding Embodiments or a stereoisomer, a racemate, a tautomer, a hydrate or a solvate, or pharmaceutically acceptable salt thereof, wherein:

$R_1$ is selected from the group consisting of:

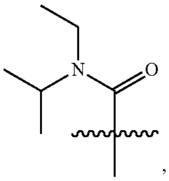 , 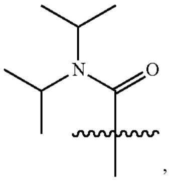 , 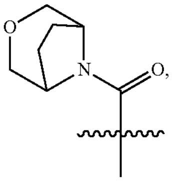

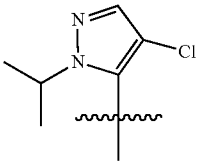 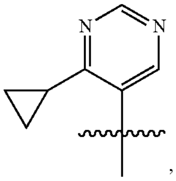 ,

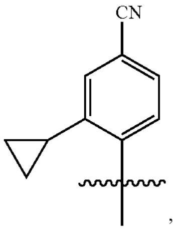 , and 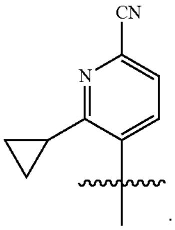 .

Embodiment 28. The compound according to any one of the preceding Embodiments or a stereoisomer, a racemate, a tautomer, a hydrate or a solvate, or pharmaceutically acceptable salt thereof, wherein:

the moiety
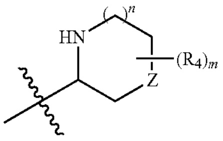
is selected from the group consisting of:
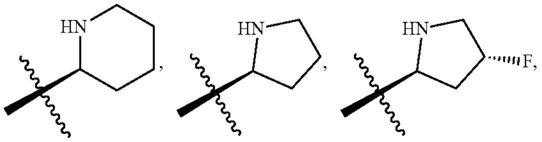
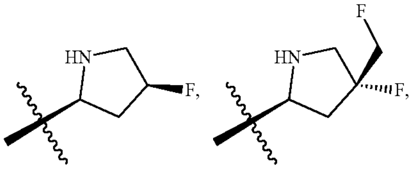
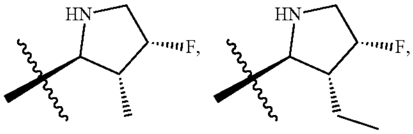
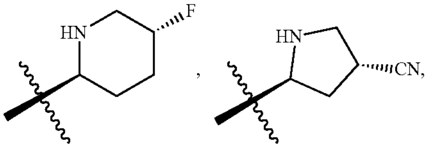
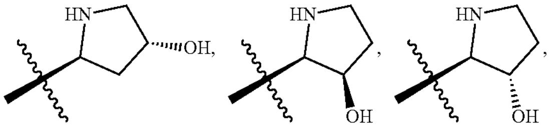
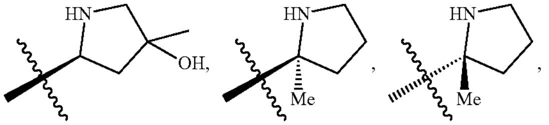
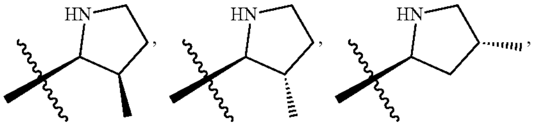
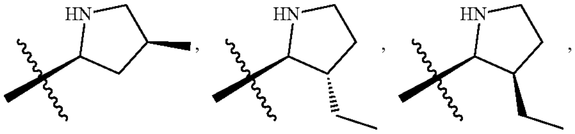
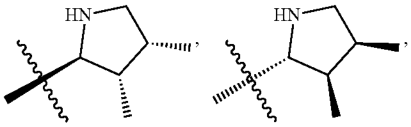
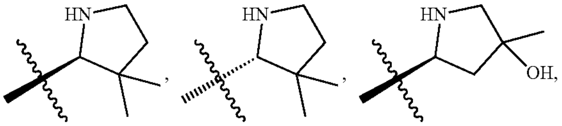
-continued
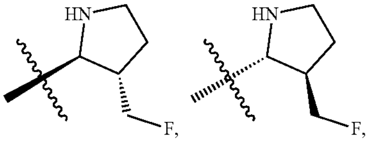
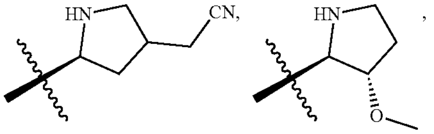
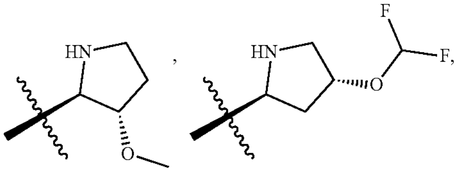
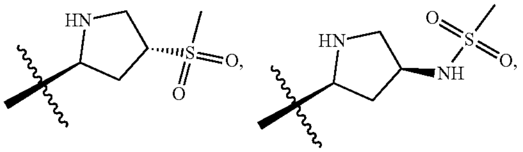
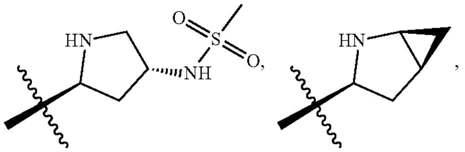
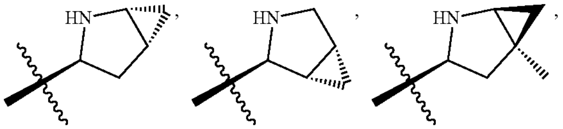
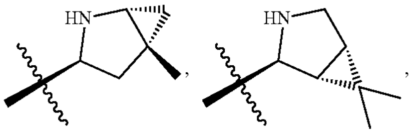
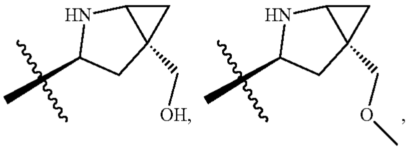
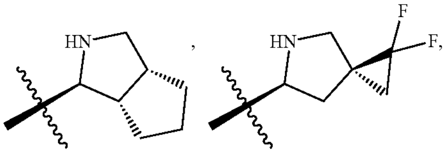
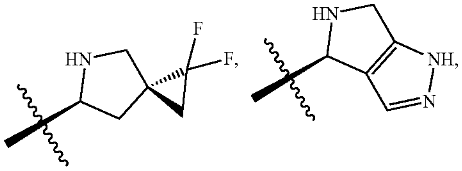
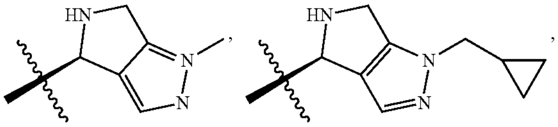

-continued

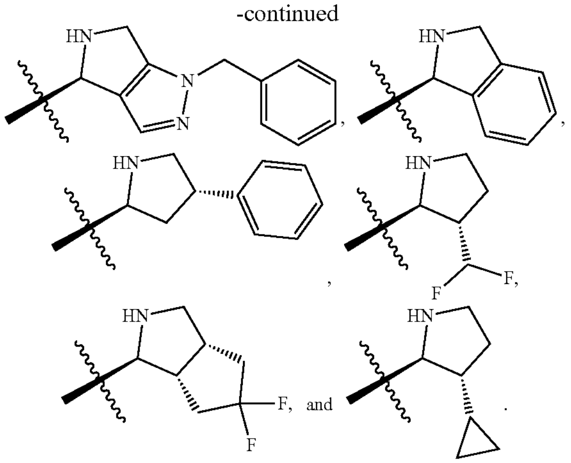

-continued

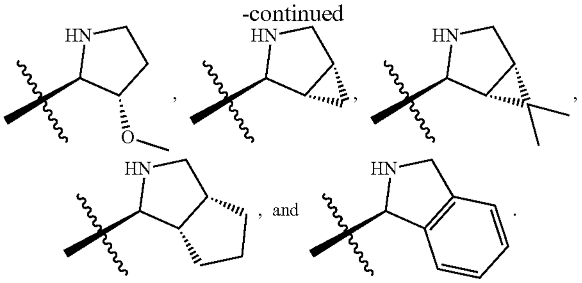

Embodiment 29. The compound according to any one of the preceding Embodiments or a stereoisomer, a racemate, a tautomer, a hydrate or a solvate, or pharmaceutically acceptable salt thereof, wherein:

the moiety

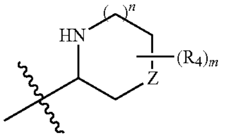

is selected from the group consisting of:

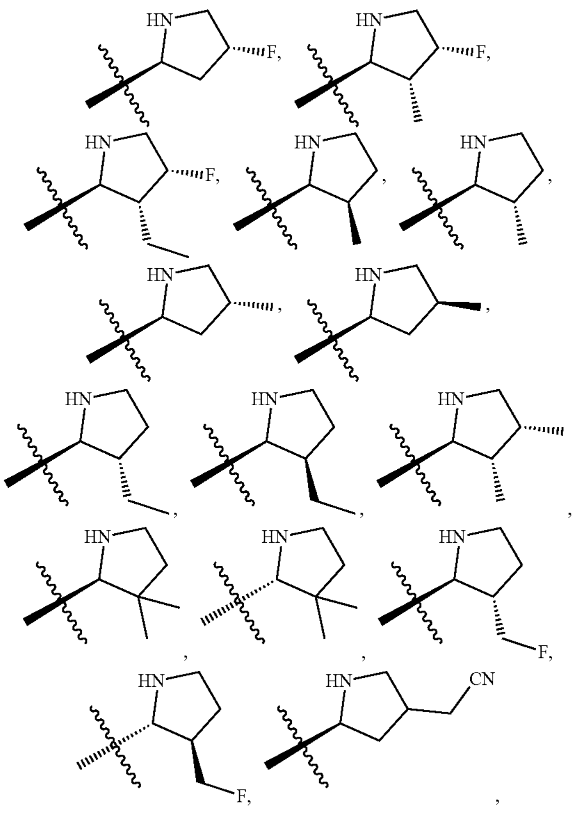

Embodiment 30. The compound according to any one of preceding Embodiments or a stereoisomer, a racemate, a tautomer, a hydrate or a solvate, or pharmaceutically acceptable salt thereof, wherein:

X is F;

Z is $CH_2$;

$R_1$ is selected from the group consisting of:

1) —(C═O)—NRaRb, wherein:

Ra and Rb are each independently selected from the group consisting of $C_{1-6}$alkyl;

or Ra and Rb, together with the nitrogen atom to which they are attached, form a 5-6 membered monocyclic or 7-9 membered bicyclic heterocyclyl ring, which is optionally substituted with 1, 2 or 3 $C_{1-6}$alkyl;

2) a 5-6 membered heteroaryl ring substituted with 1, 2 or 3 substituents selected from the group consisting of halo, CN, $C_{1-6}$alkyl and 3-5 membered cycloalkyl ring;

3) $C_{6-10}$aryl ring substituted with 1, 2 or 3 substituents selected from the group consisting of halo, CN, $C_{1-6}$alkyl and 3-5 membered cycloalkyl ring;

$R_2$ and $R_3$ are each independently H;

each $R_4$ is independently selected from the group consisting of halo; CN; OH; $C_{1-6}$alkylsulfonyl-; $C_{1-6}$alkylsulfonylamino-; phenyl; $C_{1-6}$alkyl optionally substituted with 1, 2 or 3 substituents selected from the group consisting of halo, CN and OH; and $C_{1-6}$alkoxyl optionally substituted with 1, 2 or 3 halo; and, 3-6 membered cycloalkyl ring, wherein two adjacent $R_4$, together with the carbon atoms to which they are attached, optionally form a 3-6 membered cycloalkyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl- and halo;

or, two adjacent $R_4$, together with the carbon atoms to which they are attached, optionally form a phenyl.

$R_5$ is H or halo;

each of a and b is 1;

each of c and d is 2;

n is 0; and m is 0, 1 or 2.

Embodiment 31. The compound according to any one of the preceding Embodiments or a stereoisomer, a racemate, a tautomer, a hydrate or a solvate, or pharmaceutically acceptable salt thereof, wherein $R_5$ is H or halo; preferably H.

Embodiment 32. The compound according to any one of the preceding Embodiments or a stereoisomer, a racemate, a tautomer, a hydrate or a solvate, or pharmaceutically acceptable salt thereof, wherein each $R_4$ is independently selected from the group consisting of halo; CN; OH; $C_{1-6}$alkylsulfonyl-; $C_{1-6}$alkylsulfonylamino-; phenyl; $C_{1-6}$alkyl optionally substituted with 1, 2 or 3 substituents selected from the group consisting of halo, CN and OH; and $C_{1-6}$alkoxyl optionally substituted with 1, 2 or 3 halo, wherein two adjacent $R_4$, together with the carbon atoms to which they are attached, optionally form a 3-6 membered cycloalkyl ring, which is optionally substituted with 1, 2 or 3 substituents selected from the group consisting of $C_{1-6}$alkyl, —$C_{1-6}$alkyl-OH, and $C_{1-6}$alkoxyl-$C_{1-6}$alkyl-;

or, two adjacent $R_4$, together with the carbon atoms to which they are attached, optionally form a phenyl.

Embodiment 33. The compound according to any one of the preceding Embodiments or a stereoisomer, a racemate, a tautomer, a hydrate or a solvate, or pharmaceutically acceptable salt thereof, wherein $R_1$ is —(C═O)—NRaRb, and Ra and Rb are each independently selected from the group consisting of ethyl or isopropyl.

Embodiment 34. The compound according to any one of the preceding Embodiments or a stereoisomer, a racemate, a tautomer, a hydrate or a solvate, or pharmaceutically acceptable salt thereof, wherein $R_1$ is a 5 or 6 membered heteroaryl ring or $C_{6-10}$aryl ring, which is substituted with 1 or 2 substituents selected from the group consisting of halo, CN, $C_{1-6}$alkyl and cyclopropyl.

Embodiment 35. The compound according to any one of the preceding Embodiments or a stereoisomer, a racemate, a tautomer, a hydrate or a solvate, or pharmaceutically acceptable salt thereof, wherein the moiety

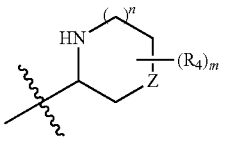

or

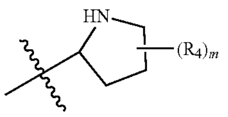

is

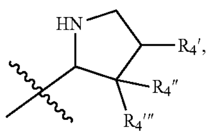

wherein $R_4$', $R_4$" and $R_4$''' are independently selected from the group consisting of H; halo; CN; OH; $C_{1-6}$alkyl optionally substituted with 1, 2 or 3 substituents selected from the group consisting of halo and CN; $C_{1-6}$alkoxyl; and, 3-6 membered cycloalkyl ring; or $R_4$' and $R_4$", together with the carbon atoms to which they are attached, optionally form a 3-6 membered cycloalkyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl- and halo; and R+''' is H.

Embodiment 36. The compound according to any one of the preceding Embodiments or a stereoisomer, a racemate, a tautomer, a hydrate or a solvate, or pharmaceutically acceptable salt thereof, wherein the moiety

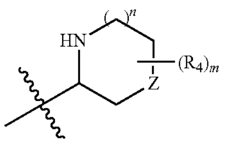

or

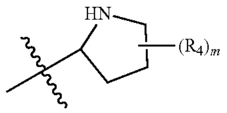

is

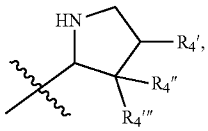

wherein Ry', $R_4$" and $R_4$''' are independently selected from the group consisting of H; halo; CN; OH; $C_{1-6}$alkyl optionally substituted with 1, 2 or 3 substituents selected from the group consisting of halo and CN; $C_{1-6}$alkoxyl; and, cyclopropyl; or $R_4$' and $R_4$", together with the carbon atoms to which they are attached, optionally form a 3-6 membered cycloalkyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl- and halo; and $R_4$''' is H.

Embodiment 37. The compound according to any one of the preceding Embodiments or a stereoisomer, a racemate, a tautomer, a hydrate or a solvate, or pharmaceutically acceptable salt thereof, wherein the moiety

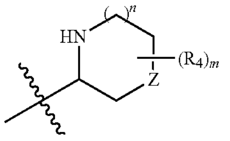

or

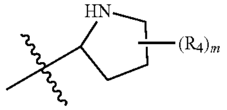

is

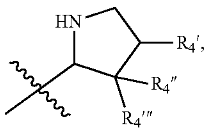

wherein $R_4$', $R_4$" and $R_4$''' are independently selected from the group consisting of H; halo; CN; $C_{1-6}$alkyl optionally substituted with 1, 2 or 3 substituents selected from the group consisting of halo and CN; and, $C_{1-6}$alkoxyl; or $R_4$' and $R_4$", together with the carbon atoms to which they are attached, optionally form a 3-6 membered cycloalkyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl- and halo; and $R_4$''' is H.

Embodiment 38. The compound according to any one of the preceding Embodiments or a stereoisomer, a racemate, a tautomer, a hydrate or a solvate, or pharmaceutically acceptable salt thereof, wherein:

wherein $R_4'$, $R_4''$ and $R_4'''$ are independently selected from the group consisting of H; halo; CN; OH; $C_{1-6}$alkyl optionally substituted with 1, 2 or 3 substituents selected from the group consisting of halo and CN; and, $C_{1-6}$alkoxyl.

Embodiment 39. The compound according to any one of the preceding Embodiments or a stereoisomer, a racemate, a tautomer, a hydrate or a solvate, or pharmaceutically acceptable salt thereof, wherein:

$R_4'$ and $R_4''$, together with the carbon atoms to which they are attached, optionally form a 3-6 membered cycloalkyl ring, which is optionally substituted with 1, 2 or 3 substituents selected from the group consisting of $C_{1-6}$alkyl, —$C_{1-6}$alkyl-OH and $C_{1-6}$alkoxyl-$C_{1-6}$alkyl-; and $R_4'''$ is H.

Embodiment 40. The compound according to any one of the preceding Embodiments or a stereoisomer, a racemate, a tautomer, a hydrate or a solvate, or pharmaceutically acceptable salt thereof, wherein:

wherein each of $R_4'$ and $R_4'''$ are H; and $R_4''$ is $C_{1-6}$alkyl substituted with 1, 2 or 3 halo.

Embodiment 41. The compound according to any one of the preceding Embodiments or a stereoisomer, a racemate, a tautomer, a hydrate or a solvate, or pharmaceutically acceptable salt thereof, wherein:

$R_4'$ and $R_4''$, together with the carbon atoms to which they are attached, optionally form a 3 or 5 membered cycloalkyl ring, which is optionally substituted with 1, 2 or 3 halo; and $R_4''$ is H.

Embodiment 42. The compound according to any one of the preceding Embodiments or a stereoisomer, a racemate, a tautomer, a hydrate or a solvate, or pharmaceutically acceptable salt thereof, wherein:

the moiety

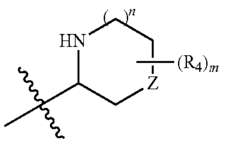

or

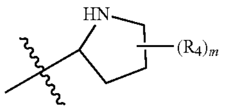

is

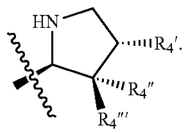

Embodiment 43. The compound according to any one of the preceding Embodiments or a stereoisomer, a racemate, a tautomer, a hydrate or a solvate, or pharmaceutically acceptable salt thereof, wherein:

the moiety

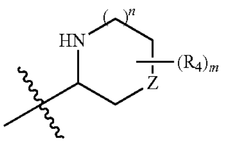

or

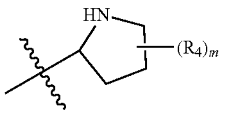

is

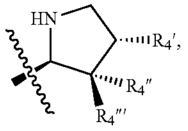

wherein $R_4'''$ is H; and $R_4'$ and $R_4''$ are independently selected from the group consisting of H; halo; $C_{1-6}$alkyl optionally substituted with 1, 2 or 3 halo; and $C_{1-6}$alkoxyl; provided that one of $R_4'$ and $R_4''$ is not H; or, $R_4'$ and $R_4''$, together with the carbon atoms to which they are attached, form a 3 or 5 membered cycloalkyl ring, which is optionally substituted with 1, 2 or 3 $C_{1-3}$alkyl.

Embodiment 44. The compound according to any one of the preceding Embodiments or a stereoisomer, a racemate, a tautomer, a hydrate or a solvate, or pharmaceutically acceptable salt thereof, wherein:

the moiety

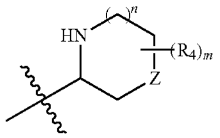

or

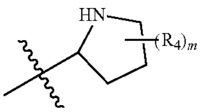

is

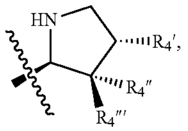

wherein $R_4'$ is H; and $R_4''$ and $R_4'''$ are independently $C_{1-3}$alkyl.

Embodiment 45. The compound according to any one of the preceding Embodiments or a stereoisomer, a racemate, a tautomer, a hydrate or a solvate, or pharmaceutically acceptable salt thereof, wherein the moiety

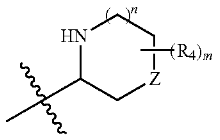

or

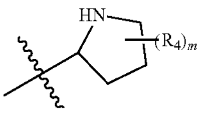

is

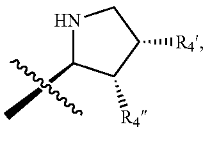

wherein one of $R_4'$ and $R_4''$ is H; and the other is $C_{1-6}$alkyl; or $R_4$' and $R_4$", together with the carbon atoms to which they are attached, optionally form a 3 or 5 membered cycloalkyl ring, which is optionally substituted with 1 or 2 $C_{1-6}$alkyl.

Embodiment 46. The compound according to any one of the preceding Embodiments or a stereoisomer, a racemate, a tautomer, a hydrate or a solvate, or pharmaceutically acceptable salt thereof, wherein the moiety

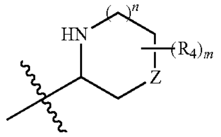 or 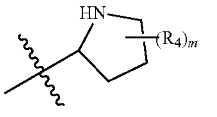

is

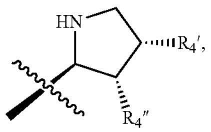

wherein $R_4$' is H; and $R_4$" is $C_{1-6}$alkyl substituted with 1 or 2 halo; or $R_4$' and $R_4$", together with the carbon atoms to which they are attached, optionally form a 3 or 5 membered cycloalkyl ring, which is optionally substituted with 1 or 2 halo.

Embodiment 47. The compound according to any one of the preceding Embodiments or a stereoisomer, a racemate, a tautomer, a hydrate or a solvate, or pharmaceutically acceptable salt thereof, wherein the moiety

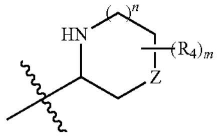 or 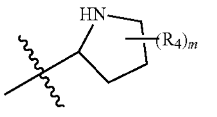

is

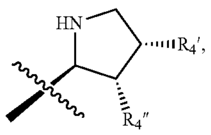

wherein $R_4$' is H; and $R_4$" is $C_{1-6}$alkyl substituted with 1, 2 or 3 halo; or $R_4$' and $R_4$", together with the carbon atoms to which they are attached, optionally form a 3 or 5 membered cycloalkyl ring.

Embodiment 48. The compound according to any one of the preceding Embodiments or a stereoisomer, a racemate, a tautomer, a hydrate or a solvate, or pharmaceutically acceptable salt thereof, wherein the moiety

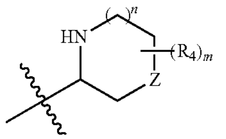 or 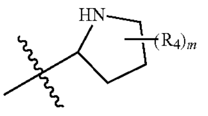

is

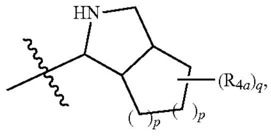

wherein each p is dependently 0 or 1; preferably both p are 0, or both p are 1;

q is 0, 1 or 2; preferably q is 0 or 2;

$R_{4a}$ is $C_{1-3}$alkyl or halo; preferably $R_{4a}$ is methyl or F.

Embodiment 49. The compound according to Embodiment 48 or a stereoisomer, a racemate, a tautomer, a hydrate or a solvate, or pharmaceutically acceptable salt thereof, wherein the moiety

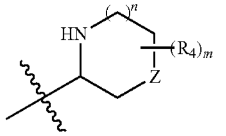 or 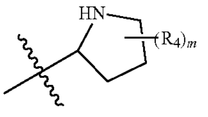

is

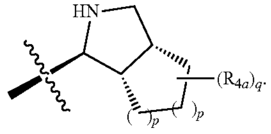

Embodiment 50. The compound according to any one of the Embodiments 1 to 2 or a stereoisomer, a racemate, a tautomer, a hydrate or a solvate, or pharmaceutically acceptable salt thereof, wherein the compound is selected from Example 2 to Example 100.

Embodiment 51. The compound of any one of the Embodiments 1-50, or a stereoisomer, a racemate, a tautomer, a hydrate or a solvate, or pharmaceutically acceptable salt thereof, for use as a medicament.

Embodiment 52. The compound of any one of the Embodiments 1-50, or a stereoisomer, a racemate, a tautomer, a hydrate or a solvate, or pharmaceutically acceptable salt thereof, for use in the treatment or prevention of cancer and other diseases mediated by the interaction of menin with MLL and/or MLL fusion proteins.

Embodiment 53. The compound of any one of the Embodiments 1-50, or a stereoisomer, a racemate, a tautomer, a hydrate or a solvate, or pharmaceutically acceptable salt thereof, for use in the treatment or prevention of cancer or diabetes;

preferably, the cancer is hematological tumor, e.g., leukemia, lymphomas, myelomas (e.g., multiple myeloma), myelodysplastic syndrome (MDS), and myeloproliferative neoplasms (MPN), polycythemia vera; or solid tumor, e.g., prostate cancer, lung cancer, breast cancer, pancreatic cancer, colon cancer, liver cancer, melanoma and glioblastoma;

more preferably, the leukemia is selected from acute leukemias, chronic leukemias, myeloid leukemias, myelogenous leukemias, lymphoblastic leukemias, lymphocytic leukemias, acute myeloid leukemias (AML), chronic myeloid leukemias (CML), acute lymphoblastic leukemias (ALL), chronic lymphocytic leukemias (CLL), T cell prolymphocytic leukemias (T-PLL), large granular lymphocytic leukemia, hairy cell leukemia (HCL), mixed lineage leukemia (MLL), MLL-rearranged leukemias (MLLr leukemia), MLL-PTD leukemias, MLL amplified leukemias, MLL-positive leukemias, nucleophosmin (NPM)-mutated leukemia, MOZ acute leukemia, NUP98 acute leukemia, CALM acute leukemia, MLL-AF4 leukemia, MLL-AF6 leukemia, MLL-AF9 leukemia, MLL-AF10 leukemia, MLL-ENL leukemia and MILL-ELL leukemia.

Embodiment 54. A pharmaceutical composition, comprising the compound of any one of the Embodiments 1-50, or a stereoisomer, a racemate, a tautomer, a hydrate or a solvate, or pharmaceutically acceptable salt thereof, and optionally a pharmaceutically acceptable carrier.

Embodiment 55. Use of the compound of any one of the Embodiments 1-50, or a stereoisomer, a racemate, a tautomer, a hydrate or a solvate, or pharmaceutically acceptable salt thereof, in the manufacture of a medicament for treatment or prevention of cancer or diabetes;

preferably, the cancer is hematological tumor, e.g., leukemia, lymphomas, myelomas (e.g., multiple myeloma), myelodysplastic syndrome (MDS), and myeloproliferative neoplasms (MPN), polycythemia vera; or solid tumor, e.g., prostate cancer, lung cancer, breast cancer, pancreatic cancer, colon cancer, liver cancer, melanoma and glioblastoma;

more preferably, the leukemia is selected from acute leukemias, chronic leukemias, myeloid leukemias, myelogenous leukemias, lymphoblastic leukemias, lymphocytic leukemias, acute myeloid leukemias (AML), chronic myeloid leukemias (CML), acute lymphoblastic leukemias (ALL), chronic lymphocytic leukemias (CLL), T cell prolymphocytic leukemias (T-PLL), Large granular lymphocytic leukemia, Hairy cell leukemia (HCL), mixed lineage leukemia (MLL), MLL-rearranged leukemias (MLLr leukemia), MLL-PTD leukemias, MLL amplified leukemias, MLL-positive leukemias, nucleophosmin (NPM)-mutated leukemia, MOZ acute leukemia, NUP98 acute leukemia, CALM acute leukemia, MLL-AF4 leukemia, MLL-AF6 leukemia, MLL-AF9 leukemia, MLL-AF10 leukemia, MLL-ENL leukemia and MILL-ELL leukemia.

Embodiment 56. A method of in vivo or in vitro inhibiting the interaction of menin with MLL and/or MLL fusion proteins, comprising contacting an effective amount of the compound of any one of the Embodiments 1-50 or a pharmaceutically acceptable salt thereof with menin and MLL and/or MLL fusion proteins.

Embodiment 57. A method of treating or preventing cancer or diabetes, comprising administering to the subject in need thereof an effective amount of the compound of any one of the Embodiments 1-50 or a stereoisomer, a racemate, a tautomer, a hydrate or a solvate, or pharmaceutically acceptable salt thereof;

preferably, the cancer is hematological tumor, e.g., leukemia, lymphomas, myelomas (e.g., multiple myeloma), myelodysplastic syndrome (MDS), and myeloproliferative neoplasms (MPN), polycythemia vera; or solid tumor, e.g., prostate cancer, lung cancer, breast cancer, pancreatic cancer, colon cancer, liver cancer, melanoma and glioblastoma;

more preferably, the leukemia is selected from acute leukemias, chronic leukemias, myeloid leukemias, myelogenous leukemias, lymphoblastic leukemias, lymphocytic leukemias, acute myeloid leukemias (AML), chronic myeloid leukemias (CML), acute lymphoblastic leukemias (ALL), chronic lymphocytic leukemias (CLL), T cell prolymphocytic leukemias (T-PLL), Large granular lymphocytic leukemia, Hairy cell leukemia (HCL), mixed lineage leukemia (MLL), MLL-rearranged leukemias (MLLr leukemia), MLL-PTD leukemias, MLL amplified leukemias, MLL-positive leukemias, nucleophosmin (NPM)-mutated leukemia, MOZ acute leukemia, NUP98 acute leukemia, CALM acute leukemia, MLL-AF4 leukemia, MLL-AF6 leukemia, MLL-AF9 leukemia, MLL-AF10 leukemia, MLL-ENL leukemia and MILL-ELL leukemia.

Embodiment 58. A combination, comprising the compound of any one of the Embodiments 1-50, or a stereoisomer, a racemate, a tautomer, a hydrate or a solvate, or pharmaceutically acceptable salt thereof, and at least one additional therapeutic agent, wherein said additional therapeutic agent preferably is an anti-neoplastic agent, e.g., a radiotherapeutic agent, a chemotherapeutic agent, an immunotherapeutic agent, or a targeted therapeutic agent.

Definitions

As used in the present disclosure, the following words, phrases and symbols have the meanings as set forth below, unless specified otherwise in the context.

As used herein, the singular forms "a", "an" and "the" are intended to include the plural forms as well, unless the context clearly indicates otherwise.

A dash ("-") that is not between two letters or symbols is used to indicate a point of attachment for a substituent. For example, $—C_{1-6}$alkyl-OH is attached to the rest of the molecule through the alkyl.

The term "alkyl" as used herein refers to a straight or branched saturated hydrocarbon radical having 1-10 carbon atoms ($C_{1-10}$), preferably 1-6 carbon atoms ($C_{1-6}$), and more preferably 1-4 carbon atoms ($C_{1-4}$) or 1-3 carbon atoms ($C_{1-3}$). For example, "$C_{1-6}$ alkyl" refers to the alkyl having 1-6 (1, 2, 3, 4, 5 or 6) carbon atoms. Examples of the alkyl include, but are not limited to, methyl, ethyl, n-propyl, i-propyl, n-butyl, i-butyl, s-butyl and t-butyl.

The term "alkenyl" as used herein refers to a straight or branched unsaturated hydrocarbon radical containing one or more, for example 1, 2, or 3 carbon-carbon double bonds (C═C) and having 2-10 carbon atoms ($C_{2-10}$), preferably 2-6 carbon atoms ($C_{2-6}$), more preferably 2-4 carbon atoms ($C_{2-4}$). For example, "$C_{2-6}$ alkenyl" refers to the alkenyl having 2-6 (2, 3, 4, 5 or 6) carbon atoms, which preferably contains 1 or 2 carbon-carbon double bonds; "$C_{2-4}$ alkenyl" refers to the alkenyl having 2-4 carbon atoms, which preferably contains 1 carbon-carbon double bond. Examples of the alkenyl include, but are not limited to, vinyl, 2-propenyl, and 2-butenyl. The point of attachment for the alkenyl may or may not be on the double bond.

The term "alkynyl" as used herein refers to a straight or branched unsaturated hydrocarbon radical containing one or more, for example 1, 2, or 3, carbon-carbon triple bonds (C≡C) and having 2-10 carbon atoms ($C_{2-10}$), preferably 2-6 carbon atoms ($C_{2-6}$), more preferably 2-4 carbon atoms ($C_{2-4}$). For example, "$C_{2-6}$ alkynyl" refers to the alkynyl having 2-6 (2, 3, 4, 5 or 6) carbon atoms, which preferably contains 1 or 2 carbon-carbon triple bonds; "$C_{2-4}$ alkynyl"

refers to the alkynyl having 2-4 carbon atoms, which preferably contains 1 carbon-carbon triple bond. Examples of the alkynyl include, but are not limited to, ethynyl, 2-propynyl, and 2-butynyl. The point of attachment for the alkynyl may or may not be on the triple bond.

The term "halogen" or "halo" as used herein refers to fluoro, chloro, bromo, and iodo, preferably fluoro, chloro and bromo, more preferably fluoro and chloro, most preferably fluoro.

The term "haloalkyl" as used herein refers to the alkyl as defined herein, in which one or more, for example 1, 2, 3, 4, or 5 hydrogen atoms are replaced with halogen atom, and when more than one hydrogen atoms are replaced with halogen atoms, the halogen atoms may be the same or different from each other. In one embodiment, the term "haloalkyl" as used herein refers to the alkyl as defined herein, in which two or more, such as 2, 3, 4, or 5 hydrogen atoms are replaced with halogen atoms, wherein the halogen atoms are the same as each other. In another embodiment, the term "haloalkyl" as used herein refers to the alkyl as defined herein, in which two or more, for example 2, 3, 4, or 5 hydrogen atoms are replaced with halogen atoms, wherein the halogen atoms may be different from each other. Examples of the haloalkyl include, but are not limited to, $—CF_3$, $—CHF_2$, $—CH_2F$, $—CH_2CF_3$, $—CF_2CF_3$, $—CF_2CH_3$, and the like. Preferably haloalkyl is $C_{1-6}$trifluoroalkyl, more preferably-$CF_3$.

The term "alkyl substituted with 1, 2 or 3 . . . halo" refers to the alkyl as defined herein, in which one or more, for example 1, 2 or 3 hydrogen atoms are replaced with halogen atom, and when more than one hydrogen atoms are replaced with halogen atoms, the halogen atoms may be the same or different from each other, including, but being not limited to, $—CF_3$, $—CHF_2$, $—CH_2F$, $—CH_2CF_3$, $—CH_2CH_2F$, $—CF_2CH_3$, and the like. Similarly, the term "alkyl substituted with 1, 2 or 3 . . . . CN" includes, but is not limited to, $—CH_2CN$ and $—CH_2CH_2CN$. The term "alkoxyl substituted with 1, 2 or 3 . . . halo" includes, but is not limited to, $—OCH_2F$, $—OCHF_2$, $—OCHF_3$, $—OCH_2CHF_3$.

The term "alkoxyl" as used herein refers to the group-O-alkyl, wherein the alkyl is as defined above. Examples of the alkoxyl include, but are not limited to, $C_{1-6}$alkoxyl, such as methoxy, ethoxy, n-propoxy, i-propoxy, n-butoxy, i-butoxy, t-butoxy, pentoxy, and hexyloxy, including their isomers. Preferably alkoxyl is methoxy.

The term "cycloalkyl" as used herein refers to saturated cyclic hydrocarbon radical having 3-10 ring carbon atoms ($C_{3-10}$), such as 3-9 ring carbon atoms ($C_{3-9}$), 3-7 ring carbon atoms ($C_{3-7}$), 3-6 ring carbon atoms ($C_{3-6}$), 3-5 ring carbon atoms ($C_{3-5}$) or 5-6 ring carbon atoms ($C_{5-6}$), which may have one or more rings, e.g., 1 or 2 rings. For example, said cycloalkyl is monocyclic cycloalkyl, preferably monocyclic $C_{3-7}$cycloalkyl, preferably monocyclic $C_{3-6}$ cycloalkyl (e.g. cyclopropyl, cyclobutyl, cyclopentyl, cyclohexyl) or monocyclic $C_{3-5}$cycloalkyl (e.g. cyclopropyl, cyclobutyl, cyclopentyl) ring. For example, said cycloalkyl is bicyclic cycloalkyl ring, preferably bicyclic $C_5$-$C_{10}$cycloalkyl ring. Bicyclic cycloalkyl include a fused ring, a bridged ring, or a spirocyclic ring.

The term "heterocyclyl" as used herein refers to a saturated or partially unsaturated ring having 3-10 ring atoms (3-10 membered), such as 5-9 ring atoms (5-9 membered), 6-8 ring atoms (6-8 membered), 5-6 ring atoms (5-6 membered) or 7-9 ring atoms (7-9 membered), with one or more of, such as 1, 2 or 3, preferably 1 or 2 of the ring atoms being heteroatoms independently selected from N, O and S, and the remaining ring atoms being carbon, and having one or more, for example 1, 2 or 3, preferably 1 or 2 rings, wherein the N or S heteroatom is optionally oxidized to various oxidation states. The point of attachment of heterocyclyl may be on N heteroatom or carbon atom. The ring(s) of the heterocyclyl also include(s) a fused ring, a bridged ring, or a spirocyclic ring. The ring(s) of the heterocyclyl may be saturated or contain(s) one or more, for example, one or two double bonds (i.e. partially unsaturated), but is (are) not fully conjugated, and not the heteroaryl as defined herein. For example, "5-9 membered heterocyclyl" refers to the monocyclic or bicyclic heterocyclyl having 5-9 ring atoms and containing 1, 2 or 3, preferably 1 or 2 ring heteroatoms independently selected from N, O and S, preferably is saturated 5-6 membered monocyclic or 7-9 membered bicyclic heterocyclyl. Examples of the heterocyclyl include, but are not limited to, pyrrolidinyl, imidazolidinyl, morpholinyl, thiomorpholinyl, piperidinyl, piperazinyl, hexahydropyrimidyl, oxazinanyl, 3-oxa-6-azabicyclo[3.2.1]octanyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, azaspiro[3.5]nonanyl, or azaspiro[2.5]octanyl ring. Preferably, the heterocyclyl is morpholinyl or 3-oxa-6-azabicyclo[3.2.1]octanyl ring.

The term "aryl" as used herein refers to carbocyclic hydrocarbon radical having 6-14 carbon atoms ($C_{6-14}$), preferably 6-10 carbon atoms ($C_{6-10}$) and consisting of one ring or more fused rings, wherein at least one ring is aromatic. Examples of the aryl include, but are not limited to, phenyl, naphthalenyl, 1,2,3,4-tetrahydronaphthalenyl, phenanthryl, indenyl, indanyl, or azulenyl ring, preferably phenyl or naphthalenyl ring, more preferably phenyl ring.

The term "heteroaryl" as used herein refers to a monocyclic, bicyclic or tricyclic ring system having 5-12 ring atoms (5-12 membered), such as 5-10 ring atoms (5-10 membered), 5-9 ring atoms (5-9 membered), 8-10 ring atoms (8-10 membered), 5-6 ring atoms (5-6 membered), 5 ring atoms (5 membered) or 6 ring atoms (6 membered), wherein at least one ring is an 5 or 6 membered aromatic ring with one or more of, such as 1, 2 or 3, preferably 1 or 2 of the ring atoms being heteroatoms independently selected from N, O and S, and the remaining ring atoms being carbon, and wherein the N or S heteroatom is optionally oxidized to various oxidation states. For example, the 5-10 membered heteroaryl is:

5-6 membered monocyclic heteroaryl, i.e. monocyclic aromatic hydrocarbon radical having 5 or 6 ring atoms (5 or 6 membered), with one or more of, for example 1, 2 or 3, preferably 1 or 2 of the ring atoms being ring heteroatoms independently selected from N, O, and S (preferably N), and the remaining ring atoms being carbon; preferably, monocyclic aromatic hydrocarbon radical having 6 ring atoms (6 membered), with 1, 2 or 3, preferably 1 or 2 of the ring atoms being heteroatoms independently selected from N, O, and S, preferably N;

or 8-10 membered bicyclic heteroaryl, i.e. bicyclic aromatic hydrocarbon radical having 8, 9, or 10 ring atoms (8, 9, or 10 membered), with one or more, for example, 1, 2, 3 or 4, preferably 1, 2 or 3 of the ring atoms are ring heteroatoms independently selected from N, O, and S (preferably N), and the remaining ring atoms being carbon, wherein at least one of the rings is aromatic.

Examples of the heteroaryl include, but are not limited to, pyridyl (e.g., pyridin-2-yl, pyridin-3-yl, pyridin-4-yl, pyridin-5-yl, pyridin-6-yl), pyridyl N-oxide, pyrazinyl (e.g., pyrazin-2-yl, pyrazin-3-yl), pyrimidinyl (e.g., pyrimidin-2-yl, pyrimidin-4-yl, pyrimidin-5-yl, pyrimidin-6-yl), pyridazinyl (e.g., pyridazin-3-yl, pyridazin-4-yl), pyrazolyl (e.g., pyrazol-1-yl, pyrazol-2-yl, pyrazol-3-yl, pyrazol-4-yl, pyrazol-5-yl), imidazolyl (e.g., imidazol-1-yl, imidazol-5-yl, imidazol-3-yl, imidazol-4-yl, imidazol-5-yl), oxazolyl, isoxazolyl, oxadiazolyl, thiazolyl, isothiazolyl, thiadiazolyl, triazolyl (e.g., triazol-1-yl, triazol-2-yl, triazol-3-yl, triazol-4-yl, triazol-5-yl), tetrazolyl, triazinyl, thienyl, furyl, pyranyl, pyrrolyl, benzodioxolyl, benzooxazolyl, benzoisoxazolyl, benzothienyl, benzothiazolyl, benzoisothiazolyl, imidazopyridyl, imidazopyrrolyl, triazolopyridyl, indazolyl, pyrrolopyridyl, pyrrolopyrimidinyl, pyrazolopyridyl, pyrazolopyrimidinyl, tetrazolopyridyl, tetrahydropyrazolopyridyl, benzofuryl, benzoimidazolinyl, or indolyl. Preferably, the heteroaryl is pyrazolyl, triazolyl or pyrimidinyl ring, more preferably pyrazol-1-yl, pyrazol-2-yl, pyrazol-3-yl, pyrazol-4-yl, pyrazol-5-yl, pyrimidin-2-yl, pyrimidin-4-yl, pyrimidin-5-yl, pyrimidin-6-yl, triazol-1-yl, triazol-2-yl, triazol-3-yl, triazol-4-yl, triazol-5-yl.

The term "oxo" as used herein refers to the group =O.

The group "D" means hydrogen atom of the moiety is replaced with its isotope deuterium.

When a structure of a compound herein contains a bond represented by a wavy line " , it means a mixture of isomers in any ratio of the compound.

When a group carries a wavy line " " on a bond, the wavy line indicates the point of attachment of the group to the rest of the molecule.

As used herein, a bond through a ring means that a group having the bond is attached to the ring at any chemically permissible position of the ring, unless indicated otherwise.

The group

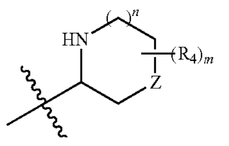

wherein Z, n, m and $R_4$ are as defined in general formulas herein represents a heterocyclyl ring substituted by $(R_4)_m$ at any chemically permissible position (e.g. at Z, when Z is $CH_2$ or NH) of the ring. Preferably, in the present disclosure, the substitution with $R_4$ is not occurred on the N atom adjacent to the attachment point of the group to the remaining structure of the compound.

The term "optional" or "optionally" as used herein means that the subsequently described event or circumstance may or may not occur, and the description includes instances wherein the event or circumstance occur and instances in which it does not occur. For example, "optionally substituted with . . . " encompasses both "unsubstituted" and "substituted with 1, 2, 3 or more" substituents as defined. It will be understood by those skilled in the art, with respect to any group containing one or more substituents, that such groups do not include any substitution or substitution patterns that are sterically impractical, chemically incorrect, synthetically non-feasible and/or inherently unstable.

The term "substituted" or "substituted with . . . " as used herein, means that one or more hydrogens on the designated atom or group are replaced with one or more substituents independently selected from the indicated group of substituents, provided that the designated atom's normal valence is not exceeded. The term "substituted with 1, 2 or 3 . . . " means that 1, 2 or 3 hydrogens on the designated atom or group are replaced with 1, 2 or 3 substituents independently selected from the indicated group of substituents, provided that the designated atom's normal valence is not exceeded. When a substituent is oxo (i.e., =O), then 2 hydrogens on a single atom are replaced by the oxo. Combinations of substituents and/or variables are permissible only if such combinations result in a chemically correct and stable compound. A chemically correct and stable compound is meant to imply a compound that is sufficiently robust to survive sufficient isolation from a reaction mixture.

It will be appreciated by a person skilled in the art that some of the compounds disclosed herein may contain one or more chiral centers or ring and therefore exist in two or more stereoisomers. The racemates of these isomers, the individual isomers and mixtures enriched in one enantiomer, as well as diastereomers and mixtures partially enriched with specific diastereomers when there are two chiral centers are within the scope of the present disclosure. It will be further appreciated by a person skilled in the art that the present disclosure includes all the individual stereoisomers (e.g. enantiomers, diastereoisomers, cis- or trans-isomers (e.g., configuration of substituents on bivalent cyclic saturated or partially saturated radicals), or atropisomers, whenever chemically possible), racemates of the compounds of the present disclosure, mixtures thereof, and, where appropriate, the individual tautomeric forms thereof.

The racemate or other mixtures of isomers can be used as such or can be resolved into their individual isomers. The resolution can afford stereochemically pure compounds or mixtures enriched in one or more isomers. Methods for separation of isomers are well known (e.g., cf. Allinger N. L. and Eliel E. L. in "*Topics in Stereochemistry*", Vol. 6, Wiley Interscience, 1971).

When a structure herein contains "(R)" and/or "(S)", it means that the chiral center of the compound marked by "(R)" or "(S)" is a single configuration in either R-configuration or S-configuration.

Such R-configuration or S-configuration of the chiral center of the compound can also be represented by " " or " " merely in the structure. For example, the compounds of the present disclosure have an enantiomeric purity of at least 60% ee (e.g., 60%, 65%, 70%, 75%, 80%, 85%, 90%, 91%, 92%, 93%, 94%, 95%, 96%, 97%, 98%, 99%, 99.5%, 99.9% ee (enantiomeric excess), or any values between those enumerated values), or have a diastereomeric purity of at least 60% de (diastereomeric excess) (e.g., 60%, 65%, 70%, 75%, 80%, 85%, 90%, 91%, 92%, 93%, 94%, 95%, 96%, 97%, 98%, 99%, 99.5%, 99.9% de, or any values between those enumerated values).

The term "pharmaceutically acceptable salt" includes, but is not limited to, acid addition salts formed by the compounds disclosed herein with an inorganic acid, such as hydrochloride, hydrobromide, carbonate, bicarbonate, phosphate, sulfate, sulfite, nitrate and the like; as well as with an organic acid, such as formate, acetate, malate, maleate, fumarate, tartrate, succinate, citrate, lactate, methanesulfonate, p-toluenesulfonate, 2-hydroxyethylsulfonate, benzoate, salicylate, stearate, and salts with alkane-dicarboxylic acid of formula $HOOC-(CH_2)_n-COOH$ wherein n is 0-4, and the like. Also, "pharmaceutically acceptable salt" includes base addition salts formed by the compound of the present disclosure carrying an acidic moiety with pharmaceutically acceptable cations, for example, sodium, potassium, calcium, aluminum, lithium, and ammonium.

In addition, if the compound described herein is obtained as an acid addition salt, the free base can be obtained by basifying a solution of the acid addition salt. Conversely, if the product is a free base, an acid addition salt, particularly a pharmaceutically acceptable acid addition salt, may be produced from a base compound by dissolving the free base in a suitable solvent and treating the solution with an acid, in accordance with conventional procedures for preparing acid addition salts. A person skilled in the art will recognize various synthetic methodologies that may be used without undue experimentation to prepare non-toxic pharmaceutically acceptable acid addition salts or base addition salts.

The term "protecting group" or "PG" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include p-methoxybenzyl (PMB), benzyl (Bn), trityl (Trt), acetyl, trifluoroacetyl, phthalimido, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include methoxymethyl, benzyl, benzyloxymethyl, methyl, triarylmethyl, acetyl, trialkylsilyl, dialkylphenylsilyl, benzoyl, and tetrahydropyranyl. For a general description of protecting groups and their use, see T. W. Greene and P. G. M. Wuts, "Protective Groups in Organic Synthesis", $5^{th}$ Edition, Wiley, New York, 2014.

The term "pharmaceutical combination" or "combination" as used herein means a product that results from the mixing or combining of more than one therapeutic agent and includes both fixed and non-fixed combinations of the therapeutic agents, e.g., kit or pharmaceutical composition. The term "fixed combination" means that the therapeutic agents, e.g. the compound of the present disclosure and an additional therapeutic agent, are both administered to a subject simultaneously in the form of a single entity or dosage. The term "non-fixed combination" means that the therapeutic agents, e.g. the compound of the present disclosure and an additional therapeutic agent, are both administered to a subject as separate entities either simultaneously, concurrently or sequentially with no specific time limits, wherein such administration provides therapeutically effective levels of the compounds in the body of the subject.

The term "treating", "treat" or "treatment" in connection with a disease refers to administering one or more pharmaceutical substances, especially the compound of the present disclosure or a pharmaceutically acceptable salt thereof described herein to a subject that has the disease or disorder, or has a symptom of a disease or disorder, with the purpose to cure, heal, alleviate, relieve, alter, remedy, ameliorate, improve, or affect the disease or disorder, the symptoms of the disease or disorder. In some embodiments, the disease or disorder is cancer or diabetes.

The term "prevent" or "preventing" in connection with a disease refer to administering one or more pharmaceutical substances, especially the compound of the present disclosure to a subject that has a predisposition toward a disease or disorder, or has a risk of suffering from a disease or disorder, with the purpose to prevent or slow down the occurrence of the disease or disorder in the subject.

The term "effective amount" as used herein refers to an amount of the compound of the present disclosure effective to "treat" or "prevent" cancer or diabetes in a subject. The effective amount may cause any changes observable or measurable in a subject as described in the definition of "treating", "treat", "treatment", "preventing", or "prevent" above. For example, in the case of cancer, the effective amount can reduce the number of cancer or tumor cells; reduce the tumor size; inhibit or stop tumor cell infiltration into peripheral organs; inhibit and stop tumor metastasis; inhibit and stop tumor growth; relieve to some extent one or more of the symptoms associated with the cancer; reduce morbidity and mortality; improve quality of life; or a combination of such effects. An effective amount may be an amount sufficient to reduce the symptoms of cancer. The term "effective amount" may also refer to an amount of the compound of the present disclosure effective to inhibit the interaction of menin with MLL and/or MLL fusion proteins.

The term "inhibition" or "inhibiting" indicates a decrease in the baseline activity of a biological activity or process.

The term "subject" as used herein means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. In some embodiments, the subject is a human.

The term "pharmaceutically acceptable" means that the substance following this term is useful in preparing a pharmaceutical composition and is generally safe, non-toxic, and neither biologically nor otherwise undesirable, especially for human pharmaceutical use.

The term "cancer" herein refers to a cellular disorder characterized by uncontrolled or disregulated cell proliferation, decreased cellular differentiation, inappropriate ability to invade surrounding tissue, and/or ability to establish new growth at other sites. The term "cancer" includes, but is not limited to, hematological tumors and solid tumors, preferably is leukemia. The term "cancer" encompasses cancer of skin, tissues, organs, bone, cartilage, blood, and vessels. The term "cancer" further encompasses primary cancers, metastatic cancers, recurrent cancers, and refractory cancers. The term "cancer" includes, but is not limited to, leukemia, lymphomas, myelomas (e.g., multiple myeloma), myelodysplastic syndrome (MDS), and myeloproliferative neoplasms (MPN), polycythemia vera; prostate cancer, lung cancer, breast cancer, pancreatic cancer, colon cancer, liver cancer, melanoma and glioblastoma. The "leukemia" herein includes, but is not limited to, acute leukemias, chronic leukemias, myeloid leukemias, myelogenous leukemias, lymphoblastic leukemias, lymphocytic leukemias, acute myeloid (myelogenous) leukemias (AML), chronic myeloid (myelogenous) leukemias (CML), acute lymphoblastic leukemias (ALL), chronic lymphocytic leukemias (CLL), T cell prolymphocytic leukemias (T-PLL), Large granular lymphocytic leukemia, Hairy cell leukemia (HCL), mixed lineage leukemia (MLL), MLL-rearranged leukemias (MLLr leukemia), MLL partial tandem duplicate leukemia (MLL-PTD leukemias), MLL amplified leukemias, MLL-positive leukemias, nucleophosmin (NPM)-mutated leukemia (NPM1-mutated leukemia, NPM1c leukemia), MOZ acute leukemia, NUP98 acute leukemia, and clathrin assembly lymphoid myeloid (CALM) acute leukemia; and MLL-AF4 (ALL-1 fused gene from chromosome 4) leukemia, MLL-AF6 leukemia, MLL-AF9 leukemia, MLL-AF10 leukemia, MLL-ENL (eleven-nineteen leukemia) leukemia and MLL-ELL (eleven-nineteen lysine-rich leukemia) leukemia.

All numerical ranges herein should be understood as disclosing each and every value within the range and each and every subset of values within the range, regardless of whether they are specifically disclosed otherwise. For example, when referring to any numerical range, it should be regarded as referring to each and every numerical value in the numerical range, for example, each and every integer in the numerical range. The present disclosure includes all values falling within these ranges, all smaller ranges, and the upper or lower limit of the range.

Technical and scientific terms used herein and not specifically defined have the meaning commonly understood by a person skilled in the art, to which the present disclosure pertains.

Pharmaceutical Composition and Administration

The compound of the present disclosure (such as any of the compounds of the Examples herein) alone or in combination with one or more additional therapeutic agents can be formulated into a pharmaceutical composition. The pharmaceutical composition includes: (a) the compound of the present disclosure; (b) a pharmaceutically acceptable carrier (for example, one or more pharmaceutically acceptable carriers); and optionally (c) at least one additional therapeutic agent.

A pharmaceutically acceptable carrier refers to an excipient or adjuvant that is compatible with the active ingredient(s) in the composition (in some embodiments, can stabilize the active ingredient) and is not harmful to the subject being treated. Suitable pharmaceutically acceptable carriers are disclosed in standard reference books in the art (e.g., Remington's Pharmaceutical Sciences, Remington: The Science and Practice of Pharmacy), including one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., the compound of the present disclosure or pharmaceutical composition thereof) or aid in the manufacturing of the pharmaceutical product (i.e., medicament).

The compound of the present disclosure can be administered in various known manners, such as orally, parenterally, by inhalation, or by implantation. The term "parenteral" as used herein includes subcutaneous, intracutaneous, intravenous, intramuscular, intraarticular, intraarterial, intrasynovial, intrasternal, intrathecal, intralesional and intracranial injection or infusion.

The compound of the present disclosure may be administered in any convenient formulation, e.g., tablets, powders, capsules, solutions, dispersions, suspensions, syrups, sprays, suppositories, gels, emulsions, patches, etc.

In one example, the effective amount of the compound of the present disclosure administered parenterally per dose will be in the range of about 0.01 to 100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 0.1 to about 1000 mg of the compound of the present disclosure.

Indications and Methods of Treatment

The present disclosure relates to a method of treating or preventing a disease or disorder mediated by the interaction of menin with MLL and/or MLL fusion proteins, comprising administering to the subject in need thereof an effective amount of the compound of the present disclosure.

The present disclosure relates to a method of treating or preventing cancer or diabetes, comprising administering to the subject in need thereof an effective amount of the compound of the present disclosure.

In one embodiment, the compound of the present disclosure is used for the treatment or prevention of a disease or disorder mediated by the interaction of menin with MLL and/or MLL fusion proteins.

In one embodiment, the compound of the present disclosure is used for the treatment or prevention of cancer or diabetes.

In one embodiment, the compound of the present disclosure is used for the treatment or prevention of hematological tumor, including but not limited to leukemia, lymphomas, myelomas (e.g., multiple myeloma), myelodysplastic syndrome (MDS), and myeloproliferative neoplasms (MPN), polycythemia vera; or solid tumor, including but not limited to prostate cancer, lung cancer, breast cancer, pancreatic cancer, colon cancer, liver cancer, melanoma and glioblastoma.

In one embodiment, the compound of the present disclosure is used for the treatment or prevention of acute leukemias, chronic leukemias, myeloid leukemias, myelogenous leukemias, lymphoblastic leukemias, lymphocytic leukemias, acute myeloid leukemias (AML), chronic myeloid leukemias (CML), acute lymphoblastic leukemias (ALL), chronic lymphocytic leukemias (CLL), T cell prolymphocytic leukemias (T-PLL), Large granular lymphocytic leukemia, Hairy cell leukemia (HCL), mixed lineage leukemia (MLL), MLL-rearranged leukemias (MLLr leukemia), MLL partial tandem duplicate leukemia (MLL-PTD leukemias), MLL amplified leukemias, MLL-positive leukemias, nucleophosmin (NPM)-mutated leukemia, MOZ acute leukemia, NUP98 acute leukemia, and clathrin assembly lymphoid myeloid (CALM) acute leukemia.

Pharmaceutical Combination

The compound of the present disclosure may be used in combination with an additional therapeutic agent in the treatment of a disease or disorder mediated by the interaction of menin with MLL and/or MLL fusion proteins. The additional therapeutic agent may be administered separately with the compound of the present disclosure or may be included with the compound of the present disclosure in a pharmaceutical composition according to the present disclosure, such as a fixed combination product. In some embodiments, the additional therapeutic agent are those that are known or discovered to be effective in the treatment of a disease or disorder mediated by the interaction of menin with MLL and/or MLL fusion proteins or a compound that antagonizes another target associated with said particular disease. The combination may serve to increase efficacy, decrease one or more side effects, or decrease the required dose of the compound of the present disclosure.

In some embodiments, the compound of the present disclosure is administered in combination with an anti-neoplastic agent. The anti-neoplastic agents include, but are not limited to: radiotherapeutic agents, chemotherapeutic agents, immunotherapeutic agents, targeted therapeutic agents.

General Synthetic Methods

Example compounds with general structure as A10 may be synthesized according to Scheme 1. Reaction between phenol A1 and 5-bromopyrimidine under basic conditions gave biaryl ether A2, which could be converted to N-oxide A3 in the presence of mCPBA. Subsequent reaction of the latter with chrolination reagent, like POCl3, readily afforded chloropyrimidine A4. Nucleophilic substitution reaction between chloride A4 and mono-protected spirodiamine A5 gave key intermediate A6. The following deprotection of A7, amide formation with N-protected cyclic amino acid A8, and N-deprotection afforded final compound A10.

Scheme 1

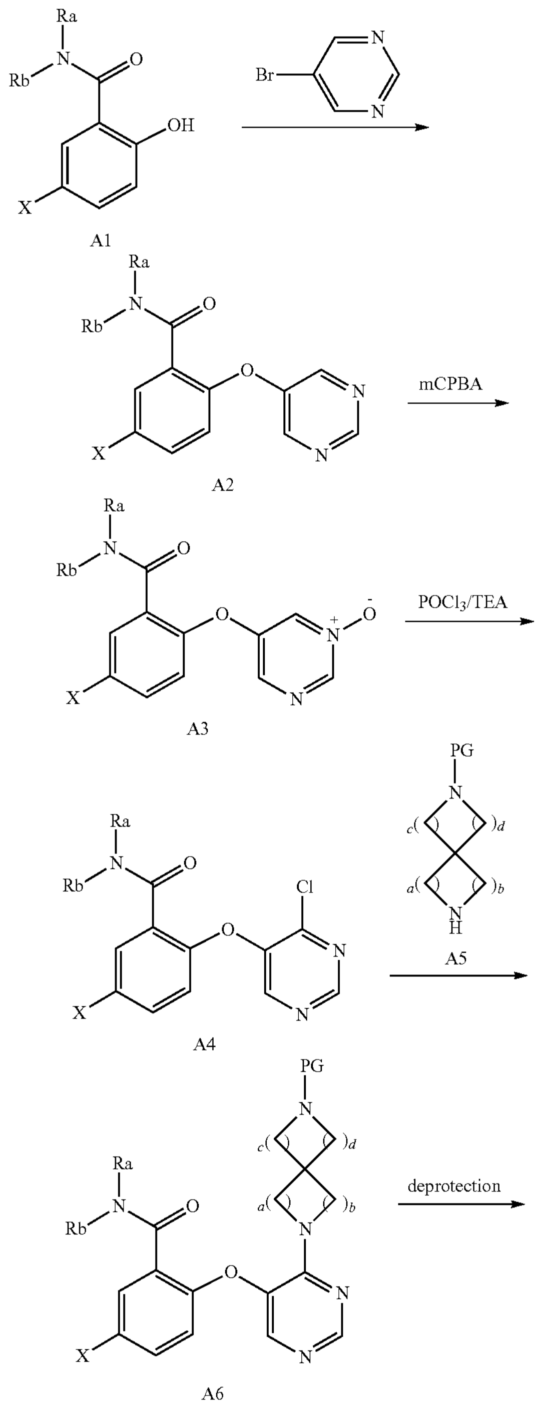

-continued

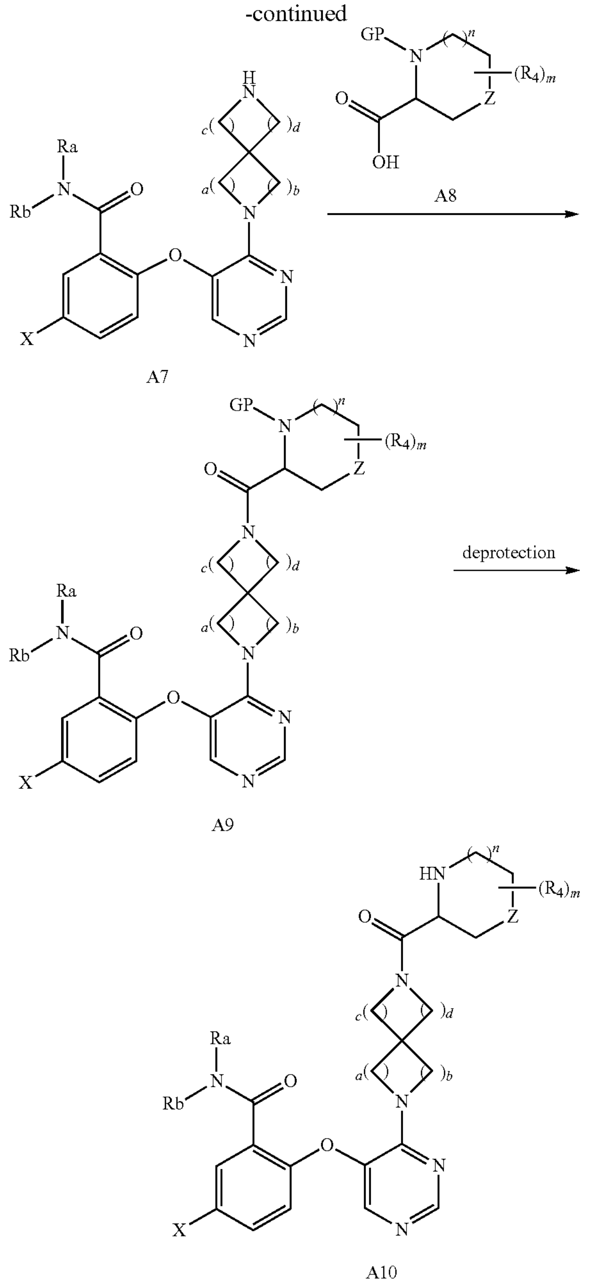

Example compounds with structure as B4 may be synthesized according to Scheme 2. B1 could be prepared from appropriate phenol according to procedure similar to that for A6 as depicted in Scheme 1. Suzuki coupling reaction between B1 and (hetero)arylboronic acid afforded compound B3. Alternatively, a two-step route could be used to prepare B3, that is, B1 was converted to boronate B2 via palladium catalyzed boronylation reaction followed by suzuki reaction of the latter with (hetero)aryl halide. Subsequent deprotection of B3, amidation with N-protected cyclic amino acid A8, and final N-deprotection could afford compound B4.

Scheme 2
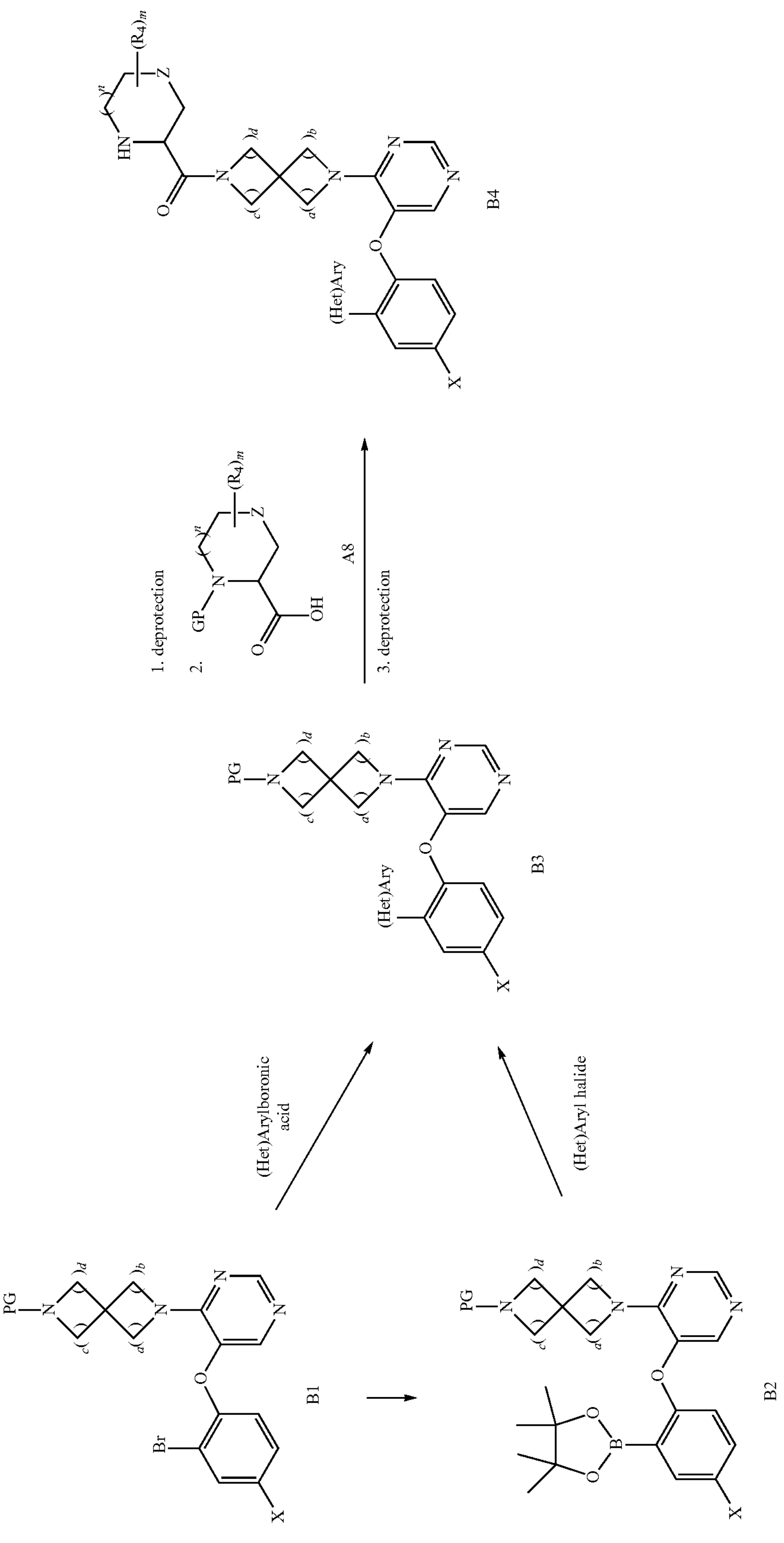

Example compounds with general structure as C6 may be synthesized according to Scheme 3. Selective nucleophilic substitution reaction between mono-protected spirodiamine A5 and 3,5,6-trichloro-1,2,4-triazine C1 afforded triazine C2. The second nucleophilic substitution with phenol C3 gave monochloride C4. Removal of the chlorine atom under reductive conditions gave triazine C5. Again, subsequent deprotection, amidation with N-protected cyclic amino acid A8, and final N-deprotection afforded compound C6.

Scheme 3

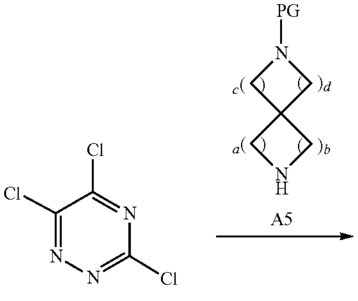

C1

A5

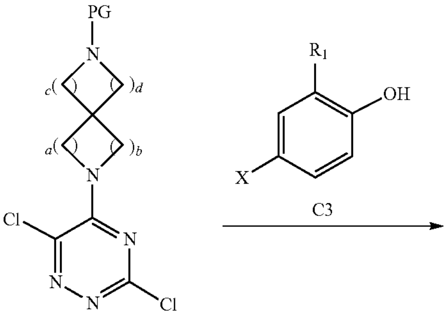

C2

C3

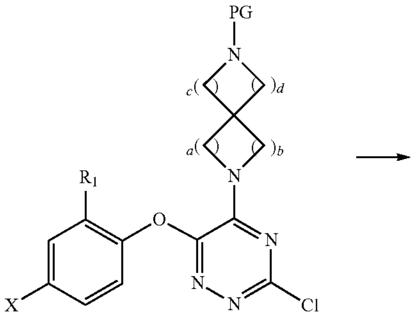

C4

-continued

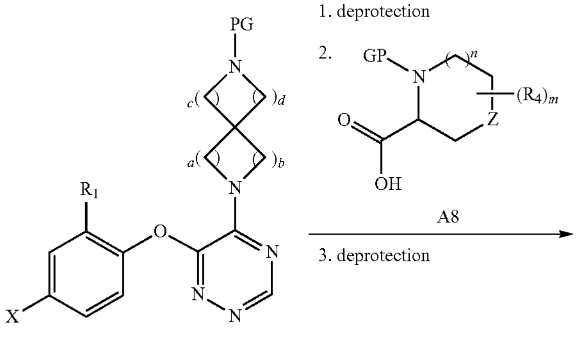

C5

A8

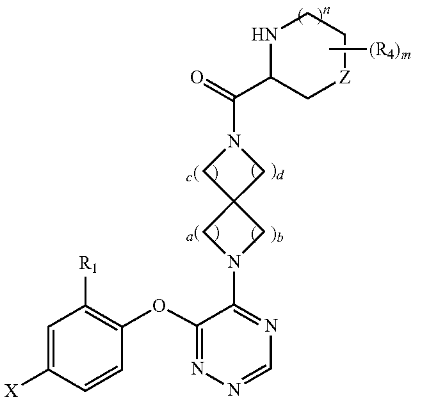

C6

Example compound with general structure as D1 in Scheme 4 could be prepared from chloride C4 in 3 steps, deprotection, amidation with N-protected cyclic amino acid A8, and N-deprotection. Chloride C4 could also react with a nucleophile under basic conditions or with a bromic reagent in the presence of palladium catalyst to give intermediate D2, which, after deprotection, amidation with N-protected cyclic amino acid A8, and N-deprotection, could afford example compound with general structure as D3 (Scheme 4).

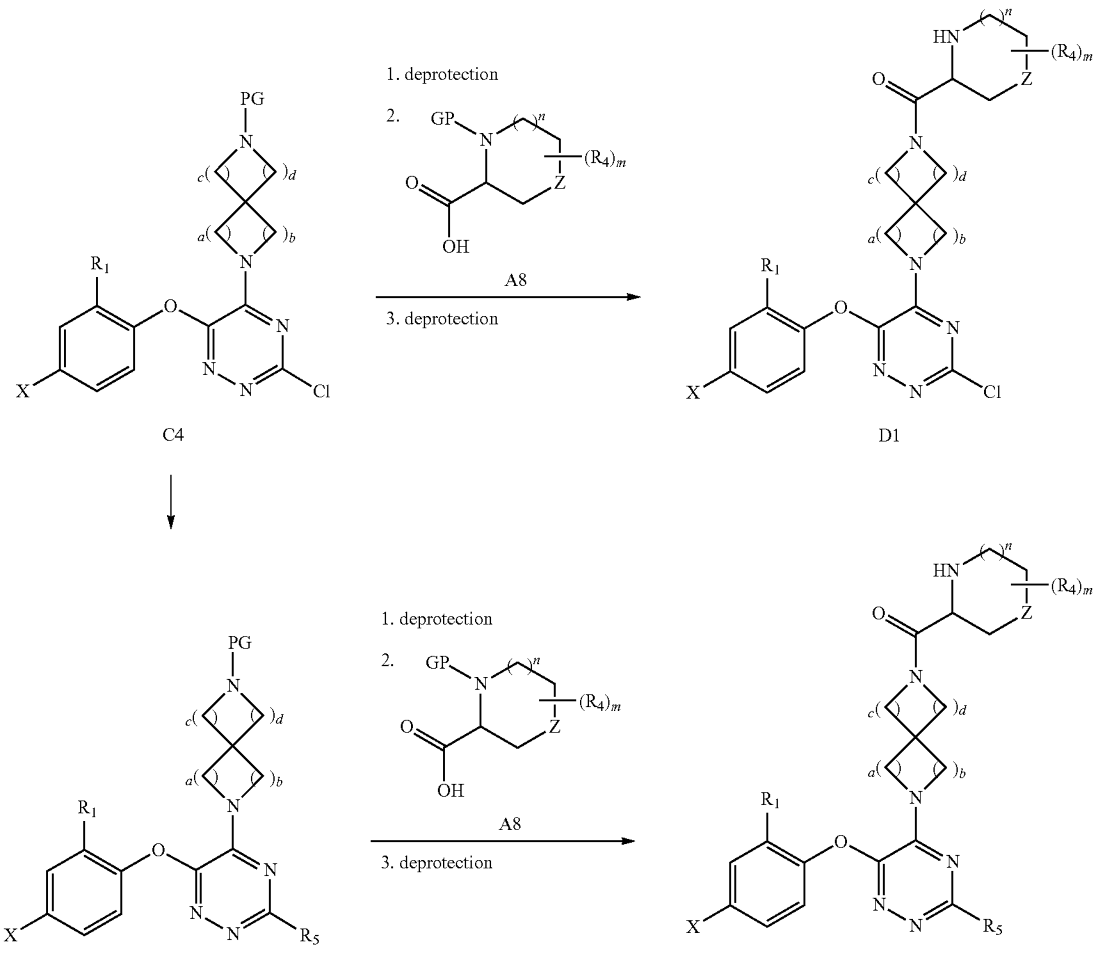

C4 D1 D2 D3

Each embodiment described in the present disclosure and the features in each embodiment should be understood as being capable of combining with each other in any manner, and those technical solutions obtained by such combination (s) are all included in the scope of the present disclosure the same as if each and every technical solution obtained by such combination(s) were specifically and individually listed, unless the context clearly shows otherwise.

All patents, patent applications, publications, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant material or prior art. The right to challenge the accuracy and pertinence of any assertion of such patents, patent applications, publications, and other references as relevant material or prior art is specifically reserved.

EXAMPLES

The examples below are intended to illustrate the invention only, and should not be contorted to be limiting in any way.

Unless indicated otherwise, temperature is in degrees Centigrade, and pressure is at or near atmospheric. All MS (mass spectrometry) data were measured by Agilent 6120B and/or Shimadzu LCMS2010. H-NMR spectra were recorded on a nuclear magic resonance spectrometer operating at Bruker AVANCE NEO 400 MHZ. When peak multiplicities are reported, the following abbreviations are used: s (singlet), d (doublet), t (triplet), m (multiplet), q (quarter), br (broadened), dd (doublet of doublets), dt (doublet of triplets). Coupling constants, when given, are reported in Herz (Hz).

All reagents and starting materials, except intermediates as prepared below, used in this invention are commercially available or prepared according to the prior art.

All compound names except the reagents were generated by Chemdraw. If there's any inconsistency between the structure and the name of a compound given in this invention, the structure prevails, unless the context shows that the structure is incorrect and the name is right.

If there's any empty valence in any atom disclosed herein, the empty valence is the hydrogen atom which is omitted for convenience.

Isomers, if isolated from the same chromatagraphy separation condition in the following Examples, are named in the same sequence as they are eluted, unless specified otherwise.

In the following examples, the abbreviations below are used:

List of Abbreviation

| Abbreviation | Full Name |
|---|---|
| AcOH | acetic acid |
| $BBr_3$ | boron tribromide |
| $CDCl_3$ | deuterated chloroform |
| $Cs_2CO_3$ | cesium carbonate |
| DAST | diethylaminosulfur trifluoride |
| DCM | dichloromethane |
| DIAD | diisopropyl azodicarboxylate |
| DIPEA | N,N-diisopropylethylamine |
| DMF | N,N-dimethylformamide |
| DMSO | dimethyl sulfoxide |
| DPPA | diphenyl phosphoryl azide |
| ESI | electrospray ionization |
| EtOAc | ethyl acetate |
| h | hour |
| HATU | O-(7-Azabenzotriazol-1-yl)-N,N,N',N'-tetramethyluronium hexafluorophosphate |
| HCl | hydrochloride |
| $K_2CO_3$ | potassium carbonate |
| KOAc | potassium acetate |
| LC/MS | liquid chromatography-mass spectrometer |
| LAH | lithium aluminium hydride |
| LDA | lithium diisopropylamide |
| mCPBA | meta-chloroperbenzoic acid |
| MeCN | acetonitrile |
| MeOD | deuterated methanol |
| mL | milliliter |
| mmol | millimole |
| MOMCl | chlormethyl methyl ether |
| $Na_2SO_4$ | sodium sulfate |
| $NaBH_4$ | sodium borohydride |
| NaH | sodium hydride |
| $NaHCO_3$ | sodium bicarbonate |
| NaOH | sodium hydroxide |
| n-BuLi | n-butyllithium |
| NCS | N-chlorosuccinimide |
| NMR | nuclear magnetic resonance |
| Pct | percentage |
| $Pd(AcO)_2$ | Palladium(II) acetate |
| $Pd(dppf)Cl_2$ | 1,1'-Bis(diphenylphosphino)ferrocene palladium(II)dichloride |
| $Pd(PPh_3)_4$ | tetrakis(triphenylphosphine)palladium |
| PE | petroleum ether |
| pH | potential of hydrogen |
| PMBCl | 4-methoxybenzylchloride |
| $PPh_3$ | triphenylphosphine |
| prep-HPLC | Preparation high performance liquid chromatography |
| prep-TLC | preparation thin layer chromatography |
| $POCl_3$ | Phosphoryl trichloride |
| p-TSA | p-toluenesulfonic acid |
| rt | room temperature |
| sat. | saturated |
| SFC | supercritical fluid chromatography |
| TBDPSCl | tert-butyl(chloro)diphenylsilane |
| TEA | triethylamine |
| TFA | trifluoroacetic acid |
| THF | tetrahydrofuran |
| TMEDA | N,N,N',N'-tetramethylethylenediamine |
| Xant-phos | 4,5-bis(diphenylphosphino)-9,9-dimethylxanthene |
| $Zn(CN)_2$ | zinc cyanide |

Preparation of Key Intermediate

Preparation of Intermediate 1, 2-((4-(2,7-diazaspiro[3.5]nonan-2-yl)pyrimidin-5-yl)oxy)-N-ethyl-5-fluoro-N-isopropylbenzamide

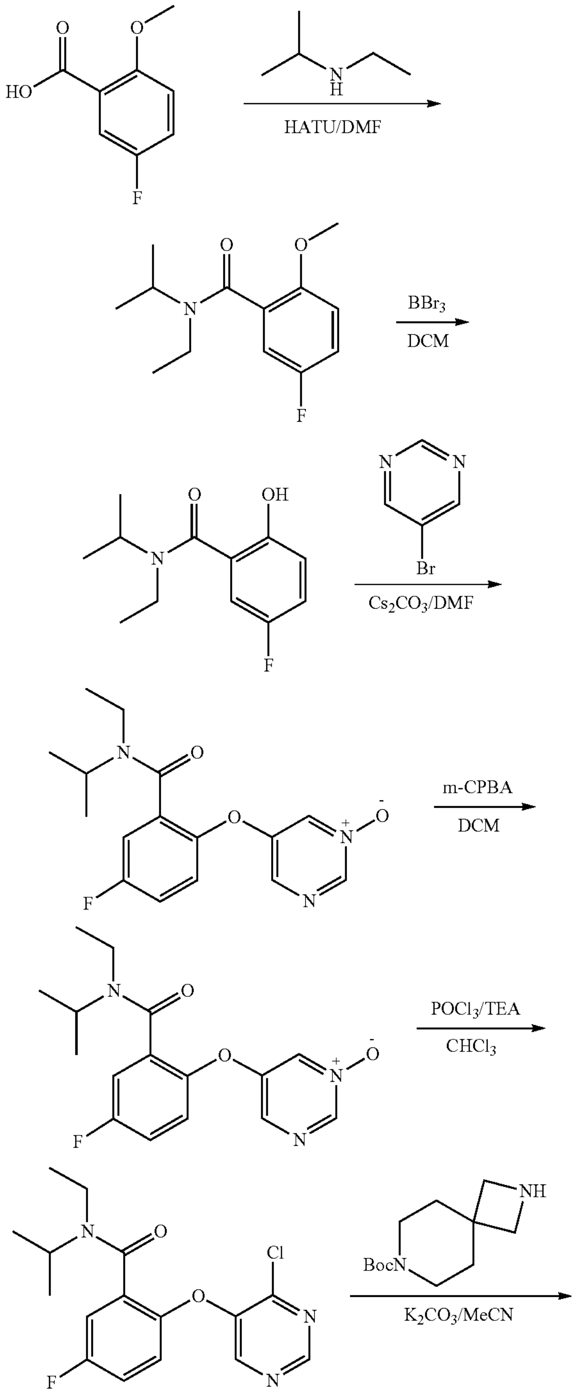

-continued

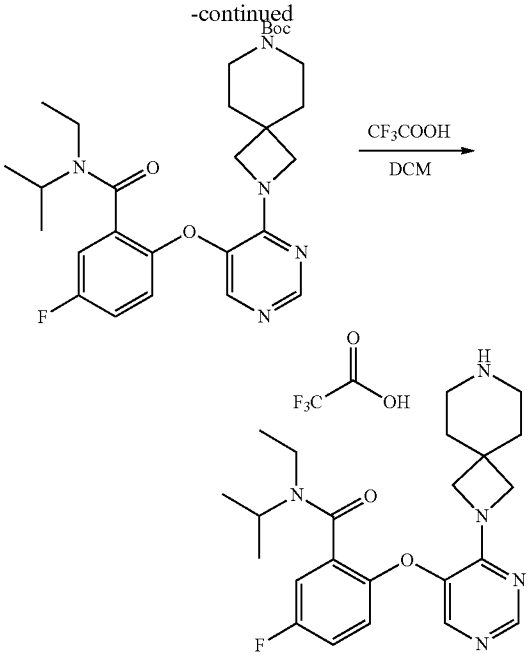

Step 1

To a solution of 5-fluoro-2-methoxybenzoic acid (7.50 g, 44.1 mmol) and HATU (16.7 g, 44.0 mmol) in DMF (50 mL) was added ethyl(propan-2-yl)amine (15.4 g, 176 mmol) dropwise at 0° C. The reaction mixture was warmed to room temperature gradually and stirred overnight. The reaction mixture was quenched with sat. $NH_4Cl$ solution (50 mL), extracted with EtOAc (100 mL×3), the combined organic phase was washed by water and brine, dried over anhydrous $Na_2SO_4$, filtered and concentrated, the residue was purified by column chromatography on silica gel (EtOAc in PE=0~30%) to give the desired product N-ethyl-5-fluoro-2-methoxy-N-(propan-2-yl)benzamide (10.0 g, yield: 94.8%) as a light yellow solid. LC/MS (ESI) m/z: 240 $(M+H)^+$.

Step 2

To a solution of N-ethyl-5-fluoro-2-methoxy-N-(propan-2-yl)benzamide (9.01 g, 37.6 mmol) in DCM (50 mL) was added $BBr_3$ (37.6 mL, 1.0 M in DCM) dropwise at −60° C. under $N_2$ atmosphere, the resulting mixture was stirred for 2 h at this temperature. Then the reaction mixture was quenched with cooled sat. $NaHCO_3$ at 0° C., the mixture was extracted with DCM (100 mL×3), the combined organic layer was washed with water and brine, dried over anhydrous $Na_2SO_4$, filtered and concentrated to give the desired product N-ethyl-5-fluoro-2-hydroxy-N-(propan-2-yl)benzamide (4.01 g, yield: 47.2%) as a light yellow solid, which can be used in next step without further purification. LC/MS (ESI) m/z: 226 $(M+H)^+$.

Step 3

To a mixture of N-ethyl-5-fluoro-2-hydroxy-N-(propan-2-yl)benzamide (4.01 g, 17.7 mmol) in DMF (20 mL) was added 5-bromopyrimidine (3.40 g, 21.3 mmol) and $Cs_2CO_3$ (11.6 g, 35.5 mmol). The reaction mixture was heated to 120° C. for 12 h. After cooled to room temperature, the mixture was quenched with sat. $NH_4Cl$ solution (50 mL), extracted with EtOAc (100 mL×3), the combined organic layer was washed with water and brine, dried over anhydrous $Na_2SO_4$, filtered and concentrated to give the crude product which was purified by column chromatography on silica gel (EtOAc in PE=0~20%) to give the desired product N-ethyl-5-fluoro-N-(propan-2-yl)-2-(pyrimidin-5-yloxy) benzamide (1.99 g, yield: 37.1%) as a yellow oil. LC/MS (ESI) m/z: 304 $(M+H)^+$.

Step 4

To a solution of N-ethyl-5-fluoro-N-(propan-2-yl)-2-(pyrimidin-5-yloxy)benzamide (1.99 g, 6.60 mmol) in DCM (20 mL) was added m-CPBA (3.41 g, 19.8 mmol) portionwise at 0° C., then the resulting mixture was stirred for 10 h at rt. The reaction mixture was quenched with sat. $NaHCO_3$, extracted with DCM (50 mL×3), and the combined organic layer was washed with water and brine, dried over anhydrous $Na_2SO_4$, filtered and concentrated to give the crude product which was purified by column chromatography on silica gel (EtOAc in PE=0~80%) to give the desired product 5-{2-[ethyl(propan-2-yl)carbamoyl]-4-fluorophenoxy}pyrimidin-1-ium-1-olate (0.901 g, yield: 42.8%) as a off-white solid. LC/MS (ESI) m/z: 320 $(M+H)^+$.

Step 5

To a solution of 5-{2-[ethyl(propan-2-yl)carbamoyl]-4-fluorophenoxy}pyrimidin-1-ium-1-olate (0.90 g, 2.8 mmol) and TEA (0.8 mL, 5.6 mmol) in $CHCl_3$ (10 mL) was added $POCl_3$ (0.80 mL, 8.4 mmol) dropwise at 0° C. Then the reaction mixture was stirred at rt for 12 h. The reaction mixture was quenched with sat. $NaHCO_3$, and extracted with DCM (100 mL×3). The combined organic layer was washed with water and brine, dried over anhydrous $Na_2SO_4$, filtered and concentrated in vacuo to give the crude product 2-[(4-chloropyrimidin-5-yl)oxy]-N-ethyl-5-fluoro-N-(propan-2-yl)benzamide (320 mg, yield: 33.6%) as a brown oil which can be used in next step without further purification. LC/MS (ESI) m/z: 338/340 $(M+H)^+$.

Step 6

To a solution of 2-[(4-chloropyrimidin-5-yl)oxy]-N-ethyl-5-fluoro-N-(propan-2-yl)benzamide (300 mg, 0.9 mmol) in MeCN (10 mL) was added tert-butyl 2,7-diazaspiro[3.5]nonane-7-carboxylate (221 mg, 1.00 mmol) and $K_2CO_3$ (246 mg, 1.80 mmol). The resulting mixture was heated to 80° C. for 5 h. After cooled to room temperature, the reaction mixture was quenched with sat. $NH_4Cl$ solution (10 mL), extracted with EtOAc (20 mL×3), the combined organic layer was washed with water and brine, dried over anhydrous $Na_2SO_4$, filtered and concentrated to give the crude product which was purified by column chromatography on silica gel (EtOAc in PE=0~50%) to give the desired product tert-butyl 2-(5-{2-[ethyl(propan-2-yl)carbamoyl]-4-fluorophenoxy}pyrimidin-4-yl)-2,7-diazaspiro[3.5]nonane-7-carboxylate (390 mg, yield: 83.2%) as a yellow solid. LC/MS (ESI) m/z: 528 $(M+H)^+$.

Step 7

To a solution of tert-butyl 2-(5-{2-[ethyl(propan-2-yl)carbamoyl]-4-fluorophenoxy}pyrimidin-4-yl)-2,7-diazaspiro[3.5]nonane-7-carboxylate (200 mg, 0.4 mmol) in DCM (5 mL) was added TFA (2.0 mL) dropwise at room temperature, the resulting mixture was stirred for 2 h at rt. The reaction mixture was concentrated to give the crude product 2-2-[(4-{2,7-diazaspiro[3.5]nonan-2-yl}pyrimidin-5-yl)oxy]-N-ethyl-5-fluoro-N-(propan-2-yl)benzamide (150 mg, yield: 92.5%) as a TFA salt which can be used in next step without further purification. LC/MS (ESI) m/z: 428 $(M+H)^+$.

The following intermediates were prepared from the corresponding chemicals according to experimental procedure for Intermediate 1 (the major different chemicals used are listed in the column of starting material):

| Intermediate | Structure | Starting material | LCMS (ESI) m/z |
|---|---|---|---|
| Intermediate 2 | 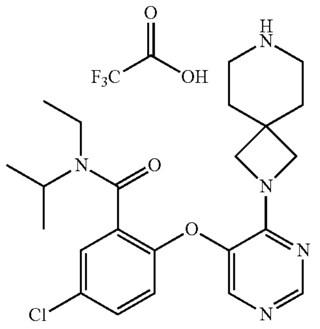 | 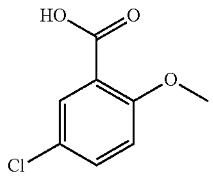 | 444 $(M + H)^+$ |
| Intermediate 3 | 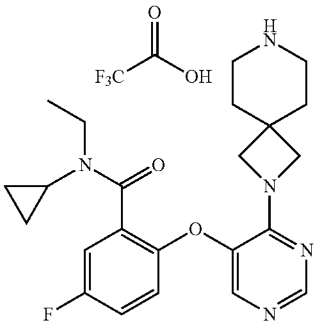 | 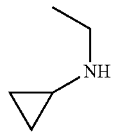 | 426 (M + H)+ |
| Intermediate 4 | 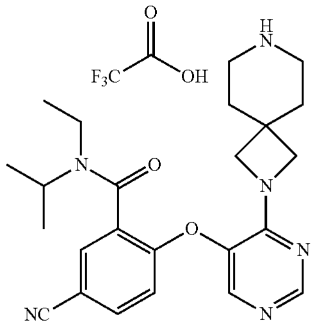 | 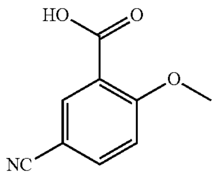 | 435 $(M + H)^+$ |
| Intermediate 5 | 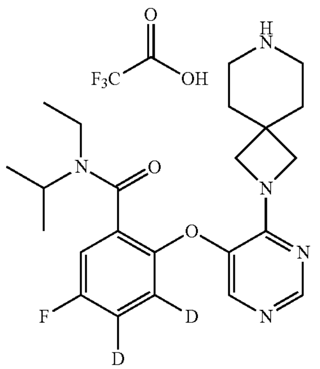 | Intermediate 41 | 430 $(M + H)^+$ |

-continued
| Intermediate | Structure | Starting material | LCMS (ESI) m/z |
|---|---|---|---|
| Intermediate 6 | 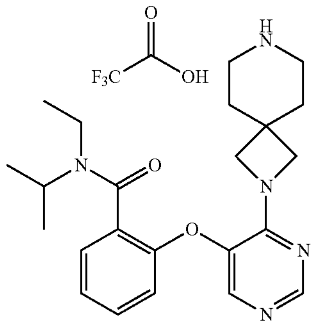 | 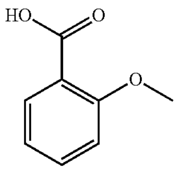 | 410 (M + H)+ |
| Intermediate 7 | 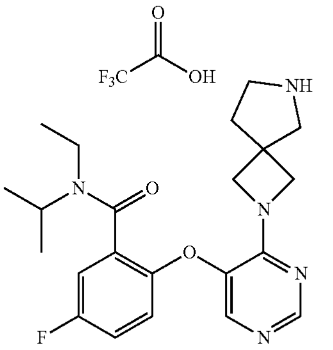 | 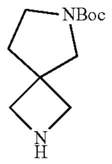 | 414 (M + H)+ |
| Intermediate 8 | 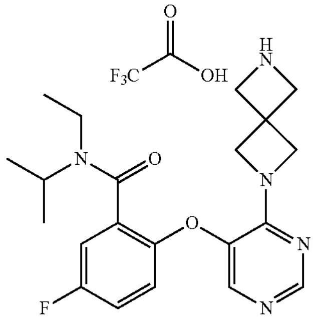 | 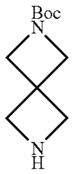 | 400 (M + H)+ |
| Intermediate 9 | 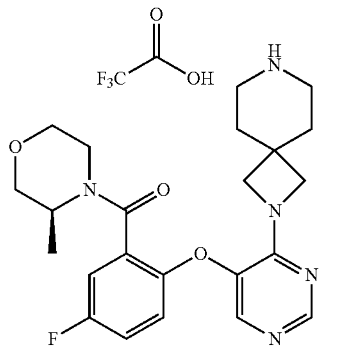 | 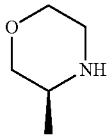 | 442 (M + H)+ |

-continued
| Intermediate | Structure | Starting material | LCMS (ESI) m/z |
|---|---|---|---|
| Intermediate 10 | 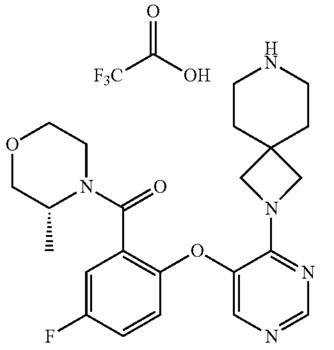 | 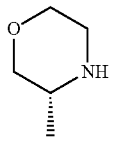 | 442 (M + H)+ |
| Intermediate 11 | 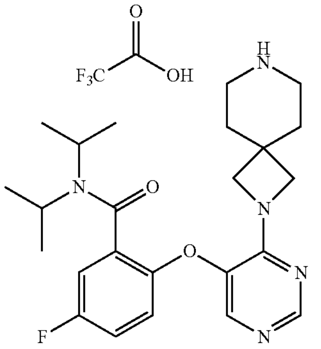 | 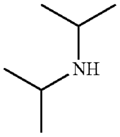 | 442 (M + H)+ |
| Intermediate 12 | TFA 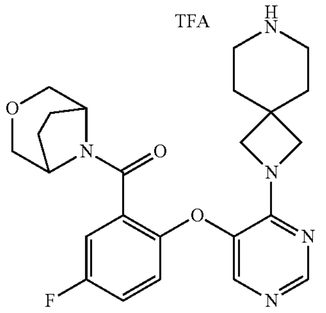 [SMILES: O=C(c1cc(F)ccc1Oc1cncnc1N1CC2(CCNCC2)C1)N1C2CCC1COC2] | 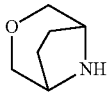 | 454 (M + H)+ |
| Intermediate 13 | TFA 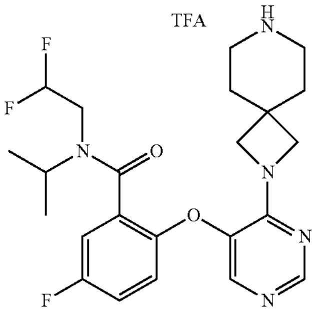 | Intermediate 22 | 240 (M + H)+ |

Preparation of Intermediate 14, 5-fluoro-2-hydroxy-N, N-diisopropylbenzamide

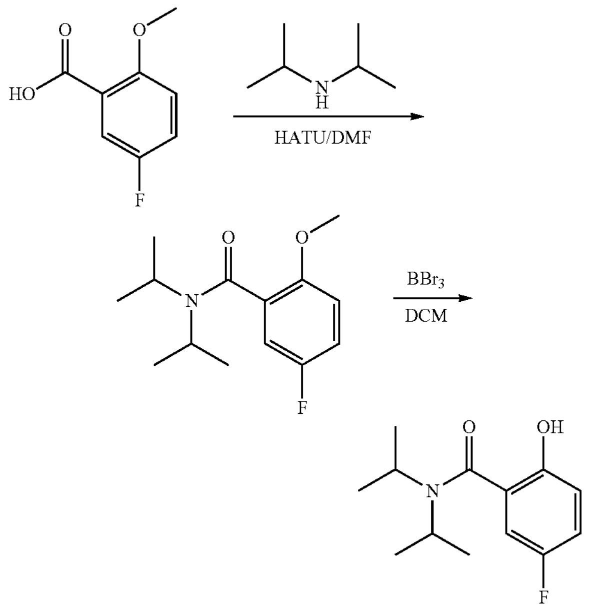

Step 1

To a solution of 5-fluoro-2-methoxybenzoic acid (1.00 g, 5.88 mmol) and HATU (2.28 g, 6.00 mmol) in DMF (10 mL) was added diisopropylamine (712 mg, 7.06 mmol) dropwise at 0° C. The reaction mixture was warmed to room temperature gradually and stirred overnight. The reaction mixture was quenched with sat. $NH_4Cl$ solution (10 mL), and extracted with EtOAc (30 mL×3). The combined organic phase was washed with water and brine, dried over anhydrous $Na_2SO_4$, filtered and concentrated, the residue was purified by column chromatography on silica gel (EtOAc in PE=0~30%) to give the desired product 5-fluoro-N, N-diisopropyl-2-methoxybenzamide (320 mg, yield: 21.5%) as a light yellow solid. LC/MS (ESI) m/z: 254 $(M+H)^+$.

Step 2

To a solution of 5-fluoro-N,N-diisopropyl-2-methoxybenzamide (320 mg, 1.26 mmol) in DCM (10 mL) was added $BBr_3$ (3 mL, 1.0 M in DCM) dropwise at −60° C. under $N_2$ atmosphere, the resulting mixture was stirred for 2 h at this temperature. Then the reaction mixture was quenched with cooled MeOH at 0° C., the mixture was extracted with DCM (15 mL×3), the combined organic layer was washed with water and brine, dried over anhydrous $Na_2SO_4$, filtered and concentrated to give the crude product which was purified by column chromatography on silica gel (EtOAc in PE=0) ~20%) to afford the desired product N-ethyl-5-fluoro-2-hydroxy-N-(propan-2-yl)benzamide (260 mg, yield: 86.3%) as a white solid, LC/MS (ESI) m/z: 240 $(M+H)^+$.

Preparation of Intermediate 15, (2S)-4-hydroxy-4-methylpyrrolidine-2-carboxylic acid

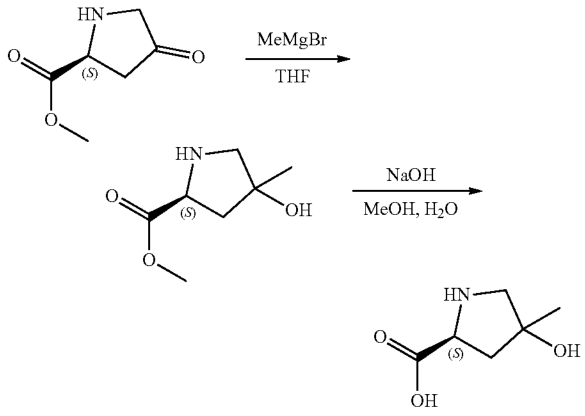

Step 1

To a solution of 1-tert-butyl 2-methyl (2S)-4-oxopyrrolidine-1,2-dicarboxylate (200 mg, 0.82 mmol) in THF (5 mL) was added MeMgBr (1.2 mL, 1.23 mmol) dropwise at 0° C. under $N_2$. The resulting mixture was stirred for 2 h at rt. The reaction mixture was quenched with sat. $NH_4Cl$ solution (5 mL), extracted with EtOAc (20 mL×3), the combined organic layer was dried over anhydrous $Na_2SO_4$, filtered and concentrated, the residue was purified by column chromatography on silica gel (EtOAc in PE=0~30%) to give the desired product 1-tert-butyl 2-methyl (2S)-4-hydroxy-4-methylpyrrolidine-1,2-dicarboxylate (180 mg, yield:80.2%) as a light yellow oil. LC/MS (ESI) m/z: 260 $(M+H)^+$.

Step 2

To a solution of 1-tert-butyl 2-methyl (2S)-4-hydroxy-4-methylpyrrolidine-1,2-dicarboxylate (180 mg, 0.69 mmol) in MeOH (3 mL) and $H_2O$ (1 mL) was added NaOH (83 mg, 2.1 mmol) at 0° C. The resulting mixture was stirred at rt for 2 h. The reaction mixture was adjusted the pH to 4-5 with 1.0 N HCl solution, diluted with $H_2O$ (10 mL), extracted with DCM (20 mL×3), the combined organic layer was dried over anhydrous $Na_2SO_4$, filtered and concentrated to give the desired product (2S)-1-[(tert-butoxy)carbonyl]-4-hydroxy-4-methylpyrrolidine-2-carboxylic acid (150 mg, yield: 83.6%) as a off-white solid which can be used in next step directly without further purification. LC/MS (ESI) m/z: 190 $(M-55)^+$.

Preparation of Intermediate 16, (2S,4R)-1-(tert-butoxycarbonyl)-4-(methylsulfonyl)pyrrolidine-2-carboxylic acid

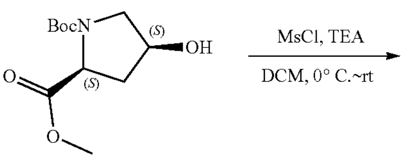

-continued

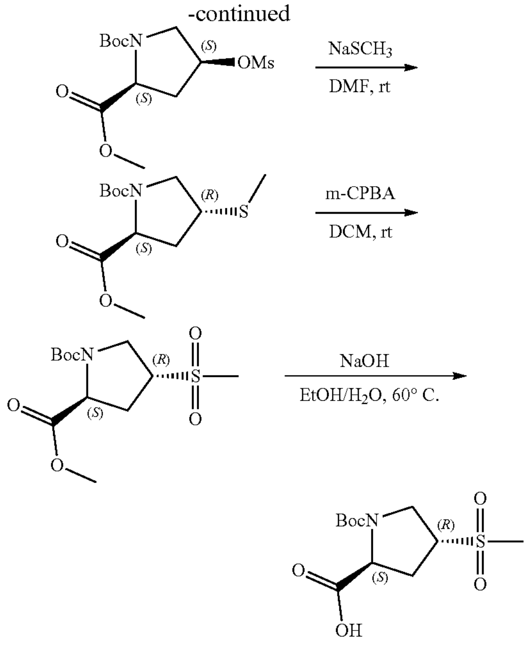

Step 1

To a solution of 1-tert-butyl 2-methyl (2S,4S)-4-hydroxypyrrolidine-1,2-dicarboxylate (1.0 g, 4.0 mmol), TEA (0.83 g, 8.2 mmol) in DCM (15 mL) was added MsCl (0.50 g, 4.5 mmol) at 0° C. under $N_2$, the resulting mixture was stirred at room temperature for 1 h. The mixture was diluted with water (30 mL), extracted with EtOAc (25 mL×3). The combined organic phase was washed with brine (25 mL), and concentrated to give the crude product 1-tert-butyl 2-methyl (2S,4S)-4-(methanesulfonyloxy)pyrrolidine-1,2-dicarboxylate (1.1 g, yield: 83.4%) as a light yellow oil which was used in next step without further purification. LC/MS(ESI)m/z: 224 $(M-100+H)^+$.

Step 2

To a solution of 1-tert-butyl 2-methyl (2S,4S)-4-(methanesulfonyloxy)pyrrolidine-1,2-dicarboxylate (1.1 g, 3.4 mmol) in DMF (15 mL) was added NaSMe (230 mg, 4.0 mmol), the resulting mixture was stirred at room temperature for 10 h. The reaction mixture was diluted with water (30 mL) and extracted with EtOAc (25 mL×3). The combined organic phase was washed with brine, dried over anhydrous $Na_2SO_4$, filtered and concentrated, the residue was purified by column chromatography on silica gel (EtOAc in PE=10~25%) to afford the desired product (2S,4R)-1-tert-butyl 2-methyl 4-(methylthio)pyrrolidine-1,2-dicarboxylate (850 mg, yield: 90.7%) as a solid, 1H NMR (400 MHZ, $CDCl_3$) δ 4.29 (dd, J=23.9, 16.0 Hz, 1H), 3.97 (dd, J=10.5, 7.0 Hz, 1H), 3.74 (s, 3H), 3.42-3.12 (m, 2H), 2.60 (dd, J=13.0, 6.4 Hz, 1H), 2.12 (s, 3H), 1.99-1.88 (m, 1H), 1.47-1.40 (m, 9H).

Step 3

To a solution of (2S,4R)-1-tert-butyl 2-methyl 4-(methylthio)pyrrolidine-1,2-dicarboxylate (850 mg, 3.10 mmol) in DCM (20 mL) was added m-CPBA (1.1 g, 6.2 mmol) at 0° C., and the resulting mixture was stirred at room temperature overnight. The reaction mixture was diluted with DCM (50 mL), washed with brine, dried over anhydrous $Na_2SO_4$, filtered and concentrated, the residue was purified by column chromatography on silica gel (EtOAc in PE=5~25%) to afford the desired product (2S,4R)-1-tert-butyl 2-methyl 4-(methylsulfonyl)pyrrolidine-1,2-dicarboxylate (500 mg, yield: 52.7%) as light yellow solid, LC/MS(ESI)m/z: 330 (M+Na).

Step 4

To a solution of (2S,4R)-1-tert-butyl 2-methyl 4-(methylsulfonyl)pyrrolidine-1,2-dicarboxylate (500 mg, 1.6 mmol) in EtOH (5 mL) was added NaOH aq. solution (2.0 mL, 2.0 N), and the resulting mixture was stirred at rt for 30 min. The reaction mixture was concentrated, and adjusted the pH to 2~3 with 1.0 N HICl solution, extracted with EtOAc (30 mL×3). The combined organic layer was washed with water and brine, dried over anhydrous $Na_2SO_4$, filtered and concentrated to give the crude product (2S,4R)-1-(tert-butoxycarbonyl)-4-(methylsulfonyl)pyrrolidine-2-carboxylic acid (400 mg, yield: 83.8%) as light yellow oil which was used in next step without further purification, LC/MS (ESI)m/z: 316 (M+Na).

Preparation of Intermediate 17, (4S,5S,7R)-6-(tert-butoxycarbonyl)-1-methyl-4,5,6,7-tetrahydro-1H-4,7-methanopyrazolo[3,4-c]pyridine-5-carboxylic acid

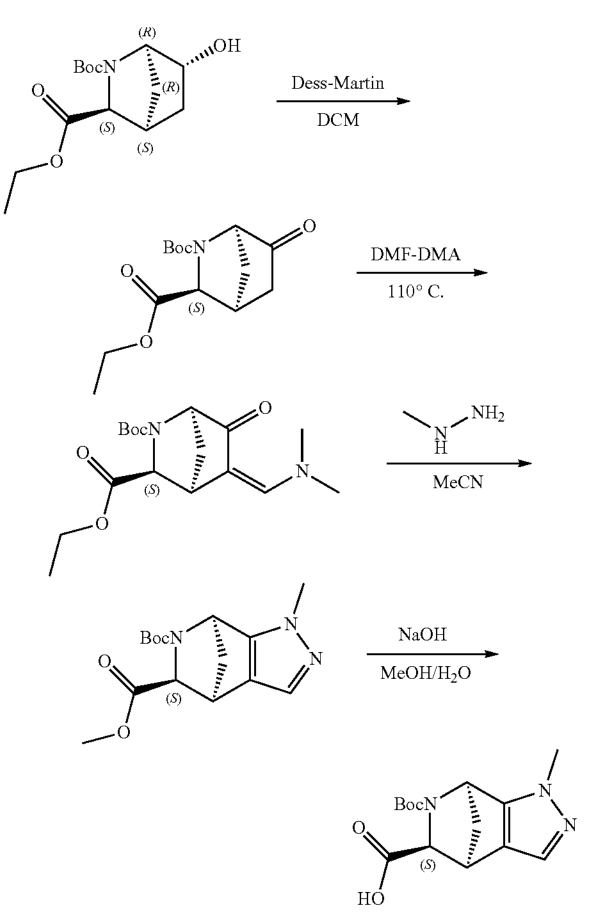

Step 1

To a solution of 2-tert-butyl 3-ethyl (1R,3S,4S,6R)-6-hydroxy-2-azabicyclo[2.2.1]heptane-2,3-dicarboxylate (1.1 g, 3.8 mmol) in DCM (30 mL) was added Dess-Martin reagent (3.3 g, 7.7 mmol) at 0° C., the resulting mixture was stirred at room temperature overnight. The reaction mixture was diluted with water (20 mL) and extracted with DCM (20 mL×3). The combined organic phase was washed with water and brine, dried over anhydrous $Na_2SO_4$, filtered and concentrated, the residue was purified by column chromatography on silica gel (EtOAc in PE=5~20%) to give the desired product 2-tert-butyl 3-ethyl (1R,3S,4S)-6-oxo-2-azabicyclo[2.2.1]heptane-2,3-dicarboxylate (800 mg, yield: 73.2%) as an oil, LC/MS(ESI)m/z:184 $(M-100+H)^+$.

Step 2

To a solution of 2-tert-butyl 3-ethyl (1R,3S,4S)-6-oxo-2-azabicyclo[2.2.1]heptane-2,3-dicarboxylate (1.2 g, 4.2 mmol) in toluene (10 mL) was added DMF-DMA (5 mL), the reaction mixture was heated to 120° C. for 24 h. The mixture was cooled to rt and the solvent was concentrated, the residue was purified by column chromatography on silica gel (EtOAc in PE=50%~100%) to afford the desired product (1R,3S,4S)-2-tert-butyl 3-ethyl 5-((dimethylamino)methylene)-6-oxo-2-azabicyclo[2.2.1]heptane-2,3-dicarboxylatee (500 mg, yield: 35.7%) as a light yellow solid, LC/MS(ESI)m/z: 283 $(M-55+H)^+$.

Step 3

To a solution of (1R,3S,4S)-2-tert-butyl 3-ethyl 5-((dimethylamino)methylene)-6-oxo-2-azabicyclo[2.2.1]heptane-2,3-dicarboxylate (300 mg, 0.9 mmol) and methylhydrazine solution (0.2 mL, 1.6 mmol) in MeCN (10 mL) was added HOAc (0.1 mL), the resulting mixture was stirred at 80° C. overnight. The reaction mixture was concentrated, the residue was purified by column chromatography on silica gel (EtOAc in PE=10~30%) to give the desired product 9-tert-butyl 8-ethyl 6-(tert-butyl) 5-ethyl (4S,5S,7R)-1-methyl-1,4,5,7-tetrahydro-6H-4,7-methanopyrazolo[3,4-c]pyridine-5,6-dicarboxylate (150 mg, yield: 52%) as a white solid, LC/MS(ESI)m/z:322 (M+H)+.

Step 4

To a solution of 6-(tert-butyl) 5-ethyl (4S,5S,7R)-1-methyl-1,4,5,7-tetrahydro-6H-4,7-methanopyrazolo[3,4-c]pyridine-5,6-dicarboxylate (150 mg, 0.5 mmol) in MeOH (8 mL) were added NaOH solution (3.0 mL, 2.0 N), the reaction mixture was stirred at 60° C. for 1 h. The mixture was concentrated, and adjusted the pH to 2-3 with 1.0 N HCl, the mixture was extracted with EtOAc (20 mL×3), the combined organic phase was dried, concentrated to give the crude product (4S,5S,7R)-6-(tert-butoxycarbonyl)-1-methyl-4,5,6,7-tetrahydro-1H-4,7-methanopyrazolo[3,4-c]pyridine-5-carboxylic acid (80 mg, yield: 58.4%) as a yellow solid, LC/MS(ESI)m/z:294 $(M+H)^+$.

Preparation of Intermediate 18, (S)—N-ethyl-5-fluoro-N-isopropyl-2-((4-(7-(1-methyl-1,4,5,6-tetrahydropyrrolo[3,4-c]pyrazole-4-car bonyl)-2,7-diazaspiro[3.5]nonan-2-yl)pyrimidin-5-yl)oxy) benzamide

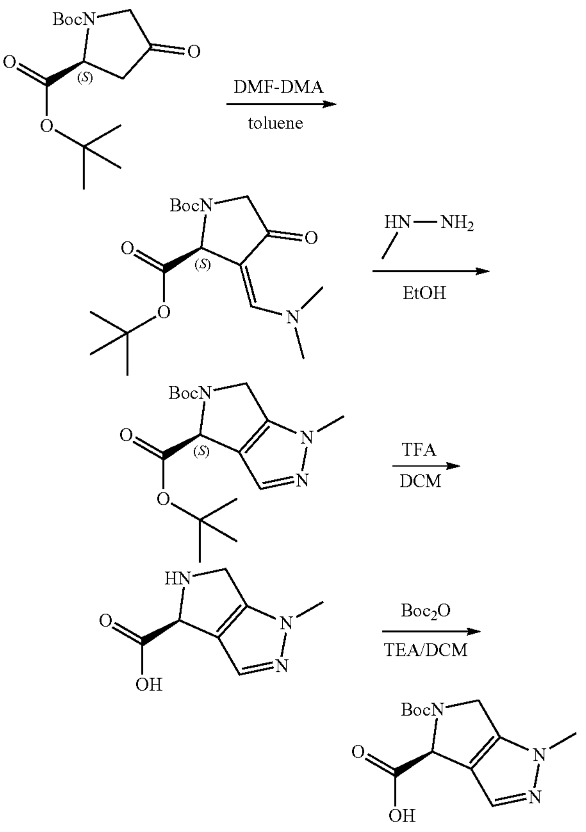

Step 1

To a solution of (S)-di-tert-butyl 4-oxopyrrolidine-1,2-dicarboxylate (2.0 g, 8.2 mmol) in toluene (20 mL) was added DMF-DMA (2.8 mL, 24.7 mmol). The resulting mixture was heated to 105° C. for 6 h. The reaction mixture was cooled to rt and concentrated, the residue was purified by column chromatography on silica gel (EtOAc in PE=0~50%) to give the desired product di-tert-butyl 3-((dimethylamino)methylene)-4-oxopyrrolidine-1,2-dicarboxylate (2.0 g, yield: 84%) as an oil. LC-MS:m/z 341 $(M+H)^+$.

Step 2

To a solution of di-tert-butyl 3-((dimethylamino)methylene)-4-oxopyrrolidine-1,2-dicarboxylate (1.3 g, 3.8 mmol) in EtOH (10 mL) was added methylhydrazine solution (0.8 mL, 5.7 mmol), the resulting mixture was heated to 85° C. for 12 h in a sealed tube. The reaction mixture was concentrated and the residue was purified by column chromatography on silica gel (EtOAc in PE=0~100%) to give the desired product (S)-di-tert-butyl 1-methyl-4,6-dihydropyrrolo[3,4-c]pyrazole-4,5(1H)-dicarboxylate (700 mg, yield: 57%) as a solid. LC-MS: m/z 324 $(M+H)^+$.

Step 3

To a solution of (S)-di-tert-butyl 1-methyl-4,6-dihydropyrrolo[3,4-c]pyrazole-4,5(1H)-dicarboxylate (300 mg, 0.93 mmol) in DCM (5 mL) at 0° C. was added TFA (2 mL) dropwise, and the resulting mixture was stirred at rt for 10 h. The reaction mixture was concentrated under reduced pressure to give the crude product (S)-1-methyl-1,4,5,6-tetrahydropyrrolo[3,4-c]pyrazole-4-carboxylic acid (240 mg, yield: 92%) as a light yellow oil which was used in next step without further purification. LC/MS (ESI) m/z: 168 $(M+H)^+$.

Step 4

To a solution of (S)-1-methyl-1,4,5,6-tetrahydropyrrolo[3,4-c]pyrazole-4-carboxylic acid (290 mg, 0.71 mmol) and TEA (0.09 mL, 0.71 mmol) in DCM (5 mL) was added $Boc_2O$ (170 mg, 0.71 mmol) dropwise at 0° C., the resulting mixture was stirred 2 h at rt. The reaction mixture was diluted with $H_2O$ (5 mL), extracted with DCM (10 mL×3), the combined organic phase was dried over anhydrous $Na_2SO_4$, filtered and concentrated to give the desired crude product (S)-5-(tert-butoxycarbonyl)-1-methyl-1,4,5,6-tetrahydropyrrolo[3,4-c]pyrazole-4-carboxylic acid (180 mg, yield: 94.6%) as a solid. LC/MS (ESI) m/z: 268 $(M+H)^+$.

The following intermediates were prepared from the corresponding chemicals according to experimental procedure for Intermediate 18 (the major different chemicals used are listed in the column of starting material):

-continued

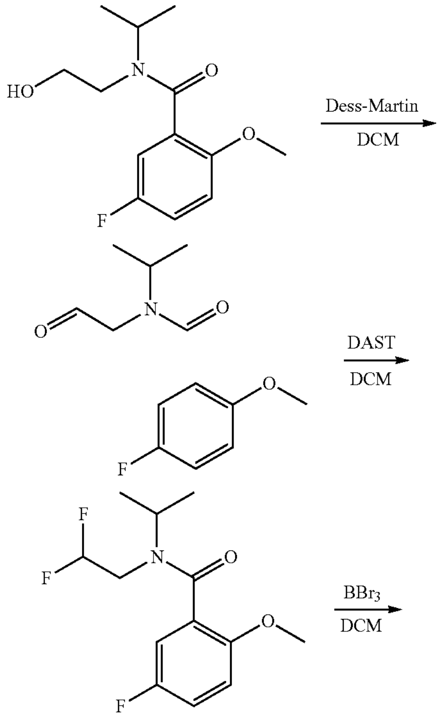

| Intermediates | Structure | Starting material | LCMS (ESI) m/z |
|---|---|---|---|
| Intermediate 19 | 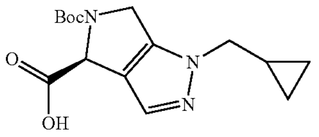 [SMILES: CC(C)(C)OC(=O)N1Cc2c(cnn2CC2CC2)[C@H]1C(=O)O] | 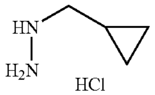 HCl | 308 $(M + H)^+$ |
| Intermediate 20 | 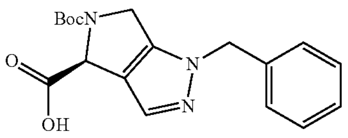 [SMILES: CC(C)(C)OC(=O)N1Cc2c(cnn2Cc2ccccc2)[C@H]1C(=O)O] | 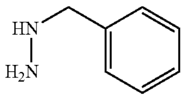 | 344 $(M + H)^+$ |
| Intermediate 21 | 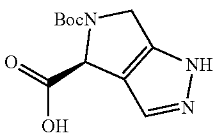 [SMILES: CC(C)(C)OC(=O)N1Cc2[nH]ncc2[C@H]1C(=O)O] | $H_2N—NH_2$ $H_2O$ | 254 $(M + H)^+$ |

Preparation of Intermediate 22, N-(2,2-difluoroethyl)-5-fluoro-2-hydroxy-N-isopropylbenzamide

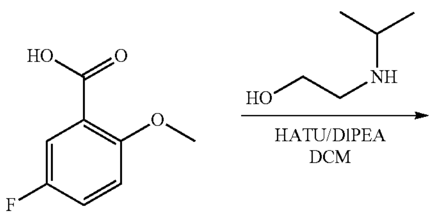

-continued

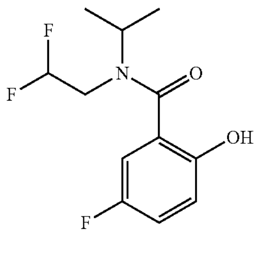

Step 1

To a stirred solution of 5-fluoro-2-methoxybenzoic acid (2.0 g, 11.7 mmol) and 2-[(propan-2-yl)amino]ethan-1-ol (1.5 mL, 13.6 mmol) in DCM (40 mL) at 0° C. were added DIPEA (2.56 mL, 15.5 mmol) and HATU (5.0 g, 13.1 mmol), then the resulting mixture was warmed to room temperature and stirred overnight. The reaction mixture was quenched with sat. $NH_4Cl$ solution, extracted with EtOAc (50 mL×3), the combined organic phase was dried over anhydrous $Na_2SO_4$, filtered and concentrated, the residue was purified by column chromatography on silica gel (EtOAc in PE=5~50%) to give the desired product 5-fluoro-N-(2-hydroxyethyl)-2-methoxy-N-(propan-2-yl)benzamide (2.5 g, yield: 83.3%) as a white solid. LC/MS (ESI) m/z: 256 $(M+H)^+$.

Step 2

To a solution of 5-fluoro-N-(2-hydroxyethyl)-2-methoxy-N-(propan-2-yl)benzamide (2.5 g, 9.79 mmol) in DCM (100 mL) at 0° C. was added Dess-Martin reagent (4.5 g, 10.6 mmol), the resulting mixture was stirred at 25° C. for 10 h. The reaction mixture was poured into ice-water (50 mL), extracted with EtOAc (50 mL×3), the combined organic phase was dried over anhydrous $Na_2SO_4$, filtered and concentrated, the residue was purified by column chromatography on silica gel (EtOAc in PE=5~30%) to give the desired product 5-fluoro-2-methoxy-N-(2-oxoethyl)-N-(propan-2-yl)benzamide (2.2 g, yield: 88.7%) as a white solid. LC/MS (ESI) m/z: 254 $(M+H)^+$.

Step 3

To a solution of 5-fluoro-2-methoxy-N-(2-oxoethyl)-N-(propan-2-yl)benzamide (2.2 g, 8.69 mmol) in DCM (50 mL) at −10° C. was added DAST (2.87 mL, 21.7 mmol) slowly, the reaction mixture was stirred at 25° C. for 5 h under $N_2$ atmosphere. The reaction mixture was poured into ice-water (50 mL), the mixture was extracted with EtOAc (50 mL×3), the combined organic phase was dried over anhydrous $Na_2SO_4$, filtered and concentrated, the residue was purified by column chromatography on silica gel (EtOAc in PE=1~30%) to give the desired product N-(2,2-difluoroethyl)-5-fluoro-2-methoxy-N-(propan-2-yl)benzamide (350 mg, yield: 14.6%) as an oil. LC/MS (ESI) m/z: 276 $(M+H)^+$.

Step 4

To a solution of N-(2,2-difluoroethyl)-5-fluoro-2-methoxy-N-(propan-2-yl)benzamide (350 mg, 1.27 mmol) in DCM (10 mL) at −60° C. was added $BBr_3$ (3.4 mL, 3.40 mmol) dropwise under $N_2$ atmosphere, the resulting mixture was stirred for 2 h at −60° C. The reaction mixture was quenched with ice sat. $NaHCO_3$ at 0° C., extracted with DCM (100 mL×3), the combined organic layer was washed with water and brine, dried over anhydrous $Na_2SO_4$, filtered and concentrated, the residue was purified by column chromatography on silica gel (EtOAc in PE=1~20%) to give the desired product N-(2,2-difluoroethyl)-5-fluoro-2-hydroxy-N-(propan-2-yl)benzamide (300 mg, yield: 90.3%) as a white solid. LC/MS (ESI) m/z: 262 $(M+H)^+$.

Preparation of Intermediate 22-1, 5-fluoro-2-hydroxy-N-(2-hydroxyethyl)-N-(propan-2-yl)benzamide

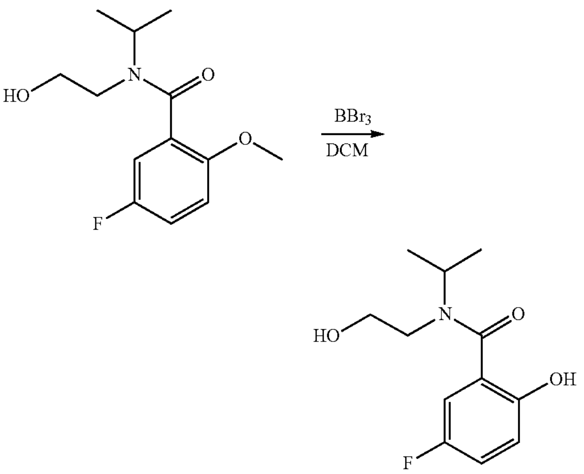

To a solution of 5-fluoro-N-(2-hydroxyethyl)-N-isopropyl-2-methoxybenzamide (510 mg, 2.00 mmol) in DCM (10 mL) was added $BBr_3$ (4 mL, 1.0 M in DCM) dropwise at −40° C. under $N_2$ atmosphere, the resulting mixture was stirred for 2 h at this temperature. Then the reaction mixture was quenched with cooled MeOH at −40° C. slowly, and then diluted with DCM (50 mL). The organic layer was separated, washed with sat. $NaHCO_3$ solution and brine, dried over anhydrous $Na_2SO_4$, filtered and concentrated to obtain the desired product 5-fluoro-2-hydroxy-N-(2-hydroxyethyl)-N-isopropylbenzamide (330 mg, yield: 68.5%) as a yellow solid, which can be used in next step without further purification. LC/MS (ESI) m/z: 242 $(M+H)^+$.

Preparation of Intermediate 23, (6S)-5-(tert-butoxycarbonyl)-1,1-difluoro-5-azaspiro[2.4]heptane-6-carboxylic acid

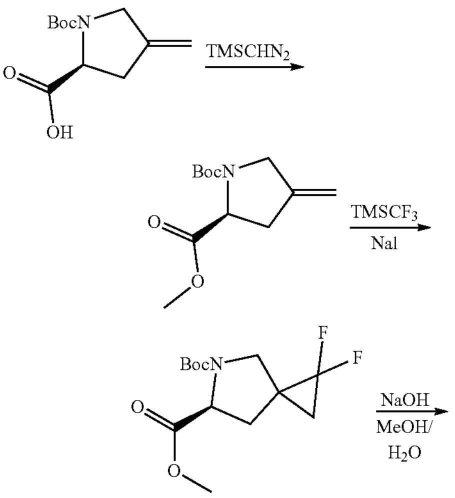

-continued

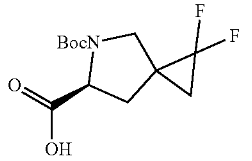

Step 1

To a solution of (2S)-1-[(tert-butoxy)carbonyl]-4-methylidenepyrrolidine-2-carboxylic acid (0.25 mL, 1.32 mmol) in DCM (5 mL) was added $TMSCHN_2$ (225.73 mg, 1.98 mmol) at room temperature, the resulting mixture was stirred for 2 h. The reaction mixture was quenched with AcOH (1.0 mL), then diluted with $H_2O$ (10 mL), extracted with DCM (10 mL×3), the combined organic layer was dried over anhydrous $Na_2SO_4$, filtered and concentrated to give the crude product (S)-1-tert-butyl 2-methyl 4-methylenepyrrolidine-1,2-dicarboxylate (300 mg, yield: 89.48%) as a colorless oil, which was used in next step without further purification. LC/MS (ESI) m/z: 242 $(M+H)^+$.

Step 2

To a stirred solution of (S)-1-tert-butyl 2-methyl 4-methylenepyrrolidine-1,2-dicarboxylate (400 mg) and NaI (82 mg, 0.54 mmol) in THF (10 mL) was added TMSCF3 (7.5 g, 53.05 mmol) at rt under $N_2$, the resulting mixture was stirred in sealed tube at 65° C. for 12 h. The mixture was diluted with $H_2O$ (10 mL), extracted with EtOAc (20 mL×3), the combined organic layer was washed with water and brine, dried over anhydrous $Na_2SO_4$, filtered and concentrated, the residue was purified by column chromatography on silica gel (EtOAc in PE=5~30%) to give the desired product (6S)-5-tert-butyl 6-methyl 1,1-difluoro-5-azaspiro[2.4]heptane-5,6-dicarboxylate (150 mg, yield: 29.5%) as a yellow oil; LCMS: ESI m/z 246 $(M+1)^+$.

Step 3

To a solution of (6S)-5-tert-butyl 6-methyl 1,1-difluoro-5-azaspiro[2.4]heptane-5,6-dicarboxylate (200 mg, 0.68 mmol) in MeOH (3 mL) and $H_2O$ (1 mL) was added NaOH (80 mg, 2 mmol) at 0° C., and the resulting mixture was stirred at rt for 30 min. The reaction mixture was concentrated, adjusted the pH to 2~3 with 1.0 N HCl, extracted with EtOAc (20 mL×3). The combined organic layer was washed with water and brine, dried over anhydrous $Na_2SO_4$, filtered and concentrated to give the crude product (6S)-5-[(tert-butoxy)carbonyl]-1,1-difluoro-5-azaspiro[2.4]heptane-6-carboxylic acid (150 mg, yield: 74.8%) as an off-white solid which can be used in next step directly without further purification. LC/MS (ESI) m/z: 222 (M−55).

Preparation of Intermediate 24, (3S,5R)-2-(tert-butoxycarbonyl)-5-(methoxymethyl)-2-azabicyclo[3.1.0]hexane-3-carboxylic acid

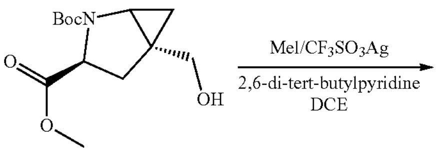

-continued

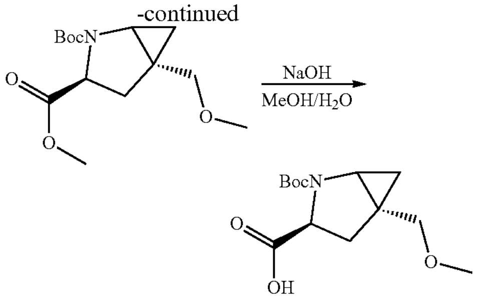

Step 1

To a solution of methyl (1S)-1-(hydroxymethyl)bicyclo[3.1.0]hexane-3-carboxylate (200 mg, 1.28 mmol) in DCE (5 mL) were added MeI (0.40 mL, 6.40 mmol), silver trifluoromethanesulfonate (1.60 g, 6.40 mmol) and 2,6-di-tert-butylpyridine (1.4 mL, 6.40 mmol). Then the reaction was stirred at 100° C. for 1 hour. The reaction mixture was cooled to rt, diluted with $H_2O$ (5 mL), extracted with EtOAc (10 mL×3). The combined organic phase was dried over anhydrous $Na_2SO_4$, filtered and concentrated to give the crude product (3S,5R)-2-tert-butyl 3-methyl 5-(methoxymethyl)-2-azabicyclo[3.1.0]hexane-2,3-dicarboxylate (150 mg, yield: 68%) as a yellow oil. LC/MS (ESI) m/z: 286 $(M+1)^+$.

Step 2

To a solution of (3S,5R)-2-tert-butyl 3-methyl 5-(methoxymethyl)-2-azabicyclo[3.1.0]hexane-2,3-dicarboxylate (200 mg, 1.17 mmol) in MeOH (3.0 mL) and $H_2O$ (1.0 mL) was added NaOH (200 mg, 5.00 mmol). Then the resulting mixture was stirred at 80° C. for 1 h. Then the pH of reaction mixture was adjusted to 5 with 1.0 N HCl, extracted with EtOAc (15 mL×3). The combined organic layer was washed with brine, dried over $Na_2SO_4$, filtered and concentrated to give the crude product (3S,5R)-2-(tert-butoxycarbonyl)-5-(methoxymethyl)-2-azabicyclo[3.1.0]hexane-3-carboxylic acid (150 mg, yield: 81%) as a white solid. LC/MS (ESI) m/z: 271 $(M+1)^+$.

Preparation of Intermediate 25, (2S,4S)-1-(tert-butoxycarbonyl)-4-(methylsulfonamido)pyrrolidine-2-carboxylic acid

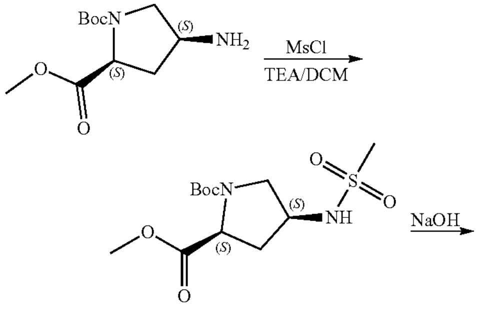

-continued

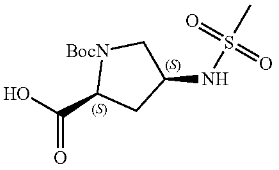

Step 1

To a solution of (2S,4S)-1-tert-butyl 2-methyl 4-amino-pyrrolidine-1,2-dicarboxylate (162 mg, 0.65 mmol) and TEA (0.20 mL, 1.3 mmol) in DCM (5 mL) was added MsCl (0.06 mL, 0.72 mmol) at 0° C., and the resulting mixture was stirred at 25° C. for 6 h. The reaction mixture was quenched with sat. $NH_4Cl$ solution (10 mL), extracted with DCM (10 mL×3), The combined organic phase was washed with water and brine, dried over with anhydrous $Na_2SO_4$, filtered and concentrated, the residue was purified by column chromatography on silica gel (EtOAc in PE=10~50%) to give the desired product (2S,4S)-1-tert-butyl 2-methyl 4-(methylsulfonamido)pyrrolidine-1,2-dicarboxylate (160 mg, yield: 75%) as colorless oil. LC/MS (ESI) m/z: 323 $(M+1)^+$.

Step 2

To a solution of (2S,4S)-1-tert-butyl 2-methyl 4-(methylsulfonamido)pyrrolidine-1,2-dicarboxylate (160 mg, 0.50 mmol) in MeOH (3.0 mL) and $H_2O$ (1.0 mL) was added NaOH (80 mg, 2.0 mmol), The resulting mixture was stirred at 20° C. for 1 h under $N_2$. Then the pH of reaction mixture was adjusted to 5 with 1.0 N HCl, extracted with EtAOc (15 mL×3). The combined organic layer was dried over $Na_2SO_4$, filtered and concentrated to give the crude product (2S,4S)-1-[(tert-butoxy)carbonyl]-4-methanesulfonamidopyrrolidine-2-carboxylic acid (130 mg, yield: 84%) as a solid. LC/MS (ESI) m/z: 309 $(M+1)^+$.

The following intermediate was prepared from the corresponding chemicals according to experimental procedure for Intermediate 25 (the major different chemicals used are listed in the column of starting material):

| Intermediate | Structure | Starting material | LCMS (ESI) m/z |
|---|---|---|---|
| Intermediate 26 | 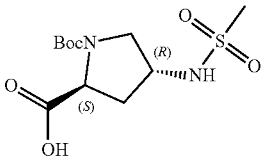 | 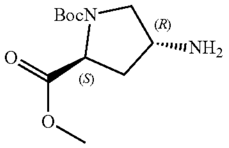 | 309 $(M + H)^+$ |

Preparation of Intermediate 27, (2S,5R)-1-(tert-butoxycarbonyl)-5-fluoropiperidine-2-carboxylic acid

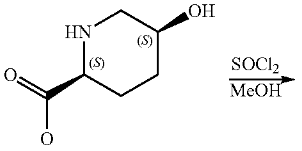

-continued

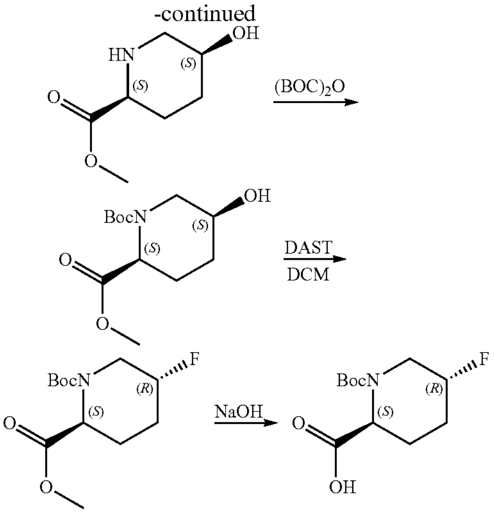

Step 1

To a solution of (2S,5S)-5-hydroxypiperidine-2-carboxylic acid (301 mg, 2.07 mmol) in MeOH (5.0 mL) was added $SOCl_2$ (0.30 mL, 4.1 mmol). The resulting mixture was stirred at 20° C. for 1 hour. The reaction mixture was concentrated to give the crude product (2S,5S)-methyl 5-hydroxypiperidine-2-carboxylate (300 mg, yield: 91%) as a light yellow oil. LC/MS (ESI) m/z: 160 $(M+1)^+$.

Step 2

To a solution of (2S,5S)-methyl 5-hydroxypiperidine-2-carboxylate (300 mg, 1.88 mmol) in acetone (5.0 mL) and $H_2O$ (1.0 mL) at 0° C. were added TEA (0.52 mL, 3.7 mmol) and $(Boc)_2O$ (0.45 g, 2.07 mmol). The resulting mixture was stirred at 20° C. for 3 h, the reaction mixture was quenched with sat. $NH_4Cl$ solution (10 mL), extracted with EtOAc (15 mL×3), the combined organic layer was washed with brine, dried over $Na_2SO_4$, filtered and concentrated to give the crude (2S,5S)-1-tert-butyl 2-methyl 5-hydroxypiperidine-1,2-dicarboxylate (400 mg, yield: 81%) as a light yellow solid which can be used in next step directly, LC/MS (ESI) m/z: 260 $(M+1)^+$.

Step 3

To a solution of (2S,5S)-1-tert-butyl 2-methyl 5-hydroxypiperidine-1,2-dicarboxylate (400 mg, 1.54 mmol) in DCM (10 mL) was added DAST (0.5 mL, 3.85 mmol) at −60° C. The resulting mixture was stirred at rt for 16 h under $N_2$. The reaction mixture was diluted with sat. $NaHCO_3$ solution (10 mL), extracted with DCM (15 mL×3), The combined organic phase was washed with brine, dried over $Na_2SO_4$, filtered and concentrated to give the crude (2S,5R)-1-tert-butyl 2-methyl 5-fluoropiperidine-1,2-dicarboxylate (270 mg, yield: 67.2%) as a yellow oil which can be used in next step without further purification, LC/MS (ESI) m/z: 262 $(M+H)^+$.

Step 4

To a solution of 1-tert-butyl 2-methyl (2S,5R)-5-fluoropiperidine-1,2-dicarboxylate (270 mg, 1.01 mmol) in MeOH (3.0 mL) and $H_2O$ (1.0 mL) was added NaOH (120 mg, 3.0 mmol), The resulting mixture was stirred at rt for 1 h. Then the pH of reaction mixture was adjusted to 5 with 1N HCl, extracted with EtAOc (15 mL×3). The combined organic layer was washed with brine, dried over $Na_2SO_4$, filtered and concentrated to give the crude product (2S,5R)-1-(tert-butoxycarbonyl)-5-fluoropiperidine-2-carboxylic acid (130 mg, yield: 48%) as a solid which can be used in next step without further purification, LC/MS (ESI) m/z: 247 $(M+H)^+$.

Preparation of Intermediate 28, (2S)-1-(tert-butoxycarbonyl)-4-(cyanomethyl)pyrrolidine-2-carboxylic acid

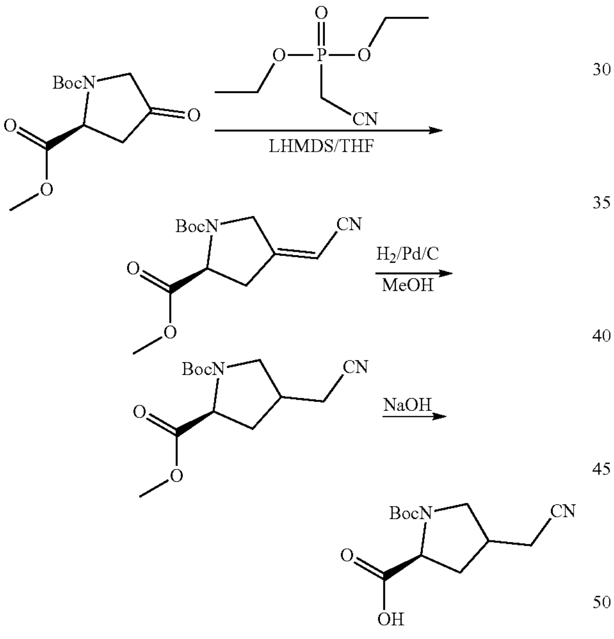

Step 1

To a solution of diethyl (cyanomethyl)phosphonate (1.5 mL, 9.0 mmol) in THF (20 mL) was added LiHMDS (9.0 mL, 1.0 M in THF) at 0° C., the resulting mixture was stirred for 1 h at 0° C., then (2S)-1-tert-butyl 2-methyl 4-oxopyrrolidine-1,2-dicarboxylate (2.01 g, 8.22 mmol) in THF (10 mL) was added to the reaction mixture at same temperature. The reaction mixture was stirred for 16 h while warmed to rt, quenched with sat. $NH_4Cl$ solution (20 mL), and extracted with EtOAc (20 mL×2). The combined organic phase was dried over $Na_2SO_4$ and concentrated, the residue was purified by column chromatography on silica gel (EtOAc in PE=0~10%) to give the desired product 1-tert-butyl 2-methyl (2S,4Z)-4-(cyanoethylidene)pyrrolidine-1,2-dicarboxylate (900 mg, yield: 41.0%) as a yellow solid. LC/MS (ESI) m/z: 247 $(M+H)^+$.

Step 2

To a solution of 1-tert-butyl 2-methyl (2S)-4-(cyanomethylidene)pyrrolidine-1,2-dicarboxylate (900 mg, 3.38 mmol) in MeOH (5 mL) was added a slurry of Pd/C (90 mg, 10%) in EtOAc (10 mL). The resulting suspension was then stirred at rt for 16 h under a balloon of $H_2$. The reaction mixture was filtered through a pad of celite, and the filtrate was concentrated to give the crude product (2S)-1-tert-butyl 2-methyl 4-(cyanomethyl)pyrrolidine-1,2-dicarboxylate (900 mg, yield: 99%) as a colorless oil which can be used in next step without further purification. LC/MS (ESI) m/z: 269 $(M+H)^+$.

Step 3

To a solution of (2S)-1-tert-butyl 2-methyl 4-(cyanomethyl)pyrrolidine-1,2-dicarboxylate (650 mg, 2.29 mmol) in MeOH (5.0 mL) and $H_2O$ (1.0 mL) at 0° C. was added NaOH (200 mg, 5.00 mmol), the resulting mixture was heated to 65° C. for 1 h. The reaction mixture was cooled to room temperature, and adjusted the pH to 5 with 1.0 N HCl, the mixture was extracted with EtOAc (10 mL×3), the combined organic phase was dried over anhydrous $Na_2SO_4$, filtered and concentrated in vacuo to give the crude product (2S)-1-[(tert-butoxy)carbonyl]-4-(cyanomethyl)pyrrolidine-2-carboxylic acid (400 mg, yield: 47%) as a light yellow solid. LC/MS (ESI) m/z: 254 $(M+H)^+$.

Preparation of Intermediate 29, 4-isopropyl-5-(4,4,5,5-tetramethyl-1,3,2-dioxaborolan-2-yl)pyrimidine

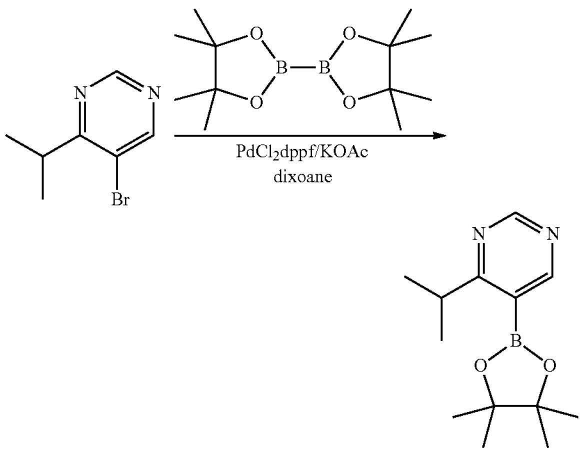

To a stirred solution of 5-bromo-4-isopropylpyrimidine (1.00 g, 4.97 mmol) and 4,4,4',4',5,5,5',5'-octamethyl-2,2'-bi(1,3,2-dioxaborolane) (1.40 g, 5.47 mmol) in dioxane (10 mL) was added KOAc (1.50 g, 15.7 mmol) and $Pd(dppf)Cl_2$ (100 mg). The resulting mixture was heated to 110° C. for 12 h under $N_2$ atmosphere. After cooled to room temperature, the mixture was diluted with $H_2O$ (10 mL), extracted with EtOAc (30 mL×3), the combined organic phase was washed with water and brine, dried over anhydrous $Na_2SO_4$, filtered and concentrated in vacuo to give the crude product which was purified by column chromatography on silica gel (EtOAc in PE=0~20%) to give the desired product 4-isopropyl-5-(4,4,5,5-tetramethyl-1,3,2-dioxaborolan-2-yl)pyrimidine (610 mg, yield: 49%) as a white solid. LC/MS (ESI) m/z: 249 $(M+H)^+$.

The following intermediate was prepared from the corresponding chemicals according to experimental procedure for Intermediate 29 (the major different chemicals used are listed in the column of starting material):

| Intermediate | Structure | Starting material | LCMS (ESI) m/z |
|---|---|---|---|
| Intermediate 30 | 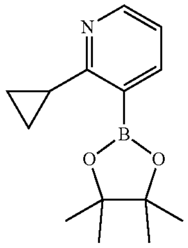 [SMILES: CC1(C)OB(c2cccnc2C2CC2)OC1(C)C] | 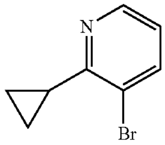 | 246 $(M + H)^+$ |

Preparation of Intermediate 31, 2-(4-(7-(tert-butoxycarbonyl)-2,7-diazaspiro[3.5]nonan-2-yl)pyrimidin-5-yloxy)-5-fluorobenzoic acid

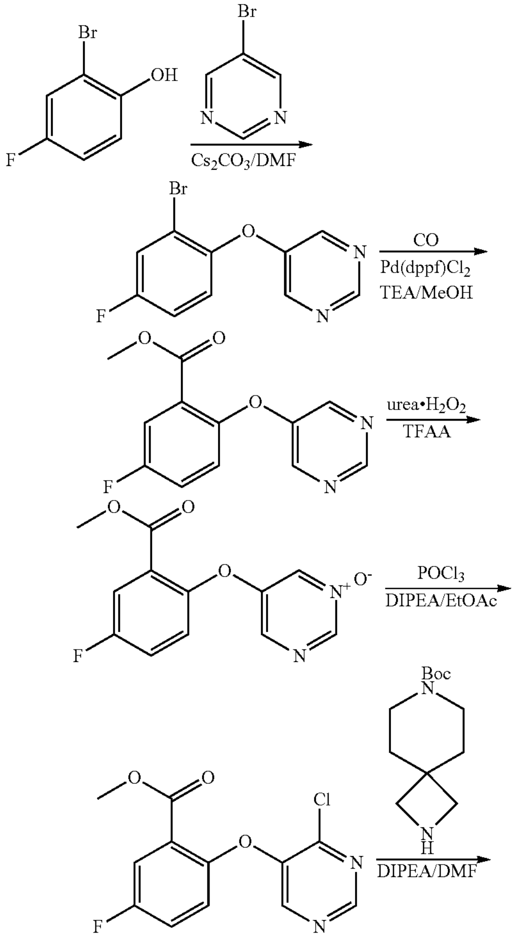

-continued

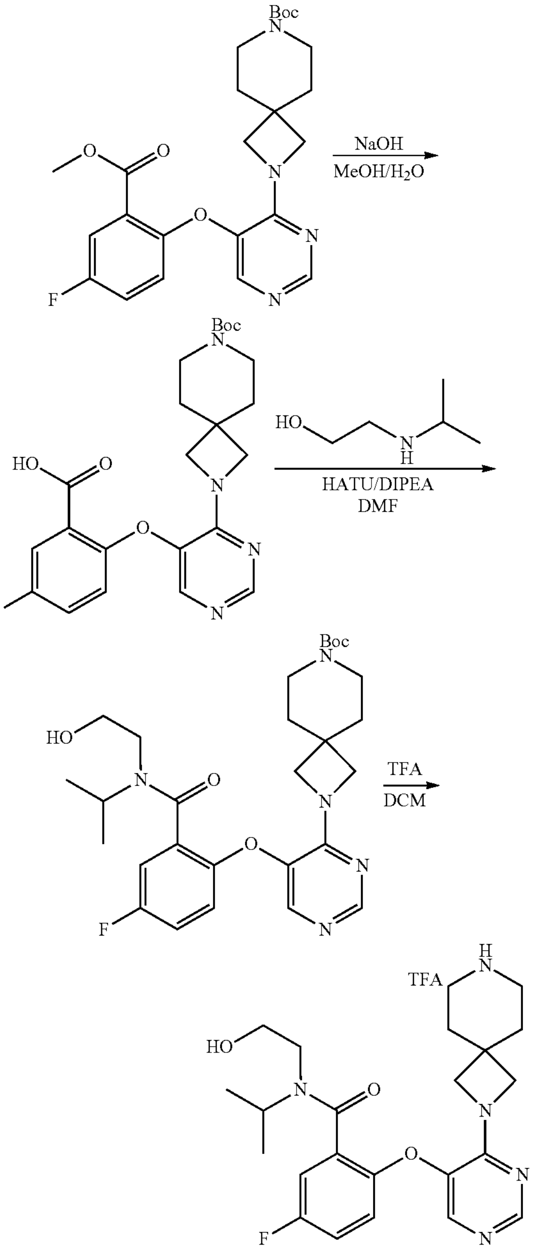

Step 1

To a solution of 2-bromo-4-fluorophenol (3.01 g, 15.7 mmol) and 5-bromopyrimidine (2.75 g, 17.3 mmol) in DMF (30 mL) was added $Cs_2CO_3$ (12.8 g, 39.3 mmol) at rt. The resulting mixture was heated to 120° C. for 12 h. The reaction mixture was cooled to room temperature, quenched with sat. $NH_4Cl$ solution (50 mL), extracted with EtOAc (100 mL×3), the combined organic layer was washed with water and brine, dried over anhydrous $Na_2SO_4$, filtered and concentrated. The residue was purified by column chromatography on silica gel (EtOAc in PE=0~30%) to give the desired product 5-(2-bromo-4-fluorophenoxy)pyrimidine (1.40 g, yield: 29.8%) as a yellow solid; LCMS: ESI m/z 270 $(M+1)^+$.

Step 2

To a solution of 5-(2-bromo-4-fluorophenoxy)pyrimidine (1.00 g, 3.70 mmol) and TEA (1.5 mL, 11 mmol) in MeOH (15 mL) was added Pd(dppf)$Cl_2$ (150 mg) at rt. The resulting mixture was stirred at 90° C. for 12 h under CO (70 psi) atmosphere. After cooled to rt, the solvent was concentrated under reduced pressure to give the crude product which was purified by column chromatography on silica gel (EtOAc in PE=0~30%) to give the desired product methyl 5-fluoro-2-(pyrimidin-5-yloxy)benzoate (900 mg, yield: 92.7%) as a colorless oil. LC/MS (ESI) m/z: 249 $(M+H)^+$.

Step 3

To a solution of methyl 5-fluoro-2-(pyrimidin-5-yloxy) benzoate (900 mg, 3.63 mmol) in THF (20 ml) was added urea. $H_2O_2$ (800 mg, 8.16 mmol) and TFAA (0.6 mL) at 0° C. under $N_2$. The resulting mixture was stirred at rt for 1 h. The reaction mixture was quenched with sat. $NaHCO_3$, extracted with EtOAc (20 mL×3), the combined organic layer was washed with water and brine, dried over anhydrous $Na_2SO_4$, filtered and concentrated in vacuo to give the crude product 5-[4-fluoro-2-(methoxycarbonyl)phenoxy] pyrimidin-1-ium-1-olate (830 mg, yield: 86.3%) as a yellow oil which can be used in next step directly without further purification. LCMS: ESI m/z 265 $(M+1)^+$.

Step 4

To a solution of 5-[4-fluoro-2-(methoxycarbonyl)phenoxy]pyrimidin-1-ium-1-olate (800 mg, 3.01 mmol) and DIPEA (5.6 mL, 34 mmol) in EtOAc (15 mL) was added $POCl_3$ (0.6 mL, 6.8 mmol) at 0° C. The resulting mixture was stirred at rt for 2 h. The reaction mixture was quenched with sat. $NaHCO_3$ solution (20 mL), extracted with EtOAc (50 mL×3), the combined organic layer was washed with water and brine, dried over anhydrous $Na_2SO_4$, filtered and concentrated in vacuo to give the crude product methyl 2-[(4-chloropyrimidin-5-yl)oxy]-5-fluorobenzoate (798 mg, yield: 93%) as a brown oil which can be used in next step directly without further purification. LCMS: ESI m/z 283 $(M+1)^+$.

Step 5

To a solution of methyl 2-[(4-chloropyrimidin-5-yl)oxy]-5-fluorobenzoate (798 mg, 2.82 mmol) and DIPEA (5.3 mL, 32 mmol) in DMF (15 mL) was added tert-butyl 2,7-diazaspiro[3.5]nonane-7-carboxylate (703 mg, 3.11 mmol) at rt. The resulting mixture was stirred at 65° C. for 3 h. After cooled to room temperature, the reaction mixture was quenched with sat. $NH_4Cl$ solution (10 mL), extracted with EtOAc (30 mL×3), the combined organic layer was washed with water and brine, dried over anhydrous $Na_2SO_4$, filtered and concentrated to give the crude product which was purified by column chromatography on silica gel (EtOAc in PE=0~50%) to give the desired product tert-butyl 2-{5-[4-fluoro-2-(methoxycarbonyl)phenoxy]pyrimidin-4-yl}-2,7-diazaspiro[3.5]nonane-7-carboxy late (610 mg, yield: 45.5%) as a yellow solid, LCMS: ESI m/z 473 $(M+1)^+$.

Step 6

To a solution of tert-butyl 2-{5-[4-fluoro-2-(methoxycarbonyl)phenoxy]pyrimidin-4-yl}-2,7-diazaspiro[3.5]nonane-7-carboxy late (610 mg, 1.29 mmol) in MeOH (12 mL) and $H_2O$ (4.0 mL) was added NaOH (228 mg, 5.71 mmol) at 0° C. the resulting mixture was stirred at rt for 1 h. Then the pH of mixture was adjusted to 5 with 1.0 N HCl, extracted with EtOAc (20 mL×3), the combined organic layer was washed with water and brine, dried over with anhydrous $Na_2SO_4$, filtered and concentrated to give the crude product 2-[(4-{7-[(tert-butoxy)carbonyl]-2,7-diazaspiro[3.5]nonan-2-yl}pyrimidin-5-yl)oxy]-5-fluorobenzoic acid (560 mg, yield:94.5%) as an off-white solid which can be used in next step without further purification. LC/MS (ESI) m/z:459 $(M+H)^+$.

Step 7

To a stirred solution of 2-[(4-{7-[(tert-butoxy) carbonyl]-2,7-diazaspiro[3.5] nonan-2-yl} pyrimidin-5-yl) oxy]-5-fluorobenzoic acid (200 mg, 0.44 mmol) and HATU (166 mg, 0.44 mmol) in DMF (4 mL) was added DIPEA (169 mg, 1.31 mmol). The resulting mixture was stirred for 10 minutes before 2-[(propan-2-yl) amino] ethan-1-ol (54 mg, 0.52 mmol) was added. The reaction mixture was stirred for 1 h at rt, and then diluted with $H_2O$ (10 mL), and extracted with EtOAc (30 mL×3). The combined organic phase was dried over anhydrous $Na_2SO_4$, filtered, and concentrated to give the desired product which was purified by Prep-TLC (MeOH in DCM=9%) to give the desired product tert-butyl 2-(5-{4-fluoro-2-[(2-hydroxyethyl) (propan-2-yl) carbamoyl] phenoxy} pyrimidin-4-yl)-2,7-diazaspiro[3.5] nonane-7-carboxylate (135 mg, yield: 56.9%) as a white solid. LCMS: ESI m/z 544 $(M+1)^+$.

Step 8

To a solution of tert-butyl 2-(5-{4-fluoro-2-[(2-hydroxyethyl) (propan-2-yl) carbamoyl] phenoxy} pyrimidin-4-yl)-2,7-diazaspiro[3.5] nonane-7-carboxylate (50 mg, 0.09 mmol) in DCM (3.0 mL) was added TFA (1.0 mL). The mixture was stirred for 1 h at rt. The resulting mixture was concentrated in vacuo to give the crude product 2-[(4-{2,7-diazaspiro [3.5]nonan-2-yl}pyrimidin-5-yl)oxy]-5-fluoro-N-(2-hydroxyethyl)-N-(propan-2-yl)benzamide (40 mg, yield: 98%) as an oil which can be used directly in next step without further purification. LC/MS (ESI) m/z: 444 $(M+H)^+$.

Preparation of Intermediate 32, 2-((4-(2,7-diazaspiro[3.5]nonan-2-yl)pyrimidin-5-yl)oxy)-5-fluoro-N-isopropyl-N-(2-methoxyethyl) benzamide

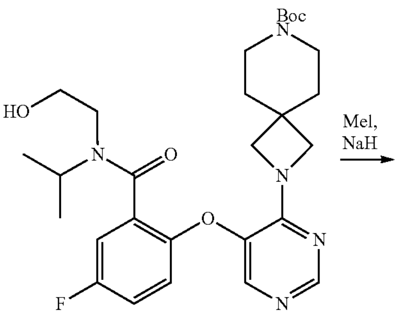

-continued

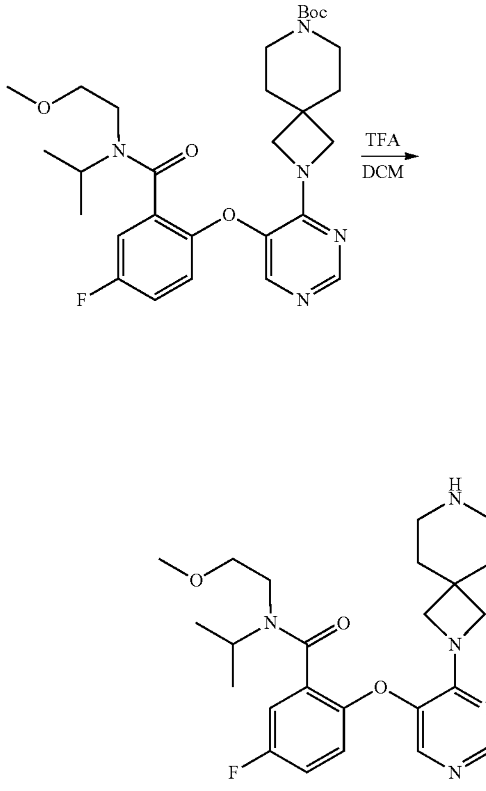

Step 1

To a solution of tert-butyl 2-(5-{4-fluoro-2-[(2-hydroxyethyl) (propan-2-yl) carbamoyl] phenoxy} pyrimidin-4-yl)-2,7-diazaspiro[3.5] nonane-7-carboxylate (60 mg, 0.11 mmol) in DMF (4 mL) was added NaH (7.0 mg, 0.17 mmol, 60%) at 0° C. The reaction mixture was stirred for 10 min, and then MeI (31 mg, 0.22 mmol) was added. The resulting mixture was stirred at rt for 1 h, quenched with sat. $NH_4Cl$ solution (10 mL), and extracted with EtOAc (30 mL×3). The combined organic layer was dried over anhydrous $Na_2SO_4$, filtered and concentrated to give the desired product which was purified by Prep-TLC (MeOH in DCM=9%) to give the desired product tert-butyl 2-(5-{4-fluoro-2-[(2-methoxyethyl) (propan-2-yl) carbamoyl] phenoxy} pyrimidin-4-yl)-2,7-diazaspiro[3.5] nonane-7-carboxylate (50 mg, yield: 81.2%) as a yellow solid. LCMS: ESI m/z 558 $(M+1)^+$.

Step 2

To a solution of tert-butyl 2-(5-{4-fluoro-2-[(2-methoxyethyl) (propan-2-yl) carbamoyl] phenoxy} pyrimidin-4-yl)-2,7-diazaspiro[3.5] nonane-7-carboxylate (50 mg, 0.09 mmol) in DCM (3.0 mL) was added TFA (1.0 mL). The resulting mixture was stirred for 1 h at rt. The reaction mixture was concentrated in vacuo to give the crude product 2-[(4-{2,7-diazaspiro[3.5] nonan-2-yl} pyrimidin-5-yl) oxy]-5-fluoro-N-(2-methoxyethyl)-N-(propan-2-yl) benzamide (30 mg, yield: 73.5%) as a brown oil which can be used directly in next step without further purification. LC/MS (ESI) m/z: 458 $(M+H)^+$.

Preparation of Intermediate 33, 2-cyclopropyl-5'-fluoro-2'-hydroxybiphenyl-4-carbonitrile

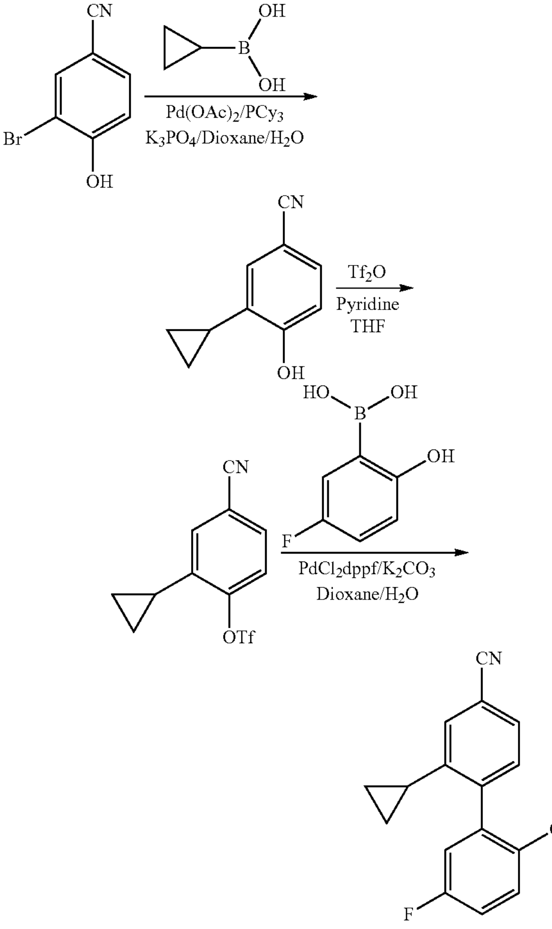

Step 1

To a solution of 3-bromo-4-hydroxybenzonitrile (1.01 g, 5.05 mmol) and cyclopropylboronic acid (520 mg, 6.06 mmol) in toluene (15 mL) were added $PCy_3$ (280 mg, 1 mmol), $Pd(OAc)_2$ (100 mg) and $K_3PO_4$ (3.2 g, 15 mmol) at rt. The resulting mixture was stirred at 100° C. for 12 h under $N_2$. The reaction mixture was cooled to rt, quenched with $H_2O$ (20 mL), extracted with EtOAc (30 mL×3), the combined organic layer was washed with water and brine, dried over anhydrous $Na_2SO_4$, filtered and concentrated, the residue was purified by column chromatography on silica gel (EtOAc in PE=0~30%) to give the desired product 3-cyclopropyl-4-hydroxybenzonitrile (700 mg, yield: 82.8%) as a yellow oil. LC/MS (ESI) m/z: 158 $(M-H)^+$.

Step 2

To a solution of 3-cyclopropyl-4-hydroxybenzonitrile (700 mg, 4.39 mmol) and pyridine (1.12 g, 8.79 mmol) in THF (10 mL) was added $Tf_2O$ (1.1 mL, 6.59 mmol) at −5° C. under $N_2$, the resulting mixture was stirred at 0° C. for 3 h. The reaction was quenched with sat. $NaHCO_3$ solution, extracted with DCM (30 mL×3), the combined organic layer was washed with water and brine, dried over anhydrous $Na_2SO_4$, filtered and concentrated, the residue was purified by column chromatography on silica gel (EtOAc in PE=0~80%) to give the desired product 4-cyano-2-cyclopropylphenyl trifluoromethanesulfonate (1.01 g, yield: 74.2%) as an oil. LC/MS (ESI) m/z: 292 $(M+H)^+$.

Step 3

To a solution of 4-cyano-2-cyclopropylphenyl trifluoromethanesulfonate (300 mg, 1.03 mmol) and 5-fluoro-2-hydroxyphenylboronic acid (177 mg, 1.13 mmol) in dioxane (5.0 mL) and $H_2O$ (1.0 mL) were added $Pd(dppf)Cl_2$ (20 mg) and $K_2CO_3$ (414 mg, 3.00 mmol), the resulting mixture was stirred at 100° C. for 10 h under $N_2$ atmosphere. The reaction mixture was cooled to rt, diluted with $H_2O$ (10 mL), extracted with EtOAc (20 mL×3), the combined organic layer was washed with water and brine, dried over anhydrous $Na_2SO_4$, filtered and concentrated to give the crude product which was purified by column chromatography on silica gel (EtOAc in PE=0~50%) to give the desired product 2-cyclopropyl-5'-fluoro-2'-hydroxybiphenyl-4-carbonitrile (125 mg, yield: 47.7%) as a yellow solid. LC/MS (ESI) m/z: 254 $(M+H)^+$.

Preparation of Intermediate 34, 2-((5-(2,7-diazaspiro[3.5]nonan-2-yl)-1,2,4-triazin-6-yl)oxy)-N-ethyl-5-fluoro-N-isopropylbenzamide

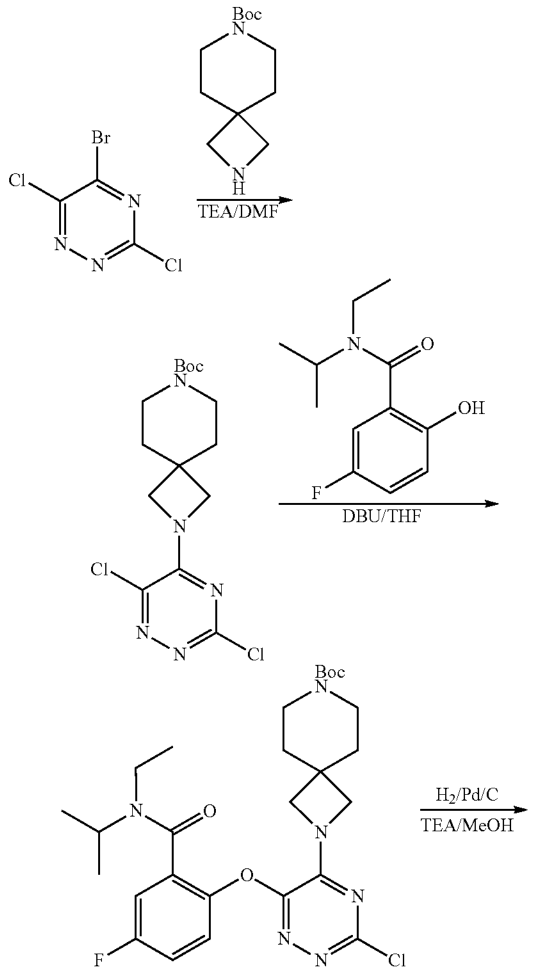

-continued

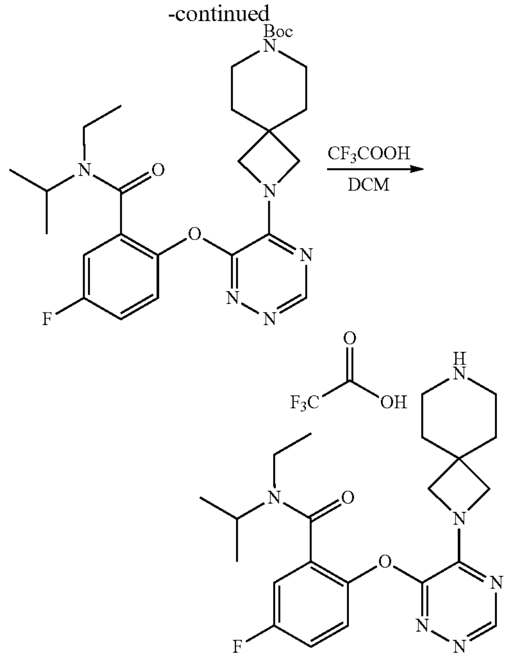

Step 1

To a stirred solution of trichloro-1,2,4-triazine (CAS 873-41-6, 0.88 g, 4.80 mmol) and TEA (1.39 mL, 9.99 mmol) in DCM (15 mL) was added tert-butyl 2,7-diazaspiro[3.5] nonane-7-carboxylate hydrochloride (1.05 g, 4.01 mmol) at 0° C. The resulting mixture was stirred at rt for 12 h. The reaction mixture was quenched with $H_2O$ (20 mL), extracted with DCM (30 mL×3), the combined organic layer was dried over anhydrous $Na_2SO_4$, filtered, and concentrated to give crude product which was purified by chromatography column on silica gel (EtOAc in PE=0~25%) to give the desired product tert-butyl 2-(dichloro-1,2,4-triazin-5-yl)-2,7-diazaspiro[3.5] nonane-7-carboxylate (1.10 g, yield: 60.4%) as a white solid. LCMS: ESI m/z 374 $(M+1)^+$.

Step 2

To a stirred solution of tert-butyl 2-(dichloro-1,2,4-triazin-5-yl)-2,7-diazaspiro[3.5] nonane-7-carboxylate (1.05 g, 2.81 mmol) and N-ethyl-5-fluoro-2-hydroxy-N-(propan-2-yl) benzamide (0.63 g, 2.81 mmol) in THF (12 mL) was added DBU (0.50 mL, 3.37 mmol) at rt. The resulting mixture was stirred at rt for 8 h. The reaction mixture was diluted with $H_2O$ (20 mL), extracted with EtOAc (20 mL×3), the combined organic layer was dried over anhydrous $Na_2SO_4$, filtered and concentrated, the residue was purified by chromatography column on silica gel (EtOAc in PE=20%~50%) to obtain the desired product tert-butyl 2-(3-chloro-6-{2-[ethyl(propan-2-yl)carbamoyl]-4-fluorophenoxy}-1,2,4-triazin-5-yl)-2,7-diazaspiro[3.5]nonane-7-carboxylate (800 mg, yield: 50.6%) as a white solid. LCMS: ESI m/z 563 $(M+1)^+$.

Step 3

To a stirred solution of tert-butyl 2-(3-chloro-6-{2-[ethyl (propan-2-yl) carbamoyl]-4-fluorophenoxy}-1,2,4-triazin-5-yl)-2,7-diazaspiro[3.5] nonane-7-carboxylate (0.80 g, 1.42 mmol) in MeOH (10 mL) were added TEA (0.24 mL, 1.71 mmol) and a slurry of Pd/C (10%, 80 mg) in EtOAc (5 mL). The resulting suspension was vacuumed and refilled with hydrogen, stirred at rt for 8 h under balloon pressure of $H_2$. The reaction mixture was filtered through a pad of celite, washed with MeOH (5 mL), the filtrate was concentrated to give the desired product tert-butyl 2-(6-{2-[ethyl(propan-2-yl) carbamoyl]-4-fluorophenoxy}-1,2,4-triazin-5-yl)-2,7-diazaspiro[3.5] nonane-7-carboxylate (750 mg, yield: 99.8%) as a white solid which can be used in next step without further purification. LCMS: ESI m/z 529 $(M+1)^+$.

Step 4

To a solution of tert-butyl 2-(6-{2-[ethyl(propan-2-yl) carbamoyl]-4-fluorophenoxy}-1,2,4-triazin-5-yl)-2,7-diazaspiro[3.5] nonane-7-carboxylate (720 mg, 1.36 mmol) in DCM (10 mL) was added TFA (5 mL) at 0° C. The resulting mixture was stirred at rt for 2 h. The reaction mixture was concentrated in vacuo to give the crude product 2-((5-(2,7-diazaspiro[3.5]nonan-2-yl)-1,2,4-triazin-6-yl)oxy)-N-ethyl-5-fluoro-N-isopropyl benzamide as a TFA salt (580 mg, yield: 99.4%) as a yellow oil which can be used directly in next step without further purification. LC/MS (ESI) m/z: 429 (M+H)+.

The following intermediate was prepared from the corresponding chemicals according to experimental procedure for Intermediate 34 (the major different chemicals used are listed in the column of starting material):

| Intermediate | Structure | Starting material | LCMS (ESI) m/z |
| --- | --- | --- | --- |
| Intermediate 35 | 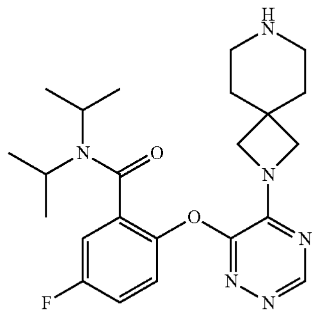 [SMILES: CC(C)N(C(=O)c1cc(F)ccc1Oc1nncnc1N1CC2(CCNCC2)C1)C(C)C] | Intermediate 14 | 443 $(M + H)^+$ |
| Intermediate 57 | 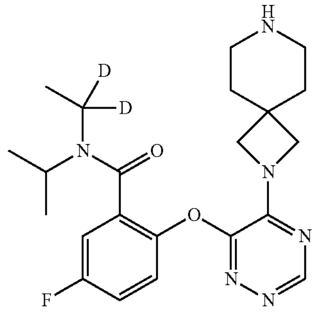 [SMILES: [2H]C([2H])(C)N(C(=O)c1cc(F)ccc1Oc1nncnc1N1CC2(CCNCC2)C1)C(C)C] | Intermediate 53 | 431 $(M + H)^+$ |
| Intermediate 60 | 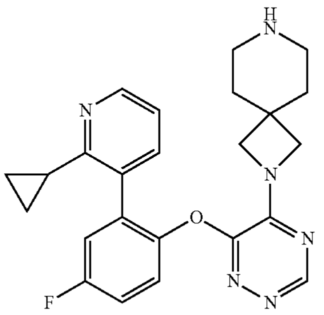 [SMILES: Fc1ccc(Oc2nncnc2N2CC3(CCNCC3)C2)c(-c2cccnc2C2CC2)c1] | Intermediate 54 | 433 $(M + H)^+$ |

-continued
| Intermediate | Structure | Starting material | LCMS (ESI) m/z |
|---|---|---|---|
| Intermediate 58 | 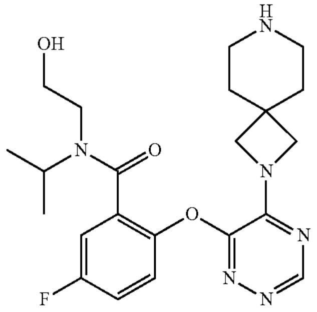 [SMILES: CC(C)N(CCO)C(=O)c1cc(F)ccc1Oc1nncnc1N1CC2(CCNCC2)C1] | Intermediate 22-1 | 445 $(M + H)^+$ |
| Intermediate 59 | 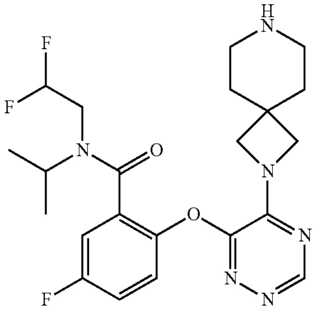 [SMILES: CC(C)N(CC(F)F)C(=O)c1cc(F)ccc1Oc1nncnc1N1CC2(CCNCC2)C1] | Intermediate 22 | 465 $(M + H)^+$ |
| Intermediate 61 | 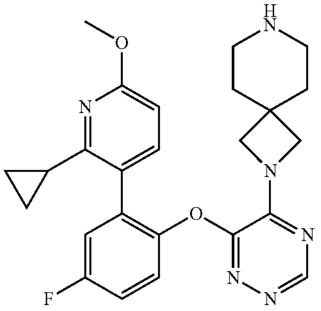 [SMILES: COc1ccc(-c2cc(F)ccc2Oc2nncnc2N2CC3(CCNCC3)C2)c(C2CC2)n1] | Intermediate 55 | 463 $(M + H)^+$ |
| Intermediate 62 | 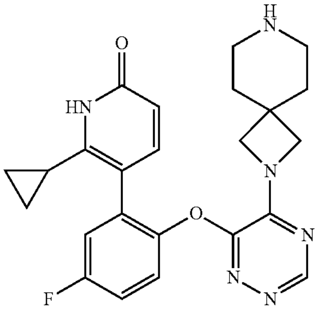 [SMILES: O=c1ccc(-c2cc(F)ccc2Oc2nncnc2N2CC3(CCNCC3)C2)c(C2CC2)[nH]1] | Intermediate 56 | 449 $(M + H)^+$ |

Preparation of Intermediate 36, 2-(6-(2-(4-chloro-1-isopropyl-1H-pyrazol-5-yl)-4-fluorophenoxy)-1,2,4-triazin-5-yl)-2,7-diazaspiro [3.5]nonane

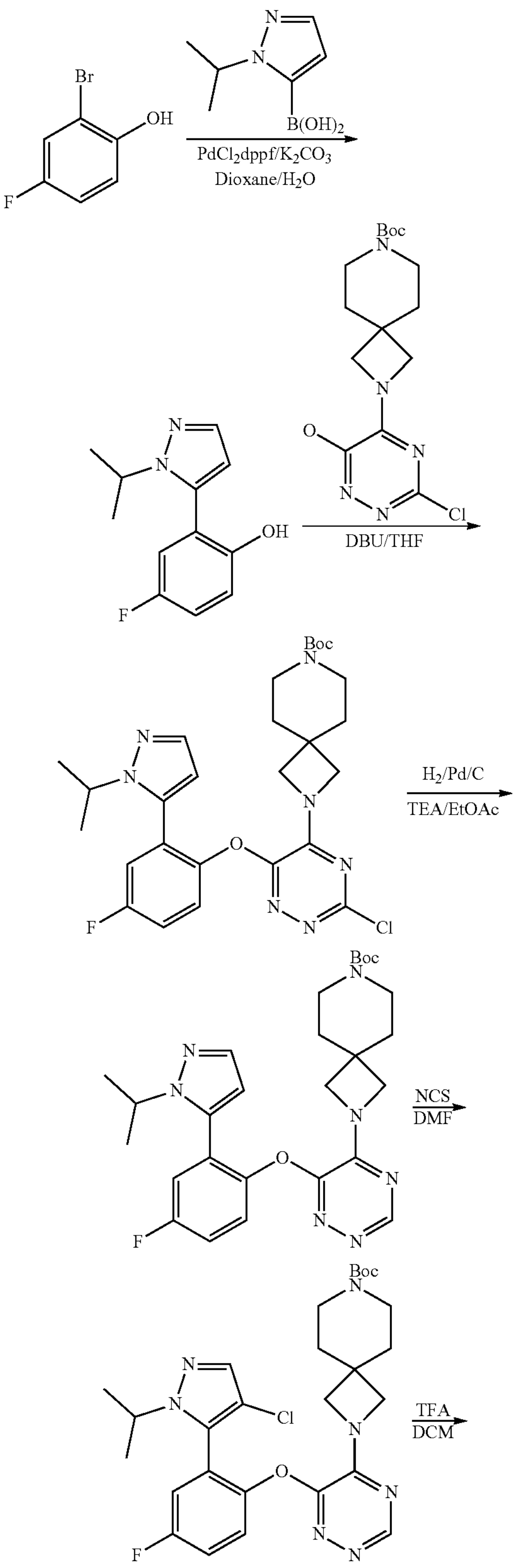

-continued

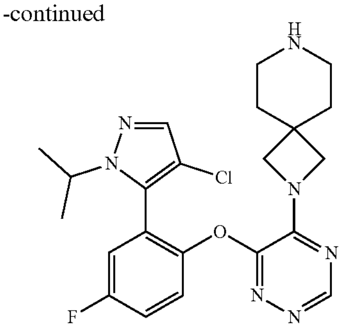

Step 1

To a solution of [1-(propan-2-yl)-1H-pyrazol-5-yl]boronic acid (605 mg, 3.93 mmol), 2-bromo-4-fluorophenol (500 mg, 2.62 mmol) in dioxane (10 mL) and $H_2O$ (2.0 mL) was added $K_2CO_3$ (1.08 g, 7.85 mmol) and Pd(dppf)$Cl_2$ (192 mg, 0.26 mmol) at room temperature, the resulting mixture was stirred at 100° C. for 2 h under $N_2$. The reaction mixture was cooled to rt, quenched with $H_2O$ (10 mL), extracted with EtOAc (30 mL×3), the combined organic layer was dried over anhydrous $Na_2SO_4$, filtered and concentrated, the residue was purified by column chromatography on silica gel (EtOAc in PE=0~50%) to obtain the desired product 4-fluoro-2-(1-isopropyl-1H-pyrazol-5-yl)phenol (200 mg, yield: 34.7%) as a yellow solid. LC/MS (ESI) m/z: 221 $(M+H)^+$.

Step 2

To a solution of tert-butyl 2-(dichloro-1,2,4-triazin-5-yl)-2,7-diazaspiro[3.5]nonane-7-carboxylate (200 mg, 0.53 mmol) and 4-fluoro-2-(1-isopropyl-1H-pyrazol-5-yl)phenol (118 mg, 0.53 mmol) in THF (5 mL) was added DBU (0.08 mL, 0.53 mmol) at room temperature, the resulting mixture was stirred overnight. The reaction mixture was diluted with $H_2O$ (10 mL), extracted with EtOAc (10 mL×3), the combined organic layer was dried over anhydrous $Na_2SO_4$, filtered and concentrated, the residue was purified by column chromatography on silica gel (EtOAc in PE=0~40%) to obtain the desired product tert-butyl 2-(3-chloro-6-(4-fluoro-2-(1-isopropyl-1H-pyrazol-5-yl)phenoxy)-1,2,4-triazin-5-yl)-2,7-diazaspiro [3.5]nonane-7-carboxylate (120 mg, yield: 40.2%) as a light yellow solid. LC/MS (ESI) m/z: 558 $(M+H)^+$.

Step 3

To a solution of tert-butyl 2-(3-chloro-6-{4-fluoro-2-[1-(propan-2-yl)-1H-pyrazol-5-yl]phenoxy}-1,2,4-triazin-5-yl)-2,7-diaza spiro[3.5]nonane-7-carboxylate (120 mg, 0.22 mmol) and TEA (0.12 mL, 0.86 mmol) in EtOAc (3 mL) was added Pd/C (12 mg) at room temperature. The reaction mixture was vacuum and refilled with hydrogen, stirred at room temperature for 2 h under a balloon of $H_2$. The reaction mixture was filtered through a pad of celite, the filtrate was concentrated to obtain the crude product tert-butyl 2-(6-(4-fluoro-2-(1-isopropyl-1H-pyrazol-5-yl)phenoxy)-1,2,4-triazin-5-yl)-2,7-diazaspiro[3.5]nonane-7-carboxylate (60 mg, yield: 53.3%) as a yellow solid which can be used in next step without further purification. LC/MS (ESI) m/z: 524 $(M+H)^+$.

Step 4

To a solution of tert-butyl 2-(6-{4-fluoro-2-[1-(propan-2-yl)-1H-pyrazol-5-yl]phenoxy}-1,2,4-triazin-5-yl)-2,7-diazaspiro[3.5] nonane-7-carboxylate (60 mg, 0.11 mmol) in DMF (2.0 mL) was added NCS (17 mg, 0.13 mmol) at 0° C., the resulting mixture was stirred for 3 h at same temperature. The reaction mixture was quenched with $H_2O$ (5 mL), extracted with EtOAc (10 mL×3), the combined organic layer was dried over anhydrous $Na_2SO_4$, filtered and concentrated, the residue was purified by column chromatography on silica gel (EtOAc in PE=0~80%) to obtain the desired product tert-butyl 2-(6-(2-(4-chloro-1-isopropyl-1H-pyrazol-5-yl)-4-fluorophenoxy)-1,2,4-triazin-5-yl)-2,7-diazaspiro [3.5]nonane-7-carboxylate (40 mg, yield: 62.1%) as a light yellow solid. LC/MS (ESI) m/z: 558 $(M+H)^+$.

Step 5

To a solution of tert-butyl 2-(6-{2-[4-chloro-1-(propan-2-yl)-1H-pyrazol-5-yl]-4-fluorophenoxy}-1,2,4-triazin-5-yl)-2,7-diaza spiro[3.5]nonane-7-carboxylate (40 mg, 0.07 mmol) in DCM (3.0 mL) was added TFA (1.0 mL) at room temperature, the resulting mixture was stirred for 1 h. The reaction mixture was concentrated to give the crude product 2-(6-(2-(4-chloro-1-isopropyl-1H-pyrazol-5-yl)-4-fluorophenoxy)-1,2,4-triazin-5-yl)-2,7-diazaspiro [3.5]nonane (30 mg, yield: 91.4%) as a yellow oil which can be used in next step without further purification. LC/MS (ESI) m/z: 458 $(M+H)^+$.

Preparation of Intermediate 37. trans-1-(tert-butoxycarbonyl)-3-ethylpyrrolidine-2-carboxylic acid

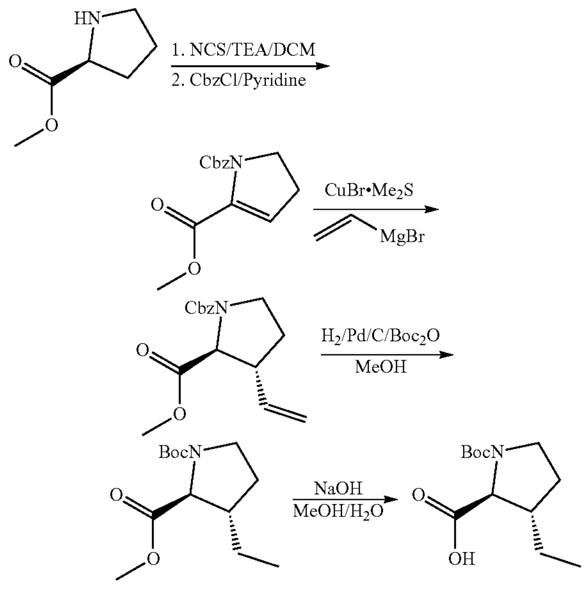

Step 1

To a mixture of methyl (2S)-pyrrolidine-2-carboxylate (2.01 g, 15.5 mmol) in DCM (30 mL) at 0° C. was added TEA (4.3 mL, 31 mmol) and NCS (2.30 g, 17.0 mmol) in small portions. The resulting mixture was stirring at rt for 3 h before pyridine (4.53 g, 35.6 mmol) was added slowly within 1 h, the reaction mixture was cooled to −20° C., then CbzCl (5.81 g, 34.1 mmol) was added, the mixture was allowed to warm to room temperature gradually and stirred for 12 h. The reaction system was diluted with $H_2O$ (50 mL), extracted with DCM (50 mL×3), the combined organic layer was washed with water and brine, dried over anhydrous $Na_2SO_4$, filtered and concentrated, the residue was purified by column chromatography on silica gel (EtOAc in PE=0~30%) to give the desired product 1-benzyl 2-methyl 4,5-dihydro-1H-pyrrole-1,2-dicarboxylate (503 mg, yield: 11.7%) as a yellow oil. LC/MS (ESI) m/z: 262 $(M+H)^+$.

Step 2

To a solution of $Me_2S{\cdot}CuBr$ (79 mg, 0.38 mmol) in THF (5.0 mL) at −40° C. was added vinylmagnesium bromide (2.8 mL, 1.0 M in THF) dropwise under $N_2$. The resulting mixture was stirred for 1 h, a solution of 1-benzyl 2-methyl 4,5-dihydro-1H-pyrrole-1,2-dicarboxylate (500 mg, 1.91 mmol) in THF (5.0 mL) was added dropwise, the reaction mixture was stirred for 4 h at this temperature. The mixture was quenched with sat. $NH_4Cl/NH_3{\cdot}H_2O$ (8:1), extracted with EtOAc (20 mL×3), the combined organic layer was washed with sat. $NH_4Cl$ solution and dried over anhydrous $Na_2SO_4$, filtered and concentrated, the residue was purified by column chromatography on silica gel (EtOAc in PE=0~30%) to give the desired product trans-1-benzyl 2-methyl-3-vinylpyrrolidine-1,2-dicarboxylate (505 mg, yield: 85.2%) as an oil. LC/MS (ESI) m/z: 292 $(M+H)^+$.

Step 3

To a solution of trans-1-benzyl 2-methyl-3-vinylpyrrolidine-1,2-dicarboxylate (500 mg, 1.72 mmol) and $(Boc)_2O$ (378 mg, 1.75 mmol) in MeOH (7.0 mL) was added Pd/C (10%, 50 mg) at rt, the resulting suspension was vacuum and refilled with hydrogen, stirred for 3 h under a balloon of $H_2$. The reaction mixture was filtered through a pad of celite, the filtrate was concentrated, the residue was purified by column chromatography on silica gel (EtOAc in PE=0~30%) to give the desired product trans-1-tert-butyl 2-methyl-3-ethylpyrrolidine-1,2-dicarboxylate (400 mg, yield: 86.1%) as a light-yellow oil. LC/MS (ESI) m/z: 202 $(M+H)^+$.

Step 4

To a solution of trans-1-tert-butyl 2-methyl-3-ethylpyrrolidine-1,2-dicarboxylate (400 mg, 1.55 mmol) in MeOH (6.0 mL) and $H_2O$ (2.0 mL) at 0° C. was added NaOH (186 mg, 4.66 mmol), the resulting mixture was stirred at rt for 1 h, the reaction mixture was acidified with HCl solution (1.0 N) to pH=4~5, and extracted with EtOAc (15 mL×3), the combined organic phase was dried over anhydrous over $Na_2SO_4$, filtered and concentrated to give the crude product trans-1-[(tert-butoxy)carbonyl]-3-ethylpyrrolidine-2-carboxylic acid (350 mg, yield: 87.9%) as white solid which can be used in next step without further purification. LC/MS (ESI) m/z: 188 $(M+H)^+$.

Preparation of Intermediate 38, (2S,3R,4R)-1-(tert-butoxycarbonyl)-4-fluoro-3-methylpyrrolidine-2-carboxylic acid

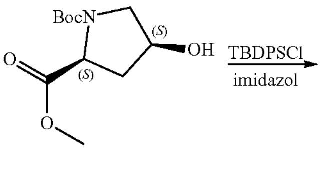

-continued

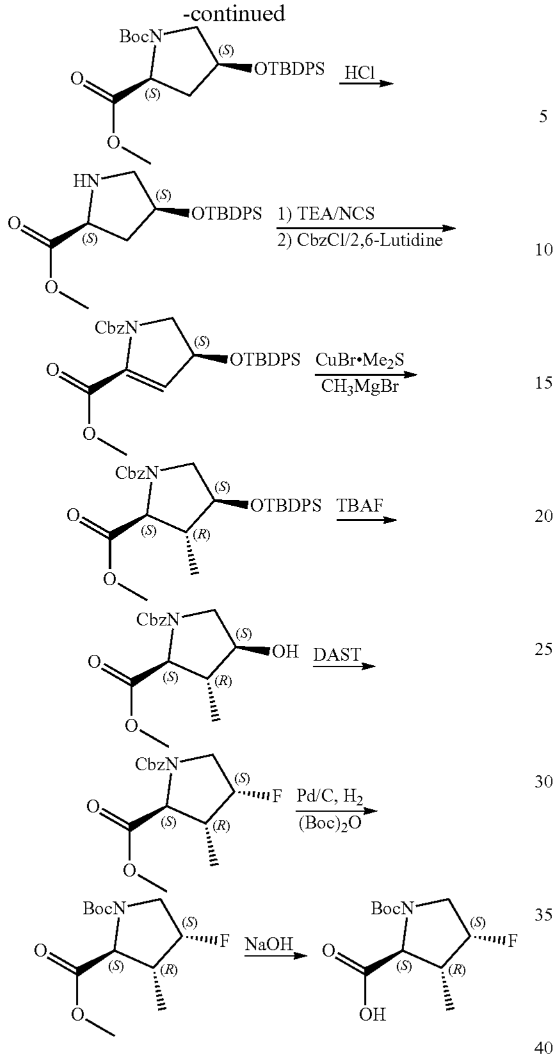

Step 1

To a solution of 1-tert-butyl 2-methyl (2S,4S)-4-hydroxypyrrolidine-1,2-dicarboxylate (4.98 g, 20.4 mmol) in DCM (50 mL) were added imidazole (1.80 g, 26.5 mmol) and TBDPSCl (7.91 g, 30.6 mmol). The resulting mixture was stirred at rt for 1 h. The reaction mixture was quenched with sat. $NH_4Cl$ solution (50 mL), extracted with DCM (100 mL×3), the combined organic layer was dried over anhydrous $Na_2SO_4$, filtered and concentrated, the residue was purified by column chromatography on silica gel (EtOAc in PE=0~50%) to give the desired product 1-tert-butyl 2-methyl (2S,4S)-4-[(tert-butyldiphenylsilyl)oxy]pyrrolidine-1,2-dicarboxylate (8.98 g, yield: 86.7%) as a colorless oil. LC/MS (ESI) m/z: 484 $(M+H)^+$.

Step 2

To a solution of 1-tert-butyl 2-methyl (2S,4S)-4-[(tert-butyldiphenylsilyl)oxy]pyrrolidine-1,2-dicarboxylate (15.0 g, 31.0 mmol) in DCM (100 mL) was added HCl in dioxane (100 mL, 4.0 M) slowly at rt for 2 h. The resulting mixture was concentrated to give the crude product 1-tert-butyl 2-methyl (2S,4S)-4-[(tert-butyldiphenylsilyl)oxy]pyrrolidine-1,2-dicarboxylate (11.9 g, yield: 95.8%) as a white solid which was used in next step without further purification. LC/MS (ESI) m/z: 384 $(M+H)^+$.

Step 3

To a solution of methyl (2S,4S)-4-[(tert-butyldiphenylsilyl)oxy]pyrrolidine-2-carboxylate (5.00 g, 13.0 mmol) in DCM (50 mL) at 0° C. was added TEA (3.3 mL, 23 mmol) and NCS (1.91 g, 14.3 mmol) in small portions, the resulting mixture was stirred at rt for 3 h before 2,6-lutidine (3 mL, 26.07 mmol) was added slowly within 1 h. The reaction mixture was cooled to −20° C. and CbzCl (4.70 g, 27.4 mmol) were added. The mixture was allowed to slowly warm to rt and stirred overnight. The reaction mixture was quenched with $H_2O$ (50 mL), extracted with EtOAc (50 mL×3), the combined organic layer was washed with water and brine, dried over anhydrous $Na_2SO_4$, filtered and concentrated, the residue was purified by column chromatography on silica gel (EtOAc in PE=0~30%) to give the desired product 1-benzyl 2-methyl (4S)-4-[(tert-butyldiphenylsilyl)oxy]-4,5-dihydro-1H-pyrrole-1,2-dicarboxylate (1.01 g, yield: 14.2%) as an oil. LC/MS (ESI) m/z: 516 $(M+H)^+$.

Step 4

To a solution of CuBr. $Me_2S$ (480 mg, 2.33 mmol) in THF (5.0 mL) was added MeMgBr (2.9 mL, 1.0 M in THF) dropwise at −40° C. under $N_2$, the mixture was stirred for 1 h at −40° C. before addition of a solution of 1-benzyl 2-methyl (4S)-4-[(tert-butyldiphenylsilyl)oxy]-4,5-dihydro-1H-pyrrole-1,2-dicarboxylate (1 g, 1.94 mmol) in THF (10 mL). The resulting mixture was stirred for 1 h at −40° C. The reaction mixture was quenched with sat. $NH_4Cl$ solution, extracted with EtOAc (20 mL×3), the combined organic layer was washed with brine and dried over anhydrous $Na_2SO_4$, filtered and concentrated, the residue was purified by column chromatography on silica gel (EtOAc in PE=0~30%) to give the desired product 1-benzyl 2-methyl (2S,3R,4S)-4-[(tert-butyldiphenylsilyl)oxy]-3-methylpyrrolidine-1,2-dicarboxylate (300 mg, yield: 27.6%) as a yellow oil. LC/MS (ESI) m/z: 532 $(M+H)^+$.

Step 5

To a solution of 1-benzyl 2-methyl (2S,3R,4S)-4-[(tert-butyldiphenylsilyl)oxy]-3-methylpyrrolidine-1,2-dicarboxylate (300 mg, 0.56 mmol) in THF (5.0 mL) was added TBAF (0.85 mL, 1.0 M in THF). The resulting mixture was stirred at rt for 1 h. The reaction mixture was diluted with sat. $NH_4Cl$ solution (5 mL), extracted with EtOAc (10 mL×3), the combined organic layer was washed with water and brine, dried over anhydrous $Na_2SO_4$, filtered and concentrated, the residue was purified by column chromatography on silica gel (EtOAc in PE=0~50%) to give the desired product 1-benzyl 2-methyl (2S,3R,4S)-4-hydroxy-3-methylpyrrolidine-1,2-dicarboxylate (100 mg, yield: 60.4%) as a light yellow oil. LC/MS (ESI) m/z: 294 $(M+H)^+$.

Step 6

To a solution of 1-benzyl 2-methyl (2S,3R,4S)-4-hydroxy-3-methylpyrrolidine-1,2-dicarboxylate (100 mg, 0.34 mmol) in DCM (2.0 mL) was added DAST (0.07 mL, 0.51 mmol) at 0° C. under $N_2$. The resulting mixture was stirred for 16 h at rt. The reaction mixture was quenched with sat. $NaHCO_3$, extracted with DCM (10 mL×3), the combined organic layer was washed with water and brine, dried over anhydrous $Na_2SO_4$, filtered and concentrated, the residue was purified by column chromatography on silica gel (EtOAc in PE=0~40%) to give the desired product 1-benzyl 2-methyl (2S,3R,4R)-4-fluoro-3-methylpyrrolidine-1,2-dicarboxylate (80 mg, yield: 75%) as a yellow oil; LCMS: ESI m/z 296 $(M+H)^+$.

Step 7

To a solution of 1-benzyl 2-methyl (2S,3R,4R)-4-fluoro-3-methylpyrrolidine-1,2-dicarboxylate (80 mg, 0.27 mmol) and $(Boc)_2O$ (0.07 mL, 0.36 mmol) in MeOH (7.0 mL) was added Pd/C (10%, 15 mg) at rt, the resulting suspension was vacuum and refilled with hydrogen, stirred at rt for 3 h under $H_2$ balloon pressure. The reaction mixture was filtered through a pad of celite, the filtrate was concentrated, the residue was purified by column chromatography on silica gel (EtOAc in PE=0~ 30%) to give the desired product 1-(tert-butyl) 2-methyl (2S,3R,4R)-4-fluoro-3-methylpyrrolidine-1,2-dicarboxylate (60 mg, yield: 80%) as an oil. LC/MS (ESI) m/z: 206 $(M+H)^+$.

Step 8

To a solution of 1-(tert-butyl) 2-methyl (2S,3R,4R)-4-fluoro-3-methylpyrrolidine-1,2-dicarboxylate (60 mg, 0.23 mmol) in MeOH (3 mL) and $H_2O$ (1 mL) was added NaOH (28 mg, 0.69 mmol) at 0° C. The resulting mixture was stirred for 4 h at room temperature, the reaction mixture was concentrated, and adjusted the pH to 4~5 with 1.0 N HCl solution, extracted with EtOAc (15 mL×3). The combined organic layer was washed with water and brine, dried over anhydrous $Na_2SO_4$, filtered and concentrated to give the crude product (2S,3R,4R)-1-(tert-butoxycarbonyl)-4-fluoro-3-methylpyrrolidine-2-carboxylic acid (50 mg, yield: 83.5%) as an off-white solid which can be used in next step directly without further purification. LC/MS (ESI) m/z: 192 $(M+1-56)^+$.

Preparation of Intermediate 39, (2S,3R,4R)-1-[(tert-butoxy)carbonyl]-3-ethyl-4-fluoropyrrolidine-2-carboxylic acid

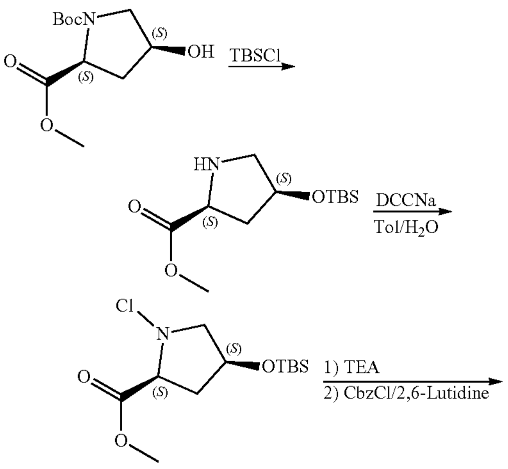

-continued

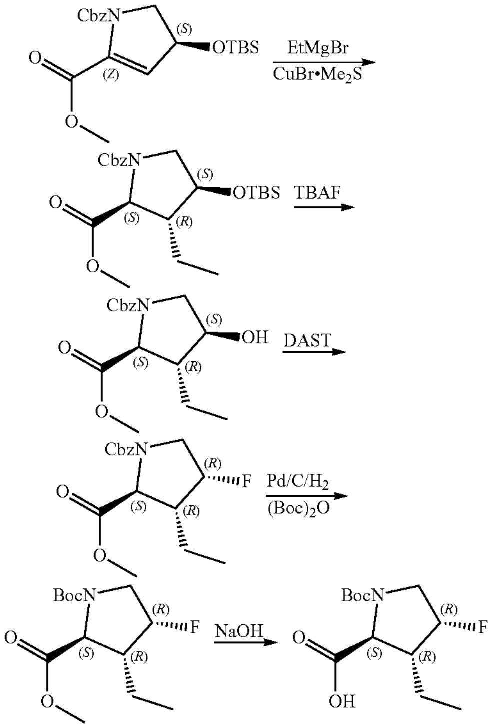

Step 1

To a solution of methyl (2S,4S)-4-hydroxypyrrolidine-2-carboxylate (2.71 g, 18.6 mmol) in DCM (40 mL) was added imidazole (2.50 g, 37.2 mmol) and TBSCl (3.30 g, 22.3 mmol). The resulting mixture was stirred at rt for 16 h. The reaction mixture was washed with 10% aq. $Na_2CO_3$ solution (50 mL), The aqueous layer was extracted with DCM (50 mL×2), the combined organic layer was dried over anhydrous $Na_2SO_4$, filtered and concentrated to give the crude product methyl (2S,4S)-4-[(tert-butyldimethylsilyl)oxy]pyrrolidine-2-carboxylate (4.50 g, yield: 88.6%) as a light yellow oil which can be used in next step without further purification. LC/MS (ESI) m/z: 260 (M+H)+.

Step 2

To a solution of methyl (2S,4S)-4-[(tert-butyldimethylsilyl)oxy]pyrrolidine-2-carboxylate (4.50 g, 17.3 mmol) in toluene (60 mL) at 0° C. was added $H_2O$ (20 mL) and sodium dichloroisocyanurate (3.60 g, 13.9 mmol), the resulting mixture was stirred for 16 h at 0° C. The reaction mixture was filtered and concentrated to give the crude product methyl (2S,4S)-4-[(tert-butyldimethylsilyl)oxy]-1-chloropyrrolidine-2-carboxylate (4.48 g, yield: 83.8%) as an oil which can be used in next step without further purification. LC/MS (ESI) m/z: 294 $(M+H)^+$.

Step 3

To a solution of methyl (2S,4S)-4-[(tert-butyldimethylsilyl)oxy]-1-chloropyrrolidine-2-carboxylate (4.48 g, 15.3 mmol) in toluene (60 mL) at −10° C. was added TEA (6.4 mL, 46 mmol), the resulting mixture was stirred at rt overnight. The reaction mixture was washed with water and brine, dried over anhydrous $Na_2SO_4$, filtered and concentrated to give the crude intermediate methyl (3S)-3-[(tert-butyldimethylsilyl)oxy]-3,4-dihydro-2H-pyrrole-5-carboxylate (3.5 g) as a clear oil, the crude intermediate was dissolved into DCM (40 mL) and cooled to −10° C., to this solution was added 2,6-lutidine (3.2 mL, 27 mmol) and CbzCl (2.80 g, 16.3 mmol) in small portions and stirred for 24 h at room temperature. Then ethylenediamine (0.25 mL, 3.7 mmol) was added to the mixture, and stirred for 15 min, the mixture was washed with citric acid solution (1.0 N, 30 mL) and aq. HCl (1.0 N, 25 mL) in turn, the organic phase was washed with water, $NaHCO_3$ solution (1.5 N) and brine, dried over anhydrous $Na_2SO_4$, filtered and concentrated, the residue was purified by column chromatography on silica gel (EtOAc in PE=0~30%) to give the desired product 1-benzyl 2-methyl (4S)-4-[(tert-butyldimethylsilyl)oxy]-4,5-dihydro-1H-pyrrole-1,2-dicarboxylate (1.51 g, yield: 26.7%) as a light yellow oil. LC/MS (ESI) m/z: 392 $(M+H)^+$.

Step 4

To a solution of CuBr·$Me_2S$ (630 mg, 3.07 mmol) in THF (5.0 mL) was added EtMgBr (1.3 mL, 3.0 M in THF) dropwise at −40° C. under $N_2$, the mixture was stirred for 1 h at −40° C. before a solution of 1-benzyl 2-methyl (4S)-4-[(tert-butyldimethylsilyl)oxy]-4,5-dihydro-1H-pyrrole-1,2-dicarboxylate (1.00 g, 2.56 mmol) in THF (10 mL) was added. The resulting mixture was stirred for 1 h at −40° C. The reaction mixture was quenched with sat. $NH_4Cl$ solution, extracted with EtOAc (20 mL×3), the combined organic layer washed with brine and dried over anhydrous $Na_2SO_4$, filtered and concentrated, the residue was purified by column chromatography on silica gel (EtOAc in PE=0~30%) to give the desired product 1-benzyl 2-methyl (2S,3R,4S)-4-[(tert-butyldimethylsilyl)oxy]-3-ethylpyrrolidine-1,2-dicarboxylate (200 mg, yield: 17.6%) as a light yellow oil. LC/MS (ESI) m/z: 422 $(M+H)^+$.

Step 5

To a solution of 1-benzyl 2-methyl (2S,3R,4S)-4-[(tert-butyldimethylsilyl)oxy]-3-ethylpyrrolidine-1,2-dicarboxylate (200 mg, 0.48 mmol) in THF (3.0 mL) was added TBAF (0.85 mL, 1.0 M in THF). The resulting mixture was stirred at rt for 1 h. The reaction mixture was diluted with sat. $NH_4Cl$ solution (5 mL), extracted with EtOAc (10 mL×3), the combined organic layer was washed with water and brine, dried over anhydrous $Na_2SO_4$, filtered and concentrated, the residue was purified by column chromatography on silica gel (EtOAc in PE=0~50%) to give the desired product 1-benzyl 2-methyl (2S,3R,4S)-3-ethyl-4-hydroxypyrrolidine-1,2-dicarboxylate (120 mg, yield: 78.2%) as a light yellow oil. LC/MS (ESI) m/z: 308 $(M+H)^+$.

Step 6

To a solution of 1-benzyl 2-methyl (2S,3R,4S)-3-ethyl-4-hydroxypyrrolidine-1,2-dicarboxylate (120 mg, 0.39 mmol) in DCM (3.0 mL) was added DAST (0.07 mL, 0.51 mmol) at 0° C. under $N_2$. The resulting mixture was stirred for 16 h at rt. The reaction mixture was quenched with sat. $NaHCO_3$, extracted with DCM (10 mL×3), the combined organic layer was washed with water and brine, dried over anhydrous $Na_2SO_4$, filtered and concentrated, the residue was purified by column chromatography on silica gel (EtOAc in PE=0~40%) to give the desired product 1-benzyl 2-methyl (2S,3R,4R)-3-ethyl-4-fluoropyrrolidine-1,2-dicarboxylate (110 mg, yield: 86.6%) as a yellow oil; LCMS: ESI m/z 310 $(M+H)^+$.

Step 7

To a solution of 1-benzyl 2-methyl (2S,3R,4R)-3-ethyl-4-fluoropyrrolidine-1,2-dicarboxylate (110 mg, 0.36 mmol) and $(Boc)_2O$ (78 mg, 0.36 mmol) in MeOH (2.0 mL) was added Pd/C (10%, 20 mg) at rt, the resulting suspension was vacuum and refilled with hydrogen, the mixture was stirred at rt for 3 h under a balloon of $H_2$. The reaction mixture was filtered through a pad of celite, the filtrate was concentrated, the residue was purified by column chromatography on silica gel (EtOAc in PE=0~30%) to give the desired product 1-tert-butyl 2-methyl (2S,3R,4R)-3-ethyl-4-fluoropyrrolidine-1,2-dicarboxylate (90 mg, yield: 87%) as an oil. LC/MS (ESI) m/z: 276 $(M+H)^+$.

Step 8

To a solution of 1-tert-butyl 2-methyl (2S,3R,4R)-3-ethyl-4-fluoropyrrolidine-1,2-dicarboxylate (90 mg, 0.38 mmol) in MeOH (3 mL) and $H_2O$ (1 mL) was added NaOH (65 mg, 1.63 mmol) at 0° C. The resulting mixture was stirred for 5 h at room temperature. The reaction mixture was concentrated, and adjusted the pH to 4~5 with 1.0 N HCl solution, extracted with EtOAc (15 mL×3). The combined organic layer was washed with water and brine, dried over anhydrous $Na_2SO_4$, filtered and concentrated to give the crude product (2S,3R,4R)-1-[(tert-butoxy)carbonyl]-3-ethyl-4-fluoropyrrolidine-2-carboxylic acid (70 mg, 78% yield) as a off-white solid which can be used in next step without further purification. LC/MS (ESI) m/z: 206 (M+1-56).

Preparation of Intermediate 40, (1-isopropyl-1H-pyrazol-5-yl)boronic acid

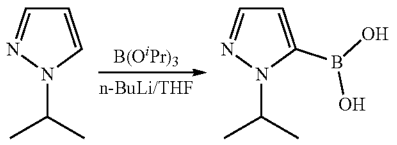

To a solution of 1-(propan-2-yl)-1H-pyrazole (2.01 g, 18.2 mmol) in THF (40 mL) was added n-BuLi (11.0 mL, 27.5 mmol) at −70° C. under $N_2$, the mixture was stirred for 1 h at −70° C. before triisopropyl borate (12.5 mL, 54.46 mmol) was added, the resulting mixture was stirred at rt for 16 h. The reaction mixture was quenched with sat. $NH_4Cl$ solution at 0° C., and adjusted the pH to 6 with 1.0 N HCl. The mixture was extracted with EtOAc (50 mL×3), and the combined organic phase was washed with water and brine, dried over with anhydrous $Na_2SO_4$, filtered and concentrated to give the crude product [1-(propan-2-yl)-1H-pyrazol-5-yl]boronic acid (2 g, yield: 71%) as a white solid which can be used in next step without further purification. LC/MS (ESI) m/z: 523 $(M+H)^+$.

Preparation of Intermediate 41, 5-fluoro-2-methoxybenzoic-3,4-d2 acid

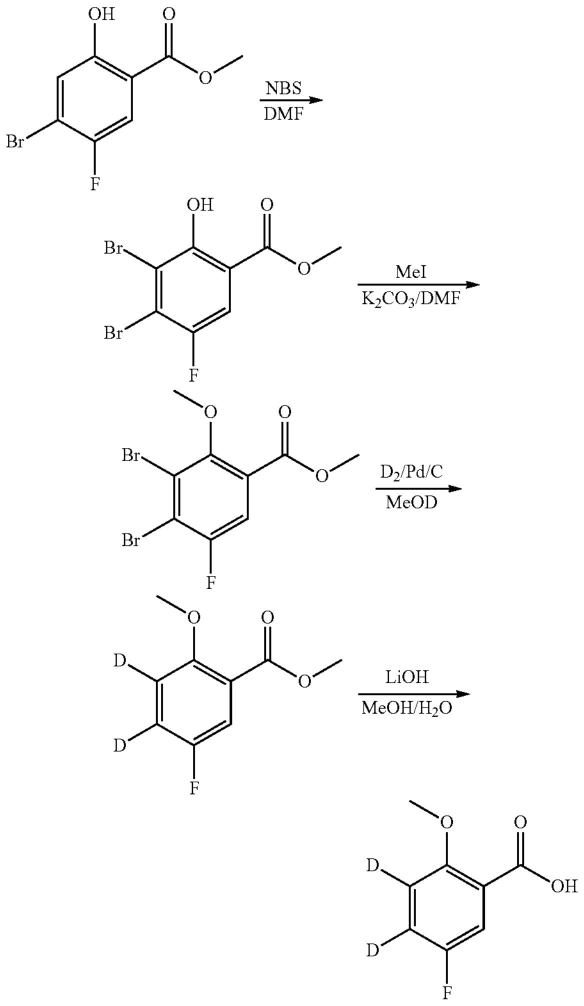

Step 1

To a solution of methyl 4-bromo-5-fluoro-2-hydroxybenzoate (500 mg, 2 mmol) in DMF (3 mL) was added NBS (464 mg, 2.6 mmol) at rt, the resulting mixture was heated to 70° C. for 4 h. After cooled down to rt, water (5 mL) was added and extract with EtOAc (10 ml×3). The combined organic layer was washed with water and brine, dried over anhydrous $Na_2SO_4$, filtered and concentrated give the crude product which was purified by column chromatography on silica gel (EtOAc in PE=0~10%) to give the desired product methyl 3,4-dibromo-5-fluoro-2-hydroxybenzoate (410 mg, yield: 62.3%) as a white solid. 1H NMR (400 MHz, DMSO) δ 11.19 (s, 1H), 7.77 (d, J=8.7 Hz, 1H), 3.94 (s, 3H).

Step 2

To a solution of methyl 3,4-dibromo-5-fluoro-2-hydroxybenzoate (400 mg, 1.2 mmol) in DMF (5 mL) was added MeI (0.2 mL, 3.6 mmol) and $K_2CO_3$ (843 mg, 6.1 mmol), the reaction mixture was stirred at r.t. for 5 h, then water (10 mL) was added and extract with EtOAc (10 mL×3). The combined organic layer was washed with water and brine, dried over $Na_2SO_4$, filtered and concentrated give the crude product which was purified by column chromatography on silica gel (EtOAc in PE=0~10%) to give the desired product methyl 3,4-dibromo-5-fluoro-2-methoxybenzoate (340 mg, yield: 81.5%) as a white solid. LC/MS (ESI) m/z: 417 $(M+H)^+$.

Step 3

To a solution of methyl 3,4-dibromo-5-fluoro-2-methoxybenzoate (340 mg, 0.99 mmol) in MeOD (5 mL) was added Pd/C (25 mg), the resulting mixture was stirred for 10 h under D2 atmosphere at 60° C. Filtered and concentrated to give the crude product methyl 5-fluoro-2-methoxybenzoate-3,4-$d_2$ (85 mg, yield: 45.9%) as a colorless oil which can be used in next step directly without further purification. LC/MS (ESI) m/z: 186 $(M+H)^+$.

Step 4

To a solution of methyl 5-fluoro-2-methoxybenzoate-3,4-$d_2$ (80 mg, 0.43 mmol) in MeOH/$H_2O$ (4 mL/2 mL) was added LiOH·$H_2O$ (72 mg, 1.72 mmol). The resulting mixture was stirred at rt for 2 h under $N_2$ atmosphere. Then the reaction mixture was diluted with $H_2O$ (50 mL), and adjusted the pH to 3-4, extracted with EtOAc (20 mL×3), the combined organic phase was washed with water and brine, dried over anhydrous $Na_2SO_4$, filtered, and concentrated in vacuo to give the crude product 5-fluoro-2-methoxybenzoic-3,4-$d_2$ acid (70 mg, yield: 94.6%) as a white solid. which was used in next step directly without further purification, LC/MS (ESI) m/z: 173 $(M+H)^+$.

Preparation of Intermediate 42, 2-[(5-{2,7-diazaspiro[3.5] nonan-2-yl}-1,2,4-triazin-6-yl) oxy]-N-ethyl-5-fluoro-N-(propan-2-yl) benzamide

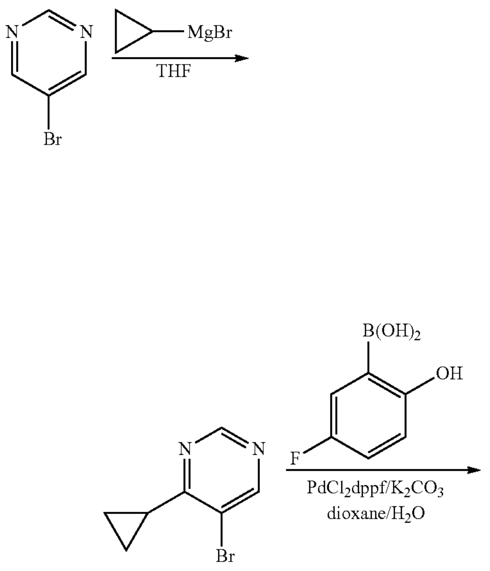

-continued

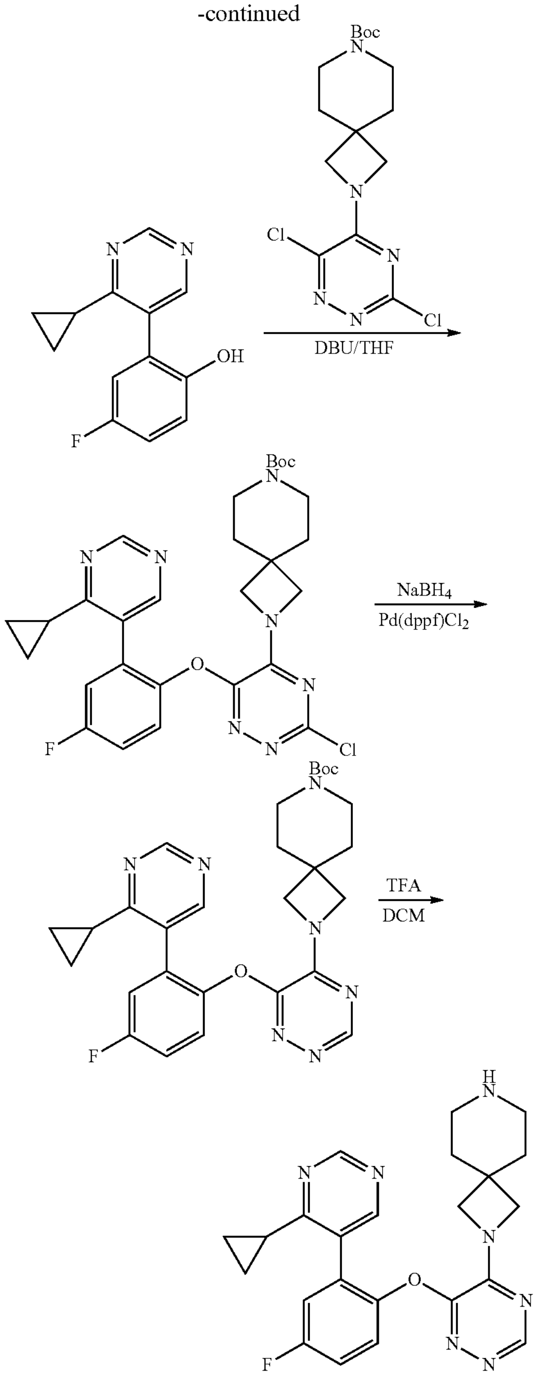

Step 1

To a solution of 5-bromopyrimidine (1.01 g, 6.29 mmol) in THF (15 mL) was added cyclopropylmagnesium bromide (9.43 mL, 9.43 mmol, 1.0 M) dropwise at −20° C. under $N_2$. The resulting mixture was stirred for 2 h at rt. The reaction mixture was quenched with $H_2O$ (0.3 mL) followed by addition of DDQ (1.60 g, 6.92 mmol), the reaction mixture was stirred at rt for 16 h. The reaction mixture was diluted with $H_2O$ (50 mL), extracted with EtOAc (20 mL×3), the combined organic layer was dried over anhydrous $Na_2SO_4$, filtered and concentrated, the residue was purified by chromatography column on silica gel (EtOAc in PE=0~10%) to give the desired product 5-bromo-4-cyclopropylpyrimidine (1.10 g, yield: 83.5%) as a white solid. LC/MS (ESI) m/z: 199 $(M+H)^+$.

Step 2

To a solution of 5-bromo-4-cyclopropylpyrimidine (200 mg, 1.00 mmol) and (5-fluoro-2-hydroxyphenyl)boronic acid (188 mg, 1.21 mmol) in dioxane (5.0 mL) and $H_2O$ (1.0 mL) was added Pd(dppf)$Cl_2$ (20 mg) and $K_2CO_3$ (347 mg, 2.51 mmol), the resulting mixture was stirred at 100° C. for 12 h under $N_2$. The reaction mixture was cooled to rt, diluted with $H_2O$ (20 mL), extracted with EtOAc (20 mL×3), the combined organic layer was washed with water and brine, dried over anhydrous $Na_2SO_4$, filtered and concentrated, the residue was purified by column chromatography on silica gel (EtOAc in PE=0~30%) to give the desired product 2-(4-cyclopropylpyrimidin-5-yl)-4-fluorophenol (200 mg, yield: 82.1%) as a light yellow solid. LC/MS (ESI) m/z: 231 $(M+H)^+$.

Step 3

To a stirred solution of 2-(4-cyclopropylpyrimidin-5-yl)-4-fluorophenol (800 mg, 3.48 mmol) and tert-butyl 2-(3,6-dichloro-1,2,4-triazin-5-yl)-2,7-diazaspiro[3.5]nonane-7-carboxylate (1.30 g, 3.48 mmol) in THF (20 mL) was added DBU (1.04 g, 6.90 mmol) at 0° C. The resulting mixture was stirred at rt for 10 h. The reaction mixture was diluted with $H_2O$ (20 mL), extracted with EtOAc (30 mL×3), the combined organic layer was dried over anhydrous $Na_2SO_4$, filtered and concentrated, the residue was purified by chromatography column on silica gel (EtOAc in PE=10~50%) to obtain the desired product tert-butyl 2-(3-chloro-6-(2-(4-cyclopropylpyrimidin-5-yl)-4-fluorophenoxy)-1,2,4-triazin-5-yl)-2,7-diazaspiro [3.5]nonane-7-carboxylate (849 mg, yield: 43.2%) as a yellow solid. LCMS: ESI m/z 568 $(M+1)^+$.

Step 4

To a solution of tert-butyl 2-(3-chloro-6-(2-(4-cyclopropylpyrimidin-5-yl)-4-fluorophenoxy)-1,2,4-triazin-5-yl)-2,7-diazaspiro [3.5]nonane-7-carboxylate (300 mg, 0.53 mmol) and $NaBH_4$ (20 mg, 0.95 mmol) in THF (5 mL) was added TMEDA (220 mg, 0.53 mmol) and Pd(dppf)$Cl_2 \cdot CH_2Cl_2$ (30 mg) at room temperature, the resulting mixture was stirred overnight at rt. The reaction mixture was diluted with $H_2O$ (10 mL), extracted with EtOAc (20 mL×3), the combined organic layer was dried over anhydrous $Na_2SO_4$, filtered and concentrated, the residue was purified by column chromatography on silica gel (EtOAc in PE-0~50%) to obtain the desired product tert-butyl 2-{6-[2-(4-cyclopropylpyrimidin-5-yl)-4-fluorophenoxy]-1,2,4-triazin-5-yl}-2,7-diazaspiro[3.5]nonane-7-carboxylate (250 mg, yield: 84.3%) as a light yellow solid. LC/MS (ESI) m/z: 534 $(M+H)^+$.

Step 5

To a solution of tert-butyl 2-(6-(2-(4-cyclopropylpyrimidin-5-yl)-4-fluorophenoxy)-1,2,4-triazin-5-yl)-2,7-diazaspiro[3.5]nonane-7-carboxylate (600 mg, 1.12 mmol) in DCM (10 mL) was added TFA (5 mL) at 0° C. The resulting mixture was stirred at rt for 2 h. The reaction mixture was concentrated to give the crude product 2-[(5-{2,7-diazaspiro [3.5] nonan-2-yl}-1,2,4-triazin-6-yl) oxy]-N-ethyl-5-fluoro-N-(propan-2-yl) benzamide (460 mg, yield: 90%) as a brown oil which can be used in next step without further purification. LC/MS (ESI) m/z: 434 $(M+H)^+$.

The following intermediate was prepared from the corresponding chemicals according to experimental procedure for Intermediate 42:

| Intermediate | Structure | Staring materials | LCMS (ESI) m/z |
|---|---|---|---|
| Intermediate 43 | 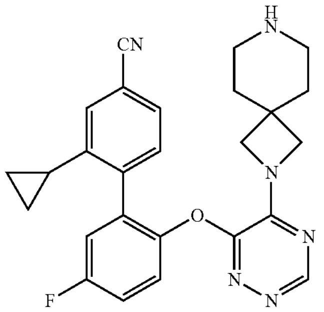 [SMILES: N#Cc1ccc(-c2cc(F)ccc2Oc2nncnc2N2CC3(CCNCC3)C2)c(C2CC2)c1] | Intermediate 33 | 457 $(M + H)^+$ |
Intermediate 44
Preparation of 2-(5-(4-fluoro-2-(1-isopropyl-1H-1,2,4-triazol-5-yl)phenoxy)pyrimidin-4-yl)-2,7-diazaspiro[3.5]no
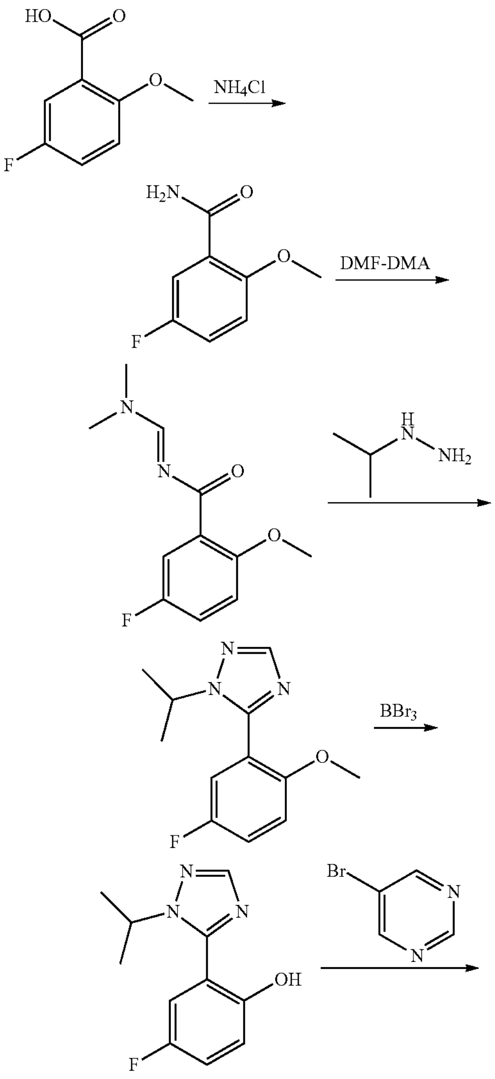
-continued
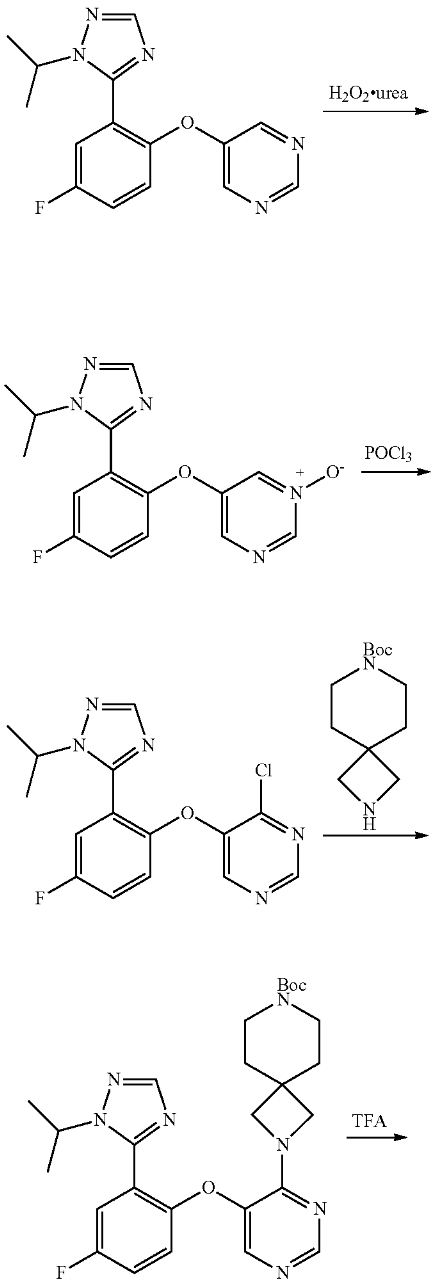

-continued

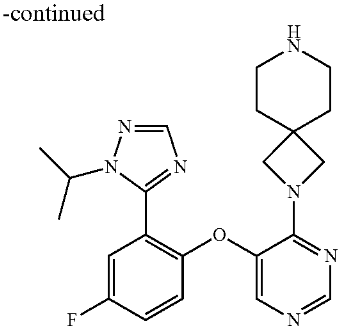

Step 1

To a solution of 5-fluoro-2-methoxybenzoic acid (4.01 g, 23.51 mmol) and DIEPA (5.8 mL, 35.33 mmol) in DCM (40 mL) was added HATU (13.4 g, 35.31 mmol) and $NH_4Cl$ (1.72 g, 31.82 mmol). The resulting mixture was stirred at rt for 3 h. The reaction mixture was quenched with Sat, $NH_4Cl$ solution, extracted with DCM (20 mL×3), the combined organic phase was washed with brine, dried over anhydrous $Na_2SO_4$, filtered and concentrated to give the crude product which was purified by column chromatography on silica gel (EtOAc in PE=10~30%) to obtain the desired product 5-fluoro-2-methoxybenzamide (3.81 g, yield: 95.6%) as a white solid. LC/MS (ESI) m/z: 170 $(M+H)^+$.

Step 2

A solution of 5-fluoro-2-methoxybenzamide (3.81 g, 22.52 mmol) in DMF-DMA (30.1 mL, 224.61 mmol) was heated to 100° C. overnight. the reaction mixture was concentrated under reduced pressure to give the crude product N-[(1E)-(dimethylamino)methylidene]-5-fluoro-2-methoxybenzamide (4.78 g, yield: 95.2%) as a colorless oil which can be used in next step directly without further purification. LC/MS (ESI) m/z 225 $(M+H)^+$.

Step 3

To a solution of N-[(1E)-(dimethylamino)methylidene]-5-fluoro-2-methoxybenzamide (4.78 g, 21.41 mmol) in AcOH (30 mL) was added (propan-2-yl)hydrazine (1.61 g, 22.0 mmol). The resulting mixture was stirred at 100° C. for 1 h. The reaction mixture was concentrated under reduced pressure, to the residue was added Sat $NaHCO_3$ solution (30 mL). Then the mixture was extracted with DCM (20 mL×3), the combined organic phase was washed with brine, dried over anhydrous $Na_2SO_4$, filtered and concentrated in vacuum to give the crude product which was purified by column chromatography on silica gel (EtOAc in PE=0~40%) to obtain the desired product 5-(5-fluoro-2-methoxyphenyl)-1-(propan-2-yl)-1H-1,2,4-triazole (3.98 g, yield: 79.4%) as a light yellow solid. LC/MS (ESI) m/z: 236 $(M+H)^+$.

Step 4

To a solution of 5-(5-fluoro-2-methoxyphenyl)-1-(propan-2-yl)-1H-1,2,4-triazole (1 g, 4.25 mmol) in DCM (10 mL) was added $BBr_3$ (10 mL, 1 mol/L in DCM) dropwise at −60° C. under $N_2$ atmosphere, $BBr_3$ (10 mL, 1.0 M in DCM) dropwise at −60° C. under $N_2$ atmosphere, the resulting mixture was stirred for 2 h at this temperature. Then the reaction mixture was quenched with cooled sat. $NaHCO_3$ at 0° C., the mixture was extracted with DCM (30 mL×3), the combined organic layer was washed with water and brine, dried over anhydrous $Na_2SO_4$, filtered and concentrated to obtain desired product4-fluoro-2-[1-(propan-2-yl)-1H-1,2,4-triazol-5-yl]phenol (700 mg, yield: 74.4%) as a yellow solid. LC/MS (ESI) m/z: 222 $(M+H)^+$.

Step 5

To a mixture of 4-fluoro-2-[1-(propan-2-yl)-1H-1,2,4-triazol-5-yl]phenol (500 mg, 2.30 mmol) and $Cs_2CO_3$ (2.21 g, 6.81 mmol) in DMF (10 mL) was added 5-bromopyrimidine (467 mg, 2.91 mmol). The reaction mixture was heated to 120° C. for 12 h. After cooled to room temperature, the mixture was quenched with sat. $NH_4Cl$ solution (50 mL), extracted with EtOAc (20 mL×3), the combined organic layer was washed with water and brine, dried over anhydrous $Na_2SO_4$, filtered and concentrated to give the crude product which was purified by column chromatography on silica gel (MeOH in DCM=0~4%) to obtain the desired product 5-{4-fluoro-2-[1-(propan-2-yl)-1H-1,2,4-triazol-5-yl]phenoxy}pyrimidine (240 mg, yield: 35.5%) as a light yellow oil. LC/MS (ESI) m/z: 300 $(M+H)^+$.

Step 6

To a solution of 5-{4-fluoro-2-[1-(propan-2-yl)-1H-1,2,4-triazol-5-yl]phenoxy}pyrimidine (240 mg, 0.81 mmol) in THF (10 mL) was added urea hydrogen peroxide (226 mg, 2.42 mmol) and TFAA (0.6 mL, 4.2 mmol) at 0° C. The resulting mixture was stirred at 20° C. for 1 h under $N_2$. The reaction mixture was washed with sat. aq. $NaHCO_3$ (30 mL) and sat. aq. $Na_2S_2O_3$ (30 mL), the water phase was extracted with DCM (15 mL×3), the combined organic phase was washed with water and brine and dried over anhydrous $Na_2SO_4$, filtered and concentrated to obtain the crude product 5-{4-fluoro-2-[1-(propan-2-yl)-1H-1,2,4-triazol-5-yl]phenoxy}pyrimidin-1-ium-1-olate (160 mg, yield: 63.3%) as a brown solid which was used in next step directly without further purification. LC/MS (ESI) m/z:254 $(M+H)^+$.

Step 7

To a solution of 5-{4-fluoro-2-[1-(propan-2-yl)-1H-1,2,4-triazol-5-yl]phenoxy}pyrimidin-1-ium-1-olate (160 mg, 0.52 mmol) in EtOAc (10 mL) was added DIEPA (0.7 mL, 4.10 mmol) and $POCl_3$ (0.15 mL, 1.52 mmol) at 0° C. Then the reaction mixture was stirred at rt for 12 h. The reaction mixture was quenched with sat. $NaHCO_3$, extracted with DCM (15 mL×3), the combined organic layer was washed with water and brine, dried over anhydrous $Na_2SO_4$, filtered and concentrated in vacuo to give the crude product 4-chloro-5-{4-fluoro-2-[1-(propan-2-yl)-1H-1,2,4-triazol-5-yl]phenoxy}pyrimidine (80 mg, yield: 47.2%) as a brown oil which can be used in next step directly without further purification. LC/MS (ESI) m/z: 334 $(M+H)^+$.

Step 8

To a solution of 4-chloro-5-{4-fluoro-2-[1-(propan-2-yl)-1H-1,2,4-triazol-5-yl]phenoxy}pyrimidine (80 mg, 0.24 mmol) and $K_2CO_3$ (132 mg, 0.96 mmol)) in MeCN (10 mL) was added tert-butyl 2,7-diazaspiro[3.5]nonane-7-carboxylate (59.7 mg, 0.31 mmol). The resulting mixture was heated to 80° C. for 5 h. After cooled to room temperature, the reaction mixture was quenched with sat. $NH_4Cl$ solution (10 mL), extracted with EtOAc (15 mL×3), the combined organic layer was washed with water and brine, dried over anhydrous $Na_2SO_4$, filtered and concentrated to give the crude product which was purified by column chromatography on silica gel (EtOAc in PE=0~40%) to obtain the desired product tert-butyl tert-butyl 2-(5-{4-fluoro-2-[1-(propan-2-yl)-1H-1,2,4-triazol-5-yl]phenoxy}pyrimidin-4-yl)-2,7-diazaspiro[3.5]nonane-7-carboxylate (30 mg, yield: 23.9%) as a white solid. LC/MS (ESI) m/z: 524 ($M+H^+$).

Step 9

To a solution of tert-butyl 2-(5-{4-fluoro-2-[1-(propan-2-yl)-1H-1,2,4-triazol-5-yl]phenoxy}pyrimidin-4-yl)-2,7-diazaspiro[3.5]nonane-7-carboxylate (30 mg, 0.06 mmol) in DCM (5 mL) was added TFA (2 mL) dropwise at room temperature, the resulting mixture was stirred for 2 h at rt. The reaction mixture was concentrated to give the crude product 2-(5-{4-fluoro-2-[1-(propan-2-yl)-1H-1,2,4-triazol-5-yl]phenoxy}pyrimidin-4-yl)-2,7-diazaspiro[3.5]nonane (15 mg, yield: 61.8%)) as a light yellow solid which can be used in next step directly without further purification. LC/MS (ESI) m/z: 213 (½ $M+H^+$).

Preparation of Intermediate 45, 2-(5-(2-(4-chloro-1-isopropyl-1H-pyrazol-5-yl)-4-fluorophenoxy)pyrimidin-4-yl)-2,7-diazaspiro[3.5]nonane

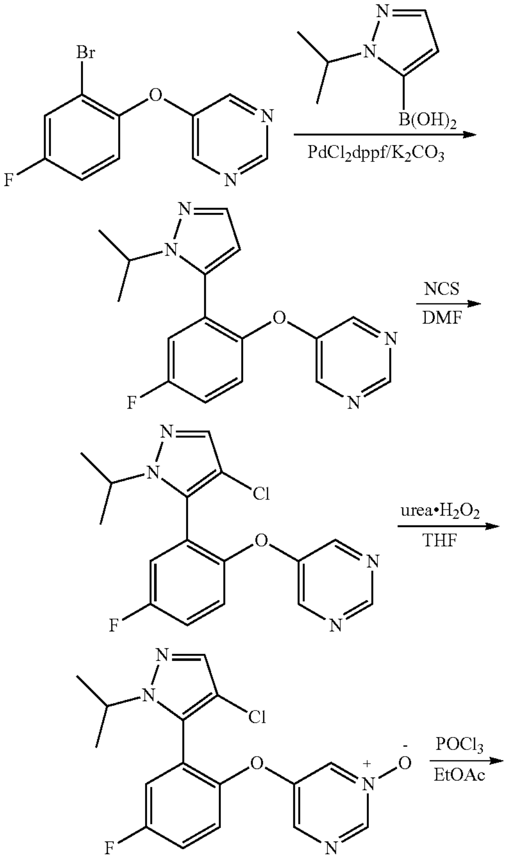

-continued

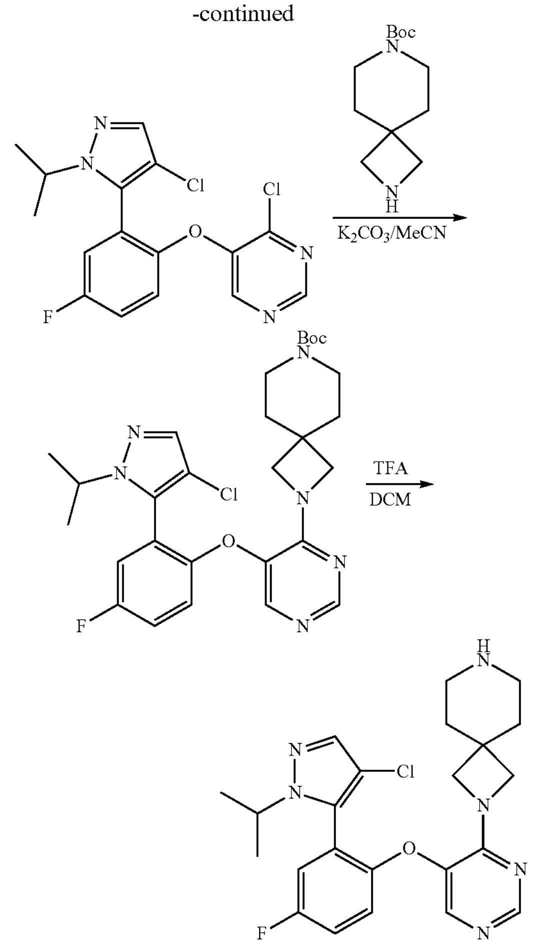

Step 1

To a solution of [1-(propan-2-yl)-1H-pyrazol-5-yl]boronic acid (686 mg, 4.46 mmol) and 5-(2-bromo-4-fluorophenoxy)pyrimidine (800 mg, 2.97 mmol) in dioxane (20 mL) and $H_2O$ (2.0 mL) was added $K_2CO_3$ (1.2 g, 8.9 mmol) and Pd(dppf)$Cl_2$ (217 mg, 0.29 mmol) at rt, the resulting mixture was stirred at 100° C. for 2 h under $N_2$. The reaction mixture was cooled to rt, quenched with $H_2O$ (5 mL), extracted with EtOAc (30 mL×3), the combined organic layer was dried over anhydrous $Na_2SO_4$, filtered and concentrated to give the crude product which was purified by column chromatography on silica gel (EtOAc in PE=0~50%) to give the desired product 5-{4-fluoro-2-[1-(propan-2-yl)-1H-pyrazol-5-yl]phenoxy}pyrimidine (602 mg, yield: 68%) as a yellow solid. 1H NMR (400 MHZ, DMSO) δ 8.91 (s, 1H), 8.47 (s, 2H), 7.46 (s, 1H), 7.44-7.40 (m, 1H), 7.39-7.34 (m, 2H), 6.25 (d, J=1.2 Hz, 1H), 4.39-4.31 (m, 1H), 1.29 (d, J=6.4 Hz, 6H), LC/MS (ESI) m/z: 299 $(M+H)^+$.

Step 2

To a solution of 5-{4-fluoro-2-[1-(propan-2-yl)-1H-pyrazol-5-yl]phenoxy}pyrimidine (600 mg, 2.01 mmol) in DMF (10 mL) was added NCS (268 mg, 2.01 mmol) dropwise at room temperature, the resulting mixture was stirred for 3 h. The reaction mixture was quenched with $H_2O$ (10 mL), extracted with EtOAc (20 mL×3), the combined organic layer was dried over anhydrous $Na_2SO_4$, filtered and concentrated, the residue was purified by column chromatography on silica gel (EtOAc in PE=0~80%) to give the desired product 5-{2-[4-chloro-1-(propan-2-yl)-1H-pyrazol-5-yl]-4-fluorophenoxy}pyrimidine (401 mg, yield: 65.7%) as a light yellow solid. $^1H$ NMR (400 MHZ, DMSO) δ 8.93 (s, 1H), 8.48 (s, 2H), 7.63 (s, 1H), 7.55-7.40 (m, 3H), 4.34-4.25 (m, 1H), 1.28 (dd, J=11.7, 6.5 Hz, 6H). LC/MS (ESI) m/z: 333 $(M+H)^+$.

Step 3

To a solution of 5-{2-[4-chloro-1-(propan-2-yl)-1H-pyrazol-5-yl]-4-fluorophenoxy}pyrimidine (150 mg, 0.45 mmol) in THF (5 mL) was added urea. $H_2O_2$ (127 mg, 1.35 mmol) and TFAA (568 mg, 2.71 mmol) portion wise at 0° C., the resulting mixture was warmed to room temperature and stirred for 3 h. The reaction mixture was quenched with sat. $NaHCO_3$, extracted with EtOAc (50 mL×3), the combined organic layer was washed with water and brine, dried over anhydrous $Na_2SO_4$, filtered and concentrated to give the crude product 5-{2-[4-chloro-1-(propan-2-yl)-1H-pyrazol-5-yl]-4-fluorophenoxy}pyrimidin-1-ium-1-olate (120 mg, yield: 76.3%) as a brown solid which can be used in next step without further purification. LC/MS (ESI) m/z: 349 $(M+H)^+$.

Step 4

To a solution of 5-{2-[4-chloro-1-(propan-2-yl)-1H-pyrazol-5-yl]-4-fluorophenoxy}pyrimidin-1-ium-1-olate (120 mg, 0.34 mmol) in EtOAc (3 mL) was added $POCl_3$ (0.10 mL, 1.0 mmol) and DIPEA (0.23 mL, 1.4 mmol) dropwise at 0° C. The resulting mixture was warmed to room temperature and stirred overnight. The reaction mixture was quenched with sat. $NaHCO_3$, extracted with DCM (10 mL×3), the combined organic layer was washed with water and brine, dried over anhydrous $Na_2SO_4$, filtered and concentrated to give the crude product 4-chloro-5-{2-[4-chloro-1-(propan-2-yl)-1H-pyrazol-5-yl]-4-fluorophenoxy}pyrimidine (110 mg, yield: 87.1%) as a brown oil which can be used in next step without further purification. LC/MS (ESI) m/z: 367 $(M+H)^+$.

Step 5

To a solution of 4-chloro-5-{2-[4-chloro-1-(propan-2-yl)-1H-pyrazol-5-yl]-4-fluorophenoxy}pyrimidine (110 mg, 0.30 mmol) in DMF (5 mL) was added tert-butyl 2,7-diazaspiro[3.5]nonane-7-carboxylate (67 mg, 0.30 mmol) and $K_2CO_3$ (124 mg, 0.89 mmol) at room temperature. The resulting reaction was stirred overnight at rt. The reaction mixture was quenched with $H_2O$ (5 mL), extracted with EtOAc (10 mL×3), the combined organic layer was washed with water and brine, dried over anhydrous $Na_2SO_4$, filtered and concentrated, the residue was purified by column chromatography on silica gel (EtOAc in PE=0~50%) to give the desired tert-butyl 2-(5-{2-[4-chloro-1-(propan-2-yl)-1H-pyrazol-5-yl]-4-fluorophenoxy}pyrimidin-4-yl)-2,7-diazaspiro[3.5]nonane-7-carboxylate (100 mg, yield: 59.9%) as a white solid. LC/MS (ESI) m/z: 557 $(M+H)^+$.

Step 6

To a solution of tert-butyl 2-(5-(2-(4-chloro-1-isopropyl-1H-pyrazol-5-yl)-4-fluorophenoxy)pyrimidin-4-yl)-2,7-diazaspiro[3.5]nonane-7-carboxylate (100 mg, 0.18 mmol) in DCM (3.0 mL) was added TFA (1.0 mL) dropwise at room temperature and the resulting mixture was stirred for 1 h at rt. The reaction mixture was concentrated to give the crude product 2-(5-{2-[4-chloro-1-(propan-2-yl)-1H-pyrazol-5-yl]-4-fluorophenoxy}pyrimidin-4-yl)-2,7-diazaspiro[3.5]nonane (60 mg, yield: 73%) as a light yellow syrup which can be used in next step directly without further purification. LC/MS (ESI) m/z: 457 $(M+H)^+$.

Preparation of Intermediate 46, Trans-1-(tert-butoxycarbonyl)-3-(fluoromethyl)pyrrolidine-2-carboxylic acid

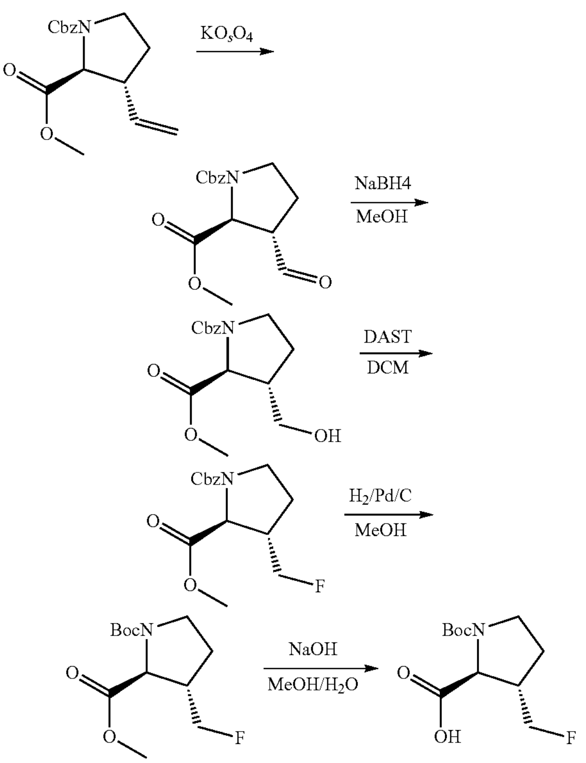

Step 1: To a solution of 1-benzyl 2-methyl trans-3-ethenylpyrrolidine-1,2-dicarboxylate (1.30 g, 4.49 mmol, see Intermediate 37 for its synthesis), $NaIO_4$ (3.00 g, 13.48 mmol) and Potassium osmate dihydrate (0.17 g, 0.45 mmol) in MeOH (30 mL) and $H_2O$ (50 mL), the resulting mixture was stirred for 4 h at room temperature. Then the reaction mixture was diluted with $H_2O$ (20 mL) and extracted with DCM (50 mL×3). The combined organic phase was washed with water and brine, dried over anhydrous $Na_2SO_4$, filtered, and concentrated to give the crude product which was purified by column chromatography on silica gel (EtOAc in PE=0~50%) to obtain the desired product 1-benzyl 2-methyl trans-3-formylpyrrolidine-1,2-dicarboxylate (700 mg, 2.40 mmol, 53.48%) as a colorless oil. LC/MS (ESI) m/z: 292 $(M+H)^+$.

Step 2

To a solution of 1-benzyl 2-methyl trans-3-formylpyrrolidine-1,2-dicarboxylate (200 mg, 0.69 mmol) in MeOH (5 mL) at 0° C. was added $NaBH_4$ (5 mg, 0.14 mmol) slowly. The resulting mixture was stirred at rt for 2 h. Then the reaction mixture was quenched with Sat. $NH_4Cl$ solution (5 mL), extracted with EtOAc (10 mL×3), the combined organic phase was washed with water and brine, dried over anhydrous $Na_2SO_4$, filtered, and concentrated to give the crude product 1-benzyl 2-methyl trans-3-(hydroxymethyl) pyrrolidine-1,2-dicarboxylate (160 mg, 79.4%) as a light yellow oil. LC/MS (ESI) m/z: 294 $(M+H)^+$.

Step 3

To a solution of 1-benzyl 2-methyl trans-3-(hydroxymethyl)pyrrolidine-1,2-dicarboxylate (160 mg, 0.55 mmol) in DCM (5 mL) was added DAST (132 mg, 0.82 mmol) at 0° C. under $N_2$. The resulting mixture was stirred for 16 h at rt. The reaction mixture was quenched with sat. $NaHCO_3$, extracted with DCM (10 mL×3), the combined organic layer was washed with water and brine, dried over anhydrous $Na_2SO_4$, filtered and concentrated, the residue was purified by column chromatography on silica gel (EtOAc in PE=0~20%) to obtain the desired product 1-benzyl 2-methyl trans-3-(fluoromethyl)pyrrolidine-1,2-dicarboxylate (80 mg, 0.27 mmol, 49.6%) as a brown oil; LCMS: ESI m/z 296 $(M+H)^+$.

Step 4

To a solution of 1-benzyl 2-methyl trans-3-(fluoromethyl) pyrrolidine-1,2-dicarboxylate (80 mg, 0.27 mmol) and $(Boc)_2O$ (77 mg, 0.35 mmol) in MeOH (5 mL) was added Pd/C (10%, 20 mg) at rt, the resulting suspension was vacuum and refilled with hydrogen, the mixture was stirred at rt for 3 h under a balloon of $H_2$. The reaction mixture was filtered through a pad of celite, the filtrate was concentrated, the residue was purified by column chromatography on silica gel (EtOAc in PE=0~ 30%) to give the desired product 1-(tert-butyl) 2-methyl trans-3-(fluoromethyl)pyrrolidine-1,2-dicarboxylate (50 mg, 70.6%) as an oil. LC/MS (ESI) m/z: 262 $(M+H)^+$.

Step 5

To a solution of 1-(tert-butyl) 2-methyl trans-3-(fluoromethyl)pyrrolidine-1,2-dicarboxylate (50 mg, 0.19 mmol) in MeOH (3 mL) and $H_2O$ (1 mL) was added NaOH (20 mg, 0.50 mmol) at 0° C. The resulting mixture was stirred for 5 h at room temperature. The reaction mixture was concentrated, and adjusted the pH to 4~5 with 1.0 N HCl solution, extracted with EtOAc (15 mL×3). The combined organic layer was washed with water and brine, dried over anhydrous $Na_2SO_4$, filtered and concentrated to give the crude product trans-1-(tert-butoxycarbonyl)-3-(fluoromethyl)pyrrolidine-2-carboxylic acid (40 mg, 85.2% yield) as a brown solid which can be used in next step without further purification. LC/MS (ESI) m/z: 248 (M+1-56).

Preparation of Intermediate 47, 5-(2-((5-(2,7-diazaspiro[3.5]nonan-2-yl)-1,2,4-triazin-6-yl)oxy)-5-fluorophenyl)-6-cyclopropylpicolinonitrile compound

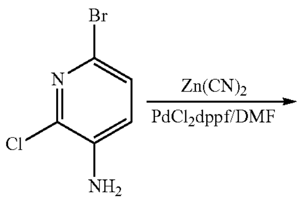

-continued

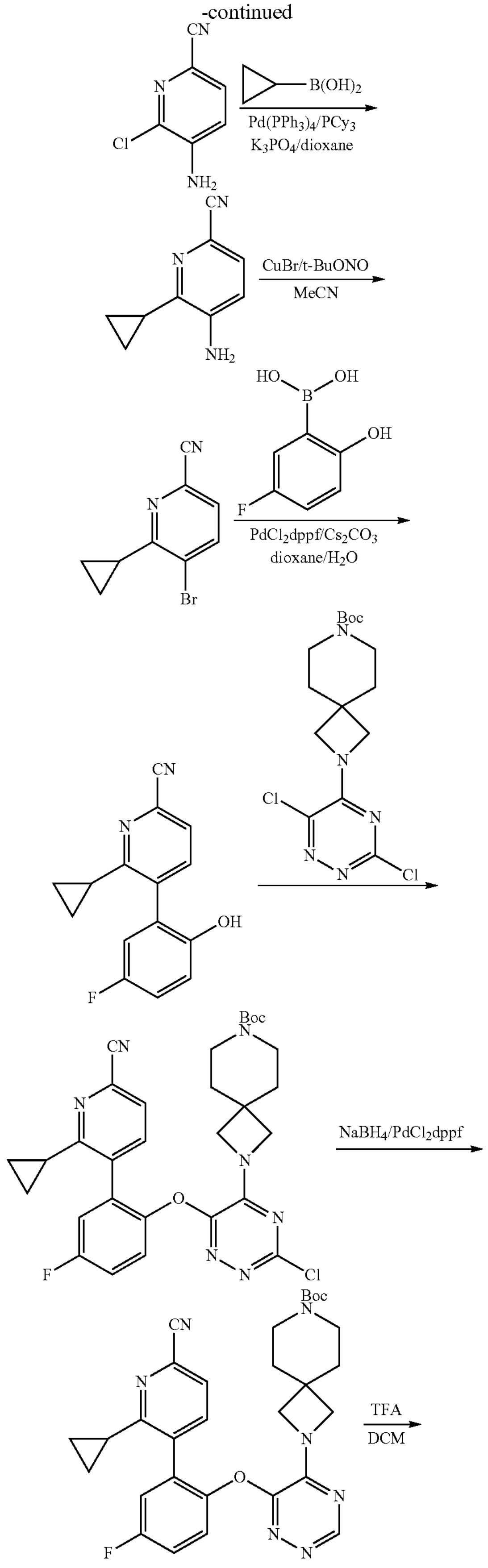

-continued

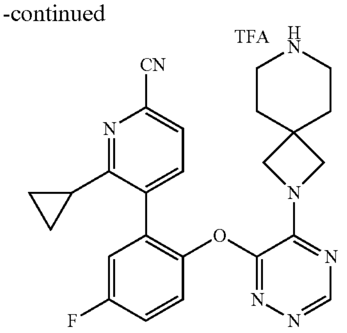

Step 1

To a solution of 6-bromo-2-chloropyridin-3-amine (2.30 g, 11.09 mmol) and $Zn(CN)_2$ (0.98 g, 8.32 mmol) in DMF (25 mL) was added $Pd(PPh_3)_4$ (0.38 g, 0.33 mmol) at rt. The resulting mixture was heated to 85° C. for 12 h under $N_2$ atmosphere. The reaction mixture was quenched with Sat. $NH_4Cl$ solution, extracted with EtOAc (20 mL×3), The combined organic layer was washed with brine, dried over $Na_2SO_4$, filtered and concentrated to give the crude product which was purified by column chromatography on silica gel (EtOAc in PE=0~30%) to afford the desired product 5-amino-6-chloropyridine-2-carbonitrile (500 mg, yield: 29.4%) as a light-yellow solid, LC/MS (ESI) m/z: 154 $(M+H)^+$.

To a solution of 5-amino-6-chloropyridine-2-carbonitrile (2.71 g, 17.58 mmol), cyclopropylboronic acid (1.96 g, 22.86 mmol) and tricyclohexylphosphane (1.97 g, 7.03 mmol) in toluene (80 mL) and $H_2O$ (10 mL) was added $Pd(AcO)_2$ (40 mg, 0.18 mmol) and $K_3PO_4$ (14.9 g, 70.33 mmol). The resulting mixture was stirred at 100° C. for 10 h under $N_2$ atmosphere. The reaction mixture was diluted with Sat. $NH_4Cl$ solution, extracted with EtOAc (20 mL×3). The combined organic phase was washed with brine, dried over $Na_2SO_4$, filtered and concentrated to give the crude product which was purified by column chromatography on silica gel (EtOAc in PE=5~30%) to afford the desired product 5-amino-6-cyclopropylpyridine-2-carbonitrile (1.12 g, yield: 40.1%) as a yellow solid. LC/MS (ESI) m/z: 160 $(M+H)^+$.

Step 3

To a stirred solution of t-BuONO (2.53 mL, 21.11 mmol) and CuBr (4.04 g, 28.14 mmol) in MeCN (20 mL) at 70° C. was added a solution of 5-amino-6-cyclopropylpyridine-2-carbonitrile (1.12 g, 7.04 mmol) in MeCN (10 mL) dropwised. The resulting mixture was stirred at the same temperature for 1 h. The reaction mixture was quenched with Sat. $NH_4Cl$ solution (30 mL), the mixture was extracted with EtOAc (20 mL×3), the combined organic layer was washed with brine, dried over $Na_2SO_4$ filtered and concentrated. The residue was purified by column chromatography on silica gel (EtOAc in PE=0~10%) to give the desired product 5-bromo-6-cyclopropylpyridine-2-carbonitrile (1 g, yield: 63.7%) as a yellow solid. LC/MS (ESI) m/z: 223 $(M+H)^+$.

Step 4

To a solution of 5-bromo-6-cyclopropylpyridine-2-carbonitrile (1.00 g, 4.48 mmol), (5-fluoro-2-hydroxyphenyl) boronic acid (1.05 g, 6.72 mmol) in dioxane (10 mL) and $H_2O$ (2 mL) was added $Pd(dppf)Cl_2$ (50 mg) and $Cs_2CO_3$ (4.38 g, 13.45 mmol), the resulting mixture was stirred at 100° C. for 2 h under $N_2$. The reaction mixture was cooled to rt, quenched with $H_2O$ (5 mL), extracted with EtOAc (30 mL×3), the combined organic layer was dried over anhydrous $Na_2SO_4$, filtered and concentrated. The residue was purified by column chromatography on silica gel (EtOAc in PE=5~30%) to give the desired product 6-cyclopropyl-5-(5-fluoro-2-hydroxyphenyl)pyridine-2-carbonitrile (740 mg, yield: 64.9%) as a colorless oil. LC/MS (ESI) m/z: 255 $(M+H)^+$.

Step 5

To a stirred solution of 6-cyclopropyl-5-(5-fluoro-2-hydroxyphenyl)pyridine-2-carbonitrile (740 mg, 2.91 mmol) and tert-butyl 2-(dichloro-1,2,4-triazin-5-yl)-2,7-diazaspiro[3.5]nonane-7-carboxylate (762 mg, 2.04 mmol, see Intermediate 34 for its synthesis) in THF (15 mL) was added DBU (0.65 mL, 4.37 mmol) at 0° C. The resulting mixture was stirred at rt for 10 h at rt. The reaction mixture was diluted with $H_2O$ (20 mL), extracted with EtOAc (30 mL×3), the combined organic layer was dried over anhydrous $Na_2SO_4$, filtered and concentrated. The residue was purified by chromatography column on silica gel (EtOAc in PE=0~50%) to afford the desired product tert-butyl 2-{3-chloro-6-[2-(6-cyano-2-cyclopropylpyridin-3-yl)-4-fluorophenoxy]-1,2,4-triazin-5-yl}-2,7-diazaspiro[3.5]nonane-7-carboxylate (440 mg, yield: 25.5%) as a white solid. LCMS: ESI m/z 592 $(M+H)^+$.

Step 6

To a solution of tert-butyl 2-{3-chloro-6-[2-(6-cyano-2-cyclopropylpyridin-3-yl)-4-fluorophenoxy]-1,2,4-triazin-5-yl}-2,7-diazaspiro[3.5]nonane-7-carboxylate (600 mg, 1.01 mmol), [3-(dimethylamino)propyl]dimethylamine (263 mg, 2.03 mmol) in THF (15 mL) was added $NaBH_4$ (63 mg, 1.86 mmol) and $Pd(dppf)Cl_2$ (30 mg). The reaction mixture was stirred at rt for 12 h under $N_2$ atmosphere, quenched with Sat. $NH_4Cl$ solution (30 mL), and extracted with EtOAc (20 mL×3). The combined organic layer was washed with brine, dried over $Na_2SO_4$, filtered and concentrated to give the crude product which was purified by column chromatography on silica gel (EtOAc in PE=0~40%) to obtain the desired product tert-butyl 2-{6-[2-(6-cyano-2-cyclopropylpyridin-3-yl)-4-fluorophenoxy]-1,2,4-triazin-5-yl}-2,7-diazaspiro[3.5]nonane-7-carboxylate (240 mg, yield: 42.5%) as a white solid. LCMS: ESI m/z 558 $(M+H)^+$.

Step 7

To a solution of tert-butyl 2-{6-[2-(6-cyano-2-cyclopropylpyridin-3-yl)-4-fluorophenoxy]-1,2,4-triazin-5-yl}-2,7-diazaspiro[3.5]nonane-7-carboxylate (240 mg, 0.43 mmol) in DCM (5.0 mL) was added TFA (2.0 mL) dropwise at room temperature and the resulting mixture was stirred for 1 h at rt. The reaction mixture was concentrated to give the crude product 5-(2-((5-(2,7-diazaspiro[3.5]nonan-2-yl)-1,2,4-triazin-6-yl)oxy)-5-fluorophenyl)-6-cyclopropylpicolinonitrile as a TFA salt (200 mg, yield: 75.1%) which can be used in next step directly without further purification. LC/MS (ESI) m/z: 458 $(M+H)^+$.

Preparation of Intermediate 48, 2-((3-chloro-5-(2,7-diazaspiro[3.5]nonan-2-yl)-1,2,4-triazin-6-yl)oxy)-N-ethyl-5-fluoro-N-isopropylbenzamide

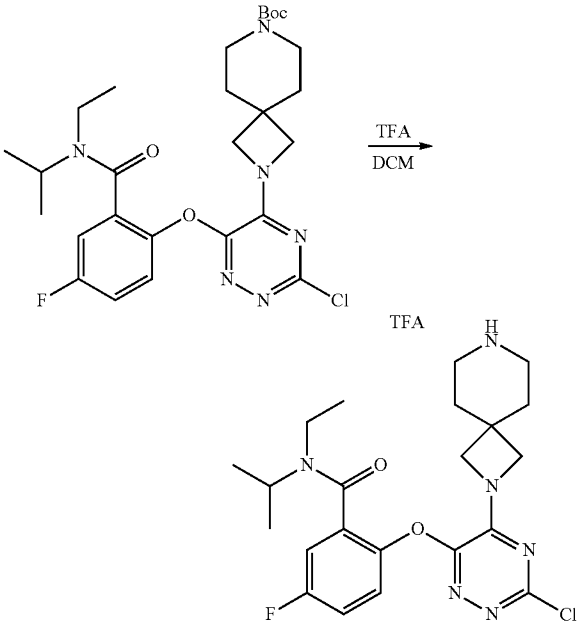

To a solution of tert-butyl 2-(3-chloro-6-(2-(ethyl(isopropyl)carbamoyl)-4-fluorophenoxy)-1,2,4-triazin-5-yl)-2,7-diazaspiro[3.5]nonane-7-carboxylate (200 mg, 0.36 mmol, see Intermediate 34 for its synthesis) in DCM (5.0 mL) was added TFA (2.0 mL) dropwise at room temperature and the resulting mixture was stirred for 1 h at rt. The reaction mixture was concentrated to give the crude product 2-((3-chloro-5-(2,7-diazaspiro[3.5]nonan-2-yl)-1,2,4-triazin-6-yl)oxy)-N-ethyl-5-fluoro-N-isopropylbenzamide as a 2,2,2-trifluoroacetate salt (150 mg, yield: 74.4%) which can be used in next step directly without further purification. LC/MS (ESI) m/z: 463 $(M+H)^+$.

Preparation of Intermediate 49, rel-(2R,3R,4S)-1-(tert-butoxycarbonyl)-3,4-dimethylpyrrolidine-2-carboxylic acid

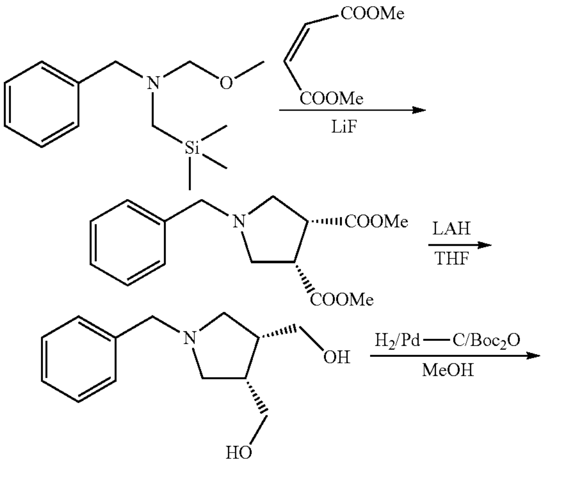

-continued

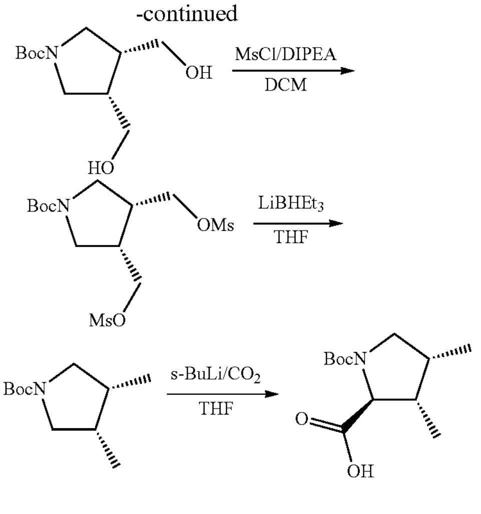

Step 1

To a stirred solution of benzyl(methoxymethyl)[(trimethylsilyl)methyl]amine (21.5 mL, 84.24 mmol) and 1,4-dimethyl (2Z)-but-2-enedioate (10.6 mL, 84.24 mmol) in MeCN (150 mL) at 25° C. was added LiF (2.66 g, 102.31 mmol), and the resulting mixture was stirred at 25° C. for 18 h under $N_2$ atmosphere. The reaction mixture was then diluted with Sat. $NH_4Cl$ solution (100 mL), and extracted with EtOAc (200 mL×3). The combined organic phase was washed by water and brine sequentially, the organic phase was dried over anhydrous $Na_2SO_4$, filtered, and concentrated to give the crude product which was purified by column chromatography on silica gel (EtOAc in PE=0~ 30%) to give the desired product cis-3,4-dimethyl 1-benzylpyrrolidine-3,4-dicarboxylate (22.1 g, yield: 94.2%) as a light-yellow oil. $^1H$ NMR (400 MHZ, $CDCl_3$) δ 7.31-7.23 (m, 5H), 3.66 (s, 8H), 3.33-3.28 (m, 2H), 3.17-3.12 (m, 2H), 2.77-2.67 (m, 2H), LC/MS (ESI) m/z: 278 $(M+H)^+$.

Step 2

To a stirred solution of cis-dimethyl 1-benzylpyrrolidine-3,4-dicarboxylate (10.0 g, 36.06 mmol) in THF (50 mL) at 0° C. was added LAH (4.5 g, 118.58 mmol) in small portions. The resulting mixture was stirred at 60° C. for 18 h under $N_2$ atmosphere, and then quenched with water (4.5 mL), 15% NaOH solution (4.5 mL) and water (13.5 mL) dropwise. The mixture was filtered through celite and the filtrate was extracted with EtOAc (100 mL×3). The combined organic phase was washed with water and brine, and the organic phase was dried over anhydrous $Na_2SO_4$, filtered and concentrated to give the crude product which was purified by column chromatography on silica gel (MeOH in DCM=1~10%) to give the desired product cis-[1-benzyl-4-(hydroxymethyl)pyrrolidin-3-yl]methanol (7.03 g, yield: 87.7%) as a colorless oil. LC/MS (ESI) m/z: 222 $(M+H)^+$.

Step 3

To a stirred solution of cis-[1-benzyl-4-(hydroxymethyl)pyrrolidin-3-yl]methanol (4.00 g, 18.07 mmol) and $Boc_2O$ (4.95 g, 22.91 mmol) in MeOH (50 mL) were added TEA (1.49 g, 14.85 mmol) and 10% Pd/C (500 mg) at rt slowly. The resulting mixture was stirred at rt for 18 h under $H_2$ atmosphere, and then poured into water (200 mL). The mixture was extracted with EtOAc (200 mL×3), and the combined organic phase was washed by water and brine, dried over anhydrous $Na_2SO_4$, filtered, and concentrated to give the crude product which was purified by column chromatography on silica gel (EtOAc in PE=0~20%) to give the desired product tert-butyl cis-3,4-bis(hydroxymethyl) pyrrolidine-1-carboxylate (3.50 g, yield: 83.7%) as a colorless oil. LC/MS (ESI) m/z: 176 $(M+H-56)^+$.

Step 4:

To a stirred solution of cis-tert-butyl 3,4-bis(hydroxymethyl)pyrrolidine-1-carboxylate (4.00 g, 17.29 mmol) and DIPEA (10.2 mL, 61.90 mmol) in DCM (50 mL) was added MsCl (4.05 mL, 52.38 mmol) at 0° C. in 10 min. The resulting mixture was stirred at 25° C. for 18 h under $N_2$ atmosphere, quenched with Sat. $NH_4Cl$ solution (20 mL), and extracted with DCM (50 mL×3). The combined organic phase was washed with water and brine, the organic phase was dried over anhydrous $Na_2SO_4$, filtered and concentrated to give the crude product which was purified by column chromatography on silica gel (EtOAc in PE=0~20%) to give the desired product tert-butyl cis-3,4-bis(((methylsulfonyl) oxy)methyl)pyrrolidine-1-carboxylate (5.81 g, yield: 86.6%) as a light yellow oil. LC/MS (ESI) m/z: 332 $(M+H-56)^+$.

Step 5

To a stirred solution of tert-butyl cis-3,4-bis(((methylsulfonyl)oxy)methyl)pyrrolidine-1-carboxylate (5.81 g, 14.97 mmol) was added $LiEt_3BH$ (100 mL, 100 mmol) at 0° C. in 30 min. The resulting mixture was stirred at 25° C. for 12 h under $N_2$ atmosphere, quenched with sat. $NH_4Cl$ solution (10 mL), and extracted with EtOAc (50 mL×3). The combined organic phase was washed with water and brine, dried over anhydrous $Na_2SO_4$, filtered, and concentrated. The crude product was purified by column chromatography on silica gel (EtOAc in PE=0~10%) to give the desired product tert-butyl cis-3,4-dimethylpyrrolidine-1-carboxylate (1.50 g, yield: 50.3%) as a light-yellow oil. 1H NMR (400 MHZ, $CDCl_3$) δ 3.46-3.42 (m, 2H), 3.04-3.00 (m, 2H), 2.34-2.14 (m, 2H), 1.46 (s, 9H), 0.92 (d, J=6.7 Hz, 6H).

Step 6

To a stirred solution of tert-butyl cis-3,4-dimethylpyrrolidine-1-carboxylate (300 mg, 1.51 mmol) in THF (3 mL) at −78° C. was added s-BuLi (1.5 mL, 1.950 mmol) dropwised in 30 min. The resulting mixture was stirred for 3 h at the same temperature, then to it was bubbled with $CO_2$ for 1 h (maintain the inner temperature below-70° C.). After warmed to room temperature, the mixture was quenched with 1N HCl to pH=5, and extracted with EtOAc (30 mL×3). The combined organic phase was washed with water and brine, dried over anhydrous $Na_2SO_4$, filtered, and concentrated to give the crude product product rel-(2S,3S,4R)-1-(tert-butoxycarbonyl)-3,4-dimethylpyrrolidine-2-carboxylic acid (120 mg, yield: 32.8%) as a yellow semisolid which can be used in next step directly without further purification. LC/MS (ESI) m/z: 144 $(M+H-100)^+$.

Preparation of Intermediate 50, 2-[(tert-butoxy)carbonyl]-5,5-difluoro-octahydrocyclopenta[c]pyrrole-1-carboxylic acid

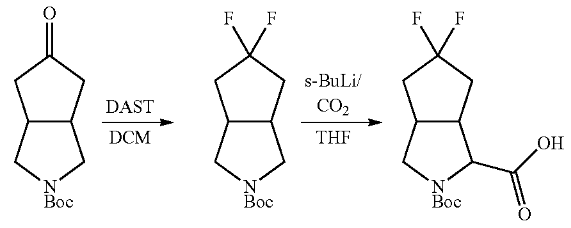

Step 1

To a solution of tert-butyl cis-5-oxo-octahydrocyclopenta[c]pyrrole-2-carboxylate (5.00 g, 22.19 mmol) in THF (30 mL) at 0° C. was added DAST (11.7 mL, 88.77 mmol) slowly, the reaction mixture was stirred at 25° C. for 72 h under $N_2$ atmosphere. The reaction mixture was quenched with Sat. $NH_4Cl$ solution (10 mL), the mixture was extracted with EtOAc (50 mL×3), the combined organic phase was washed by water and brine, dried over anhydrous $Na_2SO_4$, filtered and concentrated. The residue was purified by column chromatography on silica gel (EtOAc in PE=0~ 40%) to obtain the desired product tert-butyl cis-5,5-difluoro-octahydrocyclopenta[c]pyrrole-2-carboxylate (4 g, yield: 72.8%) as a light-yellow oil. LC/MS (ESI) m/z: 248 $(M+H)^+$.

Step 2

To a solution of tert-butyl cis-5,5-difluoro-octahydrocyclopenta[c]pyrrole-2-carboxylate (3.21 g, 12.94 mmol) in THF (20 mL) at −78° C. was added s-BuLi (29.8 mL, 38.82 mmol). After stirred at −78° C. for 4 h under $N_2$ atmosphere, the resulting mixture was stirred for 5 h under $CO_2$ atmosphere at −78° C., and then allowed to return to rt gradually, and stirred for another 12 h at rt. The mixture was quenched with 1N HCl solution, adjusted to pH of 4~5, and extracted with EtOAc (30 mL×3). The combined organic layer was washed by brine, dried over anhydrous $Na_2SO_4$, filtered and concentrated to afford the crude product 2-[(tert-butoxy)carbonyl]-5,5-difluoro-octahydrocyclopenta[c]pyrrole-1-carboxylic acid (800 mg, yield: 21.2%) as a brown oil, which was used in next step without further purification. LC/MS (ESI) m/z: 292 $(M+H)^+$.

Preparation of Intermediate 51, trans-1-((benzyloxy)carbonyl)-3-(difluoromethyl)pyrrolidine-2-carboxylic acid

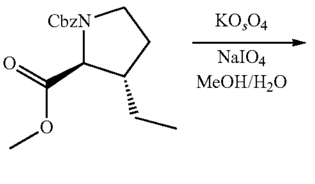

-continued

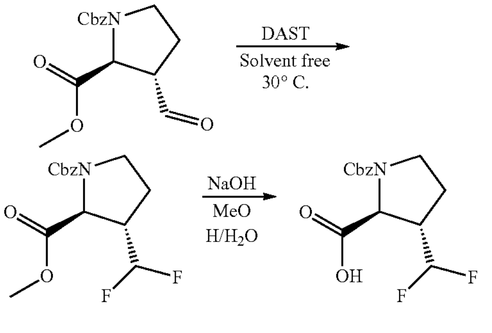

Step 1

To a solution of 1-benzyl 2-methyl trans-3-ethenylpyrrolidine-1,2-dicarboxylate (1.30 g, 4.49 mmol, see Intermediate 37 for its synthesis), $NaIO_4$ (2.88 g, 13.48 mmol) and potassium osmate dihydrate (170 mg, 0.45 mmol) in MeOH (30 mL) and $H_2O$ (50 mL), the resulting mixture was stirred for 4 h at room temperature. Then the reaction mixture was diluted with $H_2O$ (20 mL) and extracted with DCM (20 mL×3). The combined organic phase was washed with water and brine, dried over anhydrous $Na_2SO_4$, filtered, and concentrated to give the crude product which was purified by column chromatography on silica gel (EtOAc in PE=0~50%) to obtain the desired product 1-benzyl 2-methyl trans-3-formylpyrrolidine-1,2-dicarboxylate (700 mg, yield: 53.5%) as a yellow solid. LC/MS (ESI) m/z: 292 $(M+H)^+$.

Step 2

To DAST (5 mL) at 0° C. was added a solid of 1-benzyl 2-methyl (2S,3S)-3-formylpyrrolidine-1,2-dicarboxylate (500 mg, 1.72 mmol), then the resulting mixture was stirred for 24 h at 40° C. The reaction mixture was diluted with DCM (50 mL), and washed with sat. $NaHCO_3$. the organic phase was collected, and the water layer was extracted with DCM (20 mL×3). The combined organic layer was washed with water and brine, dried over anhydrous $Na_2SO_4$, filtered and concentrated, the residue was purified by column chromatography on silica gel (EtOAc in PE=0-30%) to obtain the product 1-benzyl desired 2-methyl trans-3-(fluoromethyl)pyrrolidine-1,2-dicarboxylate (300 mg, yield: 55.7%) as a yellow oil; LCMS: ESI m/z 314 $(M+H)^+$.

Step 3

To a solution of 1-benzyl 2-methyl trans-3-(difluoromethyl)pyrrolidine-1,2-dicarboxylate (300 mg, 0.96 mmol) in MeOH (5 mL) and $H_2O$ (2 mL) at 0° C. was added NaOH (115 mg, 2.88 mmol). The resulting mixture was stirred for 2 h at room temperature. The reaction mixture was concentrated, and adjusted the pH to 4~5 with 1 N HCl solution, extracted with EtOAc (15 mL×3). The combined organic layer was washed with water and brine, dried over anhydrous $Na_2SO_4$, filtered and concentrated to give the crude product 1-benzyl 2-methyl trans-3-(difluoromethyl)pyrrolidine-1,2-dicarboxylate (250 mg, yield: 82.2%) as a brown solid, which was used in next step without further purification. LC/MS (ESI) m/z: 300 $(M+1)^+$.

The following intermediate was prepared from the corresponding chemicals according to experimental procedure for Intermediate 37 (the major different chemicals used are listed in the column of starting material):

| Intermediate | Structure | Starting material | LCMS (ESI) m/z |
| --- | --- | --- | --- |
| Intermediate 52 | 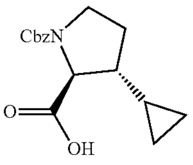 [SMILES: O=C(O)[C@@H]1[C@@H](C2CC2)CCN1C(=O)OCc1ccccc1] | 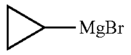 | 290 $(M + H)^+$ |

Preparation of Intermediate 53, N-(ethyl-1,1-$d_2$)-5-fluoro-2-hydroxy-N-isopropylbenzamide

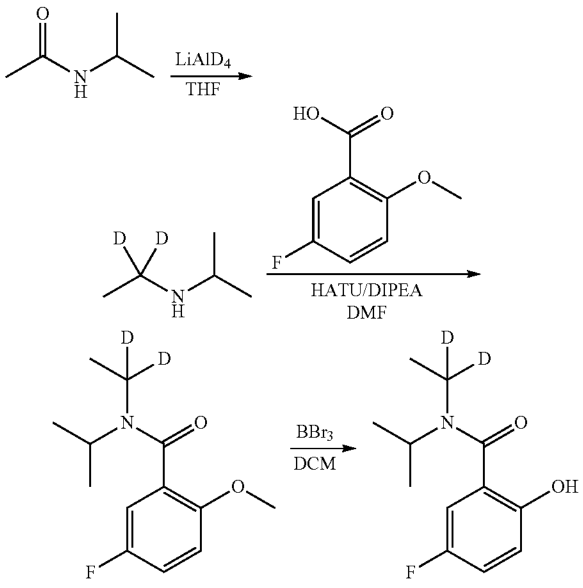

Step 1

To a solution of N-isopropylacetamide (1 g, 9.89 mmol) in dry THF (10 mL) was added LiAl$D_4$ (620 mg, 14.83 mmol) at 0° C., the resulting mixture was stirred at 70° C. for 24 h. The reaction mixture was quenched with Sat. $NH_4Cl$ (10 mL), extracted with $Et_2O$ (20 mL×3). The combined organic layer was washed with brine, then dried over anhydrous $Na_2SO_4$, filtered and concentrated to give the crude product N-(ethyl-1,1-$d_2$)propan-2-amine (400 mg, yield: 45.4%) as a colorless liquid, which was used to next step without further purification. LC/MS (ESI) m/z: 90 $(M+H)^+$.

To a solution of 5-fluoro-2-methoxybenzoic acid (700 mg, 4.11 mmol) and N-(ethyl-1,1-d2)propan-2-amine (400 mg, 4.49 mmol) in DMF (5 mL) was added HATU (2.03 g, 5.35 mmol) and DIPEA (1.06 g, 8.23 mmol) dropwise at 0° C. The reaction mixture was warmed to room temperature gradually and stirred overnight. The reaction mixture was quenched with sat. $NH_4Cl$ solution (10 mL), extracted with EtOAc (50 mL×3), the combined organic phase was washed by water and brine, dried over anhydrous $Na_2SO_4$, filtered and concentrated. The residue was purified by column chromatography on silica gel (EtOAc in PE=0~ 20%) to obtain the desired product N-(ethyl-1,1-d2)-5-fluoro-N-isopropyl-2-methoxybenzamide (400 mg, yield: 40.3%) as a white solid. LC/MS (ESI) m/z: 242 $(M+H)^+$.

Step 3

To a solution of N-[(1,1-d2)ethyl]-5-fluoro-2-methoxy-N-(propan-2-yl)benzamide (400 mg, 1.66 mmol) in DCM (10 mL) was added $BBr_3$ (2.2 mL, 1.0 M in DCM) dropwise at −60° C. under $N_2$ atmosphere, the resulting mixture was stirred for 7 h at this temperature. Then the reaction mixture was quenched with cooled sat. $NaHCO_3$ at 0° C., the mixture was extracted with DCM (30 mL×3), the combined organic layer was washed with water and brine, dried over anhydrous $Na_2SO_4$, filtered and concentrated to give desired product N-(ethyl-1,1-$d_2$)-5-fluoro-2-hydroxy-N-isopropyl-benzamide (270 mg, yield: 71.6%) as a light-yellow solid, which was used in next step without further purification. LC/MS (ESI) m/z: 228 $(M+H)^+$.

Preparation of Intermediate 54, 2-(2-cyclopropylpyridin-3-yl)-4-fluorophenol

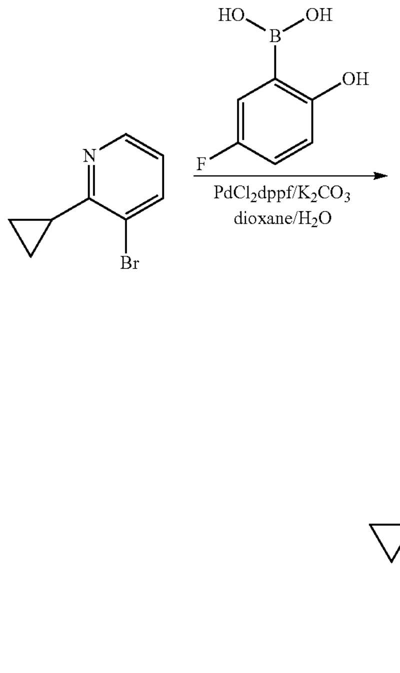

To a solution of 3-bromo-2-cyclopropylpyridine (250 mg, 1.26 mmol) and (5-fluoro-2-hydroxyphenyl)boronic acid (220 mg, 1.41 mmol) in dioxane (4.0 mL) and $H_2O$ (1.0 mL) was added Pd(dppf)$Cl_2$ (25 mg) and $K_2CO_3$ (400 mg, 2.89 mmol), the resulting mixture was stirred at 100° C. overnight under $N_2$. The reaction mixture was cooled to rt, diluted with $H_2O$ (20 mL), and extracted with EtOAc (20 mL×3). The combined organic layer was washed with water and brine, dried over anhydrous $Na_2SO_4$, filtered and concentrated, the residue was purified by column chromatography on silica gel (EtOAc in PE=0~10%) to obtain the desired product 2-(2-cyclopropylpyridin-3-yl)-4-fluorophenol (200 mg, yield:69.1%) as a yellow solid. LC/MS (ESI) m/z: 230 $(M+H)^+$.

Preparation of Intermediate 55, 2-(2-cyclopropyl-6-methoxypyridin-3-yl)-4-fluorophenol

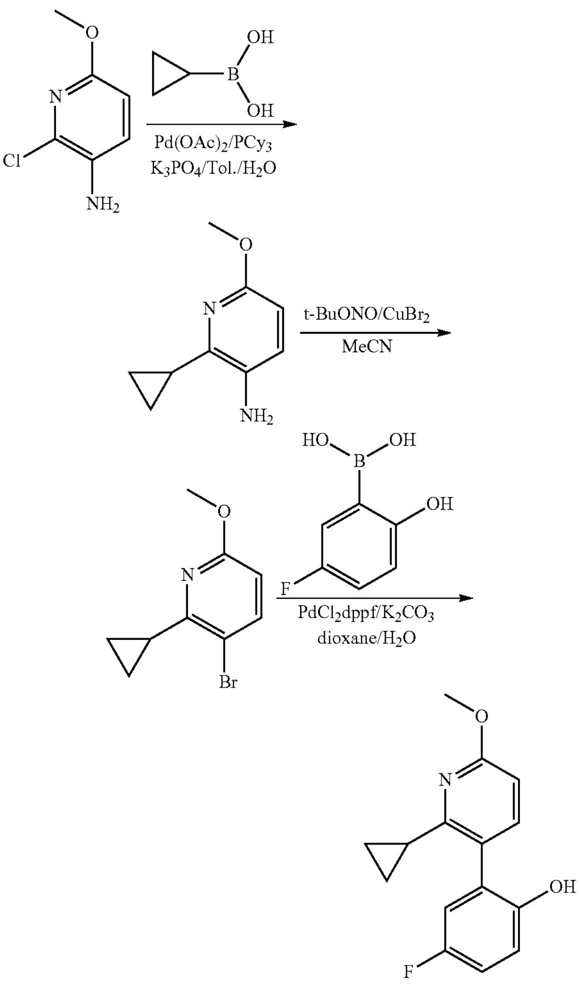

Step 1

To a solution of 2-chloro-6-methoxypyridin-3-amine (2.5 g, 15.8 mmol), cyclopropylboronic acid (1.76 g, 20.5 mmol) in toluene (20 mL) and $H_2O$ (4 mL) at rt was added $K_3PO_4$ (13.4 g, 63.1 mmol), tricyclohexylphosphane (1.77 g, 6.31 mmol) and $Pd(AcO)_2$ (40 mg, 0.16 mmol). The resulting mixture was degassed with $N_2$ for three times and stirred at 100° C. overnight under $N_2$ atmosphere.

The reaction mixture was cooled to rt, quenched with Sat. $NH_4Cl$ solution (20 mL), and extracted with EtOAc (20 mL×3). The combined organic layer was washed with water and brine, dried over anhydrous $Na_2SO_4$, filtered and concentrated to give the crude product which was purified by column chromatography on silica gel (EtOAc in PE=0~10%) to obtain the desired product 2-cyclopropyl-6-methoxypyridin-3-amine (830 mg, yield: 32.1%) as a yellow solid. LC/MS (ESI) m/z: 164 $(M+H)^+$.

Step 2

A suspension of tert-Butyl nitrite (1.82 mL, 15.2 mmol), CuBr (2.90 mg, 20.2 mmol) in MeCN (10 mL) was stirred at 70° C. for 30 min, then to this stirred mixture was added a solution of 2-cyclopropyl-6-methoxypyridin-3-amine (830 mg, 5.06 mmol) in MeCN (5 mL) dropwised. The resulting mixture was stirred at 70° C. for another 1 h. The reaction mixture was quenched with water (10 mL), and extracted with EtOAc (20 mL×3). The combined organic phase was washed by water and brine, dried over anhydrous $Na_2SO_4$, filtered and concentrated to give the crude product which was purified by column chromatography on silica gel (PE=100%) to obtain the desired product 3-bromo-2-cyclopropyl-6-methoxypyridine (400 mg, yield: 34.7%) as a light-yellow oil. LC/MS (ESI) m/z: 229 $(M+H)^+$.

Step 3

To a solution of 3-bromo-2-cyclopropyl-6-methoxypyridine (600 mg, 2.63 mmol) and (5-fluoro-2-hydroxyphenyl) boronicacid (615 mg, 3.95 mmol) in dioxane (16 mL) and $H_2O$ (4 mL) was added $Cs_2CO_3$ (2.57 g, 7.89 mmol) and $Pd(dppf)Cl_2$ (50 mg), the resulting mixture was stirred at 100° C. overnight under $N_2$ atmosphere. The reaction mixture was cooled to rt, diluted with $H_2O$ (20 mL), extracted with EtOAc (20 mL×3), the combined organic layer was washed with water and brine, dried over anhydrous $Na_2SO_4$, filtered and concentrated. The residue was purified by column chromatography on silica gel (EtOAc in PE=0~30%) to obtain the desired product 2-(2-cyclopropyl-6-methoxypyridin-3-yl)-4-fluorophenol (550 mg, yield: 80.6%) as a yellow solid. LC/MS (ESI) m/z: 260 [M+1]+.

Preparation of Intermediate 56, 6-cyclopropyl-5-(5-fluoro-2-hydroxyphenyl)pyridin-2(1H)-one

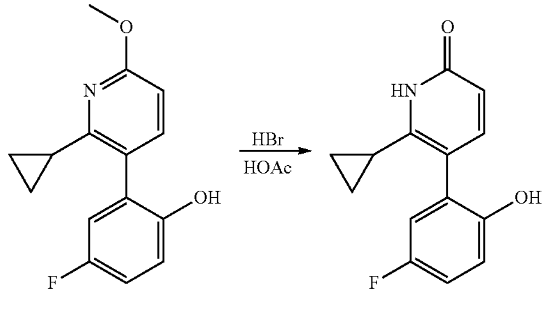 [SMILES: COc1ccc(-c2cc(F)ccc2O)c(C2CC2)n1 ; Br ; O=c1ccc(-c2cc(F)ccc2O)c(C2CC2)[nH]1 ; "HOAc"]

To a solution of 2-(2-cyclopropyl-6-methoxypyridin-3-yl)-4-fluorophenol (350 mg, 1.35 mmol, Intermediate 55) in HOAc (5 mL) was added 40% HBr solution (3 mL) at room temperature, and the resulting mixture was stirred overnight at 80° C. The reaction mixture was cooled to rt and concentrated. The residue was suspended in EtOAc (50 mL) and washed with sat $NaHCO_3$ (10 mL×3), and brine, the organic phase was dried over anhydrous $Na_2SO_4$, filtered, and concentrated to give the crude product which was purified by silica gel column (EtOAc in PE=0~70%) to obtain the desired product 6-cyclopropyl-5-(5-fluoro-2-hydroxyphenyl)-1,2-dihydropyridin-2-one (200 mg, yield: 60.4%) as a brown semi-solid, H NMR (400 MHZ, DMSO) & 10.72 (s, 1H), 9.38 (s, 1H), 7.23 (d, J=9.0 Hz, 1H), 7.02-6.92 (m, 2H), 6.89-6.85 (m, 1H), 6.21 (d, J=8.9 Hz, 1H), 1.75-1.69 (m, 1H), 0.89-0.80 (m, 2H), 0.76-0.72 (m, 2H), LC/MS (ESI) m/z: 246 $(M+H)^+$.

EXAMPLES

Example 2

Preparation of N-ethyl-5-fluoro-2-[(4-{7-[(2S,4R)-4-fluoropyrrolidine-2-carbonyl]-2,7-diazaspiro[3.5] nonan-2-yl} pyrimidin-5-yl)oxy]-N-(propan-2-yl) benzamide

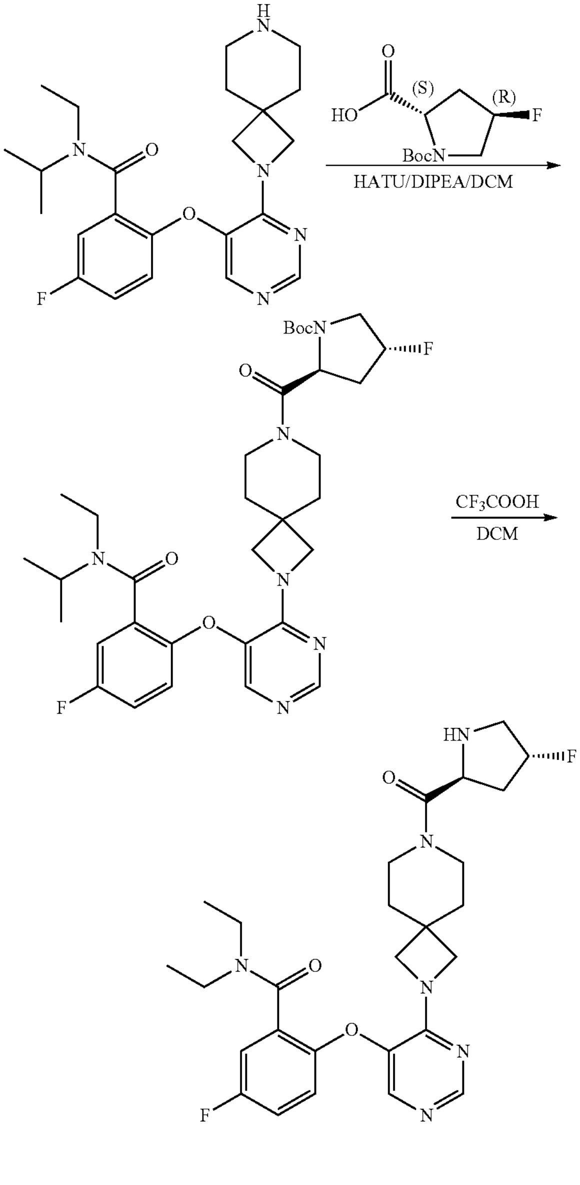

Step 1

To a solution of 2-[(4-{2,7-diazaspiro[3.5]nonan-2-yl}pyrimidin-5-yl)oxy]-N-ethyl-5-fluoro-N-(propan-2-yl) benz amide (Intermediate 1, 50 mg, 0.12 mmol) and (2S, 4R)-1-[(tert-butoxy)carbonyl]-4-fluoropyrrolidine-2-carboxylic acid (27 mg, 0.12 mmol) in DMF (2 mL) was added DIPEA (0.1 mL) and HATU (58 mg, 0.15 mmol) at room temperature. The resulting mixture was stirred for 3 h at rt and quenched with sat. $NH_4Cl$ solution (10 mL), and extracted with EtOAc (15 mL×3), the combined organic phase was washed with water and brine, dried over anhydrous $Na_2SO_4$, filtered and concentrated, the residue was purified by column chromatography on silica gel (MeOH in DCM=0~5%) to give the desired product tert-butyl(2S,4R)-2-[2-(5-{2-[ethyl(propan-2-yl)carbamoyl]-4-fluorophenoxy}pyrimidin-4-yl)-2,7-diazaspiro[3.5]nonane-7-carbonyl]-4-fluoropyrrolidine-1-carboxylate (60 mg, yield: 79%) as a light yellow solid. LC/MS (ESI) m/z: 643 $(M+H)^+$.

Step 2

To a solution of tert-butyl (2S,4R)-2-[2-(5-{2-[ethyl(propan-2-yl)carbamoyl]-4-fluorophenoxy}pyrimidin-4-yl)-2,7-diazaspiro [3.5]nonane-7-carbonyl]-4-fluoropyrrolidine-1-carboxylate (60 mg, 0.1 mmol) in DCM (3 mL) was added TFA (1.0 mL). The resulting mixture was stirred for 1 h at rt, concentrated, the residue was purified by Prep-HPLC to afford the desired product N-ethyl-5-fluoro-2-[(4-{7-[(2S,4R)-4-fluoropyrrolidine-2-carbonyl]-2,7-diazaspiro[3.5]nonan-2-yl} pyrimidin-5-yl)oxy]-N-(propan-2-yl)benzamide (35 mg, yield: 69%) as a white solid. H NMR (400 MHz, $CDCl_3$) δ 8.40 (d, J=3.1 Hz, 1H), 7.82-7.80 (m, 1H), 7.04-7.00 (m, 2H), 6.78-6.72 (m, 1H), 5.35-5.22 (m, 1H), 4.29-4.25 (m, 1H), 4.03-3.82 (m, 5H), 3.66-3.63 (m, 1H), 3.52-3.15 (m, 7H), 2.40-2.31 (m, 1H), 1.87-1.76 (m, 5H), 1.29-1.23 (m, 4H), 1.16-1.07 (m, 5H). LC/MS (ESI) m/z: 543 $(M+H)^+$.

The following compounds were prepared from the appropriate intermediates or commercially available chemicals according to experimental procedure for Example 2:

| Example | Structure | Starting materials | $^1$H-NMR (400 MHz) | LCMS (ESI) m/z |
|---|---|---|---|---|
| Example 3 | 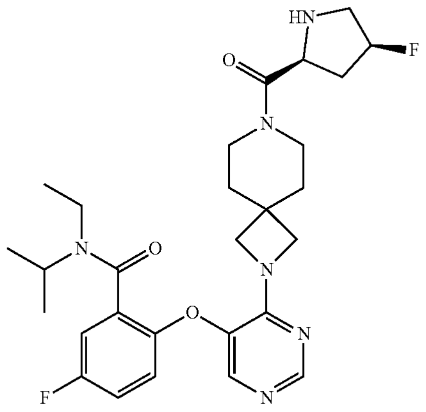 [SMILES: CCN(C(=O)c1cc(F)ccc1Oc1cncnc1N1CC2(CCN(C(=O)[C@@H]3C[C@H](F)CN3)CC2)C1)C(C)C] | Intermediate 1 and 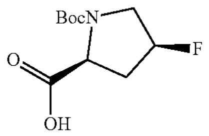 | $^1$H NMR (400 MHz, $CDCl_3$) δ 8.51-8.35 (m, 1H), 8.23 (s, 0.6H), 7.83 (d, J = 6.2 Hz, 1H), 7.04-7.01 (m, 2H), 6.77-6.73 (m, 1H), 5.33-5.20 (m, 1H), 4.60-4.56 (m, 1H), 4.06-3.73 (m, 6H), 3.64-3.56 (m, 1H), 3.40-3.16 (m, 6H), 2.65-2.55 (m, 1H), 2.21-2.12 (m, 1H), 1.83-1.79 (m, 4H), 1.29-1.23 (m, 3H), 1.17-1.09 (m, 5H). | 543 $(M + H)^+$ |
| Example 4 | 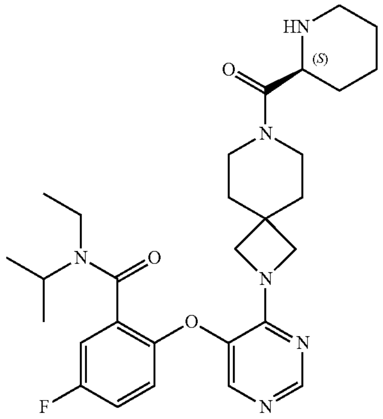 | Intermediate 1 and 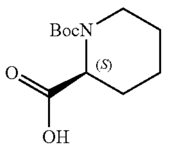 | $^1$H NMR (400 MHz, $CDCl_3$) δ 8.39 (d, J = 3.3 Hz, 1H), 7.81-7.80 (m, 1H), 7.04-7.00 (m, 2H), 6.79-6.74 (m, 1H), 4.03-3.83 (m, 6H), 3.68-3.64 (s, 1H), 3.51-3.30 (m, 6H), 2.77 (t, J = 10.8 Hz, 1H), 1.91-1.65 (m, 8H), 1.54-1.50 (m, 2H), 1.28-1.23 (m, 4H), 1.16-1.17 (m, 5H). | 539 $(M + H)^+$ |

-continued
| Example | Structure | Starting materials | $^1$H-NMR (400 MHz) | LCMS (ESI) m/z |
|---|---|---|---|---|
| Example 5 | 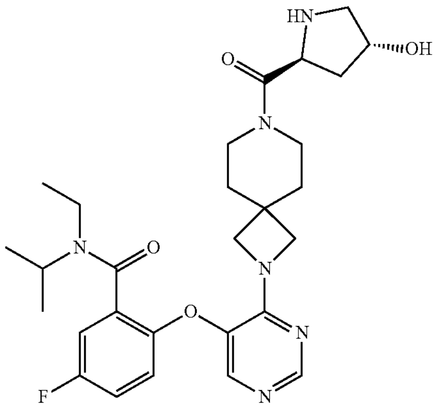 [SMILES: CCN(C(=O)c1cc(F)ccc1Oc1cncnc1N1CC2(CCN(C(=O)[C@@H]3C[C@@H](O)CN3)CC2)C1)C(C)C] | Intermediate 1 and 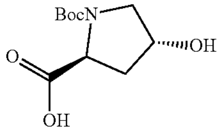 | $^1$H NMR (400 MHz, DMSO) δ 8.28 (d, J = 8.6 Hz, 1H), 7.75-7.69 (m, 1H), 7.29-7.23 (m, 2H), 7.05-7.03 (m, 1H), 4.95 (s, 1H), 4.23-4.18 (m, 3H), 3.96-3.86 (m, 5H), 3.77-3.72 (m, 1H), 3.15-3.11 (m, 3H), 2.71-2.68 (m, 1H), 1.97-1.95 (m, 1H), 1.85-1.56 (m, 6H), 1.20-1.18 (m, 2H), 1.12-0.97 (m, 9H) | 541 (M + H)$^+$ |
| Example 6 | 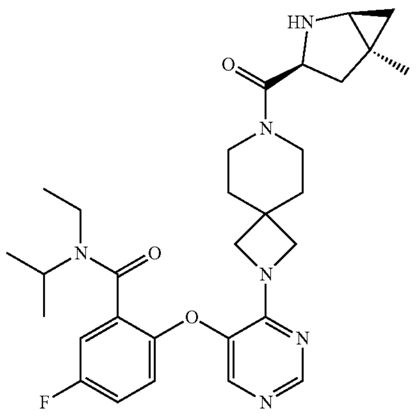 [SMILES: CCN(C(=O)c1cc(F)ccc1Oc1cncnc1N1CC2(CCN(C(=O)[C@@H]3C[C@]4(C)C[C@@H]4N3)CC2)C1)C(C)C] | Intermediate 1 and 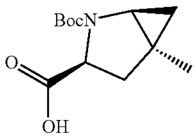 | $^1$H NMR (400 MHz, MeOD) δ 8.45 (s, 1H), 7.81-7.73 (m, 1H), 7.30-7.21 (m, 3H), 4.99 (d, J = 9.9 Hz, 1H), 4.30-4.18 (m, 4H), 3.91-3.84 (m, 1H), 3.73-3.68 (m, 1H), 3.49-3.29 (m, 5H), 3.15 (d, J = 5.0 Hz, 1H), 2.73-2.67 (m, 1H), 2.21-2.18 (m, 1H), 1.90-1.85 (m, 4H), 1.37-0.93 (m, 15H) | 551 (M + H)$^+$ |
| Example 7 | 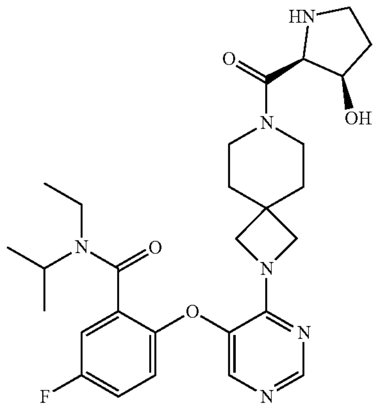 [SMILES: CCN(C(=O)c1cc(F)ccc1Oc1cncnc1N1CC2(CCN(C(=O)[C@H]3NCC[C@H]3O)CC2)C1)C(C)C] | Intermediate 1 and 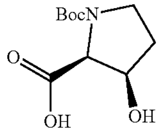 | $^1$H NMR (400 MHz, DMSO) δ 9.31 (s, 1H), 8.59 (s, 1H), 8.35 (d, J = 4.9 Hz, 1H), 7.82-7.76 (m, 1H), 7.35-7.24 (m, 2H), 7.08-7.07 (m, 1H), 5.57 (s, 1H), 4.62-4.57 (m, 2H), 4.01-3.92 (m, 4H), 3.81-3.69 (m, 1H), 3.28-3.11 (m, 5H), 2.12-2.07 (m, 1H), 1.91-1.70 (mz, 6H), 1.21-0.98 (m, 10H) | 541 (M + H)$^+$ |

-continued
| Example | Structure | Starting materials | $^1$H-NMR (400 MHz) | LCMS (ESI) m/z |
|---|---|---|---|---|
| Example 8 | 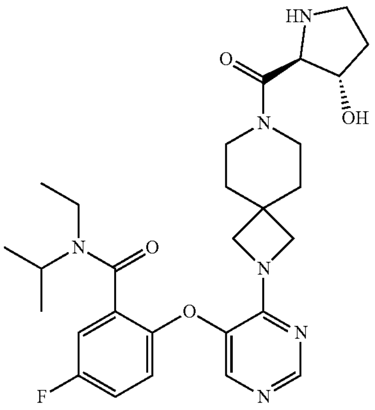 [SMILES: CCN(C(=O)c1cc(F)ccc1Oc1cncnc1N1CC2(CCN(C(=O)[C@H]3NCC[C@@H]3O)CC2)C1)C(C)C] | Intermediate 1 and 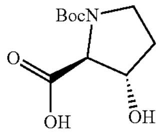 | $^1$H NMR (400 MHz, $CDCl_3$) δ 8.40-8.39 (m, 1H), 7.80 (d, J = 3.9 Hz, 1H), 7.03-6.99 (m, 2H), 6.73-6.71 (m, 1H), 4.21 (s, 1H), 4.03-3.95 (m, 2H), 3.92-3.81 (m, 4H), 3.64-3.50 (m, 4H), 3.37-3.28 (m, 1H), 3.20-3.17 (m, 1H), 3.05-2.98 (m, 1H), 2.37-2.31 (m, 3H), 1.80-1.73 (m, 4H), 1.28-1.22 (m, 5H), 1.14 (d, J = 6.4 Hz, 4H) | |
| Example 9 | 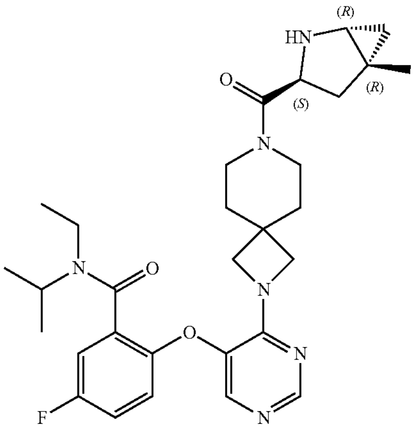 | Intermediate 1 and 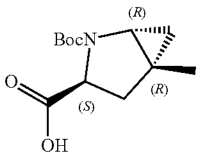 | $^1$H NMR (400 MHz, MeOD) δ 8.28 (s, 1H), 7.81-7.78 (m, 1H), 7.21-7.17 (m, 2H), 6.98-6.94 (m, 1H), 4.41-4.37 (m, 1H), 4.06-3.88 (m, 5H), 3.57-3.44 (m, 6H), 3.08 (d, J = 5.2 Hz, 1H), 2.63-2.41 (m, 1H), 1.93-1.78 (m, 6H), 1.32-1.08 (m, 14H) | 551 $(M + H)^+$ |
| Example 10 | 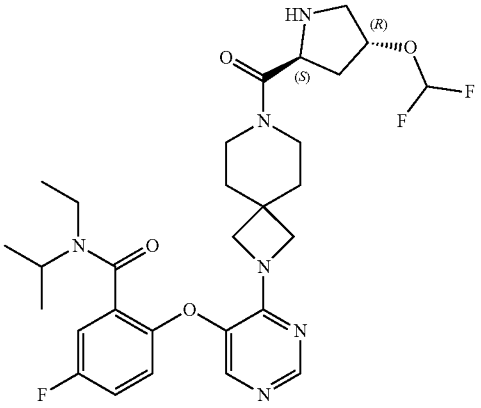 | Intermediate 1 and 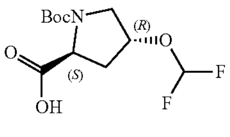 | $^1$H NMR (400 MHz, MeOD) δ 8.27 (d, J = 5.4 Hz, 1H), 7.80-7.77 (m, 1H), 7.22-7.16 (m, 2H), 6.99-6.96 (m, 1H), 6.51 (t, J = 74.1 Hz, 1H), 5.03 (s, 1H), 4.73 (t, J = 8.6 Hz, 1H), 4.07-3.85 (m, 5H), 3.85-3.33 (m, 8H), 3.31-3.20 (m, 1H), 2.66-2.60 (m, 1H), 2.19-2.16 (m, 1H), 1.86-1.80 (m, 4H), 1.32-1.03 (m, 9H) | 591 $(M + H)^+$ |

-continued

| Example | Structure | Starting materials | $^1$H-NMR (400 MHz) | LCMS (ESI) m/z |
|---|---|---|---|---|
| Example 11 | 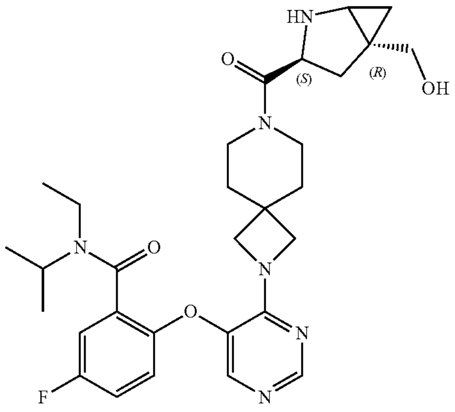 | Intermediate 1 and 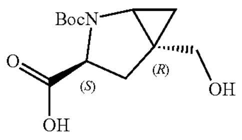 | $^1$H NMR (400 MHz, DMSO) δ 8.28 (d, J = 8.7 Hz, 1H), 7.74-7.68 (m, 1H), 7.32-7.24 (m, 2H), 7.09-7.02 (m, 1H), 4.63-4.61 (m, 1H), 4.40-4.31 (m, 1H), 3.94-3.69 (m, 6H), 3.44-3.40 (m, 6H), 3.25-3.22 (m, 2H), 2.56 (s, 1H), 1.81-1.64 (m, 6H), 1.21-1.03 (m, 9H), 0.64-0.49 (m, 2H) | 567 (M + H)+ |
| Example 12 | 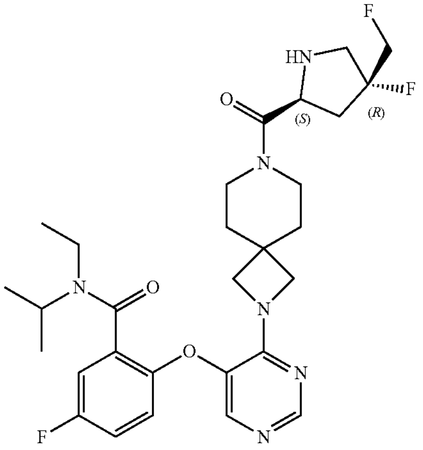 | Intermediate 1 and 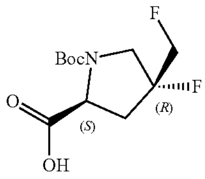 | $^1$H NMR (400 MHz, MeOD) δ 8.25 (d, J = 6.4 Hz, 1H), 7.77-7.73 (m, 1H), 7.22-7.16 (m, 2H), 7.01-6.97 (m, 1H), 4.65-4.48 (m, 2H), 4.33-4.29 (m, 1H), 4.11-3.88 (m, 5H), 3.58-3.49 (m, 5H), 3.36-3.34 (m, 1H), 3.11-3.03 (m, 1H), 2.45-2.30 (m, 1H), 1.99-1.67 (m, 6H), 1.34-1.12 (m, 9H) | 575 (M + H)+ |
| Example 13 | 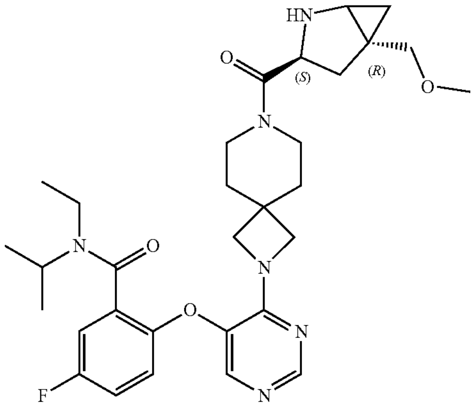 | Intermediate 1 and Intermediate 24 | $^1$H NMR (400 MHz, DMSO) δ 10.08 (s, 1H), 8.64 (s, 1H), 8.31 (d, J = 6.2 Hz, 1H), 7.78-7.72 (m, 1H), 7.32-7.20 (m, 2H), 7.11-7.04 (m, 1H), 4.91 (d, J = 8.0 Hz, 1H), 3.97-3.87 (m, 4H), 3.76-3.73 (m, 1H), 3.44-3.41 (m, 2H), 3.30-3.27 (m, 3H), 3.23-3.19 (m, 3H), 3.13-3.12 (m, 1H), 2.82-2.76 (m, 1H), 2.04-2.00 (m, 1H), 1.75-1.68 (m, 4H), 1.20-0.88 (m, 12H) | 581 (M + H)$^+$ |

-continued

| Example | Structure | Starting materials | $^1$H-NMR (400 MHz) | LCMS (ESI) m/z |
| --- | --- | --- | --- | --- |
| Example 14 | 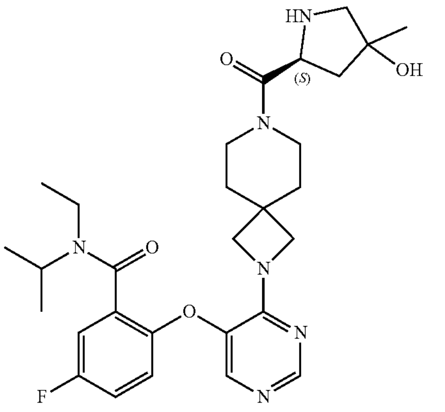 | Intermediate 1 and Intermediate 15 | $^1$H NMR (400 MHz, MeOD) δ 8.26 (d, J = 5.8 Hz, 1H), 7.79-7.76 (m, 1H), 7.20-7.17 (m, 2H), 6.99-6.98 (m, 1H), 4.41-4.38 (m, 1H), 3.99-3.93 (m, 5H), 3.59-3.51 (m, 3H), 3.45-3.42 (m, 2H), 3.19-3.16 (m, 1H), 2.92-2.90 (m, 1H), 2.42-2.35 (m, 1H), 1.85-1.80 (m, 5H), 1.32-1.10 (m, 15H) | 555 $(M + H)^+$ |
| Example 15 | 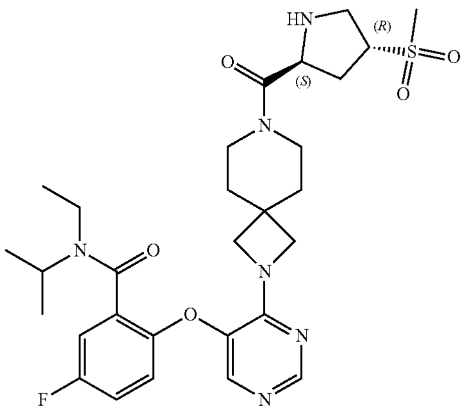 | Intermediate 1 and Intermediate 16 | $^1$H NMR (400 MHz, MeOD) δ 8.25 (d, J = 6.4 Hz, 1H), 7.77-7.73 (m, 1H), 7.21-7.16 (m, 2H), 7.05-6.95 (m, 1H), 4.17 (t, J = 7.4 Hz, 1H), 4.10-3.84 (m, 5H), 3.82-3.75 (m, 1H), 3.65-3.45 (m, 6H), 3.41-3.33 (m, 1H), 3.22-3.18 (m, 1H), 2.97 (s, 3H), 2.57-2.46 (m, 1H), 2.18-2.08 (m, 1H), 1.86-1.78 (m, 4H), 1.34-1.06 (m, 10H) | 603 $(M + H)^+$ |
| Example 16 | 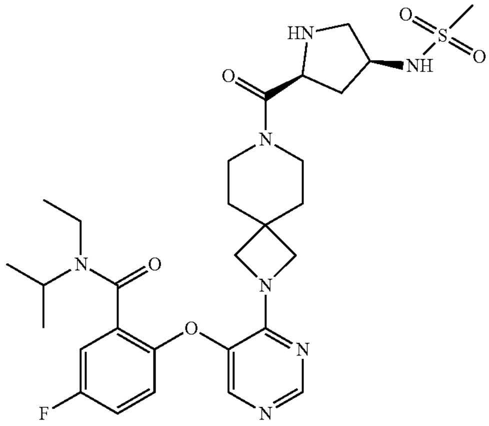 [SMILES: CCN(C(=O)c1cc(F)ccc1Oc1cncnc1N1CC2(CCN(C(=O)[C@@H]3C[C@H](NS(C)(=O)=O)CN3)CC2)C1)C(C)C] | Intermediate 1 and Intermediate 25 | $^1$H NMR (400 MHz, $CDCl_3$) δ 8.40 (d, J = 3.7 Hz, 1H), 7.82 (s, 1H), 7.04-7.00 (m, 2H), 6.76-6.72 (m, 1H), 5.59-5.49 (m, 1H), 4.08-3.98 (m, 4H), 3.97-3.79 (m, 3H), 3.70-3.41 (m, 5H), 3.37-3.26 (m, 1H), 3.20-3.13 (m, 2H), 3.07-3.04 (m, 1H), 2.95 (s, 3H), 2.36-2.23 (m, 1H), 1.81-1.72 (m, 2H), 1.33-1.07 (m, 11H) | 618 $(M + H)^+$ |

-continued

| Example | Structure | Starting materials | $^1$H-NMR (400 MHz) | LCMS (ESI) m/z |
|---|---|---|---|---|
| Example 18 | 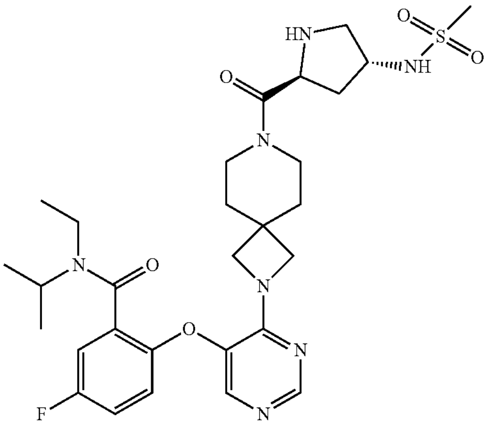 [SMILES: CCN(C(=O)c1cc(F)ccc1Oc1cncnc1N1CC2(CCN(C(=O)[C@@H]3C[C@@H](NS(C)(=O)=O)CN3)CC2)C1)C(C)C] | Intermediate 1 and Intermediate 26 | $^1$H NMR (400 MHz, MeOD) δ 8.36 (s, 1H), 8.28-8.26 (m, 1H), 7.80-7.77 (m, 1H), 7.23-7.16 (m, 2H), 7.01-6.93 (m, 1H), 4.61 (t, J = 8.1 Hz, 1H), 4.12-4.09 (m, 3H), 3.98-3.88 (m, 3H), 3.58-3.51 (m, 7H), 3.38-3.31 (m, 2H), 3.28-3.24 (m, 2H), 2.44-2.40 (m, 1H), 2.22-2.16 (m, 1H), 1.85-1.80 (m, 4H), 1.32-1.09 (m, 10H) | 618 $(M + H)^+$ |
| Example 17 | 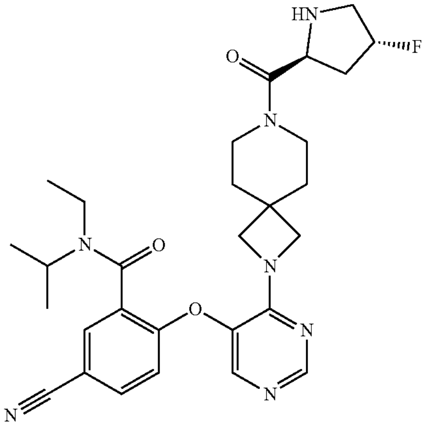 [SMILES: CCN(C(=O)c1cc(C#N)ccc1Oc1cncnc1N1CC2(CCN(C(=O)[C@@H]3C[C@@H](F)CN3)CC2)C1)C(C)C] | Intermediate 4 and 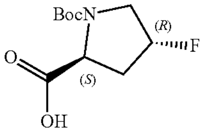 | $^1$H NMR (400 MHz, DMSO) δ 8.39 (d, J = 6.7 Hz, 1H), 8.01-7.97 (m, 1H), 7.92 (dd, J = 12.4, 2.1 Hz, 1H), 7.8-7.84 (m, 1H), 7.06-7.00 (m, 1H), 5.32-5.18 (m, 1H), 4.10 (t, J = 7.8 Hz, 1H), 3.90-3.88 (m, 2H), 3.83-3.72 (m, 3H), 3.40-3.38 (m, 5H), 3.17-3.04 (m, 2H), 2.99-2.90 (m, 1H), 2.17-1.91 (m, 3H), 1.72-1.61 (m, 4H), 1.24-1.10 (m, 9H) | 550 $(M + H)^+$ |
| Example 19 | 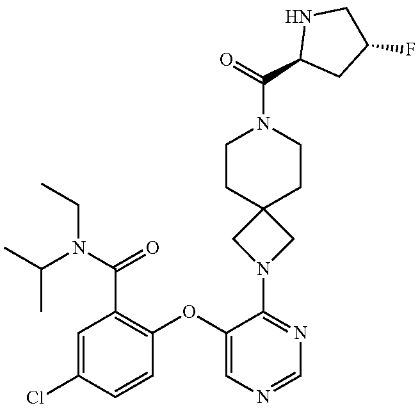 | Intermediate 2 and 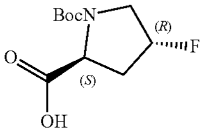 | $^1$H NMR (400 MHz, DMSO) δ 8.33 (d, J = 8.5 Hz, 1H), 8.14 (s, 0.4H), 7.87-7.82 (m, 1H), 7.48-7.41 (m, 2H), 7.00-6.93 (m, 1H), 6.42-5.28 (m, 1H), 4.43 (t, J = 8.2 Hz, 1H), 3.99-3.72 (m, 5H), 3.45-3.39 (m, 4H), 3.25-3.20 (m, 4H), 2.43-2.39 (m, 1H), 2.09-2.00 (m, 1H), 1.83-1.62 (m, 4H), 1.24-1.00 (m, 9H) | 559 $(M + H)^+$ |

-continued

| Example | Structure | Starting materials | $^1$H-NMR (400 MHz) | LCMS (ESI) m/z |
|---|---|---|---|---|
| Example 20 | 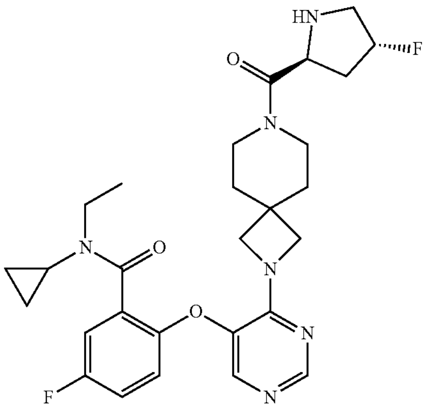 [SMILES: CCN(C(=O)c1cc(F)ccc1Oc1cncnc1N1CC2(CCN(C(=O)[C@@H]3C[C@@H](F)CN3)CC2)C1)C1CC1] | Intermediate 3 | $^1$H NMR (400 MHz, MeOD) δ 8.26 (d, J = 8.0 Hz, 1H), 7.77-7.69 (m, 1H), 7.18 (t, J = 8.2 Hz, 2H), 6.96-6.93 (m, 1H), 5.33-5.20 (m, 1H), 4.25-4.17 (m, 1H), 4.00 (br, 4H), 3.57-3.52 (m, 6H), 3.25-3.22 (m, 1H), 3.13-3.04 (m, 1H), 2.84-2.72 (m, 1H), 2.45-2.34 (m, 1H), 1.95-1.78 (m, 5H), 1.25-1.16 (m, 4H), 0.64 (d, J = 6.9 Hz, 4H) | 541 $(M + H)^+$ |
| Example 21 | 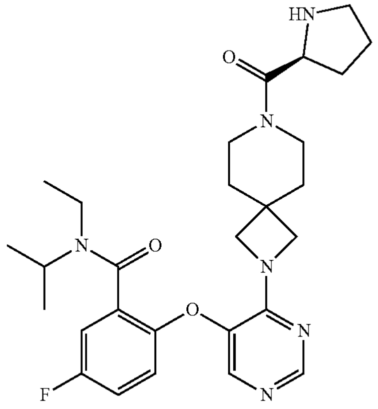 [SMILES: CCN(C(=O)c1cc(F)ccc1Oc1cncnc1N1CC2(CCN(C(=O)[C@@H]3CCCN3)CC2)C1)C(C)C] | Intermediate 1 and 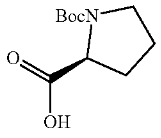 | $^1$H NMR (400 MHz, MeOD) δ 8.25 (d, J = 6.4 Hz, 1H), 7.78-7.74 (m, 1H), 7.22-7.16 (m, 2H), 7.00-6.97 (m, 1H), 4.06 (br, 2H), 3.99-3.83 (m, 4H), 3.61-3.44 (m, 5H), 3.41-3.34 (m, 1H), 3.27-3.15 (m, 1H), 3.18-3.08 (m, 1H), 2.88-2.76 (m, 1H), 2.22-2.16 (m, 1H), 1.90-1.56 (m, 7H), 1.31 (d, J = 6.7 Hz, 2H), 1.23 (t, J = 7.0 Hz, 2H), 1.20-1.10 (m, 6H). | 525 $(M + H)^+$ |
| Example 22 | 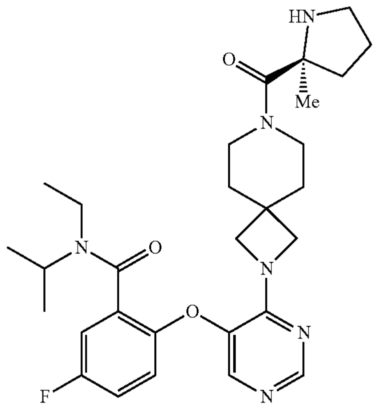 [SMILES: CCN(C(=O)c1cc(F)ccc1Oc1cncnc1N1CC2(CCN(C(=O)[C@]3(C)CCCN3)CC2)C1)C(C)C] | Intermediate 1 and 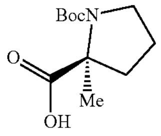 | $^1$H NMR (400 MHz, MeOD) δ 8.27-8.25 (m, 1H), 7.78-7.74 (m, 1H), 7.21-7.16 (m, 2H), 7.00-6.96 (m, 1H), 4.06 (br, 2H), 4.00-3.82 (m, 3H), 3.64-3.46 (m, 5H), 3.29-3.34 (m, 1H), 2.95-2.84 (m, 2H), 2.18-2.13 (m, 1H), 1.99-1.89 (m, 3H), 1.81 (br, 4H), 1.44 (s, 3H), 1.34-1.28 (m, 2H), 1.24 (t, J = 7.0 Hz, 2H), 1.20-1.07 (m, 6H) | 539 $(M + H)^+$ |

-continued

| Example | Structure | Starting materials | $^1$H-NMR (400 MHz) | LCMS (ESI) m/z |
|---|---|---|---|---|
| Example 23 | 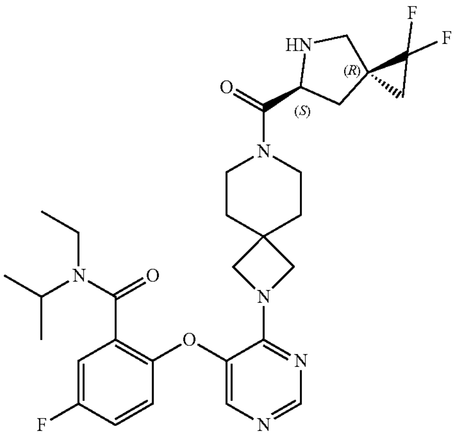 | Intermediate 1 and Intermediate 23 | $^1$H NMR (400 MHz, MeOD) δ 8.25 (d, J = 6.4 Hz, 1H), 7.77-7.73 (m, 1H), 7.24-7.14 (m, 2H), 7.01-6.97 (m, 1H), 4.28-4.16 (m, 1H), 4.10-4.03 (m, 2H), 4.00-3.95 (m, 2H), 3.91-3.88 (m, 1H), 3.59-3.46 (m, 5H), 3.42-3.33 (m, 1H), 3.13-3.07 (m, 1H), 2.44-2.25 (m, 1H), 1.90-1.75 (m, 5H), 1.47-1.28 (m, 4H), 1.23 (t, J = 6.9 Hz, 3H), 1.19-1.03 (m, 6H) | 587 $(M + H)^+$ |
| Example 24 | 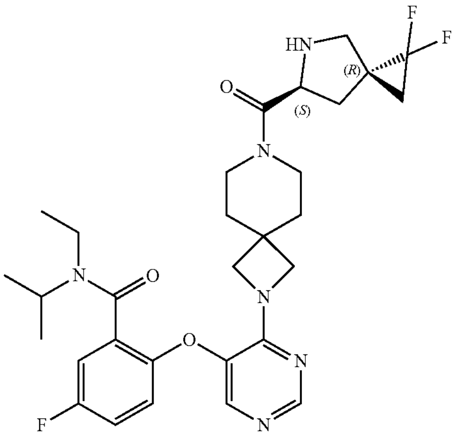 | Intermediate 1 and Intermediate 23 | $^1$H NMR (400 MHz, MeOD) δ 8.26-8.24 (m, 1H), 7.77-7.73 (m, 1H), 7.20-7.16 (m, 2H), 7.03-6.97 (m, 1H), 4.25-4.14 (m, 1H), 4.06 (s, 2H), 4.10-3.98 (m, 2H), 3.90-3.86 (m, 1H), 3.58-3.51 (m, 5H), 3.40-3.35 (m, 1H), 3.27-3.23 (m, 1H), 3.13-3.07 (m, 1H), 2.44-2.25 (m, 1H), 1.86-1.74 (m, 5H), 1.45-1.30 (m, 4H), 1.25-1.22 (t, J = 6.9 Hz, 3H), 1.20-1.07 (m, 6H) | 587 $(M + H)^+$ |
| Example 25 | 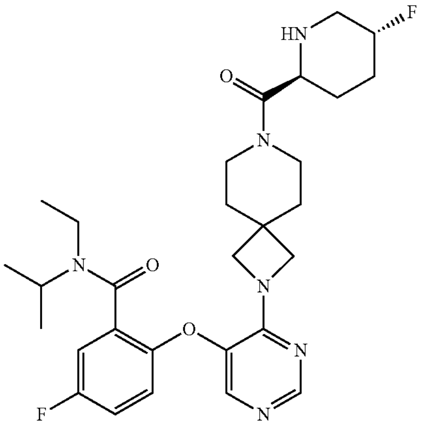 [SMILES: CCN(C(=O)c1cc(F)ccc1Oc1cncnc1N1CC2(CCN(C(=O)[C@@H]3CC[C@@H](F)CN3)CC2)C1)C(C)C] | Intermediate 1 and Intermediate 27 | $^1$H NMR (400 MHz, $CDCl_3$) δ 8.40 (s, 1H), 7.81 (s, 1H), 7.04-7.00 (m, 2H), 6.77-6.71 (m, 1H), 4.50-4.38 (m, 1H), 4.10-3.80 (m, 5H), 3.63-3.18 (m, 9H), 2.72-2.68 (m, 1H), 2.30-2.26 (m, 1H), 1.85-1.73 (m, 6H), 1.29-1.12 (m, 10H) | 557 $(M + H)^+$ |

-continued

| Example | Structure | Starting materials | $^{1}$H-NMR (400 MHz) | LCMS (ESI) m/z |
|---|---|---|---|---|
| Example 26 | 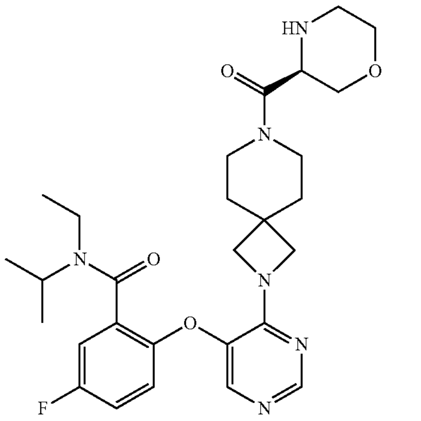 [SMILES: CCN(C(=O)c1cc(F)ccc1Oc1cncnc1N1CC2(CCN(C(=O)[C@@H]3COCCN3)CC2)C1)C(C)C] | Intermediate 1 and 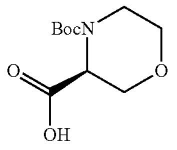 | $^{1}$H NMR (400 MHz, MeOD) δ 8.25 (d, J = 6.4 Hz, 1H), 7.77-7.73 (m, 1H), 7.25-7.14 (m, 2H), 7.05-6.97 (m, 1H), 4.14-3.94 (m, 5H), 3.95-3.88 (m, 2H), 3.78-3.75 (m, 1H), 3.64-3.57 (m, 2H), 3.52-3.42 (m, 4H), 3.40-3.32 (m, 2H), 3.27-3.25 (m, 1H), 2.95-2.93 (m, 2H), 1.84-1.76 (m, 4H), 1.34-1.14 (m, 9H) | 541 $(M + H)^+$ |
| Example 28 | 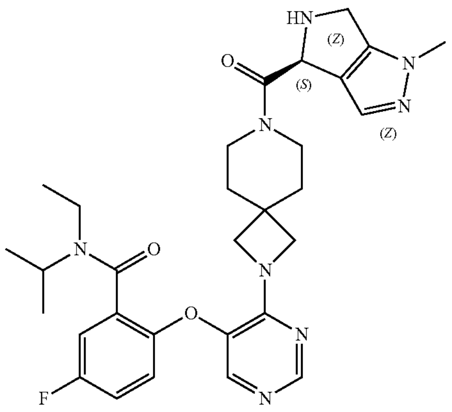 | Intermediate 1 and Intermediate 18 | $^{1}$H NMR (400 MHz, MeOD) δ 8.26 (d, J = 6.4 Hz, 1H), 7.79-7.74 (m, 1H), 7.25 (d, J = 3.2 Hz, 1H), 7.22-7.17 (m, 2H), 6.99-6.97 (m, 1H), 5.03 (s, 1H), 4.25-4.21 (m, 1H), 4.04-3.94 (m, 4H), 3.92-3.88 (m, 1H), 3.78 (s, 1H), 3.76 (s, 3H), 3.62 (s, 1H), 3.55-3.50 (m, 1H), 3.38-3.37 (m, 2H), 3.28-3.12 (m, 2H), 2.03-1.93 (m, 4H), 1.32-1.09 (m, 9H) | 577 $(M + H)^+$ |
| Example 29 | 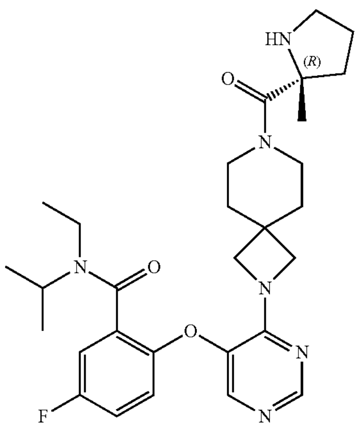 | Intermediate 1 and 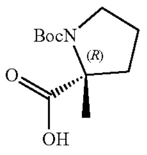 | $^{1}$H NMR (400 MHz, MeOD) δ 8.25 (d, J = 6.3 Hz, 1H), 7.78-7.74 (m, 1H), 7.21-7.16 (m, 2H), 6.99-6.96 (m, 1H), 4.03 (s, 2H), 3.98-3.85 (m, 3H), 3.59-3.48 (m, 4H), 3.39-3.33 (m, 1H), 2.90-2.84 (m, 1H), 2.82-2.75 (m, 1H), 2.15-2.10 (m, 2H), 1.94-1.84 (m, 2H), 1.80 (s, 5H), 1.39 (s, 3H), 1.32-1.08 (m, 9H) | 539 $(M + H)^+$ |

-continued
| Example | Structure | Starting materials | $^1$H-NMR (400 MHz) | LCMS (ESI) m/z |
|---|---|---|---|---|
| Example 30 | 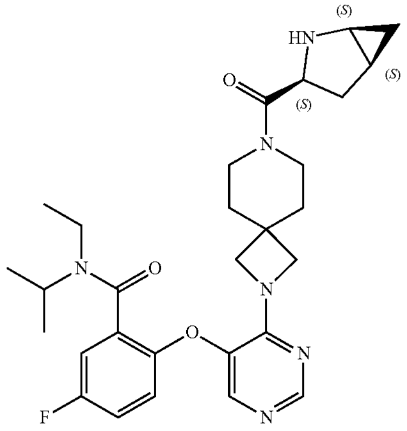 | Intermediate 1 and 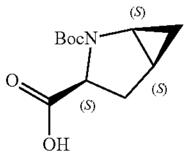 | $^1$H NMR (400 MHz, MeOD) δ 8.26-8.24 (m, 1H), 7.77-7.73 (m, 1H), 7.22-7.15 (m, 2H), 7.04-6.95 (m, 1H), 4.33-4.27 (m, 1H), 4.16-3.94 (m, 4H), 3.93-3.83 (m, 1H), 3.62-3.47 (m, 3H), 3.43-3.93 (m, 2H), 2.75-2.74 (m, 1H), 2.67-2.59 (m, 1H), 1.80-1.75 (m, 5H), 1.52-1.48 (m, 1H), 1.33-1.14 (m, 9H), 1.11-1.08 (m, 1H), 0.65-0.63 (m, 1H), 0.41-0.37 (m, 1H) | 537 $(M + H)^+$ |
| Example 31 | 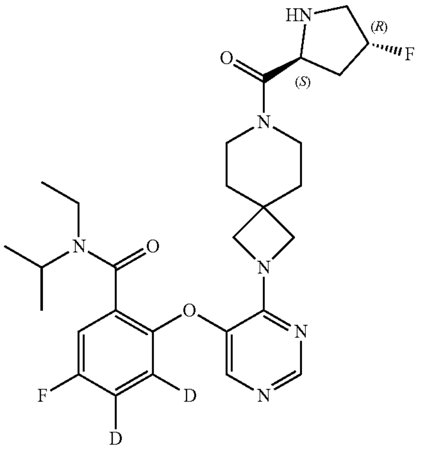 | Intermediate 5 and 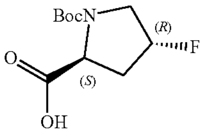 | $^1$H NMR (400 MHz, MeOD) δ 8.31 (s, 1H), 7.80-7.76 (m, 1H), 7.22-7.18 (m, 1H), 5.57-5.39 (m, 1H), 4.94-4.88 (m, 1H), 4.19 k-3.98 (m, 4H), 3.95-3.84 (m, 1H), 3.74-3.46 (m, 7H), 3.43-3.33 (m, 1H), 2.95-2.82 (m, 1H), 2.29-2.12 (m, 1H), 1.94-1.79 (m, 4H), 1.33-1.11 (m, 9H). | 545 $(M + H)^+$ |
| Example 32 | 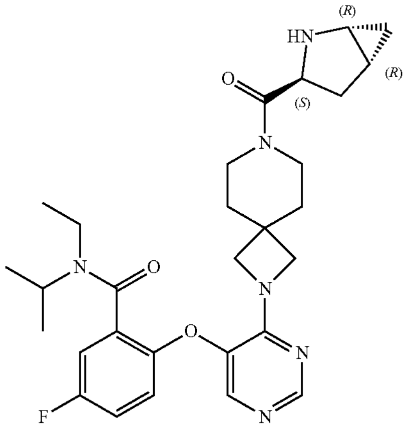 | Intermediate 1 and 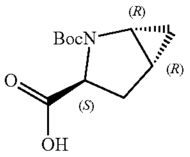 | $^1$H NMR (400 MHz, MeOD) δ 8.26-8.24 (m, 1H), 7.77-7.73 (m, 1H), 7.21-7.16 (m, 2H), 6.99-6.98 (m, 1H), 4.05-3.88 (m, 5H), 3.73-3.67 (m, 1H), 3.57-3.45 (m, 5H), 3.39-3.35 (m, 1H), 2.99-2.95 (m, 1H), 2.24-2.20 (m, 1H), 1.82-1.75 (m, 4H), 1.70-1.63 (m, 1H), 1.49-1.44 (m, 1H), 1.33-1.13 (m, 9H), 1.11-1.08 (m, 1H), 0.49 (t, J = 5.3 Hz, 2H) | 537 $(M + H)^+$ |

-continued

| Example | Structure | Starting materials | $^1$H-NMR (400 MHz) | LCMS (ESI) m/z |
|---|---|---|---|---|
| Example 33 | 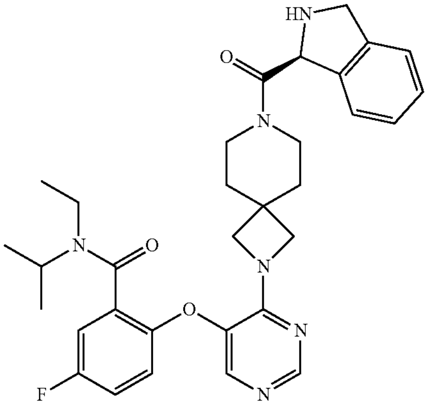 [SMILES: CCN(C(=O)c1cc(F)ccc1Oc1cncnc1N1CC2(CCN(C(=O)[C@H]3NCc4ccccc43)CC2)C1)C(C)C] | Intermediate 1 and 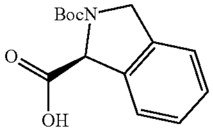 | $^1$H NMR (400 MHz, DMSO) δ 8.29 (d, J = 8.4 Hz, 1H), 7.75-7.68 (m, 1H), 7.32-7.12 (m, 7H), 7.11-7.04 (m, 1H), 5.38 (s, 1H), 4.33 (d, J = 14.3 Hz, 1H), 4.09-4.05 (m, 2H), 4.00-3.80 (m, 4H), 3.77-3.66 (m, 4H), 1.86-1.65 (m, 4H), 1.27-1.19 (m, 3H), 1.12-1.09 (m, 5H), 1.06-1.04 (m, 2H) | 573 $(M + H)^+$ |
| Example 34 | 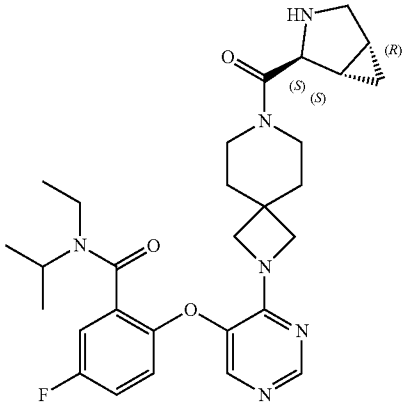 | Intermediate 1 and 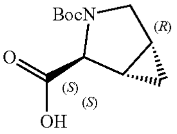 | $^1$H NMR (400 MHz, MeOD) δ 8.50 (br, 1H), 7.82-7.73 (m, 1H), 7.31-7.26 (m, 3H), 4.45-4.42 (m, 1H), 3.91-3.84 (m, 1H), 3.77-3.58 (m, 5H), 3.49-3.46 (s, 2H), 3.43-3.40 (m, 2H), 2.03-1.99 (m, 2H), 1.89-1.88 (m, 4H), 1.38-1.36 (m, 1H), 1.33-1.31 (m, 2H), 1.25-1.04 (m, 9H), 1.03-0.99 (m, 1H), 0.58 (m, 1H). | 537 $(M + H)^+$ |
| Example 36 | 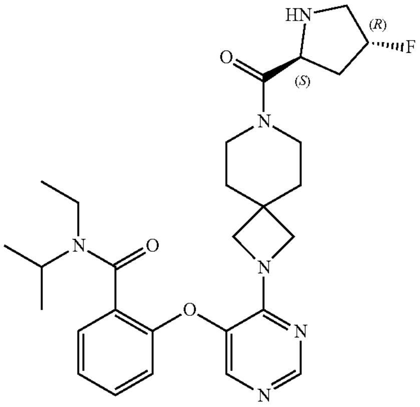 | Intermediate 6 and 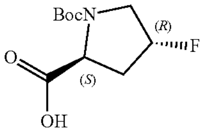 | $^1$H NMR (400 MHz, MeOD) δ 8.29-8.29 (m, 1H), 7.82-7.79 (m, 1H), 7.46-7.42 (m, 1H), 7.40-7.34 (m, 1H), 7.27-7.23 (m, 1H), 6.95-6.88 (m, 1H), 5.40-5.27 (m, 1H), 4.69-4.41 (m, 3H), 4.12-4.07 (m, 2H), 4.00-3.86 (m, 3H), 3.63-3.50 (m, 6H), 2.69-2.52 (m, 1H), 2.07-2.01 (m, 1H), 1.97-1.81 (m, 5H), 1.26 (t, J = 6.9 Hz, 3H), 1.17 (d, J = 6.4 Hz, 5H), 1.08 (t, J = 7.0 Hz, 1H) | 525 $(M + H)^+$ |
| Example 37 | 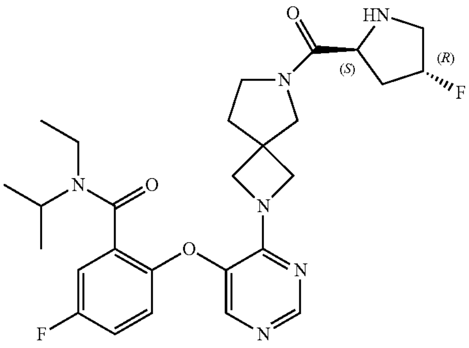 | Intermediate 7 and 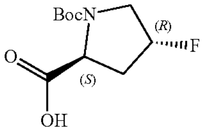 | $^1$H NMR (400 MHz, MeOD) δ 8.28-8.25 (m, 1H), 7.82-7.73 (m, 1H), 7.23-7.14 (m, 2H), 7.03-6.96 (m, 1H), 5.35-5.22 (m, 1H), 4.30-4.12 (m, 4H), 4.10-4.03 (m, 1H), 3.91-3.83 (m, 1H), 3.78-3.56 (m, 3H), 3.55-3.45 (m, 2H), 3.25-3.19 (m, 1H), 3.14-3.05 (m, 1H), 2.39-2.37 (m, 1H), 2.28-2.20 (m, 1H), 2.17-2.12 (m, 1H), 2.04-1.92 (m, 1H), 1.34-1.14 (m, 9H), 1.11-1.08 (m, 1H) | 529 $(M + H)^+$ |

-continued
| Example | Structure | Starting materials | $^1$H-NMR (400 MHz) | LCMS (ESI) m/z |
|---|---|---|---|---|
| Example 38 | 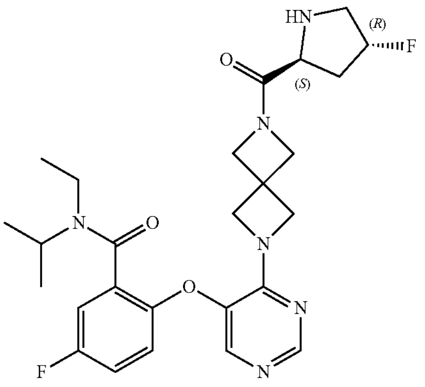 | Intermediate 8 and 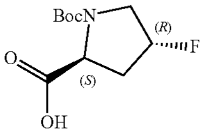 | $^1$H NMR (400 MHz, MeOD) δ 8.27-8.25 (m, 1H), 7.80-7.75 (m, 1H), 7.21-7.17 (m, 2H), 6.97-6.96 (m, 1H), 5.33-5.19 (m, 1H), 4.51-4.44 (m, 4H), 4.41-4.37 (m, 2H), 4.22-4.10 (m, 2H), 3.90-3.86 (m, 2H), 3.54-3.49 (m, 1H), 3.40-3.38 (m, 1H), 3.22-3.02 (m, 2H), 2.35-2.24 (m, 1H), 2.00-1.90 (m, 1H), 1.32-1.09 (m, 9H) | 515 $(M + H)^+$ |
| Example 40 | 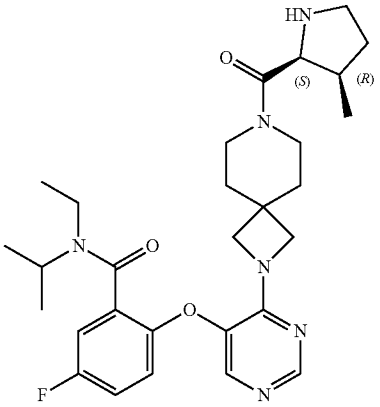 | Intermediate 1 and 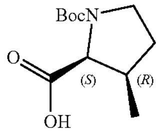 | 1HNMR (400 MHz, DMSO) δ 8.29-8.27 (m, 1H), 7.76-7.69 (m, 1H), 7.31-7.24 (m, 2H), 7.10-7.00 (m, 1H), 4.32-4.31 (m, 1H), 3.97 (s, 2H), 3.90-3.88 (m, 2H), 3.76-3.73 (m, 1H), 3.25-3.19 (m, 5H), 2.98-2.92 (m, 2H), 2.59 (s, 2H), 2.13-2.04 (m, 1H), 1.77 (s, 1H), 1.69 (s, 3H), 1.54 (s, 1H), 1.19 (s, 2H), 1.12-1.09 (m, 5H), 1.05-1.03 (m, 2H), 1.01-0.97 (m, 1H), 0.77 (d, J = 7.0 Hz, 3H). | 539 $(M + H)^+$ |
| Example 41 | 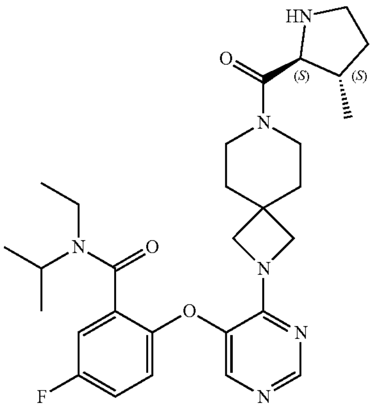 | Intermediate 1 and 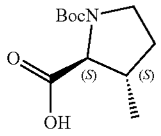 | $^1$H NMR (400 MHz, MeOD) δ 8.27-8.26 (m, 1H), 7.79-7.75 (s, 1H), 7.21-7.16 (m, 2H), 7.02-6.92 (m, 1H), 4.13-4.08 (m, 2H), 4.02-3.97 (m, 2H), 3.93-3.88 (m, 1H), 3.74-3.65 (m, 2H), 3.52-3.46 (m, 4H), 3.25-3.20 (m, 2H), 3.09-2.99 (m, 1H), 2.30-2.21 (m, 1H), 2.03-2.00 (m, 1H), 1.89-1.78 (m, 4H), 1.60-1.52 (m, 1H), 1.27-1.21 (m, 3H), 1.20-1.10 (m, 9H) | 539 $(M + H)^+$ |

-continued

| Example | Structure | Starting materials | $^1$H-NMR (400 MHz) | LCMS (ESI) m/z |
|---|---|---|---|---|
| Example 42 | 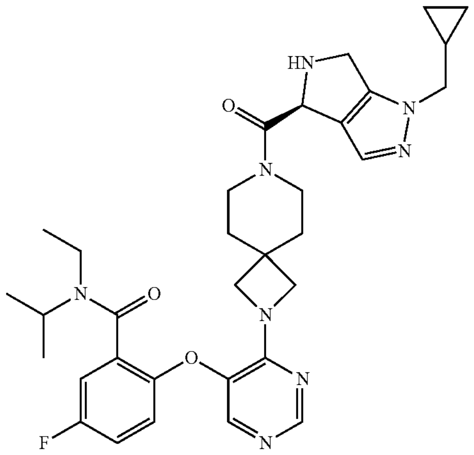 | Intermediate 1 and Intermediate 19 | $^1$H NMR (400 MHz, MeOD) δ 8.28-8.27 (m, 1H), 7.82-7.74 (m, 1H), 7.39-7.31 (m, 1H), 7.23-7.13 (m, 2H), 7.05-6.93 (m, 1H), 5.36 (s, 1H), 4.50-4.47 (m, 1H), 4.32-4.24 (m, 1H), 4.11-3.87 (m, 6H), 3.85-3.79 (m, 2H), 3.66-3.62 (m, 1H), 3.55-3.45 (m, 1H), 3.44-3.33 (m, 2H), 2.01-1.75 (m, 4H), 1.39-1.07 (m, 12H), 0.65-0.61 (m, 2H), 0.29-0.35 (m, 2H). | 539 $(M + H)^+$ |
| Example 43 | 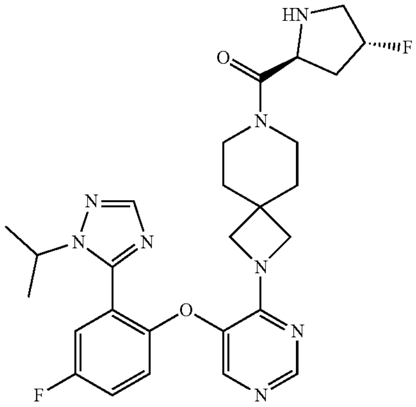 [SMILES: CC(C)n1ncnc1-c1cc(F)ccc1Oc1cncnc1N1CC2(CCN(C(=O)[C@@H]3C[C@@H](F)CN3)CC2)C1] | Intermediate 44 and 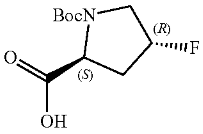 | $^1$H NMR (400 MHz, MeOD) δ 8.27 (s, 1H), 8.10 (s, 1H), 7.89 (s, 1H), 7.39-7.35 (m, 2H), 7.07-7.05 (m, 1H), 5.35-5.21 (m, 1H), 4.59-4.54 (m, 1H), 4.27-4.22 (m, 1H), 3.85 (s, 4H), 3.53-3.48 (m, 4H), 3.28-3.24 (m, 1H), 3.16-3.07 (m, 1H), 2.45-2.36 (m, 1H), 1.99-1.70 (m, 5H), 1.44 (d, J = 6.6 Hz, 6H) | 539 $(M + H)^+$ |
| Example 44 | 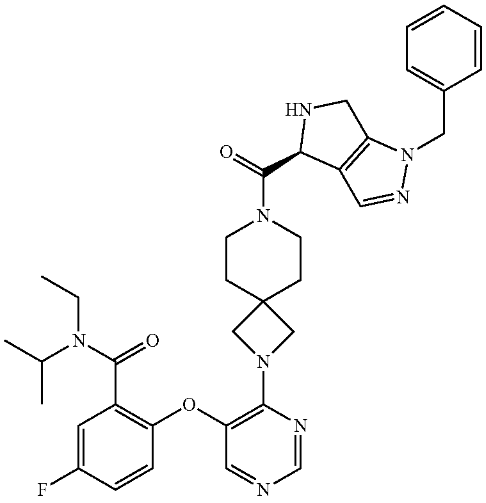 [SMILES: CCN(C(=O)c1cc(F)ccc1Oc1cncnc1N1CC2(CCN(C(=O)[C@H]3NCc4c3cnn4Cc3ccccc3)CC2)C1)C(C)C] | Intermediate 1 and Intermediate 20 | $^1$H NMR (400 MHz, DMSO) δ 8.29-8.27 (m, 1H), 7.76-7.69 (m, 1H), 7.37-7.25 (m, 8H), 7.10-7.03 (m, 1H), 5.39 (s, 1H), 5.26 (s, 2H), 4.22-4.19 (m, 1H), 3.99-3.84 (m, 5H), 3.77-3.65 (m, 3H), 3.55-3.45 (m, 3H), 1.88-1.61 (m, 4H), 1.23-0.99 (m, 10H) | 653 $(M + H)^+$ |

-continued
| Example | Structure | Starting materials | $^1$H-NMR (400 MHz) | LCMS (ESI) m/z |
|---|---|---|---|---|
| Example 45 | 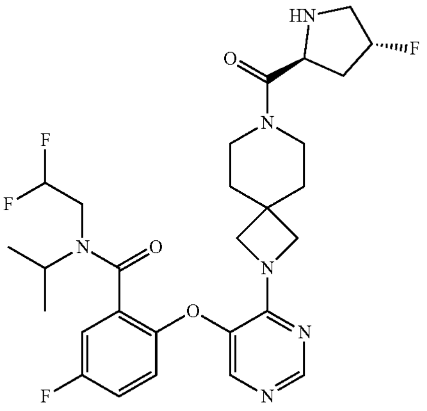 [SMILES: CC(C)N(CC(F)F)C(=O)c1cc(F)ccc1Oc1cncnc1N1CC2(CCN(C(=O)[C@@H]3C[C@@H](F)CN3)CC2)C1] | Intermediate 14 and 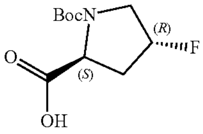 | $^1$H NMR (400 MHz, MeOD) δ 8.27 (s, 1H), 7.79 (s, 1H), 7.25-7.21 (m, 2H), 7.00-6.97 (m, 1H), 6.35-6.06 (m, 1H), 5.35-5.22 (m, 1H), 4.58 (s, 1H), 4.30-4.22 (m, 1H), 4.10-3.92 (m, 5H), 3.85-3.65 (m, 2H), 3.57-3.51 (m, 4H), 3.16-3.09 (m, 1H), 2.49-2.38 (m, 1H), 1.88-1.78 (m, 4H), 1.35-1.34 (m, 1H), 1.17 (s, 6H) | 579 $(M+H)^+$ |
| Example 46 | 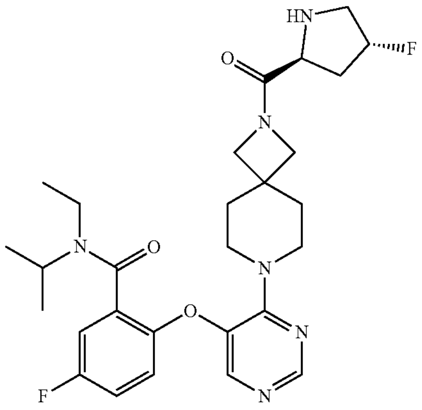 [SMILES: CCN(C(=O)c1cc(F)ccc1Oc1cncnc1N1CCC2(CC1)CN(C(=O)[C@@H]1C[C@@H](F)CN1)C2)C(C)C] | Intermediate 1 and 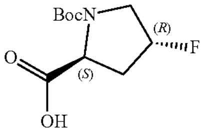 | $^1$H NMR (400 MHz, MeOD) δ 8.41-8.34 (m, 1H), 7.93-7.85 (m, 1H), 7.19-7.13 (m, 2H), 6.86-6.82 (m, 1H), 5.38-5.24 (m, 1H), 4.58-4.44 (m, 1H), 4.04-3.99 (m, 2H), 3.98-3.93 (m, 1H), 3.84-3.73 (m, 6H), 3.55-3.45 (m, 1H), 3.43-3.34 (m, 1H), 3.25-3.15 (m, 2H), 2.45-2.38 (m, 1H), 2.08-1.90 (m, 1H), 1.78 (br, 4H), 1.33-1.12 (m, 9H) | 543 $(M+H)^+$ |
| Example 47 | 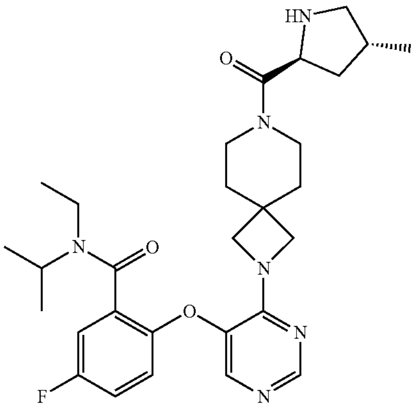 [SMILES: CCN(C(=O)c1cc(F)ccc1Oc1cncnc1N1CC2(CCN(C(=O)[C@@H]3C[C@@H](C)CN3)CC2)C1)C(C)C] | Intermediate 1 and 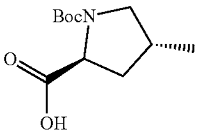 | $^1$H NMR (400 MHz, MeOD) δ 8.26-8.25 (m, 1H), 7.78-7.74 (m, 1H), 7.21-7.15 (m, 2H), 7.01-6.95 (m, 1H), 4.15-4.03 (m, 3H), 3.98-3.95 (m, 2H), 3.93-3.86 (m, 1H), 3.59-3.45 (m, 5H), 3.39-3.28 (d, J = 6.8 Hz, 1H), 2.44-2.36 (m, 1H), 2.17-2.09 (m, 1H), 1.82-1.77 (m, 5H), 1.32-1.28 (m, 3H), 1.26-1.11 (m, 9H), 1.05 (d, J = 6.6 Hz, 6H) | 539 $(M+H)^+$ |

-continued
| Example | Structure | Starting materials | $^1$H-NMR (400 MHz) | LCMS (ESI) m/z |
|---|---|---|---|---|
| Example 48 | 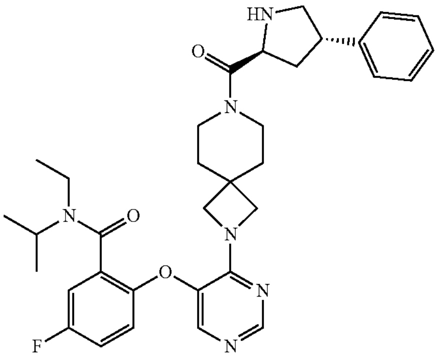 [SMILES: CCN(C(=O)c1cc(F)ccc1Oc1cncnc1N1CC2(CCN(C(=O)[C@@H]3C[C@@H](c4ccccc4)CN3)CC2)C1)C(C)C] | Intermediate 1 and 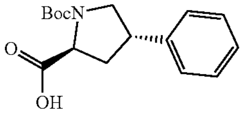 | $^1$H NMR (400 MHz, MeOD) δ 8.26-8.24 (m, 1H), 7.77-7.74 (m, 1H), 7.31-7.25 (m, 4H), 7.21-7.15 (m, 3H), 7.00-6.95 (m, 1H), 4.26-4.21 (m, 1H), 4.10-4.06 (m, 2H), 3.98-3.96 (m, 2H), 3.91-3.85 (m, 1H), 3.65-3.62 (m, 1H), 3.58-3.55 (m, 1H), 3.53-3.47 (m, 4H), 2.81-2.75 (m, 1H), 2.36-2.28 (m, 1H), 2.20-2.14 (m, 1H), 1.84-1.79 (m, 4H), 1.30 (d, J = 6.6 Hz, 2H), 1.26-1.08 (m, 9H) | 601 $(M + H)^+$ |
| Example 49 | 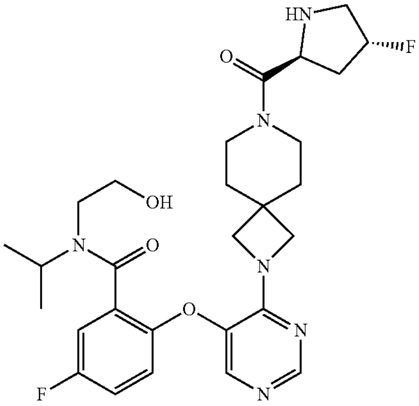 [SMILES: CC(C)N(CCO)C(=O)c1cc(F)ccc1Oc1cncnc1N1CC2(CCN(C(=O)[C@@H]3C[C@@H](F)CN3)CC2)C1] | Intermediate 31 and 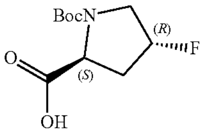 | 1H NMR (400 MHz, MeOD) δ 8.26-8.25 (m, 1H), 7.78-7.75 (m, 1H), 7.22-7.18 (m, 2H), 7.00-6.97 (m, 1H), 5.34-5.21 (m, 1H), 4.25-4.22 (m, 1H), 4.11-3.98 (m, 3H), 3.93-3.88 (m, 1H), 3.78-3.76 (m, 1H), 3.67-3.66 (m, 1H), 3.56-3.53 (m, 5H), 3.47-3.45 (m, 1H), 3.36-3.34 (m, 1H), 3.24-3.23 (m, 1H), 3.15-3.06 (m, 1H), 2.47-2.35 (m, 1H), 1.87-1.83 (m, 4H), 1.33-1.28 (m, 3H), 1.19-1.13 (m, 4H). | 559 $(M + H)^+$ |
| Example 50 | 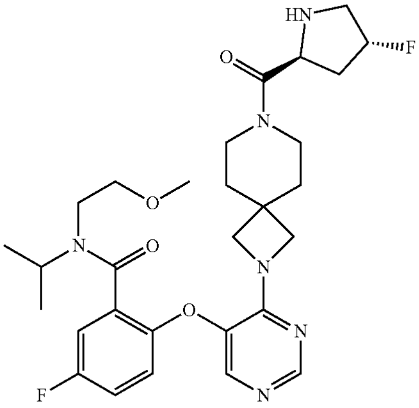 [SMILES: COCCN(C(=O)c1cc(F)ccc1Oc1cncnc1N1CC2(CCN(C(=O)[C@@H]3C[C@@H](F)CN3)CC2)C1)C(C)C] | Intermediate 32 and 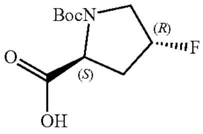 | 1HNMR (400 MHz, DMSO) δ 8.30-8.27 (m, 1H), 7.75-7.67 (m, 1H), 7.31-7.25 (m, 2H), 7.05-6.98 (m, 1H), 5.32-5.18 (m, 1H), 4.09-4.05 (m, 1H), 3.93-3.74 (m, 5H), 3.49-3.43 (m, 6H), 3.13-2.87 (m, 4H), 2.19-1.66 (m, 7H), 1.40-1.19 (m, 3H), 1.10-1.03 (m, 5H) | 573 $(M + H)^+$ |

-continued
| Example | Structure | Starting materials | ¹H-NMR (400 MHz) | LCMS (ESI) m/z |
|---|---|---|---|---|
| Example 51 | 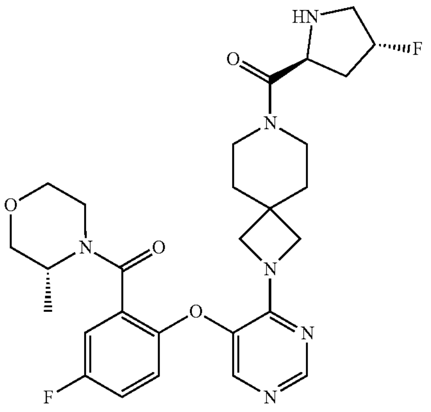 [SMILES: C[C@@H]1COCCN1C(=O)c1cc(F)ccc1Oc1cncnc1N1CC2(CCN(C(=O)[C@@H]3C[C@@H](F)CN3)CC2)C1] | Intermediate 10 and 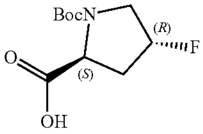 | ¹H NMR (400 MHz, DMSO) δ 8.31-8.27 (m, 1H), 7.79-7.69 (m, 1H), 7.36-7.28 (m, 2H), 7.09-7.05 (m, 1H), 5.31-5.17 (m, 1H), 4.07-3.87 (m, 6H), 3.69-3.64 (m, 1H), 3.53-3.42 (m, 6H), 3.23-3.02 (m, 5H), 2.95-2.85 (m, 1H), 2.16-1.91 (m, 2H), 1.75-1.65 (m, 4H), 1.24-1.08 (m, 3H) | 557 $(M + H)^+$ |
| Example 52 | 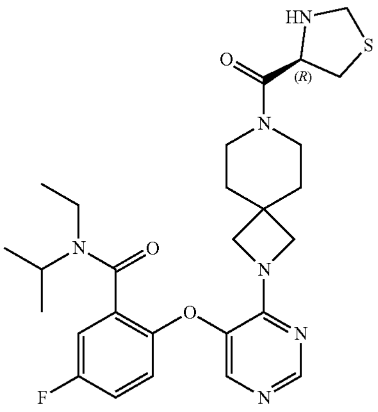 | Intermediate 1 and 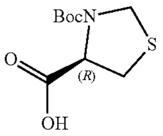 | ¹H NMR (400 MHz, MeOD) δ 8.30 (s, 1H), 7.78-7.74 (m, 1H), 7.25-7.16 (m, 2H), 7.07-7.01 (m, 1H), 4.42-4.31 (m, 2H), 4.14-4.12 (m, 2H), 4.03-4.01 (m, 2H), 3.981-3.85 (m, 1H), 3.63-3.49 (m, 5H), 3.41-3.32 (m, 2H), 3.29-3.23 (m, 1H), 2.88-2.79 (m, 1H), 1.87-1.81 (m, 4H), 1.32-1.08 (m, 9H) | 543 $(M + H)^+$ |
| Example 53 | 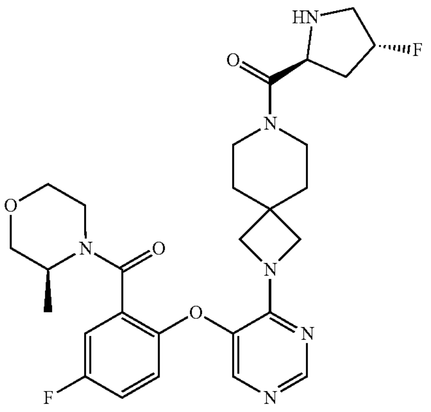 [SMILES: C[C@H]1COCCN1C(=O)c1cc(F)ccc1Oc1cncnc1N1CC2(CCN(C(=O)[C@@H]3C[C@@H](F)CN3)CC2)C1] | Intermediate 9 and 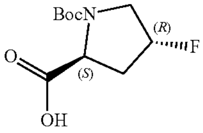 | ¹H NMR (400 MHz, MeOD) δ 8.30-8.23 (m, 1H), 7.84-7.71 (m, 1H), 7.26-7.14 (m, 2H), 7.04-6.94 (m, 1H), 5.37-5.19 (m, 1H), 4.68-4.46 (m, 1H), 4.26-4.21 (m, 1H), 4.18-3.88 (m, 5H), 3.81-3.42 (m, 9H), 3.26-3.21 (m, 1H), 3.15-3.05 (m, 1H), 2.48-2.34 (m, 1H), 1.92-1.73 (m, 5H), 1.39-1.22 (m, 3H) | 557 $(M + H)^+$ |

-continued

| Example | Structure | Starting materials | $^1$H-NMR (400 MHz) | LCMS (ESI) m/z |
|---|---|---|---|---|
| Example 54 | 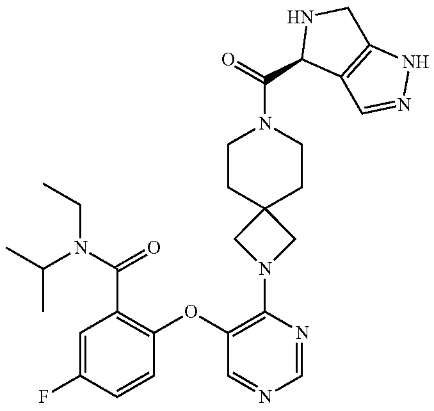 [SMILES: CCN(C(=O)c1cc(F)ccc1Oc1cncnc1N1CC2(CCN(C(=O)[C@H]3NCc4[nH]ncc43)CC2)C1)C(C)C] | Intermediate 1 and Intermediate 21 | $^1$H NMR (400 MHz, MeOD) δ 8.29-8.28 (m, 1H), 7.82-7.81 (m, 1H), 7.80-7.72 (m, 1H), 7.23-7.17 (m, 2H), 7.00-6.94 (m, 1H), 5.71 (s, 1H), 4.59-4.55 (m, 2H), 4.38-4.35 (m, 1H), 4.14-3.77 (m, 7H), 3.69-3.48 (m, 3H), 2.02-1.93 (m, 2H), 1.87-1.77 (m, 2H), 1.36-1.18 (m, 9H). | 563 $(M + H)^+$ |
| Example 58 | 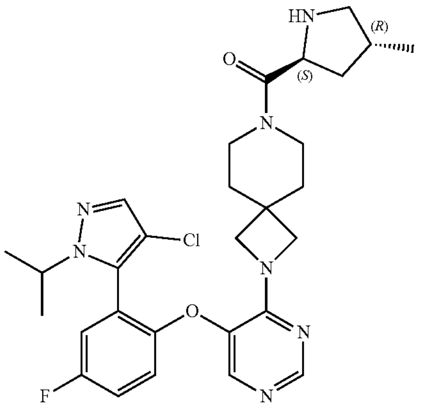 | Intermediate 45 and 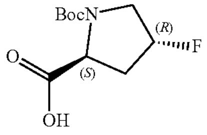 | 1H NMR (400 MHz, MeOD) δ 8.26 (s, 1H), 7.81 (s, 1H), 7.62 (s, 1H), 7.36-7.30 (m, 1H), 7.26-7.22 (m, 1H), 7.07-7.02 (m, 1H), 5.38-5.18 (m, 1H), 4.41-4.32 (m, 1H), 4.27-4.19 (m, 1H), 3.92-3.81 (m, 4H), 3.60-3.43 (m, 4H), 3.28-3.19 (m, 1H), 3.16-3.08 (m, 1H), 2.46-2.34 (m, 1H), 2.03-1.86 (m, 1H), 1.84-1.69 (m, 4H), 1.45-1.40 (m, 3H), 1.35 (d, J = 6.6 Hz, 3H) | 572 $(M + H)^+$ |
| Example 59 | 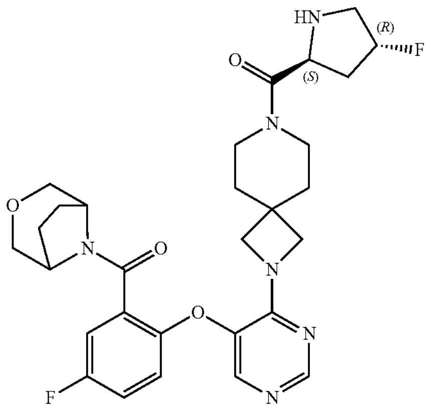 | Intermediate 12 and 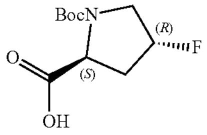 | $^1$H NMR (400 MHz, MeOD) δ 8.28 (s, 1H), 7.81 (s, 1H), 7.32-7.21 (m, 2H), 7.02-6.98 (m, 1H), 5.50-5.35 (m, 1H), 4.77-4.73 (m, 1H), 4.64-4.61 (m, 1H), 4.07-3.99 (m, 4H), 3.88-3.85 (m, 1H), 3.75-3.68 (m, 2H), 3.63-3.59 (m, 3H), 3.57-3.55 (m, 1H), 3.51-3.46 (m, 3H), 2.82-2.72 (m, 1H), 2.21-1.96 (m, 4H), 1.91-1.79 (m, 6H). | 569 $(M + H)^+$ |

Example 27

Preparation of 2-((4-(7-((2S,4R)-4-cyanopyrrolidine-2-carbonyl)-2,7-diazaspiro[3.5]nonan-2-yl)pyrimidin-5-yl)oxy)-N-ethyl-5-fluoro-N-isopropylbenzamide

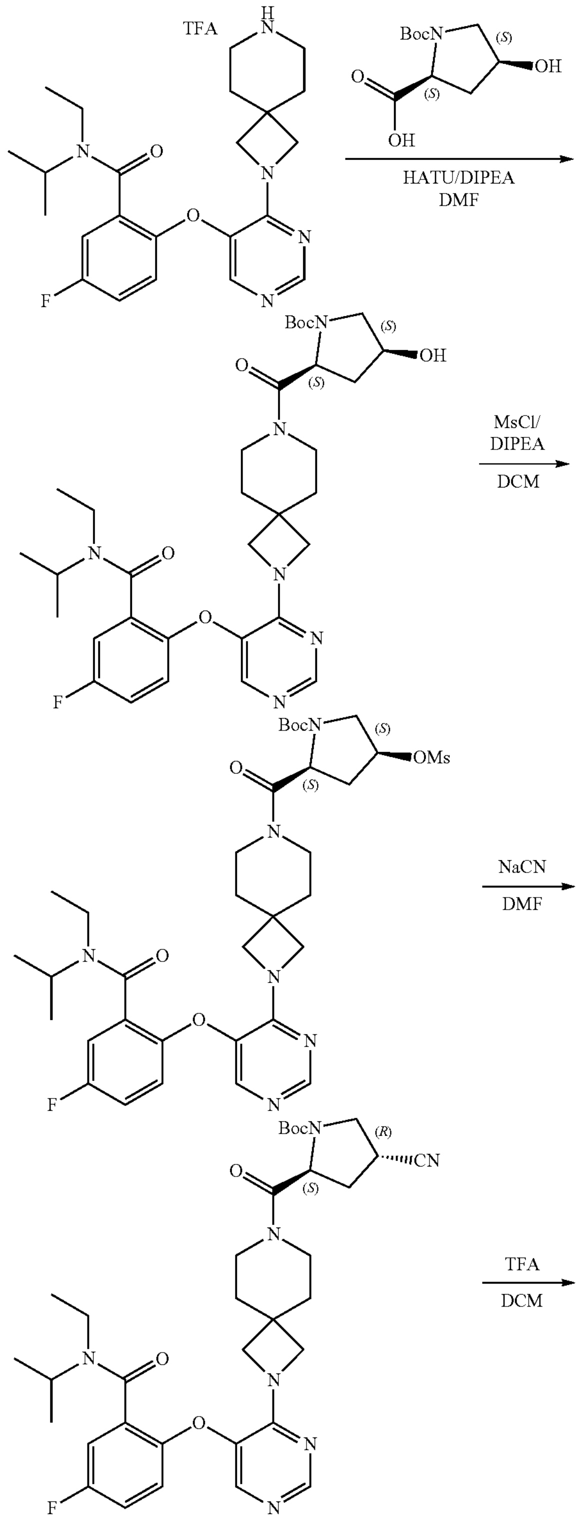

-continued

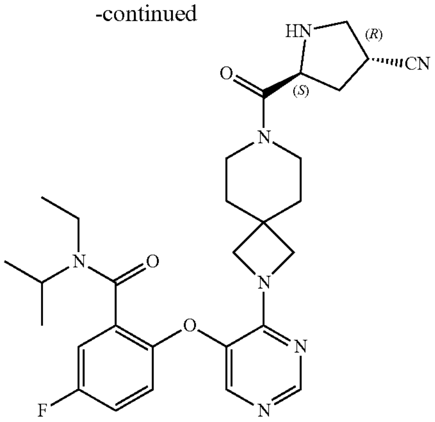

Step 1

To a solution of 2-(4-(2,7-diazaspiro[3.5]nonan-2-yl)pyrimidin-5-yloxy)-N-ethyl-5-fluoro-N-isopropylbenzamide (Intermediate 1, 280 mg, 0.53 mmol) and (2S,4S)-1-(tert-butoxycarbonyl)-4-hydroxypyrrolidine-2-carboxylic acid (277 mg, 0.60 mmol) in DMF (5 mL) was added DIPEA (0.8 mL, 3.5 mmol) and HATU (266 mg, 0.70 mmol) at 0° C. Then the reaction mixture was warmed to room temperature and stirred overnight. The reaction mixture was quenched with sat. $NH_4Cl$ solution, extracted with EtOAc (20 mL×3), the combined organic phase was washed with water and brine, dried over anhydrous $Na_2SO_4$, filtered and concentrated in vacuo to give the crude product which was purified by column chromatography on silica gel (EtOAc in PE=0~30%) to give the desired product tert-butyl (2S,4S)-2-(2-(5-(2-(ethyl(isopropyl)carbamoyl)-4-fluorophenoxy)pyrimidin-4-yl)-2,7-diazaspiro[3.5]nonane-7-carbonyl)-4-hydroxypyrrolidine-1-carboxylate (180 mg, yield: 80%) as a white solid. LCMS: m/z 641 $(M+H)^+$ Step 2

To a solution of tert-butyl (2S,4S)-2-(2-(5-(2-(ethyl(isopropyl)carbamoyl)-4-fluorophenoxy)pyrimidin-4-yl)-2,7-diazaspiro[3.5]nonane-7-carbonyl)-4-hydroxypyrrolidine-1-carboxylate (180 mg, 0.28 mmol) and DIPEA (72 mg, 0.56 mmol) in DCM (10 mL) was added MsCl (0.10 mL, 0.42 mmol) at 0° C. The resulting mixture was stirred at room temperature for 3 h. The reaction mixture was quenched with sat. $NH_4Cl$ solution (10 mL) and extracted with EtOAc (20 mL×3). The combined organic phase was washed with brine, dried over anhydrous $Na_2SO_4$ filtered and concentrated, the residue was purified by column chromatography on silica gel (EtOAc in PE=0~20%) to give the desired product tert-butyl (2S,4S)-2-(2-(5-(2-(ethyl(isopropyl)carbamoyl)-4-fluorophenoxy)pyrimidin-4-yl)-2,7-diazaspiro[3.5]nonane-7-carbonyl)-4-((methylsulfonyl)oxy)pyrrolidine-1-carboxylate (150 mg, yield: 80%) as a white solid. LCMS: m/z 719 $(M+H)^+$ Step 3

To a solution of tert-butyl (2S,4S)-2-(2-(5-(2-(ethyl(isopropyl)carbamoyl)-4-fluorophenoxy)pyrimidin-4-yl)-2,7-diazaspiro[3.5]nonane-7-carbonyl)-4-((methylsulfonyl)oxy)pyrrolidine-1-carboxylate (150 mg, 0.21 mmol) in DMF (5 mL) was added NaCN (20 mg, 0.40 mmol) at 0° C. The mixture was stirred at 100° C. for 10 h. The resulting mixture was diluted with water (10 mL) and extracted with EtOAc (15 mL×3). The combined organic phase was washed with brine, dried over anhydrous $Na_2SO_4$ filtered and concentrated, the residue was purified by column chromatography on silica gel (EtOAc in PE=0~ 20%) to give the desired product tert-butyl (2S,4R)-4-cyano-2-(2-(5-(2-(ethyl (isopropyl)carbamoyl)-4-fluorophenoxy)pyrimidin-4-yl)-2, 7-diazaspiro[3.5]nonane-7-carbonyl)pyrrolidine-1-carboxylate (60 mg, yield: 45%) as a yellow solid. LCMS: m/z 650 $(M+H)^+$ Step 4

To a solution of tert-butyl (2S,4R)-4-cyano-2-(2-(5-(2-(ethyl(isopropyl)carbamoyl)-4-fluorophenoxy)pyrimidin-4-yl)-2,7-diazaspiro[3.5]nonane-7-carbonyl)pyrrolidine-1-carboxylate (60 mg, 0.09 mmol) in DCM (3 mL) was added TFA (1.0 mL) at 0° C. The reaction mixture was stirred for 1 h at rt and concentrated under reduced pressure to give the crude product which was purified by Prep-HPLC to afford the desired product 2-((4-(7-((2S,4R)-4-cyanopyrrolidine-2-carbonyl)-2,7-diazaspiro[3.5]nonan-2-yl)pyrimidin-5-yl) oxy)-N-ethyl-5-fluoro-N-isopropylbenzamide (20 mg, yield: 30%) as a white solid. 1H NMR (400 MHz, MeOD) δ 8.26-8.25 (m, 1H), 7.78-7.74 (m, 1H), 7.21-7.15 (m, 2H), 7.00-6.96 (m, 1H), 4.20-4.16 (m, 1H), 4.06-3.87 (m, 5H), 3.58-3.46 (m, 5H), 3.39-3.36 (m, 1H), 3.27-3.26 (m, 1H), 3.15-2.91 (m, 2H), 2.40-2.17 (m, 1H), 1.84-1.78 (m, 4H), 1.32-1.09 (m, 10H). LCMS: m/z 550 $(M+H)^+$.

Example 39

Preparation of N-ethyl-5-fluoro-2-[(5-{7-[(2S,4R)-4-fluoropyrrolidine-2-carbonyl]-2,7-diazaspiro [3.5] nonan-2-yl}-1,2,4-triazin-6-yl) oxy]-N-(propan-2-yl) benzamide

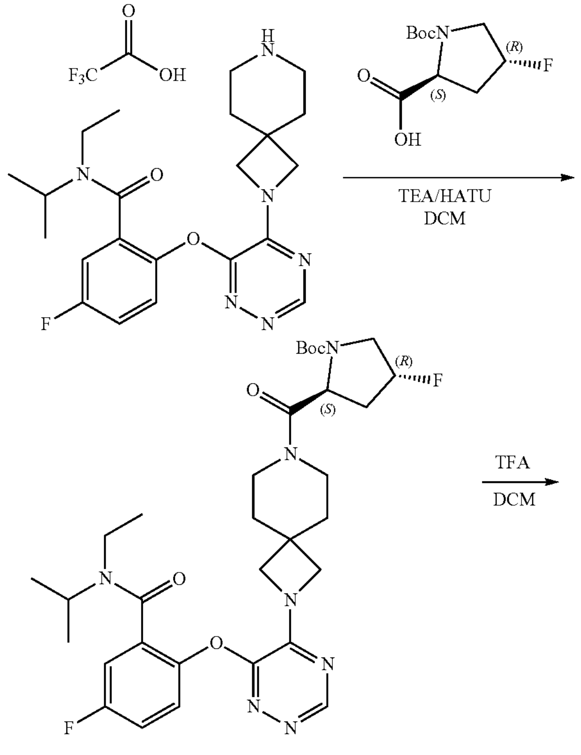

-continued

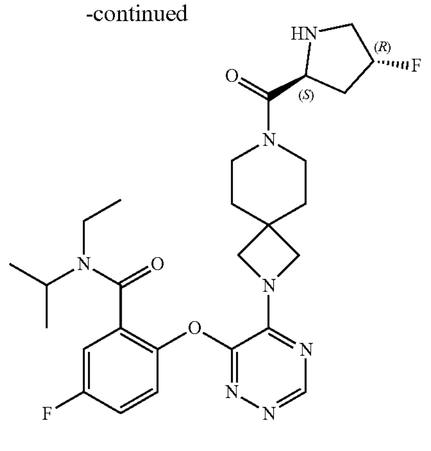

Step 1

To a stirred solution of (2S,4R)-1-[(tert-butoxy) carbonyl]-4-fluoropyrrolidine-2-carboxylic acid (381 mg, 1.63 mmol) and HATU (517 mg, 1.36 mmol) in DMF (15 mL) was added DIPEA (0.68 mL, 4.1 mmol). The reaction mixture was stirred at rt for 10 min before addition of 2-[(5-{2,7-diazaspiro[3.5] nonan-2-yl}-1,2,4-triazin-6-yl) oxy]-N-ethyl-5-fluoro-N-(propan-2-yl) benzamide (583 mg, 1.36 mmol), the resulting mixture was stirred for another 1 h at rt. The reaction mixture was quenched with $H_2O$ (50 mL), extracted with EtOAc (50 mL×3), the combined organic layer was dried over anhydrous $Na_2SO_4$, filtered and concentrated, the residue was purified by chromatography column on silica gel (MeOH in DCM=0~5%) to give the desired product tert-butyl (2S,4R)-2-[2-(6-{2-[ethyl(propan-2-yl)carbamoyl]-4-fluorophenoxy}-1,2,4-triazin-5-yl)-2,7-diazaspiro[3.5]nonane-7-carbonyl]-4-fluoropyrrolidine-1-carboxylate (650 mg, yield: 74.2%) as a white solid. LCMS: ESI m/z 644 $(M+H)^+$.

Step 2

To a solution of tert-butyl (2S,4R)-2-[2-(6-{2-[ethyl(propan-2-yl) carbamoyl]-4-fluorophenoxy}-1,2,4-triazin-5-yl)-2,7-diazaspiro[3.5] nonane-7-carbonyl]-4-fluoropyrrolidine-1-carboxylate (500 mg, 0.78 mmol) in DCM (10 mL) was added TFA (5 mL) at rt. The reaction mixture was stirred for 1 h at rt. The resulting mixture was concentrated, the residue was purified with Prep-HPLC (0.1% formic acid in $CH_3CN$) to afford desired product N-ethyl-5-fluoro-2-[(5-{7-[(2S,4R)-4-fluoropyrrolidine-2-carbonyl]-2,7-diazaspiro [3.5] nonan-2-yl}-1,2,4-triazin-6-yl) oxy]-N-(propan-2-yl) benzamide (315 mg, yield: 74.6%) as a white solid. 1H NMR (400 MHZ, MeOD) δ 8.59 (d, J=6.6 Hz, 1H), 7.46-7.43 (m, 1H), 7.35-7.22 (m, 2H), 5.56-5.43 (m, 1H), 4.98-4.93 (m, 1H), 4.54 (s, 2H), 4.13 (s, 2H), 3.87-3.80 (m, 1H), 3.71-3.51 (m, 7H), 3.17 (m, 1H), 2.95-2.85 (m, 1H), 2.29-2.14 (m, 1H), 1.97-1.90 (m, 4H), 1.25-0.87 (m, 9H), LC/MS (ESI) m/z: 544 $(M+H)^+$.

The following compounds were prepared from the appropriate intermediates or commercially available chemicals according to experimental procedure for Example 39:

| Example | Structure | Starting materials | $^1$H-NMR (400 MHz) | LCMS (ESI) m/z |
|---|---|---|---|---|
| Example 55 | 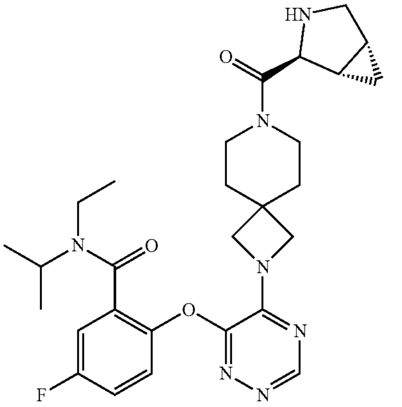 [SMILES: CCN(C(=O)c1cc(F)ccc1Oc1nncnc1N1CC2(CCN(C(=O)[C@H]3NC[C@@H]4C[C@@H]43)CC2)C1)C(C)C] | Intermediate 34 and 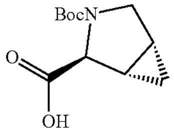 [SMILES: CC(C)(C)OC(=O)N1C[C@@H]2C[C@@H]2[C@H]1C(=O)O] | 1H NMR (400 MHz, MeOD) δ 8.40 (s, 1H), 7.43-7.40 (m, 1H), 7.30-7.25 (m, 1H), 7.22-7.20 (m, 1H), 4.45 (br, 2H), 4.05-4.01 (m, 3H), 3.84-3.81 (m, 1H), 3.66-3.45 (m, 6H), 3.21-3.19 (m, 1H), 2.95-2.92 (m, 1H), 1.94-1.85 (m, 4H), 1.55-1.53 (m, 2H), 1.22-1.07 (m, 7H), 0.82-0.80 (m, 2H), 0.67-0.65 (m, 1H), 0.39-0.38 (m, 1H) | 538(M + H)$^+$ |
| Example 56 | 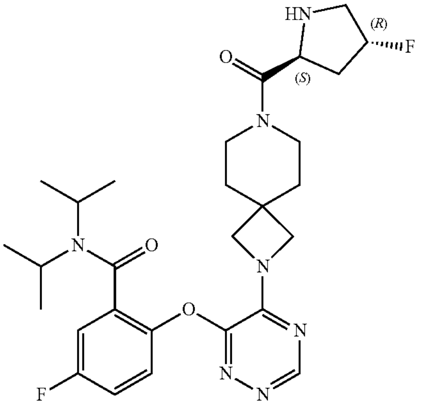 | Intermediate 35 and 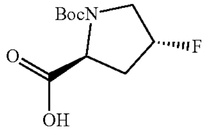 [SMILES: CC(C)(C)OC(=O)N1C[C@H](F)C[C@H]1C(=O)O] | 1H NMR (400 MHz, DMSO) δ 8.47 (s, 1H), 7.45-7.41 (m, 1H), 7.35-7.28 (m, 2H), 5.32-5.18 (m, 1H), 4.33-4.31 (m, 2H), 4.09-4.08 (m, 2H), 3.94-3.89 (m, 3H), 3.57-3.55 (m, 4H), 2.96-2.87 (m, 2H), 1.76-1.70 (m, 6H), 1.41 (d, J = 5.9 Hz, 3H), 1.29 (d, J = 5.9 Hz, 3H), 1.07 (d, J = 6.3 Hz, 3H), 0.65 (d, J = 3.9 Hz, 3H) | 558(M + H)$^+$ |
| Example 57 | 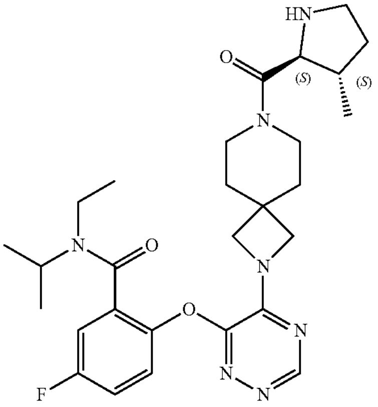 | Intermediate 34 and 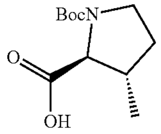 | 1H NMR (400 MHz, MeOD) δ 8.40 (s, 1H), 7.42-7.40 (m, 1H), 7.32-7.28 (m, 1H), 7.22-7.20 (m, 1H), 4.60-4.58 (m, 1H), 4.48-4.45 (m, 2H), 4.03-3.98 (m, 2H), 3.84-3.80 (m, 2H), 3.72-3.70 (m, 1H), 3.67-3.60 (m, 3H), 3.52-3.48 (m, 3H), 3.02-2.95 (m, 1H), 2.27-2.23 (m, 1H), 1.99-1.85 (m, 4H), 1.56-1.52 (m, 1H), 1.23-1.15 (m, 9H), 0.86-0.80 (m, 3H) | 540(M + H)$^+$ |

-continued
| Example | Structure | Starting materials | $^1$H-NMR (400 MHz) | LCMS (ESI) m/z |
|---|---|---|---|---|
| Example 60 | 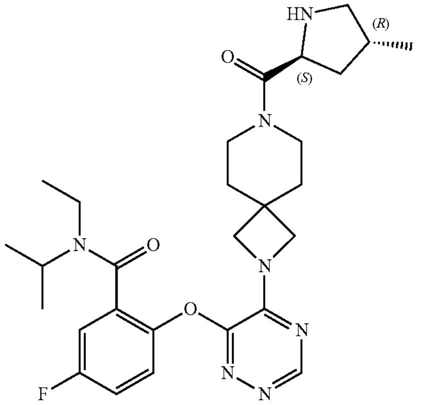 | Intermediate 34 and 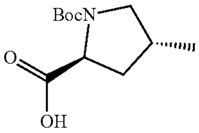 | 1H NMR (400 MHz, MeOD) δ 8.41 (s, 1H), 7.43-7.40 (m, 1H), 7.31-7.29 (m, 1H), 7.23-7.20 (m, 1H), 4.70-4.67 (m, 1H), 4.60-4.56 (m, 1H), 4.50-4.40 (m, 2H), 4.03-3.98 (m, 2H), 3.84-3.80 (m, 1H), 3.67-3.61 (m, 1H), 3.56-3.50 (m, 4H), 2.83-2.77 (m, 1H), 2.37-2.32 (m, 1H), 2.13-2.09 (m, 2H), 1.94-1.87 (m, 4H), 1.33-1.29 (m, 2H), 1.21-1.12 (m, 9H), 0.81-0.79 (m, 2H) | 540(M + H)$^+$ |
| Example 61 | 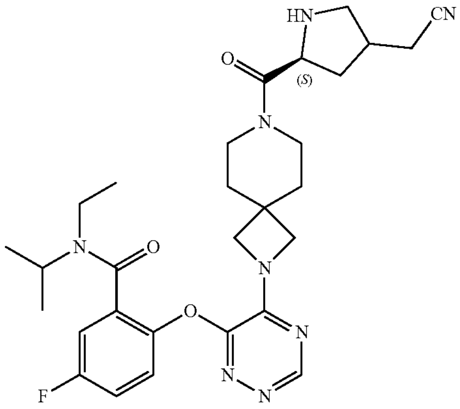 | Intermediate 34 and Intermediate 28 | $^1$H NMR (400 MHz, $CDCl_3$) δ 8.49 (s, 1H), 7.26-7.25 (m, 1H), 7.17-7.11 (m, 1H), 7.02-6.99 (m, 1H), 4.51-4.27 (m, 2H), 4.06 3.82 (m, 4H), 3.54-3.40 (m, 4H), 3.14-3.10 (m, 2H), 2.97-2.91 (m, 1H), 2.60-2.53 (m, 1H), 2.47-2.33 (m, 3H), 1.89-1.81 (m, 5H), 1.58-1.49 (m, 2H), 1.16-0.78 (m, 9H) | 565(M + H)$^+$ |
| Example 62 | 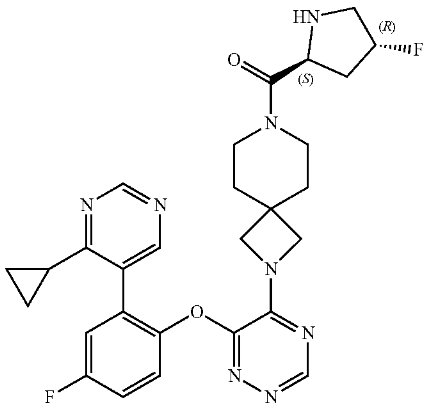 | Intermediate 42 and 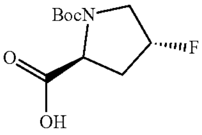 [SMILES: CC(C)(C)OC(=O)N1C[C@H](F)C[C@H]1C(=O)O] | 1H NMR (400 MHz, MeOD) δ 8.90 (s, 1H), 8.42 (s, 1H), 8.33 (s, 1H), 7.54-7.50 (m, 1H), 7.37-7.28 (m, 1H), 7.32-7.28 (m, 1H), 5.35-5.22 (m, 1H), 4.28-4.16 (m, 2H), 3.89 (br, 3H), 3.60-3.48 (m, 5H), 3.19-3.07 (m, 1H), 2.48-2.34 (m, 1H), 2.02-1.74 (m, 6H), 1.10-1.02 (m, 3H), 0.82-0.72 (m, 1H). | 549(M + H)$^+$ |

-continued
| Example | Structure | Starting materials | $^1$H-NMR (400 MHz) | LCMS (ESI) m/z |
|---|---|---|---|---|
| Example 63 | 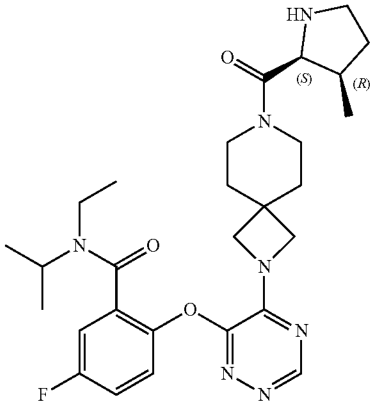 | Intermediate 34 and 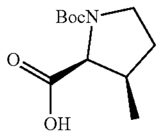 | 1H NMR (400 MHz, CDCl3) δ 8.50 (s, 1H), 7.29-7.28 (m, 1H), 7.17-7.12 (m, 1H), 7.06-6.98 (m, 1H), 5.05-5.03 (m, 1H), 4.57-4.30 (m, 2H), 3.96-3.85 (m, 4H), 3.54-3.13 (m, 7H), 2.83-2.81 (m, 1H), 2.38-2.36 (m, 1H), 1.90-1.81 (m, 5H), 1.19-0.76 (m, 13H) | 540(M + H)$^+$ |
| Example 64 | 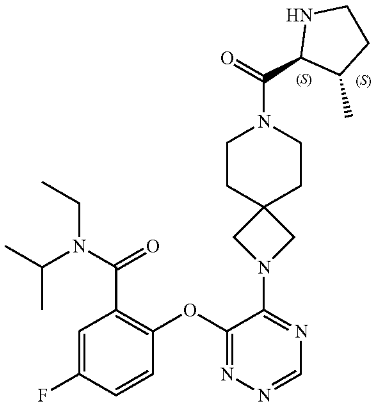 | Intermediate 35 and 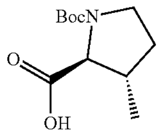 | 1H NMR (400 MHz, MeOD) δ 8.40 (s, 1H), 7.42-7.38 (m, 1H), 7.28-7.23 (m, 1H), 7.18-7.16(m, 1H), 4.51-4.43 (m, 2H), 4.04-3.97 (m, 2H), 3.79-3.74 (m, 1H), 3.67-3.48 (m, 6H), 3.17-3.13 (m, 1H), 2.97-2.91 (m, 1H), 2.27-2.20 (m, 1H), 1.96-1.84 (m, 5H), 1.54-1.48 ( m, 4H), 1.40-1.38 (m, 3H), 1.15 (t, J = 5.9 Hz, 6H), 0.75 (d, J = 6.4 Hz, 3H) | 554(M + H)$^+$ |
| Example 65 | 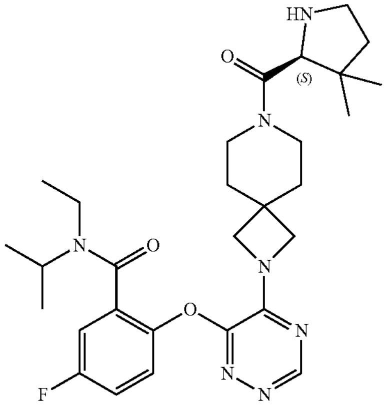 | Intermediate 34 and 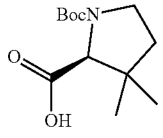 | 1H NMR (400 MHz, MeOD) δ 8.40 (s, 1H), 7.43-7.39 (m, 1H), 7.30-7.26 (m, 1H), 7.22-7.20 (m, 1H), 4.48-4.41 (m, 2H), 4.09-3.97 (m, 3H), 3.86-3.8 (m, 2H), 3.78-3.66 (m, 1H), 3.52-3.44 (m, 3H), 3.31-3.26 (m, 2H), 2.91-2.89 (m, 1H), 1.94-1.85 (m, 4H), 1.75-1.71 (m, 2H), 1.25-1.14 (m, 9H), 1.09-1.05 (m, 1H), 0.95-0.93 (m, 3H), 0.81-0.78 (m, 2H) | 554(M + H)$^+$ |

-continued
| Example | Structure | Starting materials | $^1$H-NMR (400 MHz) | LCMS (ESI) m/z |
|---|---|---|---|---|
| Example 66 | 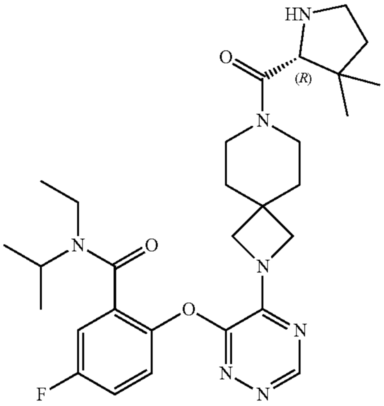 | Intermediate 34 and 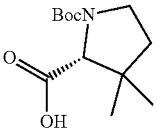 | 1H NMR (400 MHz, MeOD) δ 8.40 (s, 1H), 7.43-7.38 (m, 1H), 7.31-7.25 (m, 1H), 7.22-7.20 (m, 1H), 4.48-4.42 (m, 2H), 4.04-3.92 (m, 4H), 3.85-3.79 (m, 1H), 3.76-3.65 (m, 1H), 3.52-3.44 (m, 3H), 3.26-3.21 (m, 1H), 3.13-3.05 (m, 1H), 3.01-2.95 (m, 1H), 1.95-1.76 (m, 6H), 1.27-1.13 (m, 9H), 1.09-1.05 (m, 1H), 0.97-0.95 (m, 3H), 0.81-0.78 (m, 2H) | 554(M + H)$^+$ |
| Example 67 | 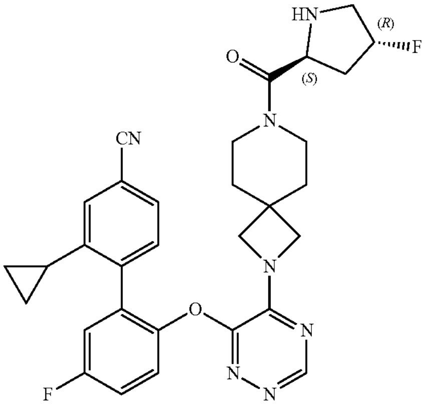 | Intermediate 43 and 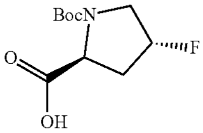 [SMILES: CC(C)(C)OC(=O)N1C[C@H](F)C[C@H]1C(=O)O] | 1H NMR (400 MHz, MeOD) δ 8.33-8.29 (m, 1H), 7.53-7.51 (m, 2H), 7.31-7.25 (m, 3H), 7.21-7.17 (m, 1H), 5.48-5.35 (m, 1H), 4.69-4.65 (m, 1H), 4.01-3.95 (m, 1H), 3.87-3.85 (m, 2H), 3.50-3.43 (m, 7H), 2.77-2.70 (m, 1H), 2.18-2.09 (m, 1H), 1.75-1.66 (m, 5H), 0.93-0.86 (m, 1H), 0.70-0.61 (m, 3H) | 572(M + H)$^+$ |
| Example 68 | 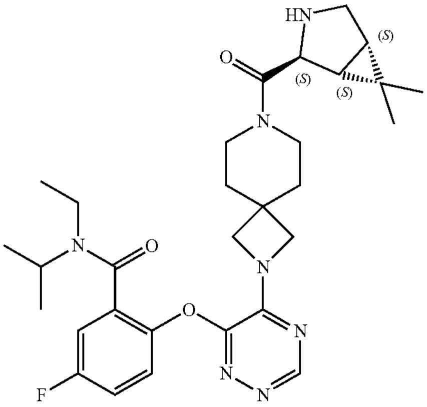 | Intermediate 34 and 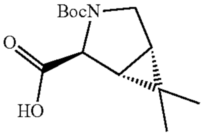 | 1H NMR (400 MHz, MeOD) δ 8.41 (s, 1H), 7.43-7.40 (m, 1H), 7.32-7.21 (m, 2H), 4.45-4.43 (m, 3H), 4.05-4.02 (m, 2H), 3.85-3.72 (m, 3H), 3.56-3.52 (m, 4H), 3.24-3.21 (m, 2H), 1.98-1.85 (m, 5H), 1.76-1.74 (m, 1H), 1.22-1.14 (m, 13H), 0.81-0.78 (m, 2H). | 566(M + H)$^+$ |

-continued

| Example | Structure | Starting materials | $^1$H-NMR (400 MHz) | LCMS (ESI) m/z |
|---|---|---|---|---|
| Example 69 | 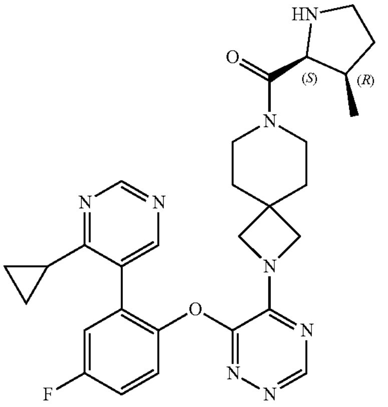 | Intermediate 42 and 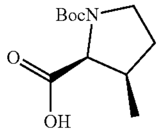 | 1H NMR (400 MHz, MeOD) δ 8.91 (s, 1H), 8.45 (s, 2H), 7.56-7.53 (m, 1H), 7.38-7.31 (m, 2H), 4.69 (d, J = 7.4 Hz, 1H), 4.26-4.23 (m, 1H), 4.00-3.97 (m, 3H), 3.76-3.73 (m, 1H), 3.57-3.44 (m, 4H), 3.34-3.33 (m, 1H), 2.88 (s, 1H), 2.37-2.32 (m, 1H), 1.86-1.82 (m, 6H), 1.11-0.95 (m, 6H), 0.83-0.80 (s, 1H) | 545(M + H)$^+$ |
| Example 70 | 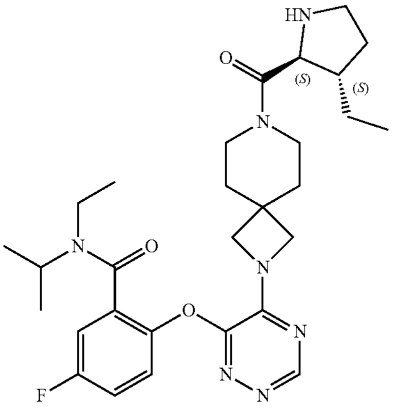 | Intermediate 34 and Intermediate 37 | 1H NMR (400 MHz, MeOD) δ 8.41 (s, 1H), 7.42-7.40 (m, 1H), 7.31-7.20 (m, 2H), 4.58 (s, 4H), 4.47-4.45 (s, 2H), 4.02-4.00 (m, 2H), 3.84-3.79 (m, 1H), 3.57-3.48 (m, 4H), 3.37-3.35 (m, 1H), 2.20-2.18 (m, 1H), 2.06-2.01 (m, 1H), 1.96-1.84 (m, 4H), 1.76-1.62 (m, 2H), 1.46 1.41 (m, 1H), 1.22-1.13 (m, 6H), 1.09-1.00 (m, 4H), 0.81-0.78 (m, 2H) | 554(M + H)$^+$ |
| Example 71 | 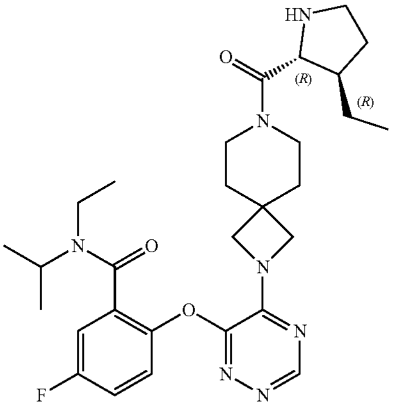 | Intermediate 34 and Intermediate 37 | $^1$H NMR (400 MHz, MeOD) δ 8.41 (s, 1H), 7.45-7.29 (m, 1H), 7.32-7.20 (m, 2H), 4.58 (s, 4H), 4.46-4.41 (m, 2H), 4.03-4.00 (d, J = 14.4 Hz, 2H), 3.86-3.80 (m, 1H), 3.59-3.45 (m, 4H), 3.40-3.35 (m, 1H), 2.28-2.24 (m, 1H), 2.15-2.10 (m, 1H), 1.7-1.93 (m, 2H), 1.90-1.83 (m, 3H), 1.75-1.67 (m, 1H), 1.54-1.46 (m, 1H), 1.22-1.12 (m, 6H), 1.09-1.01 (m, 4H), 0.84-0.76 (m, 2H) | 554(M + H)$^+$ |

-continued

| Example | Structure | Starting materials | $^1$H-NMR (400 MHz) | LCMS (ESI) m/z |
|---|---|---|---|---|
| Example 72 | 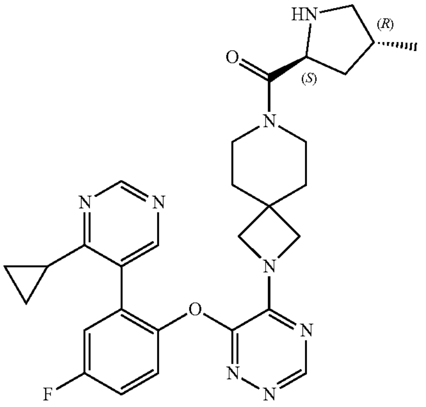 | Intermediate 42 and 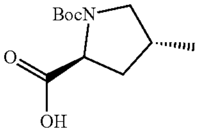 | 1H NMR (400 MHz, MeOD) 8 8.90 (s, 1H), 8.42 (s, 1H), 8.33 (s, 1H), 7.54-7.50 (m, 1H), 7.37-7.28 (m, 2H), 4.17-4.09 (m, 2H), 3.89 (s, 3H), 3.62-3.48 (m, 4H), 2.38 (t, J = 8.6 Hz, 1H), 2.15-2.10 (m, 1H), 1.92-1.88 (m, 1H), 1.85-1.76 (m, 7H), 1.10-1.01 (m, 6H), 0.77 (s, 1H) | 545 (M + H)+ |
| Example 73 | 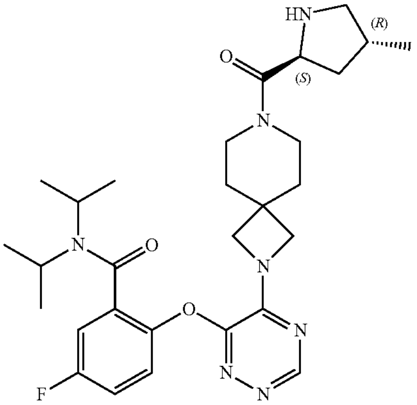 | Intermediate 35 and 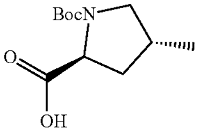 | 1H NMR (400 MHz, MeOD) δ 8.40 (s, 1H), 7.42-7.38(m, 1H), 7.28-7.23 (m, 1H), 7.18-7.16 (m, 1H), 4.52-4.41 (m, 2H), 4.10-3.98 (m, 3H), 3.77-3.74(m, 1H), 3.56-3.51 (m, 5H), 3.28-3.25 (m, 1H), 2.40-2.35 (m, 1H), 2.12-2.10 (m, 1H), 1.94-1.83 (m, 6H), 1.51 (d, J = 6.6 Hz, 3H), 1.39 (d, J = 6.6 Hz, 3H), 1.15 (d, J = 6.6 Hz, 3H), 1.05 (d, J = 6.6 Hz, 3H), 0.75 (d, J = 6.4 Hz, 3H) | 554(M + H)$^+$ |
| Example 74 | 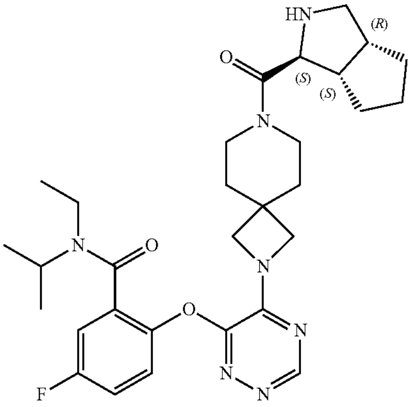 | Intermediate 34 and 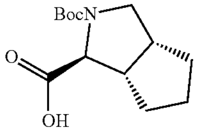 [SMILES: CC(C)(C)OC(=O)N1C[C@@H]2CCC[C@@H]2[C@H]1C(=O)O] | 1H NMR (400 MHz, MeOD) δ 8.40 (s, 1H), 7.43-7.38 (m, 1H), 7.31-7.20 (m, 2H), 4.45 (s, 2H), 4.00-3.98 (m, 3H), 3.85-3.79 (m, 1H), 3.68-3.48 (m, 5H), 3.44-3.40 (m, 1H), 3.19-3.16 (m, 1H), 2.70-2.63 (m, 3H), 2.01-1.79 (m, 7H), 1.68-1.64 (m, 2H), 1.49-1.47 (m, 1H), 1.28-1.05 (m, 7H), 0.81 (d, J = 4.7 Hz, 2H) | 566(M + H)$^+$ |

-continued

| Example | Structure | Starting materials | $^1$H-NMR (400 MHz) | LCMS (ESI) m/z |
|---|---|---|---|---|
| Example 75 | 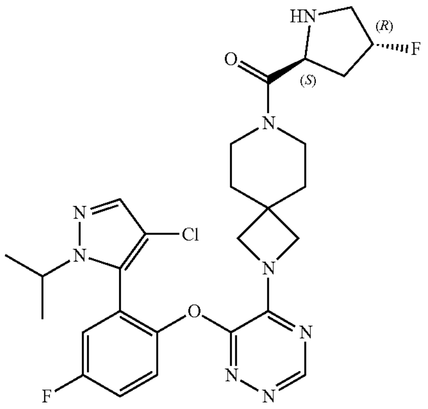 | Intermediate 36 and 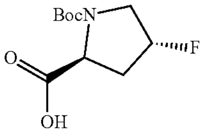 [SMILES: CC(C)(C)OC(=O)N1C[C@H](F)C[C@H]1C(=O)O] | $^1$H NMR (400 MHz, MeOD) δ 8.36 (s, 1H), 7.59 (s, 1H), 7.58-7.54 (m, 1H), 7.44-7.39 (m, 1H), 7.27-7.24 (m, 1H), 5.45-5.33 (m, 1H), 4.63-4.58 (m, 1H), 4.28-4.21 (m, 1H), 4.16-4.12 (m, 2H), 3.96-3.94 (m, 2H), 3.72-3.67 (m, 1H), 3.57-3.45 (m, 4H), 3.39-3.36 (m, 1H), 2.72-2.63 (m, 1H), 2.15-2.03 (m, 1H), 1.92-1.81 (m, 4H), 1.38 (d, J = 6.4 Hz, 3H), 1.17 (d, J = 6.4 Hz, 3H) | 573(M + H)$^+$ |
| Example 76 | 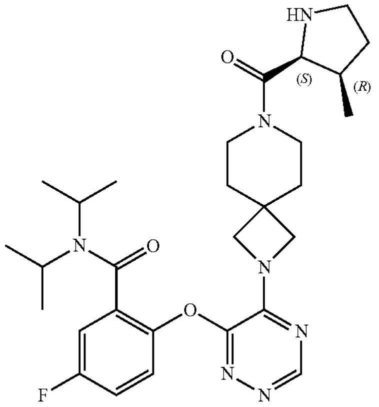 | Intermediate 35 and 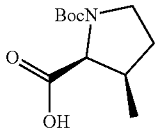 | 1H NMR (400 MHz, MeOD) δ 8.41 (s, 1H), 7.42-7.39 (m, 1H), 7.29-7.23 (m, 1H), 7.19-7.16 (m, 1H), 4.53-4.45 (m, 3H), 4.05-3.99 (m, 2H), 3.81-3.66 (m, 3H), 3.58-3.48 (m, 3H), 3.42-3.37 (m, 1H), 3.18-3.15 (m, 1H), 2.80-2.79 (m, 1H), 2.33-2.25 (m, 1H), 1.92-1.86 (m, 4H), 1.78-1.74 (m, 1H), 1.51 (d, J = 6.4 Hz, 3H), 1.39 (d, J = 5.6 Hz, 3H), 1.15 (d, J = 6.4 Hz, 3H), 0.95-0.91 (m, 3H), 0.75 (d, J = 6.4 Hz, 3H) | 554(M + H)$^+$ |
| Example 77 | 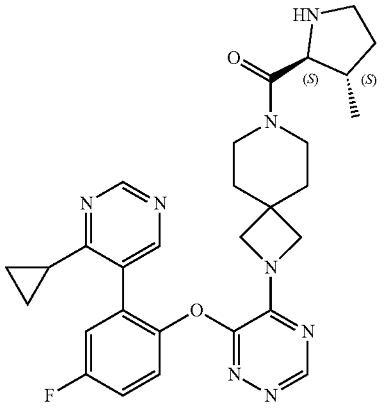 | Intermediate 42 and 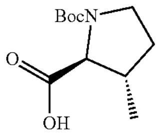 | 1H NMR (400 MHz, MeOD) δ 8.89 (s, 1H), 8.42 (s, 1H), 8.33 (s, 1H), 7.54-7.50 (m, 1H), 7.37-7.28 (m, 2H), 4.19-4.15 (m, 1H), 3.91-3.88 (m, 3H), 3.70-3.62 (m, 3H), 3.57-3.53 (m, 1H), 3.48-3.45 (m, 1H), 3.20-3.12 (m, 1H), 3.00-2.94 (m, 1H), 2.27-2.21(m, 1H), 2.01-1.94 (m, 1H), 1.86-1.77 (m, 5H), 1.57-1.49 (m, 1H), 1.17 (d, J = 6.8 Hz, 3H), 1.10-1.02 (m, 3H), 0.80-0.76 (m, 1H) | 545(M + H)+ |

-continued
| Example | Structure | Starting materials | $^1$H-NMR (400 MHz) | LCMS (ESI) m/z |
|---|---|---|---|---|
| Example 78 | 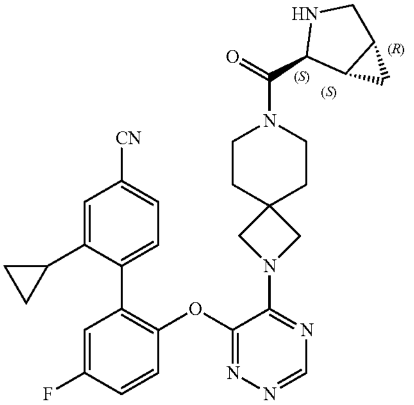 | Intermediate 43 and 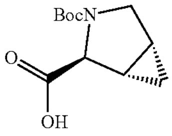 [SMILES: CC(C)(C)OC(=O)N1C[C@@H]2C[C@@H]2[C@H]1C(=O)O] | 1H NMR (400 MHz, MeOD) δ 8.32 (s, 1H), 7.54-7.49 (m, 2H), 7.31-7.25 (m, 3H), 7.20-7.17 (m, 1H), 4.09-4.02 (m, 1H), 4.01-3.92 (m, 1H), 3.89-3.84 (m, 2H), 3.69-3.54 (m, 3H), 3.52-3.42 (m, 2H), 3.24-3.16 (m, 1H), 2.95-2.91 (m, 1H), 1.84-1.80 (m, 2H), 1.76-1.70 (m, 2H), 1.68-1.64 (m, 1H), 1.56-1.52 (m, 2H), 0.94-0.85 (m, 1H), 0.72-0.61 (m, 4H), 0.44-0.37 (m, 1H) | 566(M + H)+ |
| Example 79 | 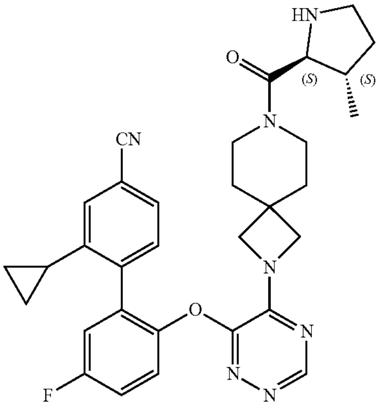 | Intermediate 43 and 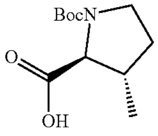 | 1H NMR (400 MHz, MeOD) δ 8.33 (s, 1H), 7.54-7.52 (m, 2H), 7.31-7.25 (m, 3H), 7.21-7.17 (m, 1H), 4.58 (, 1H), 4.00-3.95 (m, 1H), 3.88-3.85 (m, 2H), 3.78-3.7 (m, 2H), 3.60-3.53 (m, 2H), 3.43-3.39 (m, 1H), 3.20-3.15 (m, 1H), 3.05-2.99 (m, 1H), 2.28-2.21 (m, 1H), 2.03-1.93 (m, 1H), 1.83-1.70 (m, 4H), 1.68-1.63 (m, 1H), 1.59-1.52 (m, 1H), 1.22-1.14 (m, 3H), 0.92-0.88 (m, 1H), 0.70-0.60 (m, 3H) | 568(M + H)+ |
| Example 80 | 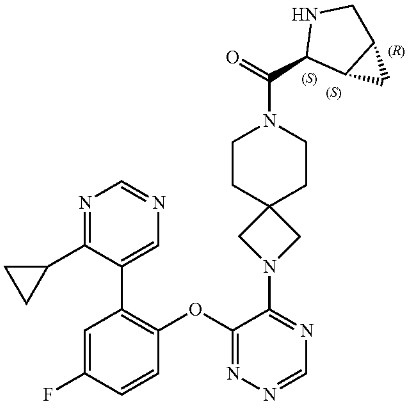 | Intermediate 42 and 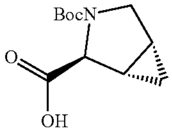 [SMILES: CC(C)(C)OC(=O)N1C[C@@H]2C[C@@H]2[C@H]1C(=O)O] | 1H NMR (400 MHz, MeOD) δ 8.90 (s, 1H), 8.43 (s, 1H), 8.34 (s, 1H), 7.54-7.51 (m, 1H), 7.37-7.29 (m, 1H), 7.32-7.29 (m, 1H), 4.69 (s, 1H), 3.92-3.90 (m, 3H), 3.65-3.47 (m, 6H), 3.40-3.37 (m, 1H), 1.89-1.81 (m, 7H), 1.09-1.03 (m, 4H), 0.78-0.75 (m, 1H), 0.57-0.55 (m, 1H) | 543(M + H)+ |

-continued

| Example | Structure | Starting materials | $^1$H-NMR (400 MHz) | LCMS (ESI) m/z |
|---|---|---|---|---|
| Example 81 | 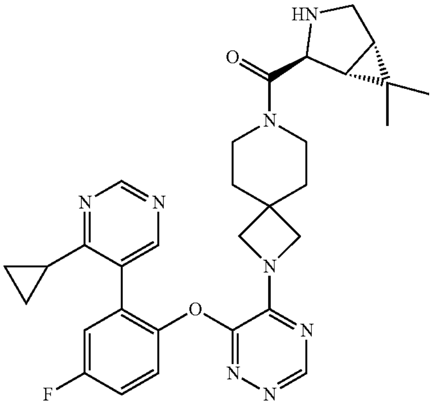 [SMILES: CC1(C)[C@@H]2[C@@H](C(=O)N3CCC4(CC3)CN(c3ncnnc3Oc3ccc(F)cc3-c3cncnc3C3CC3)C4)NC[C@@H]21] | Intermediate 42 and 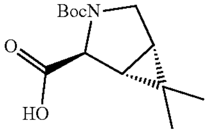 | 1H NMR (400 MHz, MeOD) δ 8.90 (s, 1H), 8.42 (s, 1H), 8.33 (s, 1H), 7.54-7.50 (m, 1H), 7.37-7.33 (m, 1H), 7.32-7.28 (m, 1H), 4.19-4.15 (m, 1H), 3.90-3.87 (m, 4H), 3.66-3.47 (m, 4H), 3.36-3.33 (m, 1H), 2.89-2.85 (m, 1H), 1.85-1.78 (m, 5H), 1.55-1.52 (m, 1H), 1.42 (d, J = 7.6 Hz, 1H), 1.14-1.08 (m, 9H), 0.79-0.75 (m, 1H) | 571(M + H)$^+$ |
| Example 82 | 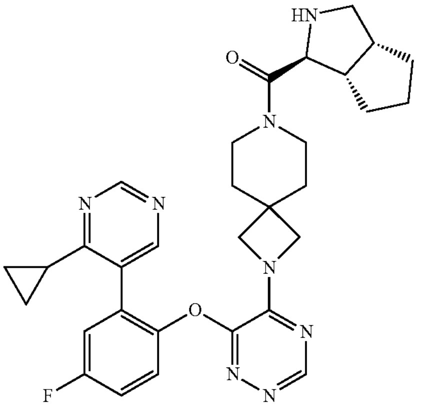 | Intermediate 42 and 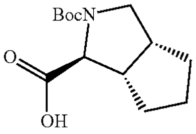 [SMILES: CC(C)(C)OC(=O)N1C[C@@H]2CCC[C@@H]2[C@H]1C(=O)O] | 1H NMR (400 MHz, MeOD) δ 8.90 (s, 1H), 8.42 (s, 1H), 8.33 (s, 1H), 7.54-7.50 (m, 1H), 7.37-7.33 (m, 1H), 7.32-7.29 (m, 1H), 4.19-4.15 (m, 1H), 3.90 (br, 3H), 3.82-3.79 (m, 1H), 3.60-3.47 (m, 4H), 3.38-3.34 (m, 1H), 2.38-2.65 (m, 1H), 2.59-2.54 (m, 2H), 1.93-1.91 (m, 1H), 1.84-1.77 (m, 7H), 1.67-1.60 (m, 2H), 1.49-1.44 (m, 1H), 1.13-1.01 (m, 3H), 0.80-0.76 (s, 1H). | 571(M + H)$^+$ |
| Example 83 | 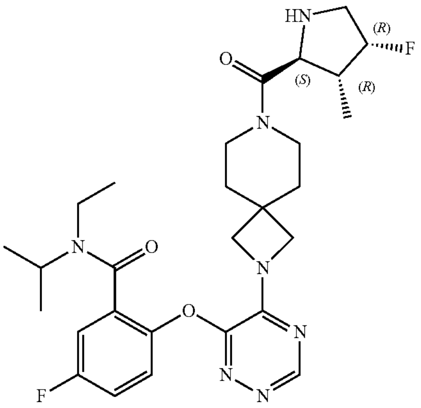 | Intermediate 34 and Intermediate 38 | $^1$H NMR (400 MHz, MeOD) δ 8.40 (s, 1H), 7.43-7.39 (m, 1H), 7.31-7.25 (m, 1H), 7.22-7.20 (m, 1H), 5.12-4.96 (m, 1H), 4.47-4.42 (m, 2H), 4.02-3.98 (m, 2H), 3.91 (d, J = 9.8 Hz, 1H), 3.84-3.79 (m, 1H), 3.74-3.70 (m, 1H), 3.61-3.48 (m, 3H), 3.44-3.34 (m, 1H), 3.18-3.06 (m, 3H), 2.35-2.37 (m, 1H), 1.93-1.85 (m, 4H), 1.22-1.05 (m, 10H), 0.82-0.80 (m, 2H) | 544(M + H)$^+$ |

-continued

| Example | Structure | Starting materials | $^1$H-NMR (400 MHz) | LCMS (ESI) m/z |
|---|---|---|---|---|
| Example 84 | 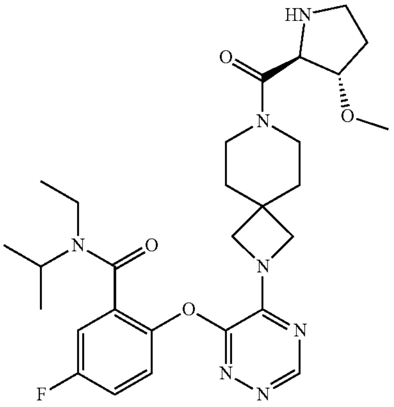 [SMILES: CCN(C(=O)c1cc(F)ccc1Oc1nncnc1N1CC2(CCN(C(=O)[C@H]3NCC[C@@H]3OC)CC2)C1)C(C)C] | Intermediate 34 and 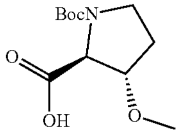 | $^1$H NMR (400 MHz, $CDCl_3$) δ 8.49 (s, 1H), 7.28 (d, J = 4.6 Hz, 1H), 7.16-7.11 (m, 1H), 7.05-6.99 (m, 1H), 4.50-4.29 (m, 3H), 3.95-3.79 (m, 5H), 3.62-3.51 (m, 5H), 3.33 (s, 3H), 3.21-3.16 (m, 2H), 3.01-2.93 (m, 1H), 1.95-1.91 (m, 2H), 1.92-1.84 (m, 5H), 1.15-1.03 (m, 7H), 0.80-0.76 (s, 2H) | $556(M + H)^+$ |
| Example 85 | 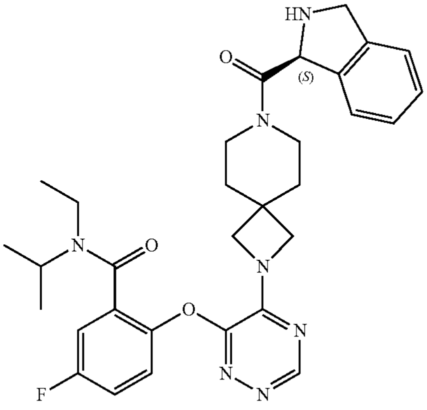 | Intermediate 34 and 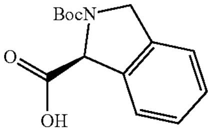 | $^1$H NMR (400 MHz, MeOD) δ 8.41 (s, 1H), 7.44-7.41 (m, 1H), 7.33-7.27 (m, 6H), 5.43 (s, 1H), 4.52-4.43 (m, 3H), 4.17-4.14 (m, 1H), 4.09-4.00 (m, 4H), 3.86-3.80 (m, 2H), 3.52-3.48 (m, 1H), 2.05-1.91 (m, 5H), 1.30-1.28 (m, 1H), 1.22-1.14 (m, 6H), 1.08 (t, J = 7.0 Hz, 1H), 0.82 (d, J = 5.6 Hz, 2H) | $574(M + H)^+$ |
| Example 86 | 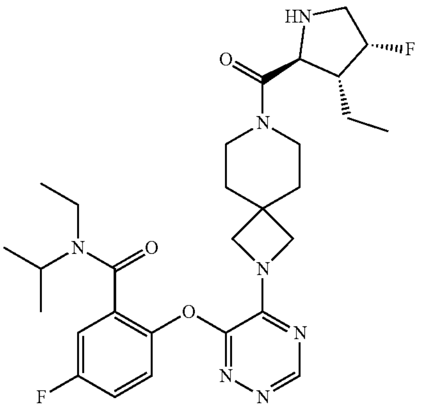 [SMILES: CC[C@@H]1[C@@H](C(=O)N2CCC3(CC2)CN(c2ncnnc2Oc2ccc(F)cc2C(=O)N(CC)C(C)C)C3)NC[C@@H]1F] | Intermediate 34 and Intermediate 39 | 1H NMR (400 MHz, MeOD) δ 8.40 (s, 1H), 7.43-7.39 (m, 1H), 7.31-7.20 (m, 2H), 5.25-5.11 (m, 1H), 4.46-4.42 (m, 2H), 4.02-3.90 (m, 3H), 3.85-3.79 (m, 1H), 3.71-3.48 (m, 5H), 3.23-3.09 (m, 3H), 2.30-2.21 (m, 1H), 1.91-1.86 (m, 4H), 1.61-1.47 (m, 2H), 1.22-1.13 (m, 6H), 1.07 (t, J = 7.1 Hz, 1H), 1.03-1.00 (m, 3H), 0.81-0.78 (m, 2H) | $572(M + H)^+$ |

-continued

| Example | Structure | Starting materials | $^1$H-NMR (400 MHz) | LCMS (ESI) m/z |
|---|---|---|---|---|
| Example 87 | 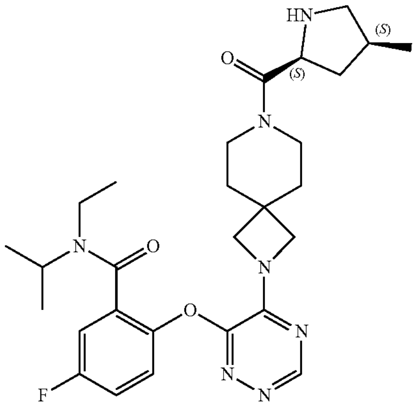 | Intermediate 34 and 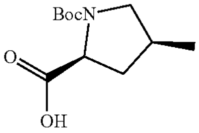 | $^1$H NMR (400 MHz, MeOD) δ 8.41 (s, 1H), 7.43-7.38 (m, 1H), 7.12-7.20 (m, 2H), 4.68-4.64 (m, 1H), 4.46-4.44 (m, 2H), 4.03-4.01 (m, 2H), 3.84-3.80 (m, 1H), 3.71-3.69 (m, 1H), 3.49-3.49 (m, 5H), 3.16-3.12 (m, 1H), 2.93-2.88 (m, 1H), 2.70-2.67 (m, 1H), 2.50-2.48 (m, 1H), 1.92-1.88 (m, 4H), 1.54-1.45 (m, 1H), 1.21-1.09 (m, 11H), 0.81-0.79 (m, 2H) | 540(M + H)$^+$ |
| Example 88 | 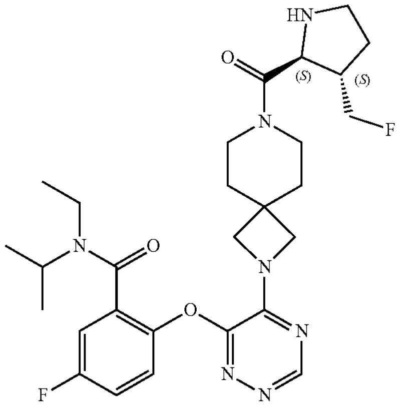 | Intermediate 34 and intermediate 46 | $^1$H NMR (400 MHz, MeOD) δ 8.40 (s, 1H), 7.44-7.38 (m, 1H), 7.31-7.25 (m, 1H), 7.24-7.18 (m, 1H), 4.58-4.55 (m, 2H), 4.52-4.38 (m, 3H), 4.06-4.00 (m, 3H), 3.84-3.80 (m, 1H), 3.65-3.48 (m, 4H), 3.23-3.19 (m, 1H), 2.97 2.90 (m, 1H), 2.66-2.62 (m, 1H), 1.98-1.83 (m, 5H), 1.69-1.63 (m, 1H), 1.29-1.27 (m, 1H), 1.22-1.13 (m, 6H), 1.09-1.04 (m, 1H), 0.14-0.78 (m, 2H) | 558(M + H)$^+$ |
| Example 89 | 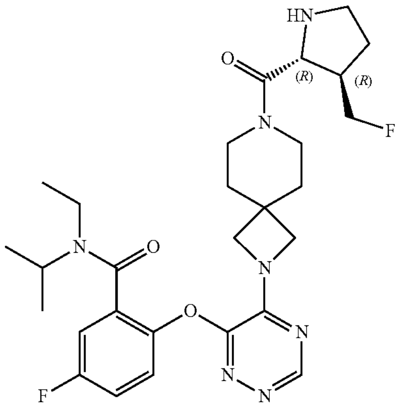 | Intermediate 34 and Intermediate 46 | $^1$H NMR (400 MHz, MeOD) δ 8.40 (s, 1H), 7.43-7.38 (m, 1H), 7.31-7.25 (m, 1H), 7.23-7.20 (m, 1H), 4.61-4.55 (m, 2H), 4.52-4.45 (m, 3H), 4.27-4.22 (m, 1H), 4.01-3.98 (m, 2H), 3.85-3.80 (m, 1H), 3.67-3.48 (m, 4H), 3.23-3.18 (m, 1H), 3.13-3.08 (m, 1H), 2.69-2.65 (m, 1H), 2.06-2.02 (m, 1H), 1.93-1.87 (m, 4H), 1.79-1.70 (m, 1H), 1.28-1.27 (m, 1H), 1.22-1.20 (m, 2H), 1.17-1.13 (m, 4H), 1.09 1.04 (m, 1H), 0.81-0.78 (m, 2H) | 558(M + H)$^+$ |

-continued
| Example | Structure | Starting materials | $^1$H-NMR (400 MHz) | LCMS (ESI) m/z |
|---|---|---|---|---|
| Example 90 | 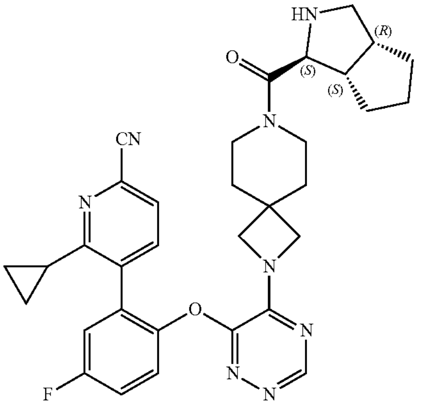 | Intermediate 47 and 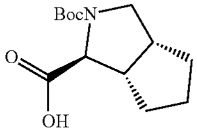 | $^1$H NMR (400 MHz, MeOD) δ 8.35 (s, 1H), 7.71-7.52 (m, 3H), 7.34-7.25 (m, 2H), 4.06-3.97 (m, 2H), 3.90-3.85 (m, 2H), 3.68-3.43 (m, 6H), 2.79-2.59 (m, 3H), 2.07-1.94 (m, 1H), 1.80-1.66 (m, 9H), 1.50-1.42 (m, 1H), 0.99-0.92 (m, 3H), 0.72-0.52 (m, 1H) | 595(M + H)$^+$ |
| Example 91 | 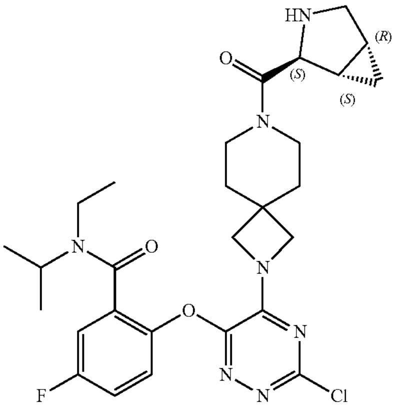 | Intermediate 48 and 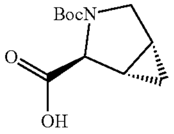 | $^1$H NMR (400 MHz, MeOD) δ 7.45-7.39 (m, 1H), 7.31-7.20 (m, 2H), 4.48 (s, 2H), 4.05 (s, 3H), 3.85-3.78 (m, 1H), 3.64-3.48 (m, 5H), 3.21-3.13 (m, 2H), 2.93 (d, J = 10.4 Hz, 1H), 1.94-1.93 (m, 2H), 1.86-1.84 (m, 2H), 1.56-1.52 (m, 2H), 1.24-1.07 (m, 7H), 0.88 (s, 2H), 0.67-0.63 (m, 1H), 0.39-0.37 (m, 1H). | 573(M + H)$^+$ |
| Example 92 | 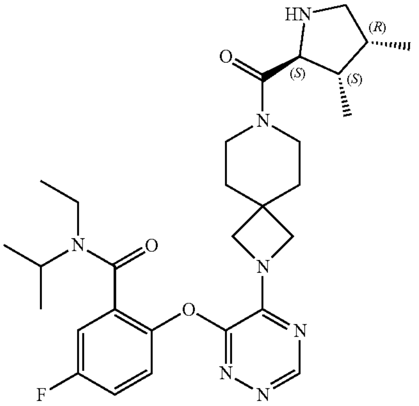 | Intermediate 34 and Intermediate 49 | $^1$H NMR (400 MHz, MeOD) δ 8.42 (s, 1H), 7.44-7.29 (m 1H), 7.31-7.20 (m, 2H), 4.48-4.46 (m, 3H), 4.04-4.00 (m, 2H), 3.85-3.80 (m, 1H), 3.59-3.50 (m, 5H), 3.05-3.00 (m, 1H), 2.42 (s, 2H), 1.95-1.89 (m, 4H), 1.420-1.35 (m, 1H), 1.22 1.04 (m, 14H), 0.84-0.80 (s, 2H) | 554(M + H)$^+$ |

-continued
| Example | Structure | Starting materials | $^1$H-NMR (400 MHz) | LCMS (ESI) m/z |
|---|---|---|---|---|
| Example 93 | 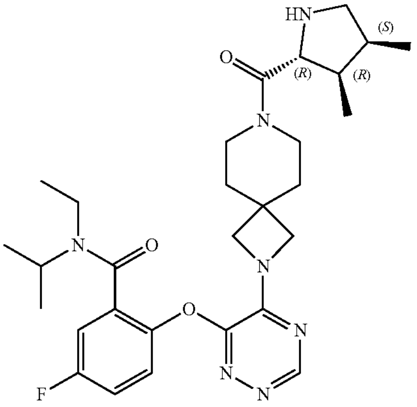 | Intermediate 34 and Intermediate 49 | $^1$H NMR (400 MHz, MeOD) δ 8.41 (s, 1H), 7.43-7.38 (m, 1H), 7.31-7.20 (m, 2H), 4.48-4.40 (m, 2H), 4.19-4.177 (m, 1H), 4.02-3.99 (m, 2H), 3.84-3.79 (m, 2H), 3.51-3.45 (m, 5H), 2.84-2.80 (m, 1H), 2.35-2.29 (m, 2H), 1.95-1.87 (m, 4H), 1.21-1.00 (m, 14H), 0.80 (d, J = 5.0 Hz, 2H) | 554(M + H)$^+$ |
| Example 94 | 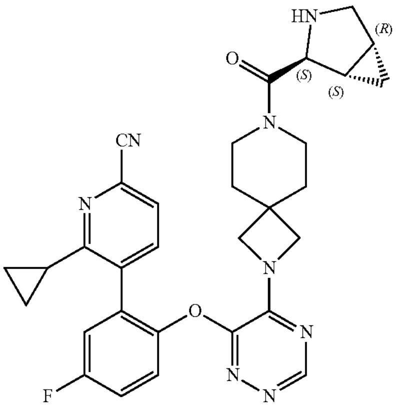 | Intermediate 47 and 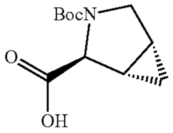 | $^1$H NMR (400 MHz, MeOD) δ 8.35 (s, 1H), 7.68-7.55 (m, 3H), 7.36-7.25 (m, 2H), 4.38-4.35 (m, 1H), 4.02-3.90 (m, 3H), 3.61-3.42 (m, 6H), 3.18-3.16 (m, 1H), 1.83-1.72 (m, 7H), 1.33-1.28 (m, 1H), 0.99-0.85 (m, 4H), 0.49-0.45 (m, 1H) | 567(M + H)$^+$ |
| Example 95 | 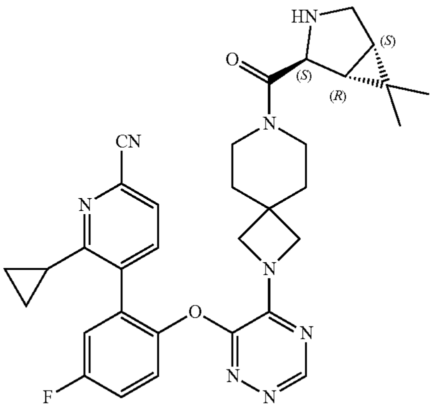 | Intermediate 47 and 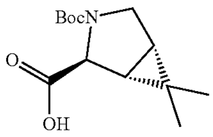 | $^1$H NMR (400 MHz, MeOD) δ 8.37 (s, 1H), 7.68-7.53 (m, 3H), 7.37-7.27 (m, 2H), 4.42 (s, 1H), 4.06-4.04 (m, 1H), 3.95-3.90 (m, 3H), 3.76-3.71 (m, 1H), 3.64-3.42 (m, 4H), 3.24-3.21 (m, 1H), 1.94-1.74 (m, 7H), 1.20-1.14 (m, 6H), 1.03-0.90 (m, 3H), 0.71-0.47 (m, 1H). | 595(M + H)$^+$ |

-continued
| Example | Structure | Starting materials | $^1$H-NMR (400 MHz) | LCMS (ESI) m/z |
|---|---|---|---|---|
| Example 96 | 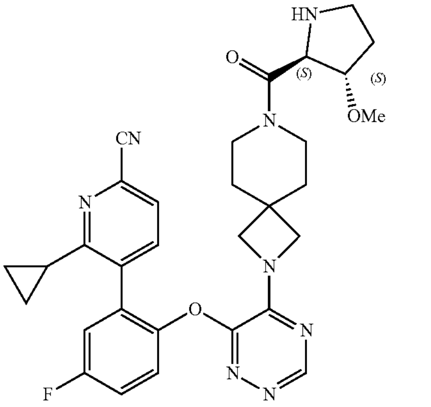 | Intermediate 43 and 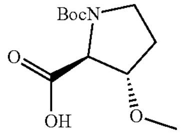 | $^1$H NMR (400 MHz, MeOD) δ 8.34 (s, 1H), 7.55-7.50 (m, 2H), 7.31-7.25 (m, 3H), 7.22-7.19 (m, 1H), 5.49 (s, 1H), 4.54-4.51 (m, 1H), 4.13-4.07 (m, 1H), 4.03-3.94 (m, 1H), 3.89-3.86 (m, 2H), 3.72-3.54 (m, 4H), 3.50-3.39 (m, 7H), 2.24-2.18 (m, 1H), 1.91-1.82 (m, 5H), 1.69-1.61 (m, 1H), 0.94-0.85 (m, 1H), 0.72-0.60 (m, 3H) | 584(M + H)$^+$ |
| Example 97 | 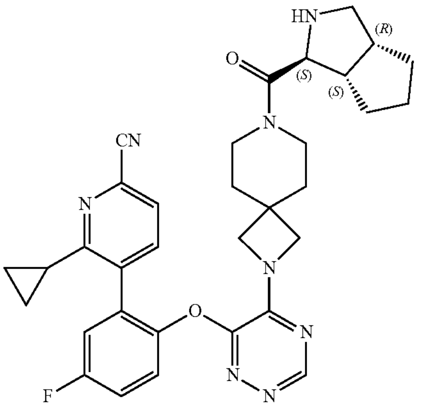 | Intermediate 43 and 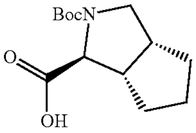 | $^1$H NMR (400 MHz, MeOD) δ 8.32 (s, 1H), 7.54-7.50 (m, 2H), 7.31-7.25 (m, 3H), 7.20-7.19 (m, 1H), 4.02-3.93 (m, 1H), 3.86 (s, 2H), 3.74 (d, J = 5.0 Hz, 1H), 3.67-3.55 (m, 2H), 3.43-3.40 (m, 2H), 3.35-3.33 (m, 1H), 2.68-2.61 (m, 1H), 2.56-2.43 (m, 2H), 1.81-1.59 (m, 11H), 0.91-0.87 (m, 3H), 0.71-0.64 (m, 2H) | 595(M + H)$^+$ |
| Example 101 | 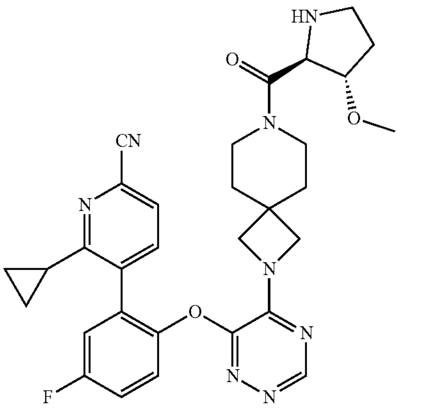 [SMILES: CO[C@H]1CCN[C@@H]1C(=O)N1CCC2(CC1)CN(c1ncnnc1Oc1ccc(F)cc1-c1ccc(C#N)nc1C1CC1)C2] | Intermediate 47 and 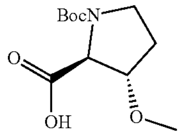 | 1H NMR (400 MHz, MeOD) δ 8.36 (s, 1H), 7.71-7.52 (m, 3H), 7.36-7.25 (m, 2H), 4.64 (s, 1H), 4.14 (br, 1H), 4.05-3.87 (m, 3H), 3.82-3.67 (m, 1H), 3.64-3.32 (m, 9H), 2.31-2.20 (m, 1H), 2.03-1.73 (m, 6H), 1.05-0.85 (m, 3H), 0.70-0.55 (m, 1H). | 585(M + H)$^+$ |

-continued

| Example | Structure | Starting materials | $^1$H-NMR (400 MHz) | LCMS (ESI) m/z |
|---|---|---|---|---|
| Example 102 | 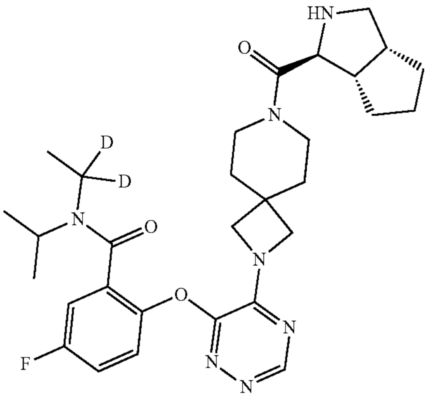 [SMILES: [2H]C([2H])(C)N(C(=O)c1cc(F)ccc1Oc1nncnc1N1CC2(CCN(C(=O)[C@H]3NC[C@@H]4CCC[C@@H]43)CC2)C1)C(C)C] | Intermediate 57 and 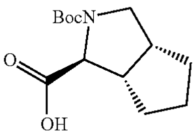 | 1H NMR (400 MHz, MeOD) δ 8.41 (s, 1H), 7.43-7.38 (m, 1H), 7.31-7.20 (m, 2H), 4.50-4.32 (m, 3H), 4.11-3.91 (m, 2H), 3.85-3.78 (m, 1H), 3.72-3.45 (m, 5H), 3.01-2.94 (m, 1H), 2.91-2.80 (m, 1H), 2.78-2.67 (m, 1H), 2.11-2.01 (m, 1H), 1.97-1.79 (m, 6H), 1.77-1.65 (m, 2H), 1.59-1.50 (m, 1H), 1.21-1.10 (m, 6H), 1.06 (s, 1H), 0.80 (d, J = 5.4 Hz, 2H). | 568(M + H)$^+$ |
| Example 103 | 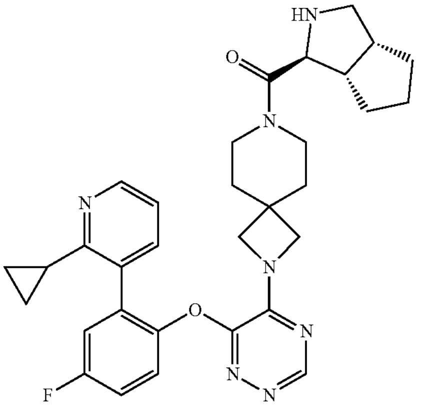 | Intermediate 60 and 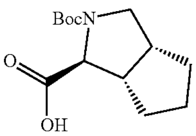 | 1H NMR (400 MHz, MeOD) δ 8.38 (d, J = 4.2 Hz, 1H), 8.33 (s, 1H), 7.53-7.48 (m, 2H), 7.31-7.12 (m, 3H), 4.35 (d, J = 4.5 Hz, 1H), 4.04-3.95 (m, 1H), 3.90-3.83 (m, 2H), 3.78-3.74 (m, 1H), 3.63-3.37 (m, 5H), 3.00-2.93 (m, 1H), 2.90-2.81 (m, 1H), 2.79-2.69 (m, 1H), 2.11-2.03 (m, 1H), 1.90-1.71 (m, 9H), 1.59-1.53 (m, 1H), 0.97-0.81 (m, 3H), 0.59-0.50 (m, 1H). | 570(M + H)$^+$ |
| Example 104 | 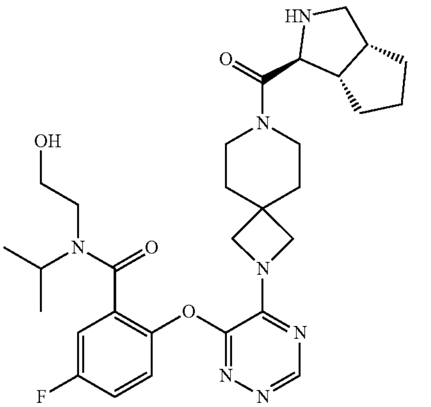 [SMILES: CC(C)N(CCO)C(=O)c1cc(F)ccc1Oc1nncnc1N1CC2(CCN(C(=O)[C@H]3NC[C@@H]4CCC[C@@H]43)CC2)C1] | Intermediate 58 and 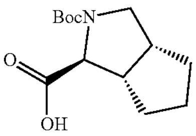 | 1H NMR (400 MHz, MeOD) δ 8.40 (s, 1H), 7.43-7.37 (m, 1H) 7.34-7.23 (m, 2H), 4.49-4.40 (m, 2H), 4.31-4.26 (m, 1H), 4.06-3.98 (m, 2H), 3.85-3.79 (m, 1H), 3.74-3.65 (m, 2H), 3.64-3.47 (m, 7H), 2.95-2.78 (m, 2H), 2.76-2.67 (m, 1H), 2.11-2.06 (m, 1H), 1.99-1.81 (m, 7H), 1.73-1.68 (m, 2H), 1.56-1.62 (m, 1H), 1.24 (d, J = 6.8 Hz, 1H), 1.17-1.12 (m, 2H), 0.83-0.74 (m, 2H). | 582(M + H)$^+$ |

-continued

| Example | Structure | Starting materials | $^1$H-NMR (400 MHz) | LCMS (ESI) m/z |
| --- | --- | --- | --- | --- |
| Example 105 | 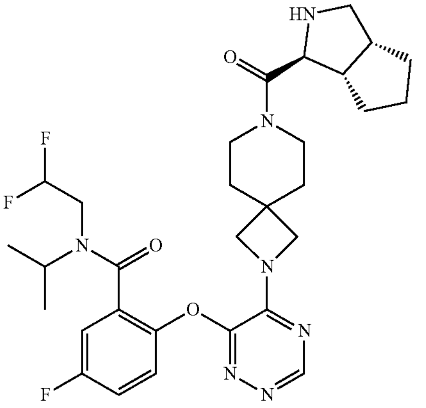 [SMILES: CC(C)N(CC(F)F)C(=O)c1cc(F)ccc1Oc1nncnc1N1CC2(CCN(C(=O)[C@H]3NC[C@@H]4CCC[C@@H]43)CC2)C1] | Intermediate 59 and 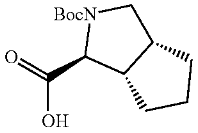 | 1H NMR (400 MHz, MeOD) δ 8.47 (s, 1H), 8.41 (s, 1H), 7.43-7.40 (m, 1H), 7.34-7.25 (m, 2H), 6.31-6.00 (m, 1H), 4.49-4.38 (m, 3H), 4.05-3.99 (m, 2H), 3.95-3.88 (m, 1H), 3.67-3.48 (m, 6H), 3.05-3.01 (m, 1H), 2.91-2.75 (m, 2H), 2.15-2.05 (m, 2H), 1.96-1.84 (m, 7H), 1.76-1.68 (m, 2H), 1.59-1.54 (m, 1H), 1.24-1.09 (m, 3H), 0.86-0.78 (m, 2H). | 602(M + H)$^+$ |
| Example 106 | 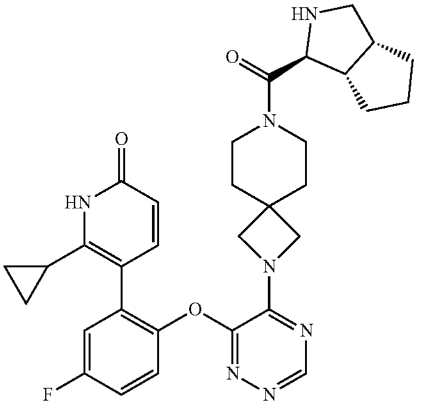 [SMILES: O=C([C@H]1NC[C@@H]2CCC[C@@H]21)N1CCC2(CC1)CN(c1ncnnc1Oc1ccc(F)cc1-c1ccc(=O)[nH]c1C1CC1)C2] | Intermediate 62 and 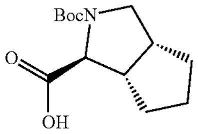 | 1H NMR (400 MHz, MeOD) δ 8.35 (s, 1H), 7.47-7.44 (m, 1H), 7.38 (d, J = 9.2 Hz, 1H), 7.27-7.21 (m, 2H), 6.34 (d, J = 9.2 Hz, 1H), 4.61-4.58 (m, 1H), 4.45 (d, J = 4.6 Hz, 1H), 4.25-4.13 (m, 2H), 3.97-3.91 (m, 2H), 3.68-3.43 (m, 4H), 3.05-3.01 (m, 1H), 2.93-2.85 (m, 1H), 2.80-2.73 (m, 1H), 2.16-2.06 (m, 1H), 1.92-1.68 (m, 9H), 1.59-1.53 (m, 1H), 0.92-0.69 (m, 4H). | 586(M + H)$^+$ |
| Example 107 | 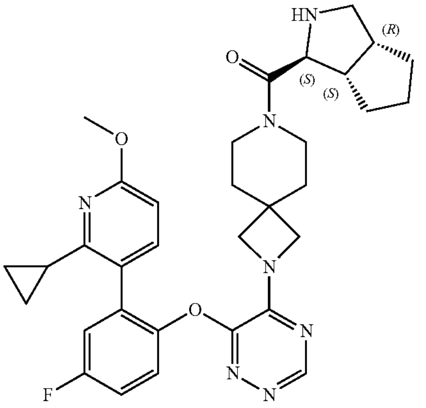 | Intermediate 61 and 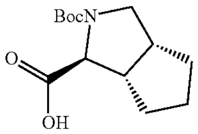 | 1H NMR (400 MHz, MeOD) δ 8.34 (s, 1H), 7.53-7.47 (m, 1H), 7.35-7.33 (m, 1H), 7.27-7.22 (m, 1H), 7.17-7.14 (m, 1H), 6.55-6.51 (m, 1H), 4.51-4.46 (m, 1H), 4.08-4.00 (m, 1H), 3.92-3.82 (m, 5H), 3.77-3.48 (m, 5H), 3.41-3.34 (m, 1H), 3.10-3.03 (m, 1H), 2.95-2.86 (m, 1H), 2.81-2.74 (m, 1H), 2.21-2.06 (m, 1H), 1.94-1.56 (m, 10H), 1.02-0.72 (m, 3H), 0.48-0.30 (m, 1H). | 600(M + H)$^+$ |

Example 98

Preparation of 2-((5-(7-5,5-difluorooctahydrocyclopenta[c]pyrrole-1-carbonyl)-2,7-diazaspiro[3.5]nonan-2-yl)-1,2, 4-triazin-6-yl)oxy)-N-ethyl-5-fluoro-N-isopropylbenzamide

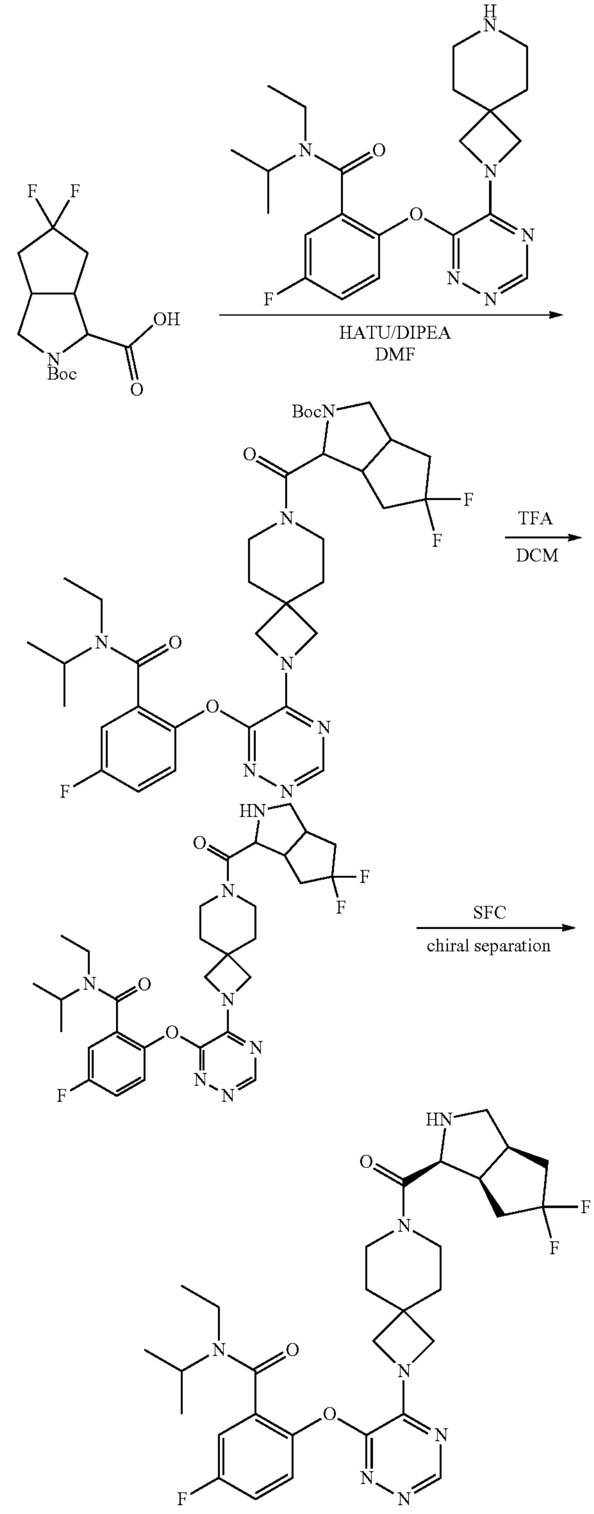

-continued

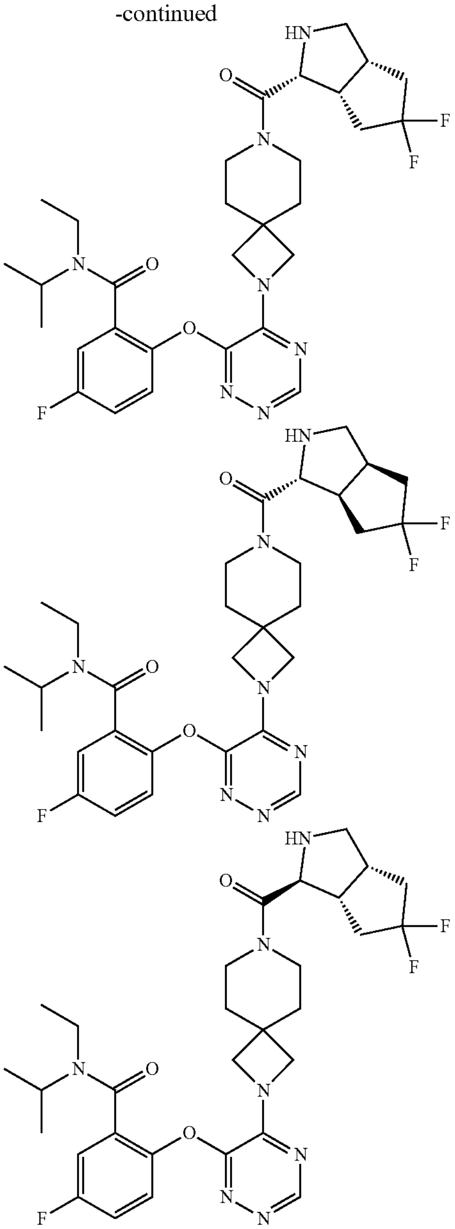

Step 1

To a solution of 2-((5-(2,7-diazaspiro[3.5]nonan-2-yl)-1,2,4-triazin-6-yl)oxy)-N-ethyl-5-fluoro-N-isopropylbenzamide (100 mg, 0.23 mmo, Intermediate 34) and 2-(tert-butoxycarbonyl)-5,5-difluorooctahydrocyclopenta[c]pyrrole-1-carboxylic acid (67.9 mg, 0.23 mmol, Intermediate 50) in DMF (3 mL) was added DIPEA (50 mg, 0.39 mmol) and HATU (133 mg, 0.35 mmol) at room temperature. The resulting mixture was stirred for 3 h at rt and quenched with sat. $NH_4Cl$ solution (10 mL), and extracted with EtOAc (15 mL×3), the combined organic phase was washed with water and brine, dried over anhydrous $Na_2SO_4$, filtered and concentrated, the residue was purified by column chromatography on silica gel (MeOH in DCM=0~5%) to give the desired product tert-butyl-1-(2-(6-(2-(ethyl(isopropyl)carbamoyl)-4-fluorophenoxy)-1,2,4-triazin-5-yl)-2,7-diazaspiro[3.5]nonane-7-carbonyl)-5,5-difluorohexahydrocyclopenta[c]pyrrole-2(1H)-carboxylate (40 mg, yield:24.4%) as a light yellow solid. LC/MS (ESI) m/z: 702 $(M+H)^+$.

Step 2

To a solution of tert-butyl-1-(2-(6-(2-(ethyl(isopropyl) carbamoyl)-4-fluorophenoxy)-1,2,4-triazin-5-yl)-2,7-diazaspiro[3.5]nonane-7-carbonyl)-5,5-difluorohexahydrocyclopenta[c]pyrrole-2(1H)-carboxylate (150 mg, 0.21 mmol) in DCM (10 mL) was added TFA (4 mL). The resulting mixture was stirred for 1 h at rt, and concentrated. The residue was diluted with EtOAc (20 mL), and the pH was adjusted to 9 with sat. $NaHCO_3$ solution. The organic phase was collected, and dried with anhydrous $Na_2SO_4$, filtered and concentrated. The resulting crude product was purified by Prep-HPLC to obtain the desired product 2-((5-(7-5,5-difluorooctahydrocyclopenta[c]pyrrole-1-carbonyl)-2,7-diazaspiro[3.5]nonan-2-yl)-1,2, 4-triazin-6-yl)oxy)-N-ethyl-5-fluoro-N-isopropylbenzamide (90 mg, yield: 69.9%) as a white solid, which was submitted to SFC chiral separation to give four isomers. (Two conditions were used. The first condition gave the pure isomer 3 and isomer 4 respectively and a mixture of isomers 1 and 2. The latter was then submitted to the second condition to afford pure isomer 1 and isomer 2 respectively)

Example 98a: isomer 1 (9.8 mg, yield: 10.8%) as a white solid, (SFC condition: SHIMADZA PREP SPLUTION SFC, Column: ChiralPak IH, 250×21.1 um, I.D., 5 um; Mobile phase: A for $CO_2$ and B for EtOH+0.1% $NH_3H_2O$, Gradient: B 17%, Flow rate: 40 mL/min, Back pressure: 100 bar, Column temperature: 35° C., Wavelength: 254 nm, Cycle-time: 18 min, Eluted time: 3.5 h. retention time: 8.39 min); 1H NMR (400 MHZ, MeOD) δ 8.40 (s, 1H), 7.43-7.38 (m, 1H), 7.31-7.20 (m, 2H), 4.48-4.42 (m, 2H), 4.03-3.97 (m, 3H), 3.84-3.75 (m, 1H), 3.64-3.48 (m, 5H), 3.13-3.06 (m, 2H), 2.96-2.87 (m, 3H), 2.34-2.26 (m, 1H), 2.06-1.81 (m, 7H), 1.23-1.14 (m, 6H), 1.06 (d, J=7.1 Hz, 1H), 0.82-0.79 (m, 2H), LC/MS (ESI) m/z: 602 $(M+H)^+$.

Example 98b: isomer 2, (16.3 mg, yield: 18.1%) as a white solid, (SFC condition: SHIMADZA PREP SPLUTION SFC, Column: ChiralPak IH, 250×21.1 um, I.D., 5 um; Mobile phase: A for $CO_2$ and B for EtOH+0.1% $NH_3H_2O$, Gradient: B 17%, Flow rate: 40 mL/min, Back pressure: 100 bar, Column temperature: 35° C., Wavelength: 254 nm, Cycle-time: 18 min, Eluted time: 3.5 h. retention time: 11.09 min); 1H NMR (400 MHZ, MeOD) δ 8.40 (s, 1H), 7.43-7.38 (m, 1H), 7.31-7.20 (m, 2H), 4.48-4.38 (m, 2H), 4.03-4.00 (m, 2H), 3.91 (d, J=3.9 Hz, 1H), 3.85-3.80 (m, 1H), 3.69-3.45 (m, 5H), 3.40-3.35 (m, 1H), 3.27-3.20 (m, 1H), 2.80-2.66 (m, 3H), 2.45-2.37 (m, 1H), 2.33-2.24 (m, 1H), 2.20-2.07 (m, 1H), 1.97-1.82 (m, 5H), 1.22-1.14 (m, 6H), 1.06 (d, J=7.1 Hz, 1H), 0.82-0.78 (m, 2H), LC/MS (ESI) m/z: 602 $(M+H)^+$.

Example 98c: isomer 3, (8.8 mg, yield: 9.7%) as a white solid, (SFC condition: SHIMADZA PREP SPLUTION SFC, Column: ChiralPak CIG, 250×21.1 um, I.D., 5 um; Mobile phase: A for $CO_2$ and B for IPA+0.1% $NH_3H_2O$, Gradient: B 50%, Flow rate: 40 mL/min, Back pressure: 100 bar, Column temperature: 35° C., Wavelength: 254 nm, Cycle-time: 45 min, Eluted time:5 h. retention time: 12.61 min); 1H NMR (400 MHZ, MeOD) δ 8.40 (s, 1H), 7.43-7.38 (m, 1H), 7.31-7.21 (m, 2H), 4.49-4.41 (m, 2H), 4.13 (d, J=7.0 Hz, 1H), 4.05-3.96 (m, 2H), 3.85-3.79 (m, 1H), 3.72-3.48 (m, 5H), 3.17-3.13 (m, 2H), 3.02-2.90 (m, 3H), 2.36-2.27 (m, 1H), 2.03-1.84 (m, 7H), 1.23-1.12 (m, 6H), 1.07 (t, J=7.1 Hz, 1H), 0.81 (d, J=5.1 Hz, 2H). LC/MS (ESI) m/z: 602 $(M+H)^+$.

Example 98d: isomer 4, (20.1 mg, yield: 22.3%) as a white solid, (SFC condition: SHIMADZA PREP SPLUTION SFC, Column: ChiralPak CIG, 250×21.1 um, I.D., 5 um; Mobile phase: A for $CO_2$ and B for IPA+0.1% $NH_3H_2O$, Gradient: B 50%, Flow rate: 40 mL/min, Back pressure: 100 bar, Column temperature: 35° C., Wavelength: 254 nm, Cycle-time: 45 min, Eluted time:5 h. retention time: 28.06 min); 1H NMR (400 MHZ, MeOD) δ 8.40 (s, 1H), 7.43-7.38 (m, 1H), 7.31-7.18 (m, 2H), 4.47-4.30 (m, 2H), 4.02-3.98 (m, 3H), 3.84-3.80 (m, 1H), 3.62-3.42 (m, 6H), 3.25-3.20 (m, 1H), 2.85-2.74 (m, 3H), 2.48-2.40 (m, 1H), 2.36-2.25 (m, 1H), 2.17-2.16 (m, 1H), 2.03-1.86 (m, 5H), 1.22-1.11 (m, 6H), 1.06 (d, J=7.1 Hz, 1H), 0.81 (d, J=5.2 Hz, 2H), HNMR, LC/MS (ESI) m/z: 602 $(M+H)^+$.

Example 99

Preparation of 2-((5-(7-(trans-3-(difluoromethyl) pyrrolidine-2-carbonyl)-2,7-diazaspiro[3.5]nonan-2-yl)-1,2,4-triaz in-6-yl)oxy)-N-ethyl-5-fluoro-N-isopropylbenzamide

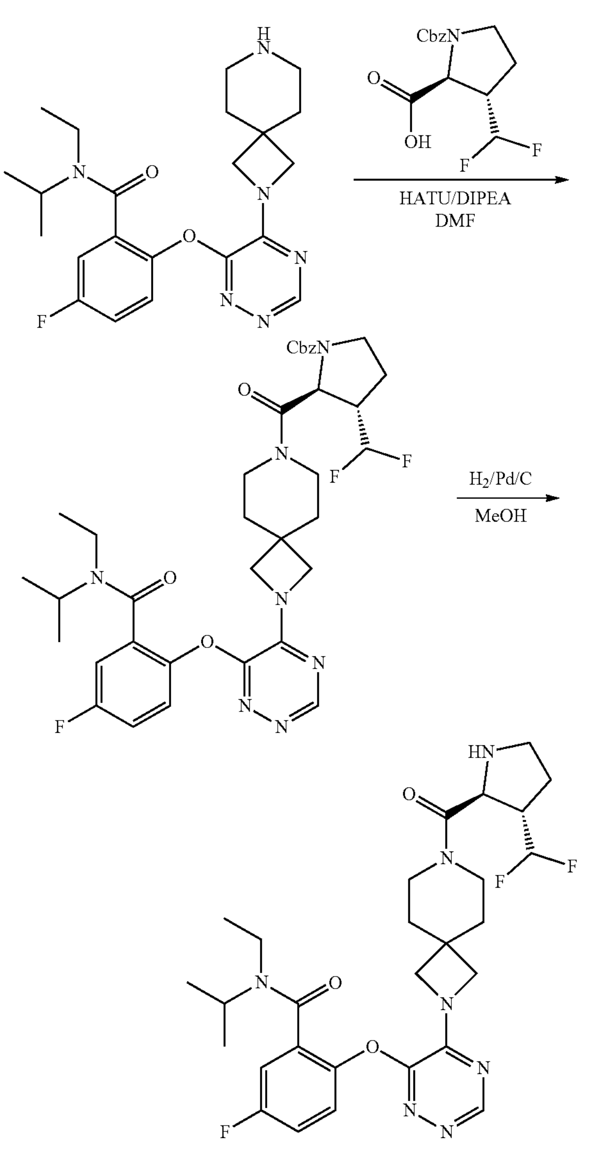

Step 1

To a solution of trans-1-[(benzyloxy)carbonyl]-3-(difluoromethyl)pyrrolidine-2-carboxylic acid (250 mg, 0.83 mmol, Intermediate 51) and 2-[(5-{2,7-diazaspiro[3.5]nonan-2-yl}-1,2,4-triazin-6-yl)oxy]-N-ethyl-5-fluoro-N-(propan-2-yl)benzamide (357 mg, 0.83 mmol, Intermediate 34) in DMF (5 mL) was added HATU (476 mg, 1.25 mmol) and DIPEA (323 mg, 2.51 mmol) at room temperature. The resulting mixture was stirred for 3 h at rt and quenched with sat. $NH_4Cl$ solution (10 mL), and extracted with EtOAc (20 mL×3), the combined organic phase was washed with water and brine, dried over anhydrous $Na_2SO_4$, filtered and concentrated. The residue was purified by column chromatography on silica gel (MeOH in DCM=0~5%) to give the desired product benzyl trans-3-(difluoromethyl)-2-[2-(6-{2-[ethyl(propan-2-yl)carbamoyl]-4-fluorophenoxy}-1,2,4-triazin-5-yl)-2,7-diazaspiro[3.5]nonane-7-carbonyl]pyrrolidine-1-carboxylate (200 mg, yield: 33.7%) as a off-white solid, LC/MS (ESI) m/z: 710 $(M+H)^+$.

Step 2

To a solution of benzyl trans-3-(difluoromethyl)-2-[2-(6-{2-[ethyl(propan-2-yl)carbamoyl]-4-fluorophenoxy}-1,2,4-triazin-5-yl)-2,7-diazaspiro[3.5]nonane-7-carbonyl]pyrrolidine-1-carboxylate (200 mg, 0.28 mmol) in MeOH (10 mL) was added Pd/C (30 mg, 10% Palladium on activated charcoal) at rt. The reaction mixture was stirred at rt for 5 h under $H_2$ atmosphere (balloon). The reaction mixture was filtered and concentrated. The resulting crude product was purified by Prep-HPLC to obtain the desired product 2-[(5-{7-[trans-3-(difluoromethyl)pyrrolidine-2-carbonyl]-2,7-diazaspiro[3.5]nonan-2-yl}-1,2,4-triazin-6-yl)oxy]-N-ethyl-5-fluoro-N-(propan-2-yl)benzamide (30 mg, yield: 36.9%) as a white solid. which was separated by SFC to give two isomers. (SFC conditions: Waters Thar 80 preparative SFC, Column: ChiralCel, 250×21.1 um, I.D., 5 um; Mobile phase: A for $CO_2$ and B for MeOH+0.1% $NH_3H_2O$, Gradient: B 40%, Flow rate: 40 mL/min, Back pressure: 100 bar, Column temperature: 35° C., Wavelength: 254 nm, Cycle-time: 5 min, Eluted time:2 h. retention time: 5.5 min for 99a, and 7.8 min for 99b)

Example 99a 2-((5-(7-((2S,3S)-3-(difluoromethyl)pyrrolidine-2-carbonyl)-2,7-diazaspiro[3.5]nonan-2-yl)-1,2,4-triazin-6-yl)oxy)-N-ethyl-5-fluoro-N-isopropylbenzamide (35.3 mg, yield: 21.4%) as a white solid. 1H NMR (400 MHZ, MeOD) δ 8.40 (s, 1H), 7.43-7.38 (m, 1H), 7.31-7.19 (m, 2H), 6.10-5.81 (m, 1H), 4.48-4.41 (m, 2H), 4.14 (d, J=5.4 Hz, 1H), 4.04-3.97 (m, 2H), 3.84-3.80 (m, 1H), 3.71-3.47 (m, 5H), 3.25-3.11 (m, 2H), 2.94-2.78 (m, 2H), 2.06-1.81 (m, 6H), 1.22-1.12 (m, 6H), 1.07 (t, J=7.1 Hz, 1H), 0.81 (d, J=4.9 Hz, 2H). LC/MS (ESI) m/z: 576 $(M+H)^+$.

Example 99b 2-((5-(7-((2R,3R)-3-(difluoromethyl)pyrrolidine-2-carbonyl)-2,7-diazaspiro[3.5]nonan-2-yl)-1,2,4-triazin-6-yl)oxy)-N-ethyl-5-fluoro-N-isopropylbenzamide (36.8 mg, yield: 22.9%) as a white solid. 1H NMR (400 MHZ, MeOD) δ 8.40 (s, 1H), 7.43-7.38 (m, 1H), 7.31-7.19 (m, 2H), 6.11-5.82 (m, 1H), 4.48-4.39 (m, 2H), 4.17 (d, J=5.2 Hz, 1H), 4.02-3.96 (m, 2H), 3.85-3.79 (m, 1H), 3.72-3.48 (m, 5H), 3.24-3.11 (m, 2H), 2.97-2.81 (m, 2H), 2.05-1.84 (m, 6H), 1.22-1.13 (m, 6H), 1.07 (t, J=7.1 Hz, 1H), 0.87-0.74 (m, 2H). LC/MS (ESI) m/z: 576 $(M+H)^+$.

The following compounds were prepared from the appropriate intermediates or commercially available chemicals according to experimental procedure for Example 99:

| Example | Structure | Starting materials | 1H-NMR (400 MHz) | LCMS (ESI) m/z |
|---|---|---|---|---|
| Example 100a | 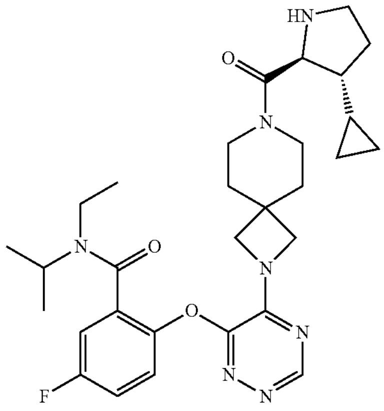 [SMILES: CCN(C(=O)c1cc(F)ccc1Oc1nncnc1N1CC2(CCN(C(=O)[C@H]3NCC[C@@H]3C3CC3)CC2)C1)C(C)C] | Intermediate 52 and 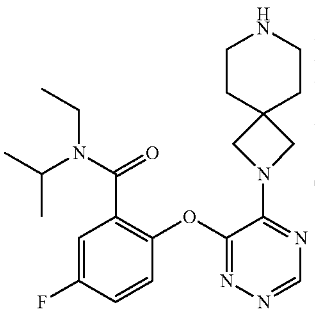 | $^1$H NMR (400 MHz, MeOD) δ 8.41 (s, 1H), 7.43-7.39 (m, 1H), 7.31-7.20 (m, 2H), 4.55-4.44 (m, 3H), 4.05-3.99 (m, 2H), 3.86-3.79 (m, 2H), 3.59-3.35 (m, 5H), 3.27-3.20 (m, 1H), 2.19-2.12 (m, 1H), 2.03-1.85 (m, 5H), 1.68-1.63 (m, 1H), 1.21-1.13 (m, 6H), 1.07 (t, J = 7.1 Hz, 1H), 0.91-0.81 (m, 4H), 0.68-0.61 (m, 2H), 0.27 (s, 2H). | $566(M + H)^+$ |

-continued

| Example | Structure | Starting materials | 1H-NMR (400 MHz) | LCMS (ESI) m/z |
|---|---|---|---|---|
| Example 100b | 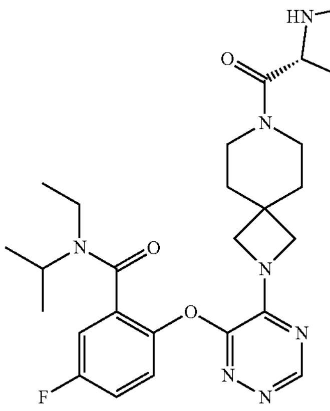 | Intermediate 52 and 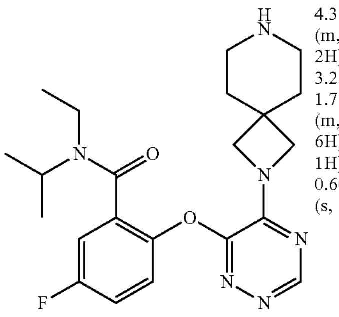 | $^1$H NMR (400 MHz, MeOD) δ 8.40 (s, 1H), 7.43-7.40 (m, 1H), 7.31-7.20 (m, 2H), 4.50-4.38 (m, 2H), 4.05-3.96 (m, 3H), 3.84-3.75 (m, 2H), 3.59-3.45 (m, 3H), 3.23-3.02 (m, 3H), 2.04-1.71 (m, 6H), 1.54-1.45 (m, 1H), 1.22-1.14 (m, 6H), 1.07 (t, J = 7.0 Hz, 1H), 0.88-0.82 (m, 4H), 0.60-0.49 (m, 2H), 0.19 (s, 2H). | 566(M + H)$^+$ |

Pharmacological Examples

SNDX-5613 used in the following assays was either sourced from MCE, cat. No. HY-136175, or prepared according to procedures reported in WO2017214367.

1. Menin-MLL1 Inhibition Assay

1× assay bu9ffer (Tris 7.5 50 mM, NaCl 50 mM, DTT 1 mM, Tween-20 0.01%) was prepared and test compounds solution (10 mM in DMSO, Sigma, Cat. No. 34869) were transferred to assay plate (384-well plate, Perkin Elmer, Cat. No. 6007279) by Echo. The final fraction of DMSO is 1%. 20 nM of Menin protein (Menin (2-610) isform2, ChemPartner, Cat. No. 2020111101) in 1× assay buffer was added to prepare 2× enzyme solution. Then 10 nM of MLL-peptide (Ac-SRWRFPARPGTGRR-Ahx-Ahx-K(FAM)-$NH_2$, GL Biochem (Shanghai)), Cat. No. 833831/202009220104) in 1× assay buffer was added to prepare 2× substrate solution. 10 μL of 2× enzyme solution was transferred to assay plate or 10 μL of 1× assay buffer for low control group. 10 μL of 2× substrate solution was added to each well to start reaction. mP data on Envision (Ex480/Em535(s), Em535(p)) was collected.

$$Y=\text{Bottom}+(\text{Top}-\text{Bottom})/(1+(IC50/X)^{*}\text{HillSlope}),$$
where $Y$ is % inhibition and $X$ is compound concentration (Equation 2)

The test results of the compounds of the present disclosure were showed in Table 1.

2. Cell Proliferation Assay

RPMI1640 (from Invitrogen, Cat. No. 11875-093; Lot. No. 2327411)

IMDM (from Invitrogen, Cat. No. 12440-053; Lot. No. 2192731)

FBS (from Gibco, Cat. No. 10099141C, Lot. No. 2233792CP)

Penicillin-Streptomycin solution (from Invitrogen, Cat. No. 15140-122, Lot. No. 2321118)

Glutamax (from Invitrogen, Cat. No. 35050-061; Lot. No. 2248972)

0.25% Trypsine-EDTA (from Invitrogen, Cat. No. 25200-072; Lot. No. 2276876)

Staurosporine (from selleck, Cat. No. S1421, Lot. No. #S142106)

DMSO (from Sigma, Cat. No. 276855-1L, Lot. No. 276855-1L)

| Cell Line | Vendor | Cat# | Lot. No | Description | Growth properties | Complete medium | Seeding Density | Incubation time |
|---|---|---|---|---|---|---|---|---|
| MV-4-11 | ATCC | CRL-9591 | 58352230 | leukemia, biphenotypic B myelomonocytic | suspension | IMDM + 10% FBS | 7500 | 4 Days |
| MOLM-13 | Addex Bio | C0003003 | 126132 | leukemia, acute myeloid | suspension | RPMI1640 + 20% FBS | 3000 | 12 Days |
| OCI-AML-3 | DSMZ | ACC-582 | 10 | leukemia, acute myeloid | supension | RPMI 1640 + 20% FBS | 6000 | 5 Days |
| HL-60 | ATCC | CCL-240 | 5036502 | leukemia, acute promyelocytic | suspension | IMDM + 20% FBS | 4000 | 4 Days |

Compound potencies were determined by first calculating % inhibition at each compound concentration according to equation 1:

$$\text{Inhibition }\%=(\text{Max}-\text{Signal})/(\text{Max}-\text{Min})^{*}100 \quad \text{(Equation 1)}$$

$IC_{50}$ values of the compounds of the present disclosure was obtained by using equation 2 and showed in the following Table 1:

The antiproliferative activity of test compounds was assessed in human leukemia cell lines. The cell line MV4-11, MOLM13 and OCI-AML3, which expresses the MLL fusion protein MLL-AF4, MLL-AF9 and carry the NPM1c gene mutation, respectively, were tested. HL-60 was used as a control cell line containing two MLL wildtype alleles in order to exclude compounds that display general cytotoxic effect. MV4-11 cells were cultured in IMDM supplemented with 10% FBS, MOLM13 and OCI-AML3 cells were cultured in RPMI1640 supplemented with 20% FBS, and HL-60 cells were cultured in IMDM supplemented with 20% FBS. Corresponding cells (MV4-11, MOLM13, OCI-AML3 or HL-60 cell line) were seeded in 100 uL medium per well in 96-well plate (white wall with clear bottom, tissue culture treated, Corning, Cat. No. CLS3903; Lot.No. 30419025). Plates were placed in the $CO_2$ incubator overnight. Compounds solution (2 mM starting, 4-fold serial dilution) were prepared and added to the wells containing 100 μL of the culture medium with HPD300 according to the plate map and centrifuge at 1000 rpm for 1 minutes (200-fold dilution totally). MV4-11, MOLM13, OCI-AML3 and HL-60 cells were incubated with the compounds for 4, 12, 5 and 4 days, respectively, under 5% $CO_2$ at 37° C., respectively. 100 μL of CellTiter-Glo reagent (Promega, Cat. No. G7573, Lot. No. 0000416710) was added to the assay plate by Multidrop Combi instrument, contents were mixed for 10 minutes on an orbital shaker to induce cell lysis. After incubation at room temperature for 10 mins, clear bottom with white back seal was pasted and luminescence with Envision was read.

The test results of the compounds of the present disclosure were showed in Table 1.

TABLE 1

| Biological data | | | | | | |
|---|---|---|---|---|---|---|
| | Biochemical | Cell antiproliferation assay | | | | |
| Compounds | assay Menin-MLL1 IC50 (nM) | MV-4-11 IC50 (nM) | OCI-AML3 IC50 (nM) | MOLM13 IC50 (nM) | HL-60 IC50 (nM) | HL-60 (Pct of inhibition at 10 μM) |
| SNDX-5613 | 3.4 | 8.0 | 74.7 | 21.6 | 7970 | 98.9% |
| Example 2 | 4.3 | 20.3 | 102.0 | 62.4 | >10000 | −30.1% |
| Example 3 | 20.9 | 329.2 | | | | |
| Example 4 | 5.0 | 33.1 | | | | |
| Example 5 | 7.0 | 440.0 | | | | |
| Example 6 | 6.0 | 33.8 | | | | |
| Example 7 | 7.5 | 219.8 | | | | |
| Example 8 | 5.5 | 331.7 | | | | |
| Example 9 | 12.9 | 40.7 | | | | |
| Example 10 | 8.3 | 238.5 | | | | |
| Example 11 | 6.3 | 128.3 | | | | |
| Example 12 | 4.7 | 68.2 | | | | |
| Example 13 | 16.7 | | | | | |
| Example 14 | 9.2 | | | | | |
| Example 15 | 55.2 | | | | | |
| Example 16 | 22.3 | | | | | |
| Example 17 | 25.3 | 316.6 | | | | |
| Example 18 | 13.5 | | | | | |
| Example 19 | 5.0 | 40.2 | | | | |
| Example 20 | 10.1 | 267.1 | | | | |
| Example 21 | 5.8 | 42.2 | | | | |
| Example 22 | 4.9 | 134.4 | | | | |
| Example 23 | 8.7 | 127.1 | | | | |
| Example 24 | 8.0 | 102.1 | | | | |
| Example 25 | 8.4 | 232.5 | | | | |
| Example 26 | 10.2 | 647.2 | | | | |
| Example 27 | 18.4 | 419.9 | | | | |
| Example 28 | 5.2 | 107.4 | | | | |
| Example 29 | 7.0 | 271.4 | | | | |
| Example 30 | 4.7 | 33.8 | | | | |
| Example 31 | 6.7 | 41.0 | | | | |
| Example 32 | 6.5 | 75.4 | | | | |
| Example 33 | 4.5 | 19.3 | | | | |
| Example 34 | 4.1 | 18.0 | | | >10000 | −12.2% |
| Example 36 | 4.0 | 66.0 | | | | |
| Example 37 | 15.4 | | | | | |
| Example 38 | 3.3 | 69.0 | | | | |
| Example 39 | 4.2 | 43.0 | | | >10000 | −24.9% |
| Example 40 | 5.4 | 26.2 | | | | |
| Example 41 | 3.6 | 7.7 | 31.4 | 23.7 | >10000 | −22.2% |
| Example 42 | 5.5 | 93.5 | | | | |
| Example 43 | 4.8 | 169.7 | | | | |
| Example 44 | 3.9 | 30.7 | | | | |
| Example 45 | 3.4 | 36.1 | | | | |
| Example 46 | 7.7 | 494.5 | | | | |
| Example 47 | 3.7 | 15.9 | | | >10000 | −10.6% |
| Example 48 | 11.4 | 144.3 | | | | |
| Example 49 | 3.6 | 57.3 | | | >10000 | −8.4% |
| Example 50 | 4.4 | 120.1 | | | | |
| Example 51 | 4.3 | 221.0 | | | | |
| Example 52 | 21.0 | | | | | |
| Example 53 | 10.9 | 786.1 | | | | |
| Example 54 | 4.3 | 582.3 | | | | |
| Example 55 | 2.3 | 14.2 | 186.2 | 61.9 | >10000 | −5.0% |
| Example 56 | 3.7 | 16.8 | 132.2 | 68.3 | >10000 | −12.2% |
| Example 57 | 5.3 | 13.0 | 143.9 | 57.8 | >10000 | −16.4% |

TABLE 1-continued

| Biological data | | | | | | |
|---|---|---|---|---|---|---|
| | Biochemical assay | Cell antiproliferation assay | | | | |
| Compounds | Menin-MLL1 IC50 (nM) | MV-4-11 IC50 (nM) | OCI-AML3 IC50 (nM) | MOLM13 IC50 (nM) | HL-60 IC50 (nM) | HL-60 (Pct of inhibition at 10 μM) |
| Example 58 | 3.5 | 27.1 | | | >10000 | −4.5% |
| Example 59 | 5.5 | 158.6 | | | | |
| Example 60 | 4.5 | 40.1 | | | >10000 | −8.4% |
| Example 61 | 6.1 | 153.3 | | | | |
| Example 62 | 3.4 | 39.5 | | | >10000 | −9.1% |
| Example 63 | 3.5 | 43.4 | | | | |
| Example 64 | 1.9 | 9.6 | | 20.2 | >10000 | 11.2% |
| Example 65 | 3.1 | 15.1 | | 57.0 | >10000 | −3.7% |
| Example 66 | 11.0 | 308.0 | | | | |
| Example 67 | 2.8 | 20.5 | | 61.1 | >10000 | 23.8% |
| Example 68 | 4.1 | 13.8 | 68.3 | 46.1 | >10000 | 14.1% |
| Example 69 | 4.4 | 56.4 | | | | |
| Example 70 | 4.6 | 9.5 | 52.7 | 49.5 | >10000 | 1.0% |
| Example 71 | 16.0 | 1252.4 | | | | |
| Example 72 | 5.5 | 56.3 | | | | |
| Example 73 | 4.1 | 22.0 | | | | |
| Example 74 | 4.6 | 5.6 | 30.9 | 14.9 | >10000 | 7.9% |
| Example 75 | 5.8 | 40.6 | | | | |
| Example 76 | 3.7 | 16.7 | | | | |
| Example 77 | 3.4 | 17.3 | | | >10000 | 17.5% |
| Example 78 | 2.9 | 6.5 | 28.1 | 14.2 | >10000 | 40.0% |
| Example 79 | 9.9 | 5.9 | 25.9 | 15.6 | >10000 | 33.8% |
| Example 80 | 4.3 | 39.0 | | | >10000 | 0.0% |
| Example 81 | 3.9 | 7.7 | 25.5 | 16.6 | >10000 | 21.4% |
| Example 82 | 4.2 | 5.6 | 11.2 | 12.3 | >10000 | 22.3% |
| Example 83 | 3.6 | 51.0 | | | | |
| Example 84 | 5.1 | 20.0 | 67.1 | 60.9 | >10000 | 15.1% |
| Example 85 | 5.5 | 76.7 | | | >10000 | −2.8% |
| Example 86 | 3.6 | 76.0 | 281.6 | 199.3 | >10000 | 10.8% |
| Example 87 | 4.9 | 41.6 | | | | |
| Example 88 | 3.2 | 24.2 | 101.9 | 68.6 | >10000 | 11.4% |
| Example 89 | 24.0 | 1006.0 | | | | |
| Example 90 | 2.8 | 2.6 | | 6.1 | | |
| Example 91 | 7.3 | 248.0 | | | | |
| Example 92 | 8.0 | 18.8 | | | | |
| Example 93 | 24.8 | 457.0 | | | | |
| Example 94 | 3.4 | 11.8 | | | | |
| Example 95 | 2.5 | 5.5 | | | | |
| Example 96 | 4.0 | 5.6 | | | | |
| Example 97 | 4.4 | 2.3 | | | | |
| Example 98a | 5.4 | 333.4 | | | | |
| Example 98b | 22.0 | 2643 | | | | |
| Example 98c | 44.5 | | | | | |
| Example 98d | 2.3 | 29.5 | | | | |
| Example 99a | 5.4 | 46.4 | | | | |
| Example 99b | 43.0 | 1934.0 | | | | |
| Example 100a | 2.7 | 6.9 | | | | |
| Example 100b | 11.7 | 284.5 | | | | |
| Example 101 | 6.0 | 6.8 | | | | |
| Example 102 | 5.4 | 4.6 | | | | |
| Example 103 | 4.4 | 1.5 | | | | |
| Example 104 | 4.5 | 26.7 | | | | |
| Example 105 | 4.0 | 17.1 | | | | |
| Example 106 | 2.0 | 9.4 | | | | |
| Example 107 | 2.4 | 2.4 | | | | |

3. Liver Microsome Stability Study

Studies were carried out in liver microsomes (Corning, 0.5 mg/mL). Stock solutions were prepared at 10 mM in DMSO for the test compounds. Aliquots of the stock solutions were diluted to 0.5 mM with acetonitrile, and then further diluted upon the addition of liver microsomes/buffer to 1.5 μM. An aliquot of 30 μL of 1.5 μM solutions was mixed with 15 μL of 6 mM NADPH and the final concentration of NADPH was 2 mM, which had been pre-warmed to 37° C. Test compounds and Ketanserin final concentrations were 1 μM. The plates were kept in a 37° C. water bath for the duration of the experiment. At each time point (0, 5, 15, 30, 45 minutes), 135 μL of acetonitrile was added into corresponding wells. After the final time point was quenched by acetonitrile, the assay plates were shaken at the vibrator (IKA, MTS 2/4) for 10 min (600 rpm/min) and then centrifuged at 5,594 g for 15 min (Thermo Multifuge×3R). Aliquots of the supernatant were taken, diluted 1:1 into distilled water, and analyzed by LC-MS/MS. The peak area response ratio to internal standard (PARR) of the compounds at 5, 15, 30, 45 minutes was compared to the PARR at time 0 to determine the percent of test compound remaining at each time point. Half-lives were calculated using Excel software, fitting to a single-phase exponential decay equation.

TABLE 2

| Human liver microsome stability | |
|---|---|
| Compounds | Human liver microsome T1/2 (min) |
| SNDX-5613 | 12 |
| Example 22 | 92 |
| Example 38 | 60 |
| Example 39 | 94 |
| Example 55 | 159 |
| Example 57 | 105 |
| Example 60 | 119 |
| Example 62 | 86 |
| Example 63 | 125 |
| Example 65 | 67 |
| Example 69 | 154 |
| Example 72 | 158 |
| Example 77 | 81 |
| Example 84 | 68 |
| Example 87 | 66 |

4. hERG Inhibition Study

The inhibition effects of the test compounds on hERG were carried out in CHO-hERG cells (cell density: 21.5× 10~6/mL). 10 μL compound mother liquor was added to 20 μL DMSO solution, and then continuously diluted to 6 concentrations by 3-fold. The compound solution (4 uL) of six different concentrations were added to the extracellular solution (996 uL) and diluted to the final concentration to be tested (250-fold dilution totally). The highest test concentration was 40.00 μM, followed by 40.0, 13.3, 4.4, 1.48, 0.49 and 0.16 μM. The content of DMSO in the final test concentration did not exceed 0.2%, at which DMSO had no effect on the hERG potassium channel. The high impedance sealing of single cell and the formation of whole cell model were all completed automatically by Qpatch instrument.

TABLE 3

| hERG inhibition data | |
|---|---|
| Compounds | hERG (μM) |
| SNDX-5613 | 9.6 |
| Example 2 | >40 |
| Example 55 | >40 |
| Example 57 | >40 |
| Example 60 | >40 |
| Example 68 | >40 |
| Example 74 | >40 |
| Example 77 | >40 |
| Example 82 | 29.4 |

The invention claimed is:

1. A compound of formula I:

(I)

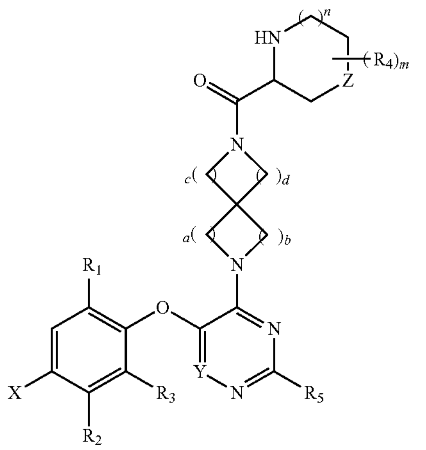

or a stereoisomer, a racemate, a tautomer, a hydrate or a solvate, or pharmaceutically acceptable salt thereof, wherein:

X is halo or CN;

Y is N or CH;

Z is selected from the group consisting of $CH_2$, O, S and NH;

$R_1$ is selected from the group consisting of:

1) —(C═O)—NRaRb, wherein:

Ra and Rb are each independently selected from the group consisting of $C_{1-6}$alkyl, 3-6 membered cycloalkyl ring and 5-9 membered heterocyclyl ring, which is optionally substituted with 1, 2 or 3 substituents selected from the group consisting of deuterium, halo, OH, CN and $C_{1-6}$alkoxyl;

or Ra and Rb, together with the nitrogen atom to which they are attached, form a 5-9 membered heterocyclyl ring, which is optionally substituted with 1, 2 or 3 substituents selected from the group consisting of $C_{1-6}$alkyl, halo, OH and CN; and 2) A 5-10 membered heteroaryl ring or $C_{6-10}$aryl ring, optionally substituted with 1, 2 or 3 substituents selected from the group consisting of halo, CN, $C_{1-6}$alkyl optionally substituted with 1, 2 or 3 substituents selected from the group consisting of halo, CN and OH, 3-5 membered cycloalkyl ring, oxo and $C_{1-6}$alkoxyl;

$R_2$ and $R_3$ are each independently H or D;

each $R_4$ is independently selected from the group consisting of halo, CN, OH, oxo, $C_{1-6}$alkylsulfonyl-, $C_{1-6}$alkylsulfonylamino-, $C_{1-6}$alkylcarbonylamino-, $C_{6-10}$aryl ring, $C_{1-6}$alkyl, $C_{2-6}$alkenyl, $C_{2-6}$alkynyl, $C_{1-6}$alkoxyl, 3-9 membered cycloalkyl ring, 5-10 membered heteroaryl ring and 4-9 membered heterocyclyl ring, wherein the alkyl, alkenyl, alkynyl, alkoxyl, cycloalkyl ring, heteroaryl ring or heterocyclyl ring is optionally substituted with 1, 2 or 3 substituents selected from the group consisting of halo, CN and OH;

wherein two adjacent $R_4$, together with the carbon atoms to which they are attached, optionally form a 3-9 membered cycloalkyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl-, halo, CN and OH;

or, two $R_4$ attached to the same carbon atom together with said carbon atom optionally form a 3-6 membered cycloalkyl ring or 4-6 membered heterocyclyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl-, halo, CN and OH;

or, two adjacent $R_4$, together with the carbon atoms to which they are attached, optionally form a 5-10 membered heteroaryl ring, $C_{6-10}$aryl ring or 5-9 membered heterocyclyl ring, wherein said heteroaryl ring or aryl ring is optionally substituted with 1, 2 or 3 substituents selected from the group consisting of $C_{1-6}$alkyl, $C_{1-6}$haloalkyl, —$C_{1-6}$alkyl-OH, $C_{1-6}$alkoxyl-$C_{1-6}$alkyl-, halo, CN and OH, wherein the alkyl is optionally substituted with one 3-6 membered cycloalkyl ring or phenyl; said heterocyclyl ring is optionally substituted with 1, 2 or 3 substituents selected from the group consisting of $C_{1-6}$alkyl, $C_{1-6}$haloalkyl, —$C_{1-6}$alkyl-OH, $C_{1-6}$alkoxyl-$C_{1-6}$alkyl-, oxo, halo, CN and OH;

$R_5$ is selected from the group consisting of H, halo, methyl optionally substituted by 1, 2 or 3 deuterium or halo, methoxyl optionally substituted by 1, 2 or 3 deuterium or halo, $NH_2$, $NHCH_3$ and $N(CH_2)_2$;

a, b, c and d are each independently 1 or 2;

n is 0, 1 or 2; and m is 0, 1, 2, 3 or 4;

provided that $R_4$, if present, is substituted at any chemically permissible position(s) on the heterocyclyl except for the N atom adjacent to the attachment point of the heterocyclyl to the remaining structure of the compound.

2. The compound according to claim 1 or a stereoisomer, a racemate, a tautomer, a hydrate or a solvate, or pharmaceutically acceptable salt thereof, wherein:

X is F, Cl or CN;

Y is N or CH;

Z is selected from the group consisting of $CH_2$, O, S and NH;

$R_1$ is selected from the group consisting of:

1) —(C═O)—NRaRb, wherein:

Ra and Rb are each independently selected from the group consisting of $C_{1-6}$alkyl and 3-5 membered cycloalkyl ring, wherein the $C_{1-6}$alkyl is optionally substituted with 1, 2 or 3 substituents selected from the group consisting of deuterium, halo, OH and $C_{1-6}$alkoxyl;

or Ra and Rb, together with the nitrogen atom to which they are attached, form a 5-6 membered monocyclic or 7-9 membered bicyclic heterocyclyl ring, which is optionally substituted with 1, 2 or 3 substituents selected from the group consisting of $C_{1-6}$alkyl and halo;

2) A 5-6 membered heteroaryl ring, optionally substituted with 1, 2 or 3 substituents selected from the group consisting of halo, CN, $C_{1-6}$alkyl optionally substituted with 1, 2 or 3 substituents selected from the group consisting of halo and CN, 3-5 membered cycloalkyl ring, oxo and $C_{1-6}$alkoxyl; and 3) $C_{6-10}$aryl ring substituted with 1, 2 or 3 substituents selected from the group consisting of halo, CN, $C_{1-6}$alkyl optionally substituted with 1, 2 or 3 substituents selected from the group consisting of halo and CN, 3-5 membered cycloalkyl ring and $C_{1-6}$alkoxyl;

$R_2$ and $R_3$ are each independently H or D;

each $R_4$ is independently selected from the group consisting of halo, CN, OH, $C_{1-6}$alkylsulfonyl-, $C_{1-6}$alkylsulfonylamino-, $C_{1-6}$alkylcarbonylamino-, phenyl, $C_{1-6}$alkyl, $C_{1-6}$alkoxyl, 3-6 membered cycloalkyl ring, 5-10 membered heteroaryl ring and 5-9 membered heterocyclyl ring, wherein the alkyl, alkoxyl, cycloalkyl ring, heteroaryl ring or heterocyclyl ring is optionally substituted with 1, 2 or 3 substituents selected from the group consisting of halo, CN and OH;

wherein two adjacent $R_4$, together with the carbon atoms to which they are attached, optionally form a 3-6 membered cycloalkyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl- and halo;

or, two $R_4$ attached to the same carbon atom together with said carbon atom optionally form a 3-6 membered cycloalkyl ring, which is optionally substituted with 1, 2 or 3 substituents selected from the group consisting of halo, CN and OH;

or, two adjacent $R_4$, together with the carbon atoms to which they are attached, optionally form a 5-10 membered heteroaryl ring, phenyl or 5-9 membered heterocyclyl ring, which is optionally substituted with 1, 2 or 3 substituents selected from the group consisting of halo, $C_{1-6}$alkyl and $C_{1-6}$haloalkyl, wherein the alkyl is optionally substituted with one 3-6 membered cycloalkyl ring or phenyl;

$R_5$ is H or halo;

a, b, c and d are each independently 1 or 2;

n is 0 or 1; and m is 0, 1, 2 or 3;

provided that $R_4$, if present, is substituted at any chemically permissible position(s) the heterocyclyl except for the N atom adjacent to the attachment point of the heterocyclyl to the remaining structure of the compound.

3. The compound according to claim 1 or a stereoisomer, a racemate, a tautomer, a hydrate or a solvate, or pharmaceutically acceptable salt thereof, wherein the compound is of formula II or formula III:

II

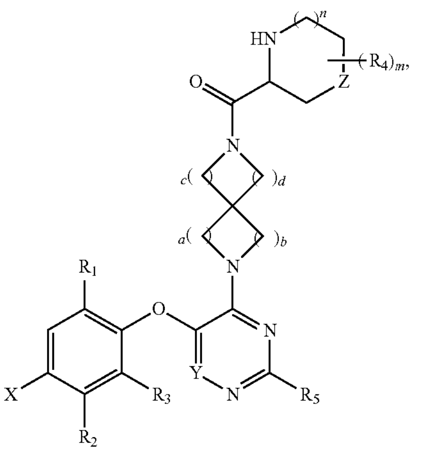

-continued

III

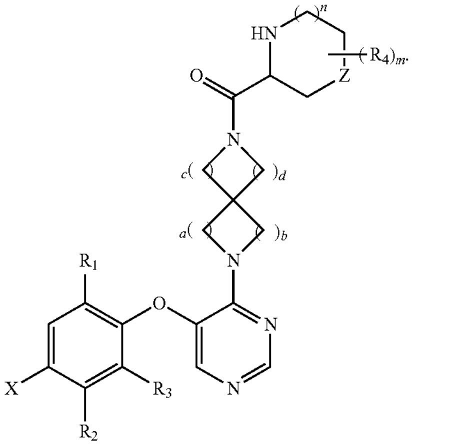

4. The compound according to claim 1 or a stereoisomer, a racemate, a tautomer, a hydrate or a solvate, or pharmaceutically acceptable salt thereof, wherein X is F.

5. The compound according to claim 1 or a stereoisomer, a racemate, a tautomer, a hydrate or a solvate, or pharmaceutically acceptable salt thereof, wherein Z is selected from the group consisting of $CH_2$, O and S.

6. The compound according to claim 1 or a stereoisomer, a racemate, a tautomer, a hydrate or a solvate, or pharmaceutically acceptable salt thereof, wherein $R_2$ and $R_3$ are each independently H.

7. The compound according to claim 1 or a stereoisomer, a racemate, a tautomer, a hydrate or a solvate, or pharmaceutically acceptable salt thereof, wherein:

$R_1$ is

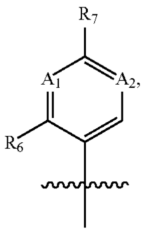

wherein $A_1$ or $A_2$ is N or CH; $R_6$ is selected from the group consisting of halo, CN and cyclopropyl; and $R_7$ is selected from the group consisting of H, halo, CN and cyclopropyl;

or $R_1$ is

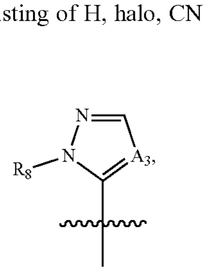

wherein $A_3$ is N or C substituted by halo, and $R_8$ is $C_{1-3}$alkyl.

8. The compound according to claim 1 or a stereoisomer, a racemate, a tautomer, a hydrate or a solvate, or pharmaceutically acceptable salt thereof, wherein:

each of a and b is 1;

each of c and d is 2;

n is 0 or 1; and m is 0, 1 or 2.

9. The compound according to claim 1 or a stereoisomer, a racemate, a tautomer, a hydrate or a solvate, or pharmaceutically acceptable salt thereof, wherein:

each $R_4$ is independently selected from the group consisting of halo; CN; OH; $C_{1-6}$alkylsulfonyl-; $C_{1-6}$alkylsulfonylamino-; phenyl; $C_{1-6}$alkyl optionally substituted with 1, 2 or 3 substituents selected from the group consisting of halo, CN and OH; $C_{1-6}$alkoxyl optionally substituted with 1, 2 or 3 halo; and cyclopropyl, wherein two adjacent $R_4$, together with the carbon atoms to which they are attached, optionally form a 3-6 membered cycloalkyl ring, which is optionally substituted with 1, 2 or 3 substituents selected from the group consisting of $C_{1-6}$alkyl, —$C_{1-6}$alkyl-OH, $C_{1-6}$alkoxyl-$C_{1-6}$alkyl- and halo;

or, two $R_4$ attached to the same carbon atom together with said carbon atom optionally form a 3-6 membered cycloalkyl ring, which is optionally substituted with 1, 2 or 3 halo;

or, two adjacent $R_4$, together with the carbon atoms to which they are attached, optionally form a 5-6 membered heteroaryl ring, which is optionally substituted with 1, 2 or 3 $C_{1-6}$alkyl, wherein the alkyl is optionally substituted with one 3-6 membered cycloalkyl ring or phenyl;

or, two adjacent $R_4$, together with the carbon atoms to which they are attached, optionally form a phenyl.

10. The compound according to claim 1 or a stereoisomer, a racemate, a tautomer, a hydrate or a solvate, or pharmaceutically acceptable salt thereof, wherein: the moiety

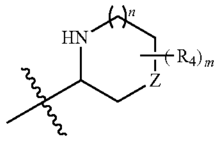

is selected from the group consisting of:

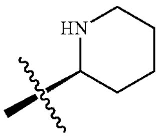, 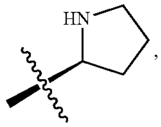, 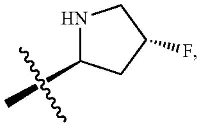

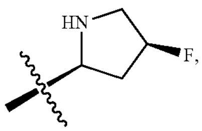 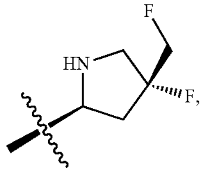

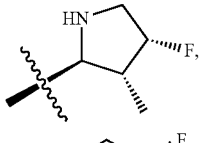 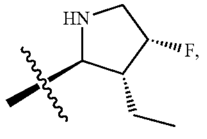

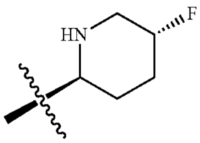, 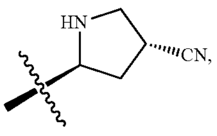

-continued
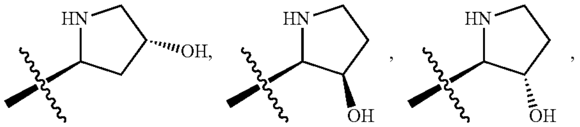
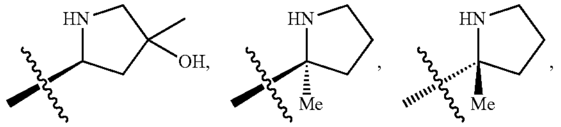
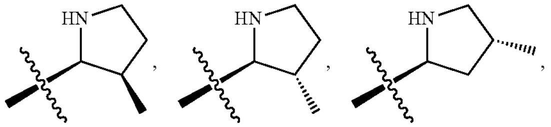
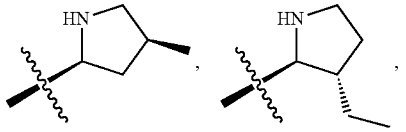
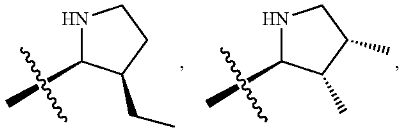
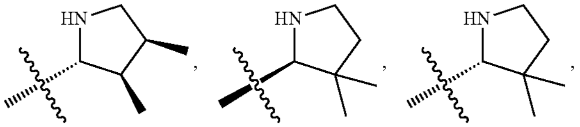
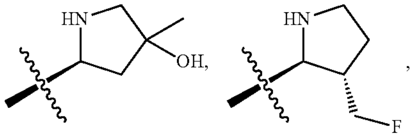
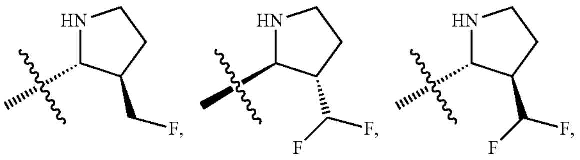
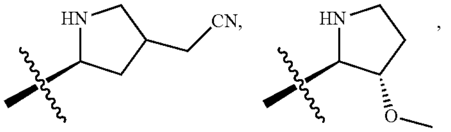
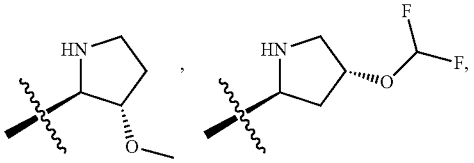
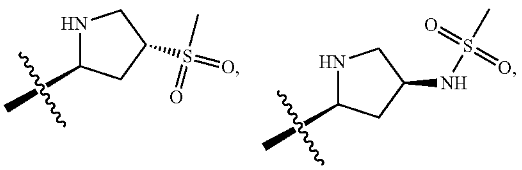
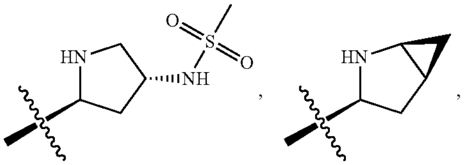
-continued
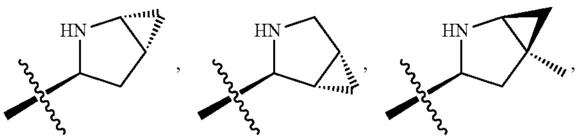
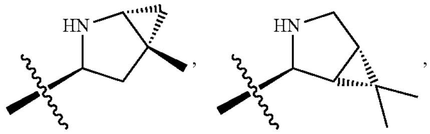
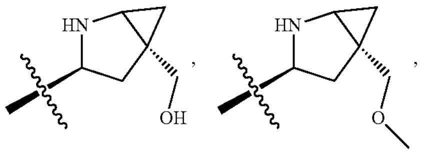
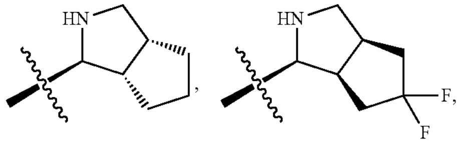
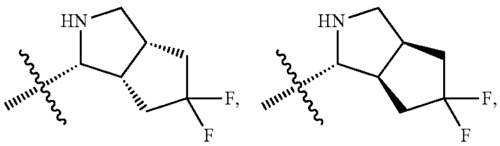
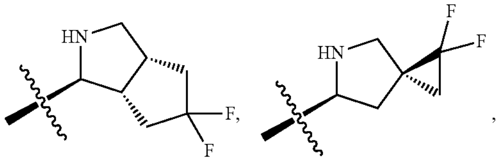
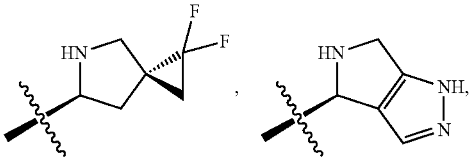
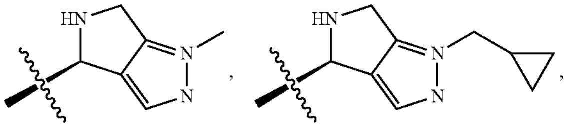
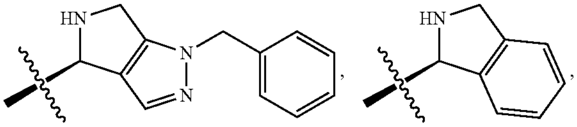
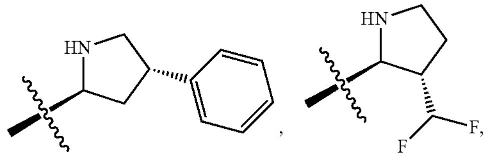
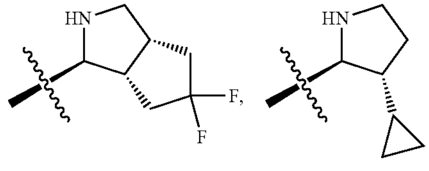
and -continued

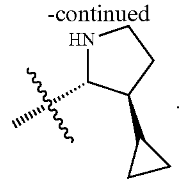

11. The compound according to claim 1 or a stereoisomer, a racemate, a tautomer, a hydrate or a solvate, or pharmaceutically acceptable salt thereof, wherein:

X is F;

Z is $CH_2$;

$R_1$ is selected from the group consisting of:

1) —(C═O)—NRaRb, wherein:

Ra and Rb are each independently selected from the group consisting of $C_{1-6}$alkyl optionally substituted by 1, 2 or 3 deuterium;

or Ra and Rb, together with the nitrogen atom to which they are attached, form a 5-6 membered monocyclic or 7-9 membered bicyclic heterocyclyl ring, which is optionally substituted with 1, 2 or 3 $C_{1-6}$alkyl;

2) A 5-6 membered heteroaryl ring substituted with 1, 2 or 3 substituents selected from the group consisting of halo, CN, $C_{1-6}$alkyl, $CF_3$, 3-5 membered cycloalkyl ring, oxo and $C_{1-6}$alkoxyl; and 3) $C_{6-10}$aryl ring substituted with 1, 2 or 3 substituents selected from the group consisting of halo, CN, $C_{1-6}$alkyl, $CF_3$, 3-5 membered cycloalkyl ring and $C_{1-6}$alkoxyl;

$R_2$ and $R_3$ are each independently H;

each $R_4$ is independently selected from the group consisting of halo; CN; OH; $C_{1-6}$alkylsulfonyl-; $C_{1-6}$alkylsulfonylamino-; phenyl; $C_{1-6}$alkyl optionally substituted with 1, 2 or 3 substituents selected from the group consisting of halo, CN and OH; $C_{1-6}$alkoxyl optionally substituted with 1, 2 or 3 halo; and 3-6 membered cycloalkyl ring, wherein two adjacent $R_4$, together with the carbon atoms to which they are attached, optionally form a 3-6 membered cycloalkyl ring, which is optionally substituted with 1, 2 or 3 substituents selected from the group consisting of $C_{1-6}$alkyl and halo;

or, two adjacent $R_4$, together with the carbon atoms to which they are attached, optionally form a phenyl;

$R_5$ is H or halo;

each of a and b is 1;

each of c and d is 2;

n is 0; and m is 0, 1 or 2;

provided that $R_4$, if present, substituted at any chemically permissible position(s) the heterocyclyl except for the N atom adjacent to the attachment point of the heterocyclyl to the remaining structure of the compound.

12. The compound according to claim 1 or a stereoisomer, a racemate, a tautomer, a hydrate or a solvate, or pharmaceutically acceptable salt thereof, wherein the moiety

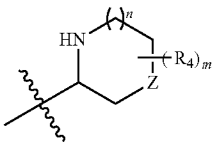

is

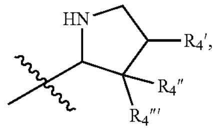

wherein $R_4'$, $R_4''$ and $R_4'''$ are independently selected from the group consisting of H; halo; CN;

OH; $C_{1-6}$alkyl optionally substituted with one halo; and $C_{1-6}$alkoxyl; or $R_4'$ and $R_4''$, together with the carbon atoms to which they are attached, optionally form a 3-6 membered cycloalkyl ring, which is optionally substituted with 1 or 2 $C_{1-6}$alkyl; and $R_4'''$ is H.

13. The compound according to claim 1 or a stereoisomer, a racemate, a tautomer, a hydrate or a solvate, or pharmaceutically acceptable salt thereof, wherein:

the moiety

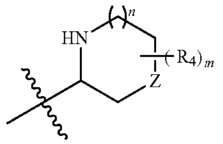

is

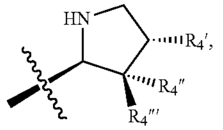

wherein $R_4'''$ is H; and $R_4'$ and $R_4''$ are independently selected from the group consisting of H; halo; $C_{1-6}$alkyl optionally substituted with one halo; and $C_{1-6}$alkoxyl; provided that one of $R_4'$ and $R_4''$ is not H; or, $R_4'$ and $R_4''$, together with the carbon atoms to which they are attached, form a 3 or 5 membered cycloalkyl ring optionally substituted with 1 or 2 $C_{1-3}$alkyl, or form a phenyl ring.

14. The compound according to claim 1 or a stereoisomer, a racemate, a tautomer, a hydrate or a solvate, or pharmaceutically acceptable salt thereof, wherein the moiety

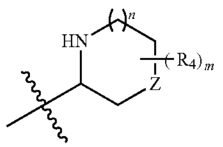

is

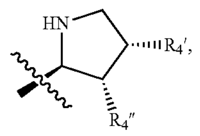

wherein $R_4'$ is H; and $R_4''$ is $C_{1-6}$alkyl substituted with one halo; or $R_4'$ and $R_4''$, together with the carbon atoms to which they are attached, optionally form a 3 or 5 membered cycloalkyl ring.

15. The compound according to claim 1 or a stereoisomer, a racemate, a tautomer, a hydrate or a solvate, or pharmaceutically acceptable salt thereof, wherein the moiety

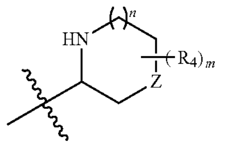

is

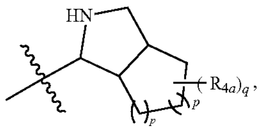

wherein each p is dependently 0 or 1;

q is 0, 1 or 2; and $R_{4a}$ is $C_{1-3}$alkyl.

16. The compound according to claim 1 or a stereoisomer, a racemate, a tautomer, a hydrate or a solvate, or pharmaceutically acceptable salt thereof, wherein the compound is selected from the group consisting of:

| Compound Nos. | Structures |
| --- | --- |
| Example 2 | 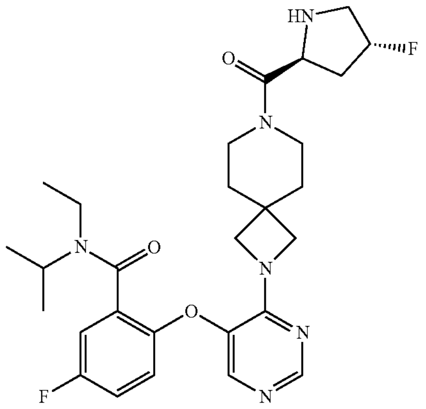 [SMILES: CCN(C(=O)c1cc(F)ccc1Oc1cncnc1N1CC2(CCN(C(=O)[C@@H]3C[C@@H](F)CN3)CC2)C1)C(C)C] |
| Example 3 | 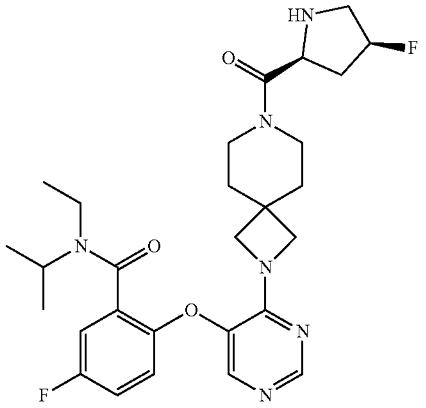 [SMILES: CCN(C(=O)c1cc(F)ccc1Oc1cncnc1N1CC2(CCN(C(=O)[C@@H]3C[C@H](F)CN3)CC2)C1)C(C)C] |

-continued
| Compound Nos. | Structures |
|---|---|
| Example 4 | 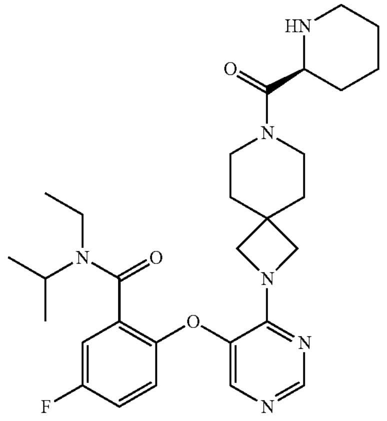 [SMILES: CCN(C(=O)c1cc(F)ccc1Oc1cncnc1N1CC2(CCN(C(=O)[C@@H]3CCCCN3)CC2)C1)C(C)C] |
| Example 5 | 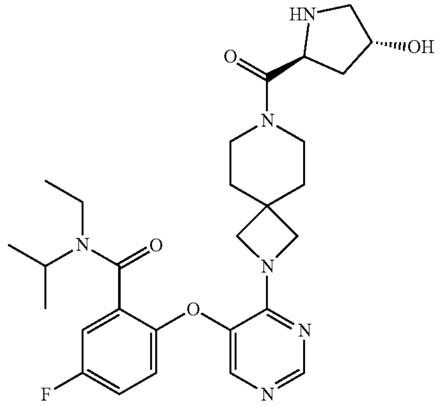 [SMILES: CCN(C(=O)c1cc(F)ccc1Oc1cncnc1N1CC2(CCN(C(=O)[C@@H]3C[C@@H](O)CN3)CC2)C1)C(C)C] |
| Example 6 | 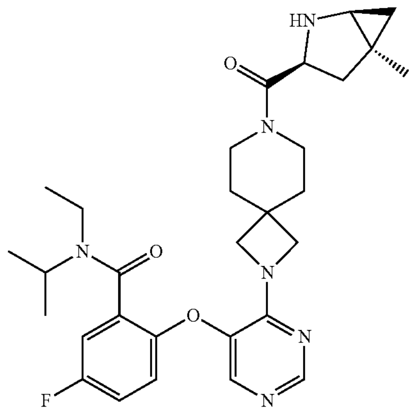 [SMILES: CCN(C(=O)c1cc(F)ccc1Oc1cncnc1N1CC2(CCN(C(=O)[C@@H]3C[C@]4(C)C[C@@H]4N3)CC2)C1)C(C)C] |

-continued
| Compound Nos. | Structures |
|---|---|
| Example 7 | 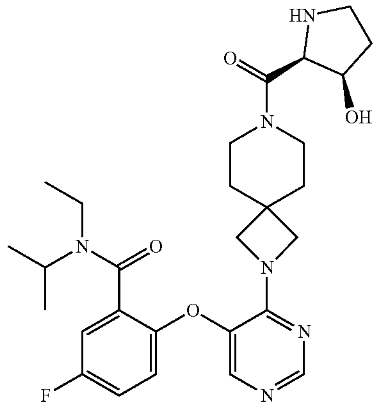 [SMILES: CCN(C(=O)c1cc(F)ccc1Oc1cncnc1N1CC2(CCN(C(=O)[C@H]3NCC[C@H]3O)CC2)C1)C(C)C] |
| Example 8 | 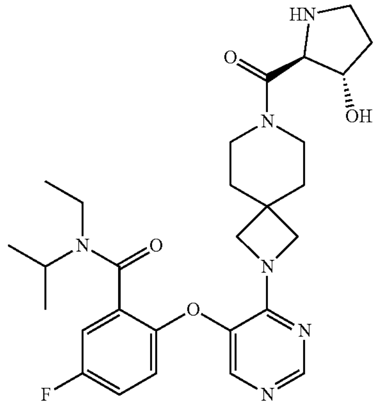 [SMILES: CCN(C(=O)c1cc(F)ccc1Oc1cncnc1N1CC2(CCN(C(=O)[C@H]3NCC[C@@H]3O)CC2)C1)C(C)C] |
| Example 9 | 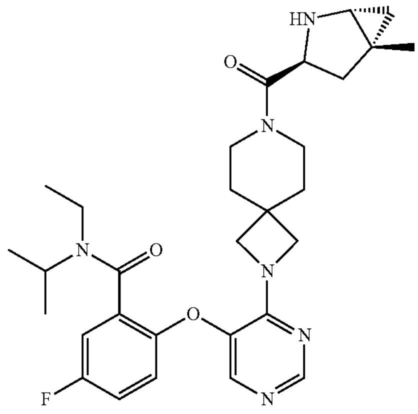 [SMILES: CCN(C(=O)c1cc(F)ccc1Oc1cncnc1N1CC2(CCN(C(=O)[C@@H]3C[C@@]4(C)C[C@H]4N3)CC2)C1)C(C)C] |

-continued
| Compound Nos. | Structures |
|---|---|
| Example 10 | 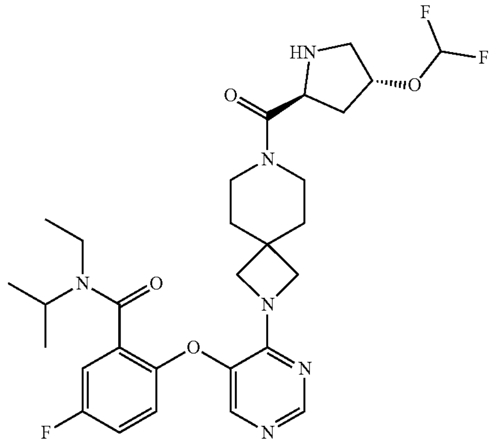 [SMILES: CCN(C(=O)c1cc(F)ccc1Oc1cncnc1N1CC2(CCN(C(=O)[C@@H]3C[C@@H](OC(F)F)CN3)CC2)C1)C(C)C] |
| Example 11 | 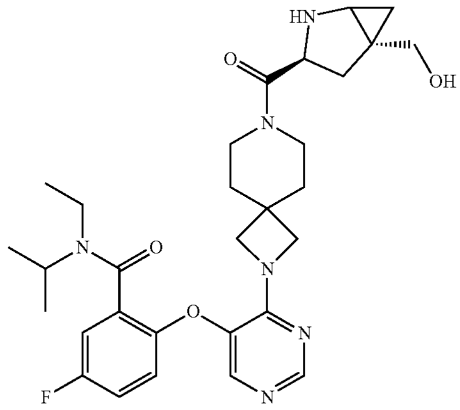 [SMILES: CCN(C(=O)c1cc(F)ccc1Oc1cncnc1N1CC2(CCN(C(=O)[C@@H]3C[C@]4(CO)CC4N3)CC2)C1)C(C)C] |
| Example 12 | 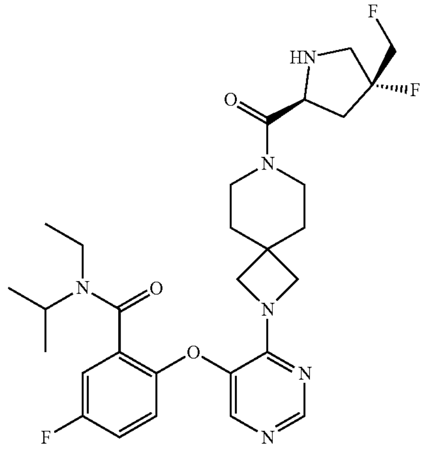 [SMILES: CCN(C(=O)c1cc(F)ccc1Oc1cncnc1N1CC2(CCN(C(=O)[C@@H]3C[C@](F)(CF)CN3)CC2)C1)C(C)C] |

-continued
| Compound Nos. | Structures |
| --- | --- |
| Example 13 | 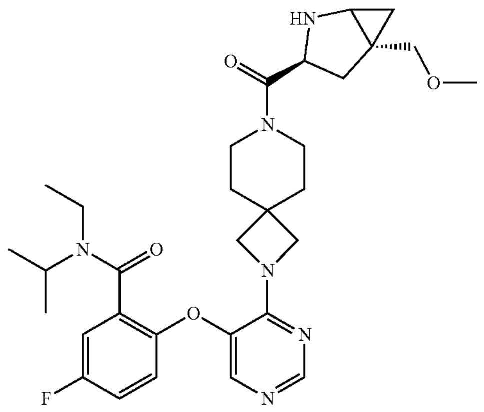 [SMILES: CCN(C(=O)c1cc(F)ccc1Oc1cncnc1N1CC2(CCN(C(=O)[C@@H]3C[C@]4(COC)CC4N3)CC2)C1)C(C)C] |
| Example 14 | 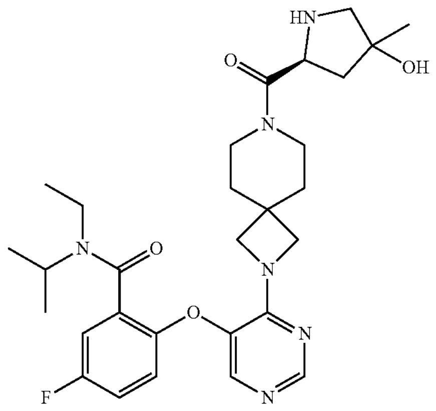 [SMILES: CCN(C(=O)c1cc(F)ccc1Oc1cncnc1N1CC2(CCN(C(=O)[C@@H]3CC(C)(O)CN3)CC2)C1)C(C)C] |
| Example 15 | 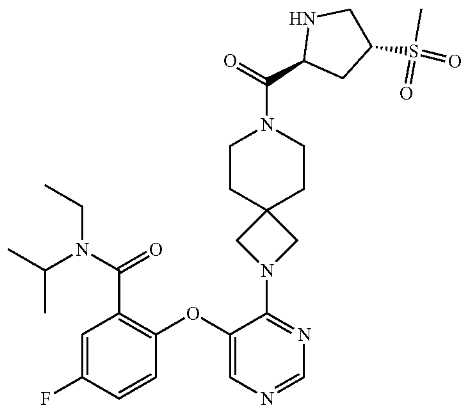 [SMILES: CCN(C(=O)c1cc(F)ccc1Oc1cncnc1N1CC2(CCN(C(=O)[C@@H]3C[C@@H](S(C)(=O)=O)CN3)CC2)C1)C(C)C] |

-continued
| Compound Nos. | Structures |
|---|---|
| Example 16 | 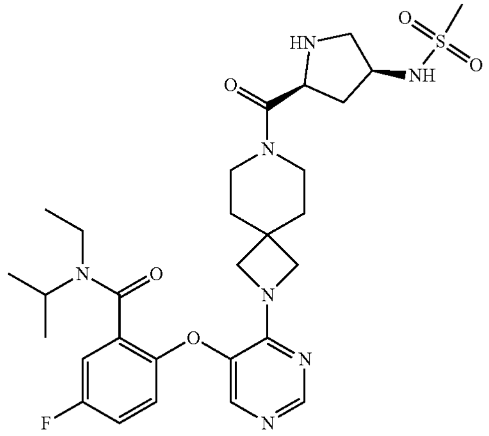 [SMILES: CCN(C(=O)c1cc(F)ccc1Oc1cncnc1N1CC2(CCN(C(=O)[C@@H]3C[C@H](NS(C)(=O)=O)CN3)CC2)C1)C(C)C] |
| Example 17 | 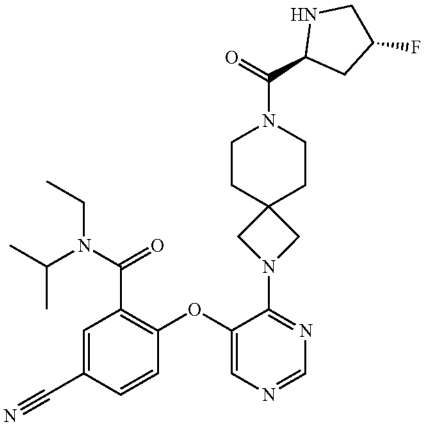 [SMILES: CCN(C(=O)c1cc(C#N)ccc1Oc1cncnc1N1CC2(CCN(C(=O)[C@@H]3C[C@@H](F)CN3)CC2)C1)C(C)C] |
| Example 18 | 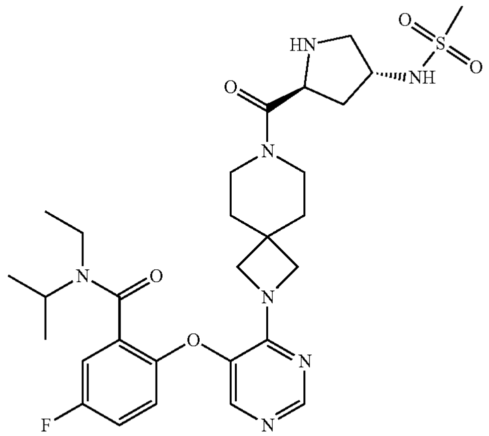 [SMILES: CCN(C(=O)c1cc(F)ccc1Oc1cncnc1N1CC2(CCN(C(=O)[C@@H]3C[C@@H](NS(C)(=O)=O)CN3)CC2)C1)C(C)C] |

-continued
| Compound Nos. | Structures |
|---|---|
| Example 19 | 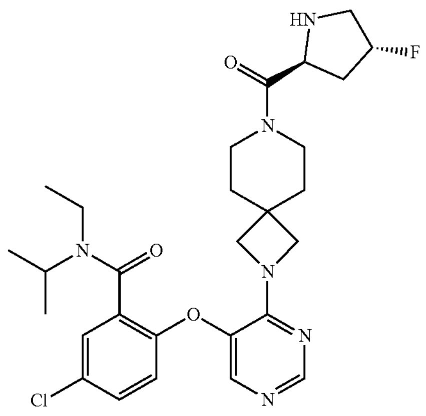 [SMILES: CCN(C(=O)c1cc(Cl)ccc1Oc1cncnc1N1CC2(CCN(C(=O)[C@@H]3C[C@@H](F)CN3)CC2)C1)C(C)C] |
| Example 20 | 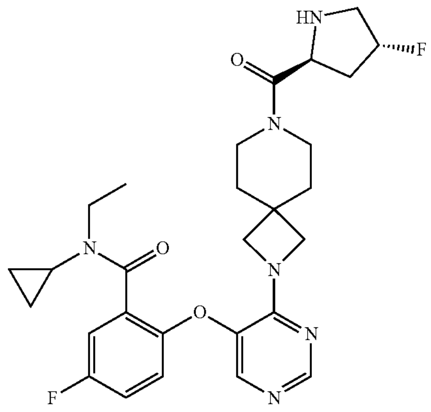 [SMILES: CCN(C(=O)c1cc(F)ccc1Oc1cncnc1N1CC2(CCN(C(=O)[C@@H]3C[C@@H](F)CN3)CC2)C1)C1CC1] |
| Example 21 | 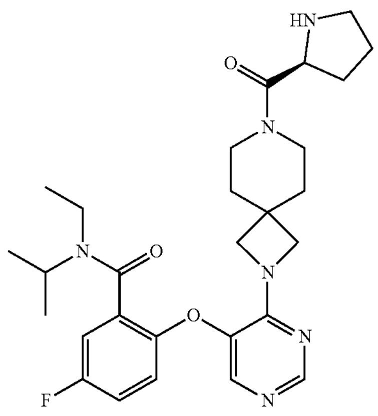 [SMILES: CCN(C(=O)c1cc(F)ccc1Oc1cncnc1N1CC2(CCN(C(=O)[C@@H]3CCCN3)CC2)C1)C(C)C] |

-continued
| Compound Nos. | Structures |
|---|---|
| Example 22 | 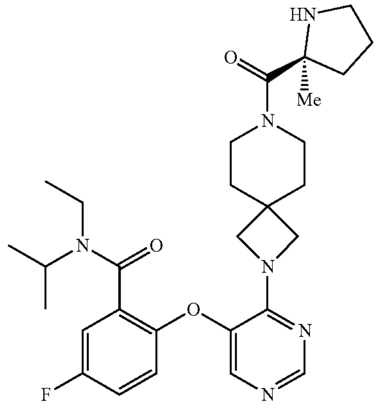 [SMILES: CCN(C(=O)c1cc(F)ccc1Oc1cncnc1N1CC2(CCN(C(=O)[C@]3(C)CCCN3)CC2)C1)C(C)C] |
| Example 23 | 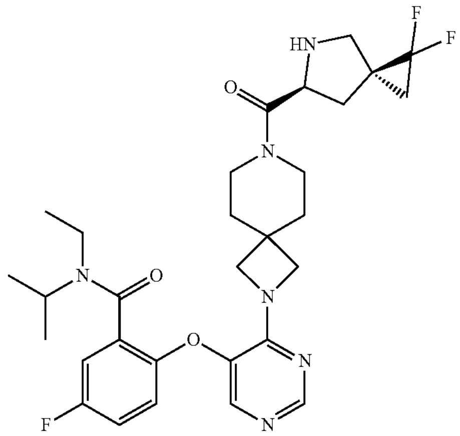 [SMILES: CCN(C(=O)c1cc(F)ccc1Oc1cncnc1N1CC2(CCN(C(=O)[C@@H]3C[C@]4(CN3)CC4(F)F)CC2)C1)C(C)C] |
| Example 24 | 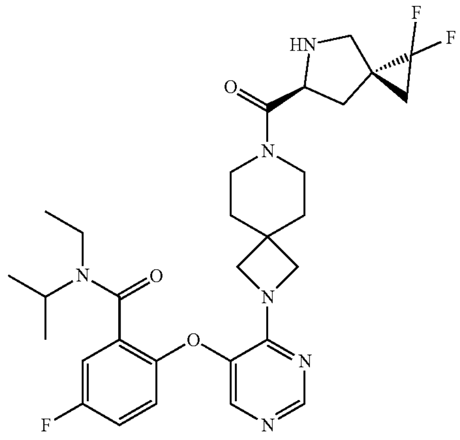 [SMILES: CCN(C(=O)c1cc(F)ccc1Oc1cncnc1N1CC2(CCN(C(=O)[C@@H]3C[C@@]4(CN3)CC4(F)F)CC2)C1)C(C)C] |

-continued
| Compound Nos. | Structures |
|---|---|
| Example 25 | 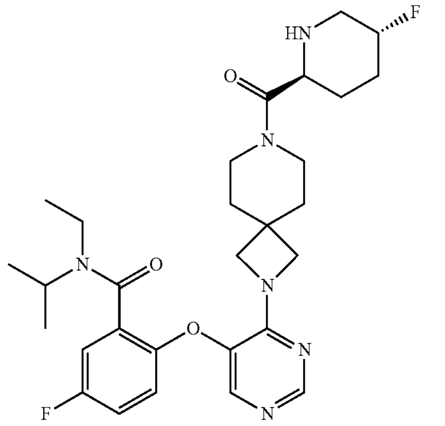 [SMILES: CCN(C(=O)c1cc(F)ccc1Oc1cncnc1N1CC2(CCN(C(=O)[C@@H]3CC[C@@H](F)CN3)CC2)C1)C(C)C] |
| Example 26 | 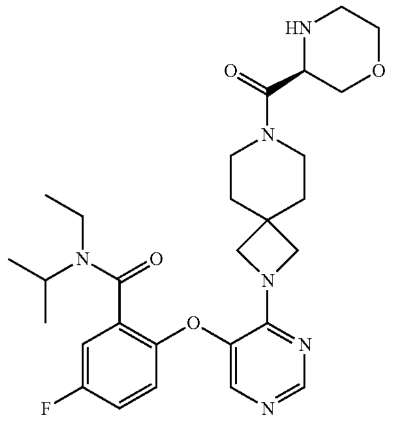 [SMILES: CCN(C(=O)c1cc(F)ccc1Oc1cncnc1N1CC2(CCN(C(=O)[C@@H]3COCCN3)CC2)C1)C(C)C] |
| Example 27 | 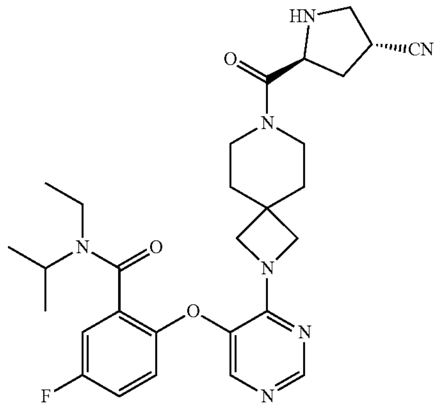 [SMILES: CCN(C(=O)c1cc(F)ccc1Oc1cncnc1N1CC2(CCN(C(=O)[C@@H]3C[C@@H](C#N)CN3)CC2)C1)C(C)C] |

-continued
| Compound Nos. | Structures |
|---|---|
| Example 28 | 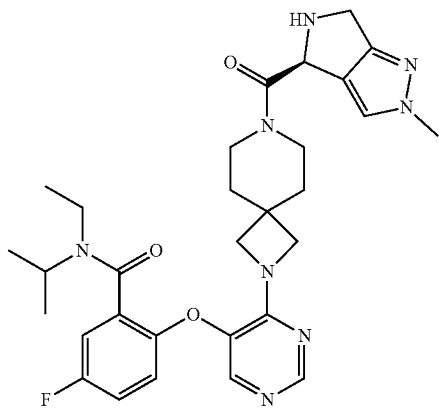 [SMILES: CCN(C(=O)c1cc(F)ccc1Oc1cncnc1N1CC2(CCN(C(=O)[C@H]3NCc4nn(C)cc43)CC2)C1)C(C)C] |
| Example 29 | 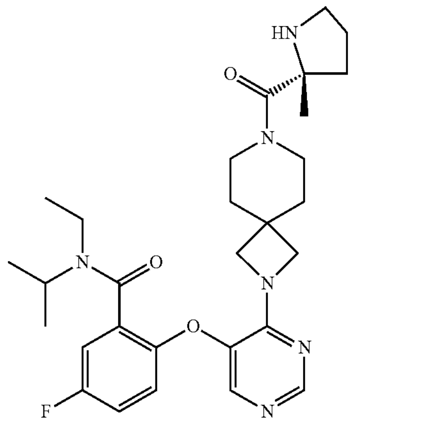 [SMILES: CCN(C(=O)c1cc(F)ccc1Oc1cncnc1N1CC2(CCN(C(=O)[C@@]3(C)CCCN3)CC2)C1)C(C)C] |
| Example 30 | 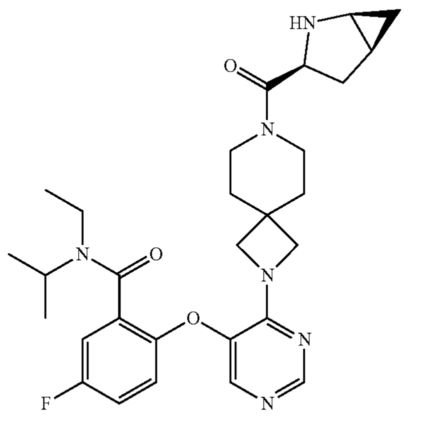 [SMILES: CCN(C(=O)c1cc(F)ccc1Oc1cncnc1N1CC2(CCN(C(=O)[C@@H]3C[C@@H]4C[C@@H]4N3)CC2)C1)C(C)C] |

-continued
| Compound Nos. | Structures |
|---|---|
| Example 31 | 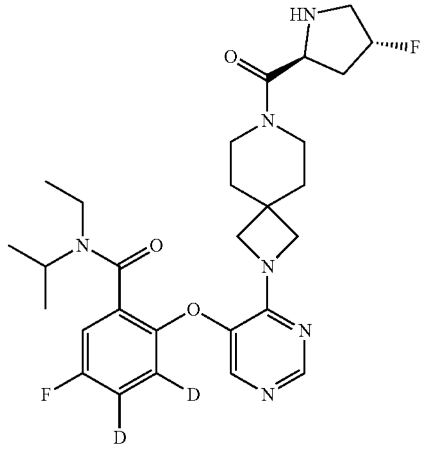 [SMILES: [2H]c1c(F)cc(C(=O)N(CC)C(C)C)c(Oc2cncnc2N2CC3(CCN(C(=O)[C@@H]4C[C@@H](F)CN4)CC3)C2)c1[2H]] |
| Example 32 | 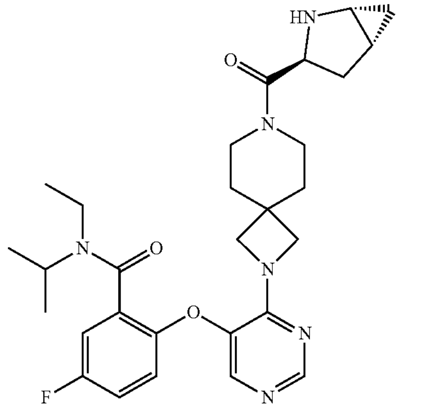 [SMILES: CCN(C(=O)c1cc(F)ccc1Oc1cncnc1N1CC2(CCN(C(=O)[C@@H]3C[C@H]4C[C@H]4N3)CC2)C1)C(C)C] |
| Example 33 | 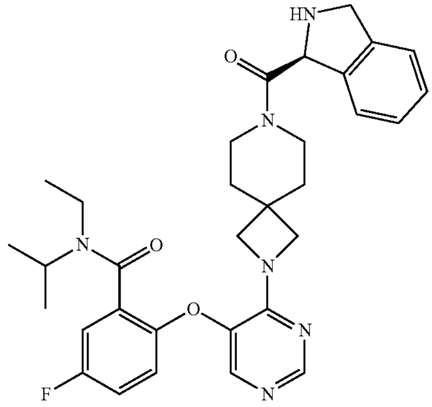 [SMILES: CCN(C(=O)c1cc(F)ccc1Oc1cncnc1N1CC2(CCN(C(=O)[C@H]3NCc4ccccc43)CC2)C1)C(C)C] |

-continued
| Compound Nos. | Structures |
|---|---|
| Example 34 | 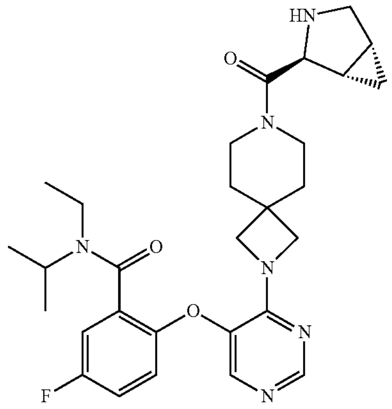 [SMILES: CCN(C(=O)c1cc(F)ccc1Oc1cncnc1N1CC2(CCN(C(=O)[C@H]3NC[C@@H]4C[C@@H]43)CC2)C1)C(C)C] |
| Example 36 | 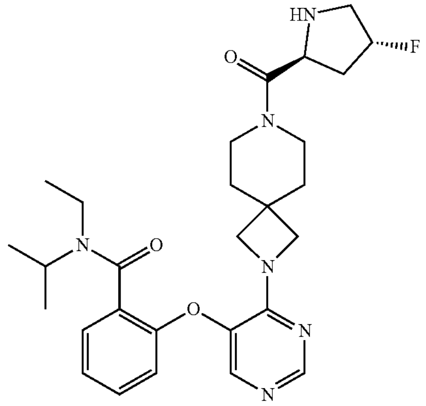 [SMILES: CCN(C(=O)c1ccccc1Oc1cncnc1N1CC2(CCN(C(=O)[C@@H]3C[C@@H](F)CN3)CC2)C1)C(C)C] |
| Example 37 | 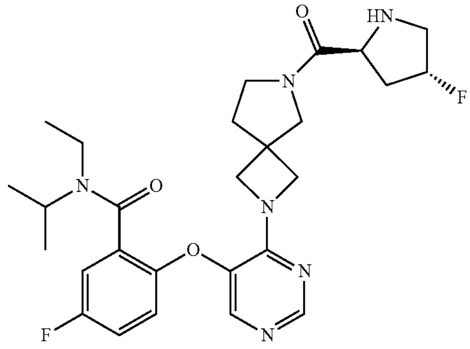 [SMILES: CCN(C(=O)c1cc(F)ccc1Oc1cncnc1N1CC2(CCN(C(=O)[C@@H]3C[C@@H](F)CN3)C2)C1)C(C)C] |
| Example 38 | 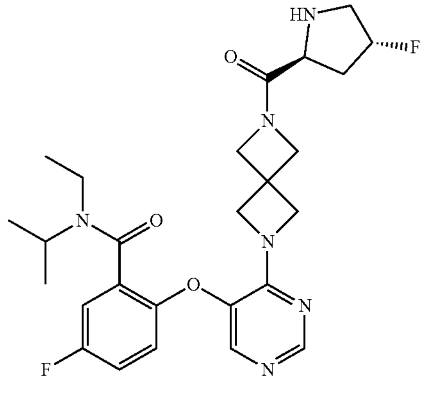 [SMILES: CCN(C(=O)c1cc(F)ccc1Oc1cncnc1N1CC2(CN(C(=O)[C@@H]3C[C@@H](F)CN3)C2)C1)C(C)C] |

-continued
| Compound Nos. | Structures |
|---|---|
| Example 39 | 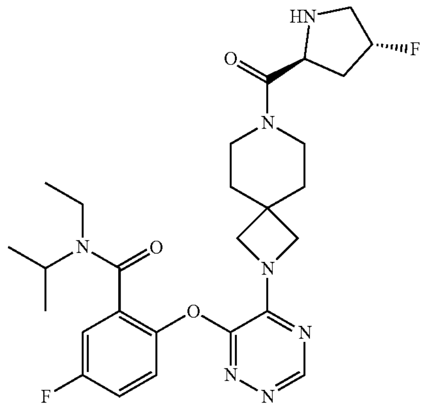 |
| Example 40 | 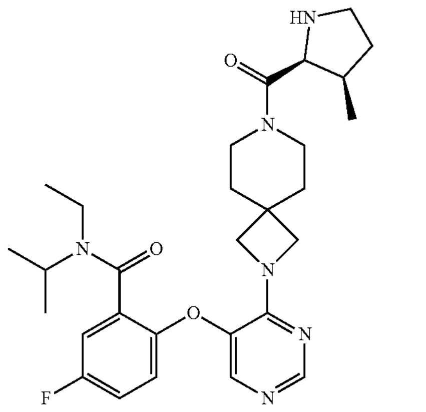 [SMILES: CCN(C(=O)c1cc(F)ccc1Oc1cncnc1N1CC2(CCN(C(=O)[C@H]3NCC[C@H]3C)CC2)C1)C(C)C] |
| Example 41 | 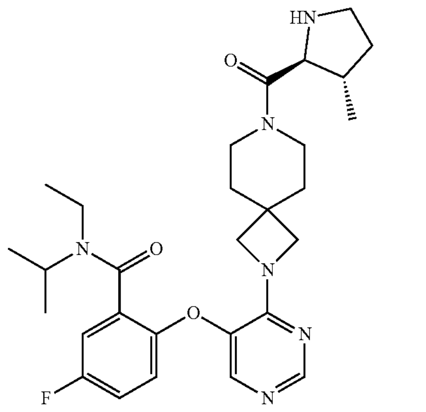 [SMILES: CCN(C(=O)c1cc(F)ccc1Oc1cncnc1N1CC2(CCN(C(=O)[C@H]3NCC[C@@H]3C)CC2)C1)C(C)C] |

-continued
Compound Nos. Structures
Example 42
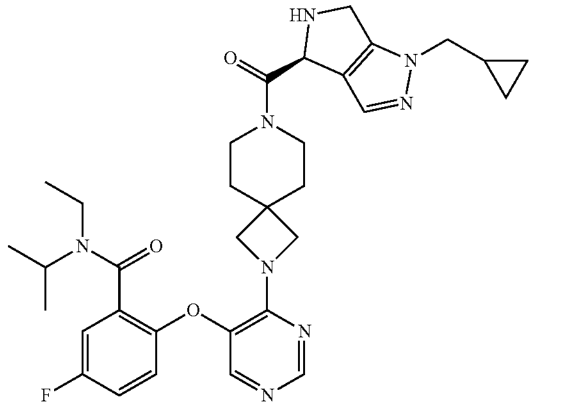 [SMILES: CCN(C(=O)c1cc(F)ccc1Oc1cncnc1N1CC2(CCN(C(=O)[C@H]3NCc4c3cnn4CC3CC3)CC2)C1)C(C)C]
Example 43
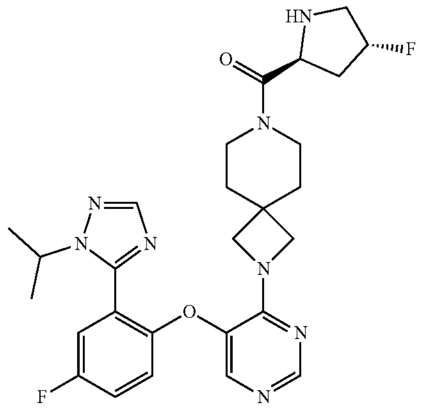 [SMILES: CC(C)n1ncnc1-c1cc(F)ccc1Oc1cncnc1N1CC2(CCN(C(=O)[C@@H]3C[C@@H](F)CN3)CC2)C1]
Example 44
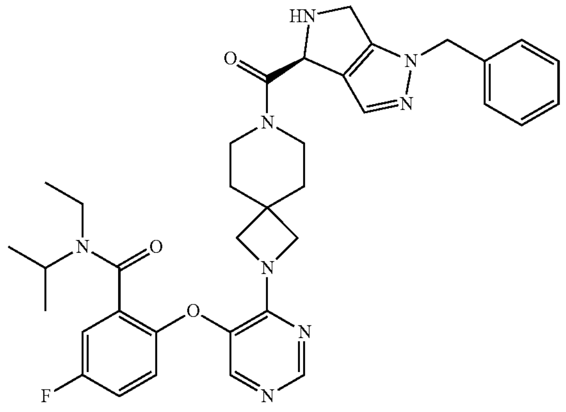 [SMILES: CCN(C(=O)c1cc(F)ccc1Oc1cncnc1N1CC2(CCN(C(=O)[C@H]3NCc4c3cnn4Cc3ccccc3)CC2)C1)C(C)C]

-continued
| Compound Nos. | Structures |
| --- | --- |
| Example 45 | 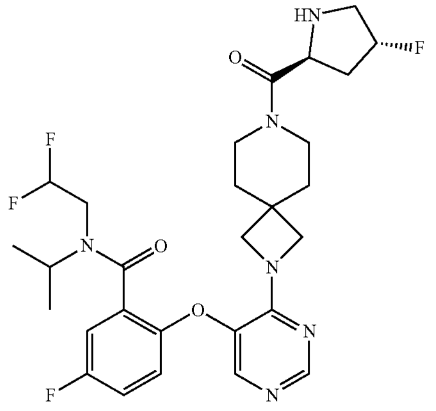 [SMILES: CC(C)N(CC(F)F)C(=O)c1cc(F)ccc1Oc1cncnc1N1CC2(CCN(C(=O)[C@@H]3C[C@@H](F)CN3)CC2)C1] |
| Example 46 | 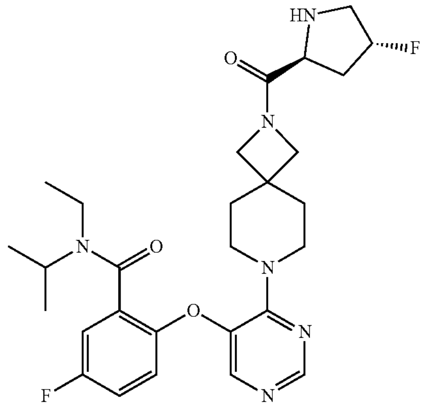 [SMILES: CCN(C(=O)c1cc(F)ccc1Oc1cncnc1N1CCC2(CC1)CN(C(=O)[C@@H]1C[C@@H](F)CN1)C2)C(C)C] |
| Example 47 | 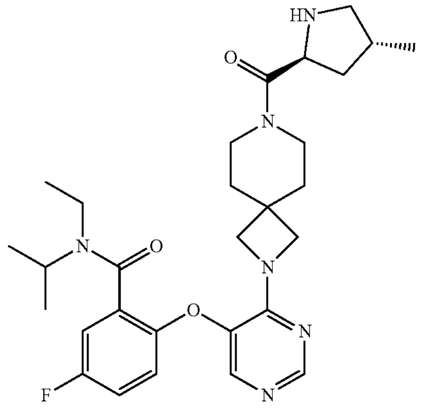 [SMILES: CCN(C(=O)c1cc(F)ccc1Oc1cncnc1N1CC2(CCN(C(=O)[C@@H]3C[C@@H](C)CN3)CC2)C1)C(C)C] |

-continued
| Compound Nos. | Structures |
|---|---|
| Example 48 | 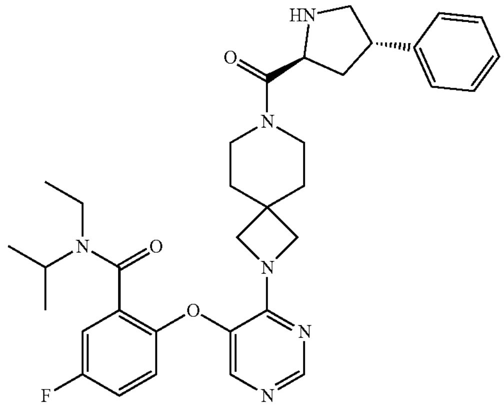 [SMILES: CCN(C(=O)c1cc(F)ccc1Oc1cncnc1N1CC2(CCN(C(=O)[C@@H]3C[C@@H](c4ccccc4)CN3)CC2)C1)C(C)C] |
| Example 49 | 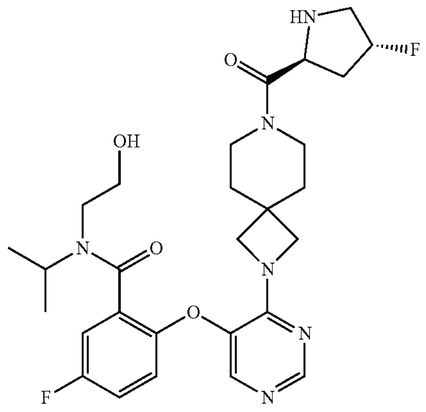 [SMILES: CC(C)N(CCO)C(=O)c1cc(F)ccc1Oc1cncnc1N1CC2(CCN(C(=O)[C@@H]3C[C@@H](F)CN3)CC2)C1] |
| Example 50 | 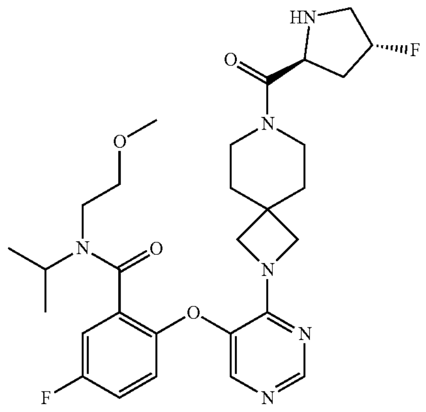 [SMILES: COCCN(C(=O)c1cc(F)ccc1Oc1cncnc1N1CC2(CCN(C(=O)[C@@H]3C[C@@H](F)CN3)CC2)C1)C(C)C] |

-continued
| Compound Nos. | Structures |
| --- | --- |
| Example 51 | 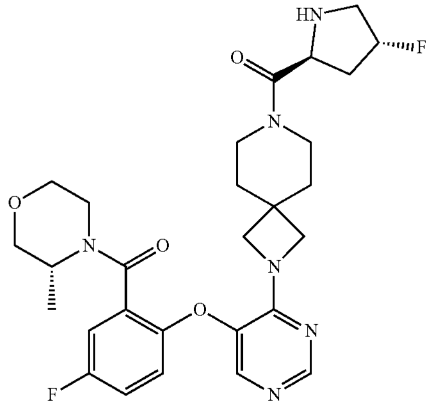 [SMILES: C[C@@H]1COCCN1C(=O)c1cc(F)ccc1Oc1cncnc1N1CC2(CCN(C(=O)[C@@H]3C[C@@H](F)CN3)CC2)C1] |
| Example 52 | 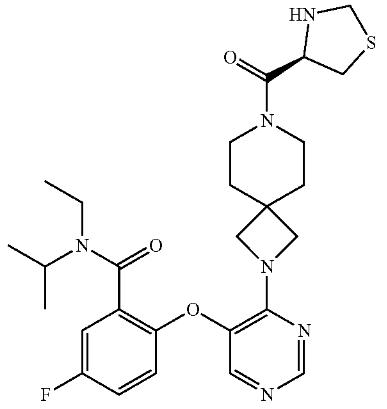 [SMILES: CCN(C(=O)c1cc(F)ccc1Oc1cncnc1N1CC2(CCN(C(=O)[C@@H]3CSCN3)CC2)C1)C(C)C] |
| Example 53 | 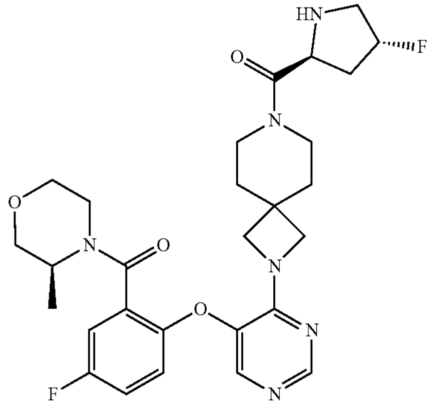 [SMILES: C[C@H]1COCCN1C(=O)c1cc(F)ccc1Oc1cncnc1N1CC2(CCN(C(=O)[C@@H]3C[C@@H](F)CN3)CC2)C1] |

-continued
| Compound Nos. | Structures |
|---|---|
| Example 54 | 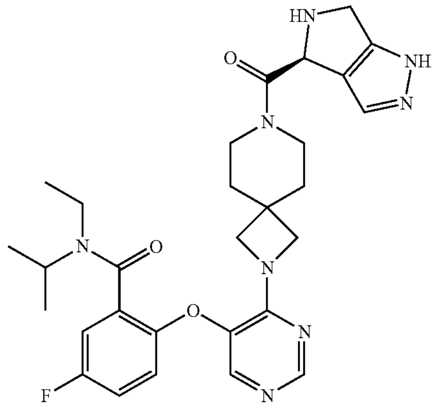 [SMILES: CCN(C(=O)c1cc(F)ccc1Oc1cncnc1N1CC2(CCN(C(=O)[C@H]3NCc4[nH]ncc43)CC2)C1)C(C)C] |
| Example 55 | 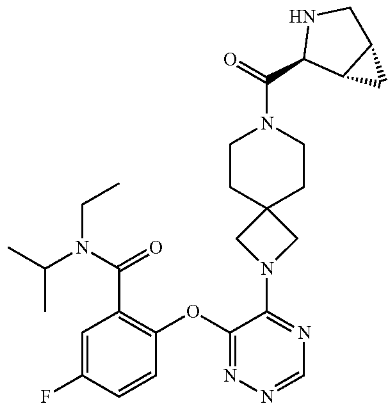 [SMILES: CCN(C(=O)c1cc(F)ccc1Oc1nncnc1N1CC2(CCN(C(=O)[C@H]3NC[C@@H]4C[C@@H]43)CC2)C1)C(C)C] |
| Example 56 | 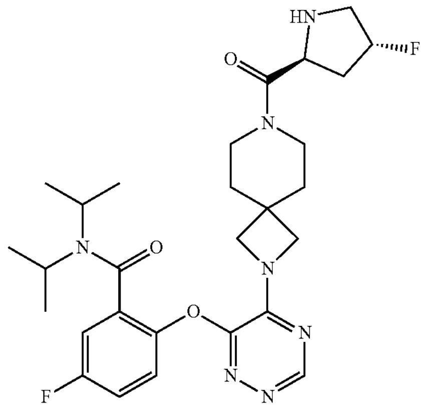 [SMILES: CC(C)N(C(=O)c1cc(F)ccc1Oc1nncnc1N1CC2(CCN(C(=O)[C@@H]3C[C@@H](F)CN3)CC2)C1)C(C)C] |

-continued
| Compound Nos. | Structures |
|---|---|
| Example 57 | 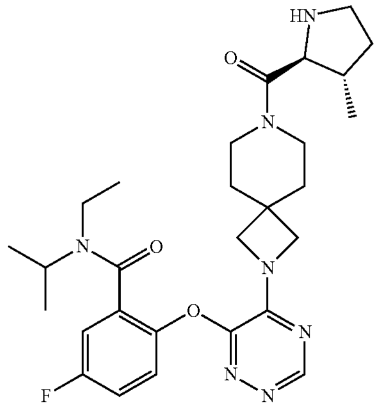 [SMILES: CCN(C(=O)c1cc(F)ccc1Oc1nncnc1N1CC2(CCN(C(=O)[C@H]3NCC[C@@H]3C)CC2)C1)C(C)C] |
| Example 58 | 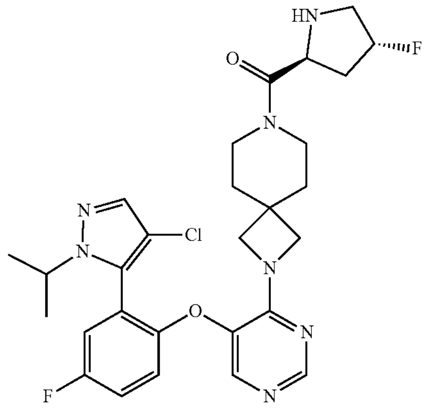 [SMILES: CC(C)n1ncc(Cl)c1-c1cc(F)ccc1Oc1cncnc1N1CC2(CCN(C(=O)[C@@H]3C[C@@H](F)CN3)CC2)C1] |
| Example 59 | 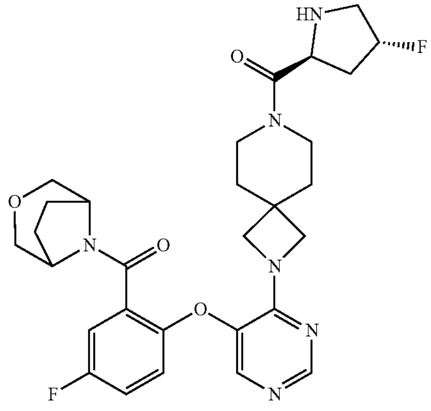 [SMILES: O=C([C@@H]1C[C@@H](F)CN1)N1CCC2(CC1)CN(c1ncncc1Oc1ccc(F)cc1C(=O)N1C3CCC1COC3)C2] |

-continued
| Compound Nos. | Structures |
| --- | --- |
| Example 60 | 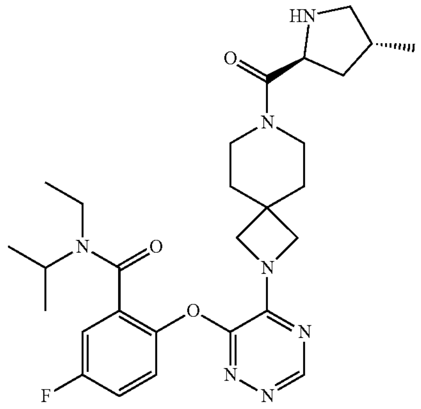 [SMILES: CCN(C(=O)c1cc(F)ccc1Oc1nncnc1N1CC2(CCN(C(=O)[C@@H]3C[C@@H](C)CN3)CC2)C1)C(C)C] |
| Example 61 | 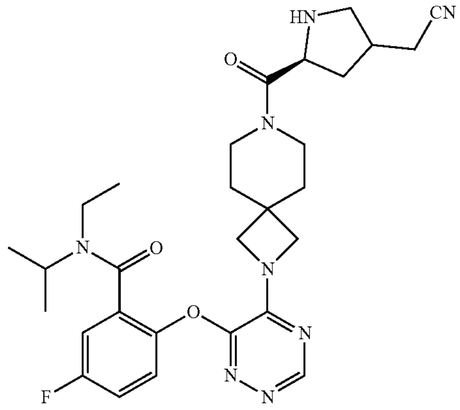 [SMILES: CCN(C(=O)c1cc(F)ccc1Oc1nncnc1N1CC2(CCN(C(=O)[C@@H]3CC(CC#N)CN3)CC2)C1)C(C)C] |
| Example 62 | 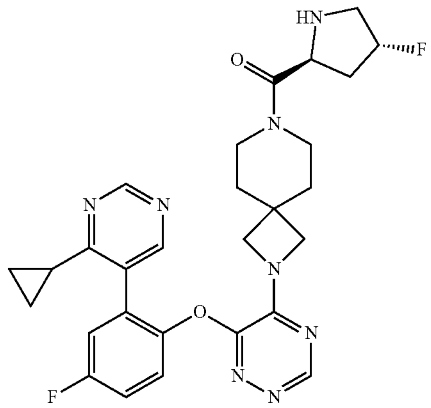 [SMILES: O=C([C@@H]1C[C@@H](F)CN1)N1CCC2(CC1)CN(c1ncnnc1Oc1ccc(F)cc1-c1cncnc1C1CC1)C2] |

-continued
| Compound Nos. | Structures |
|---|---|
| Example 63 | 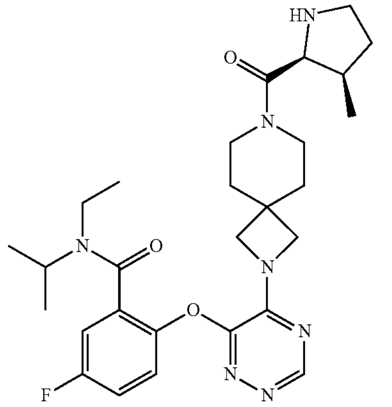 [SMILES: CCN(C(=O)c1cc(F)ccc1Oc1nncnc1N1CC2(CCN(C(=O)[C@H]3NCC[C@H]3C)CC2)C1)C(C)C] |
| Example 64 | 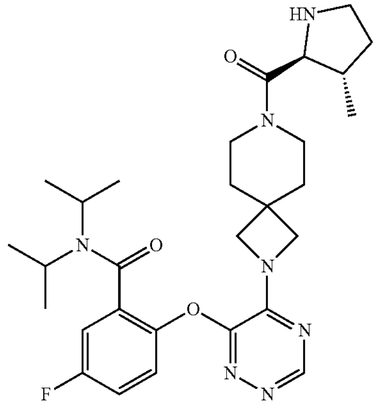 [SMILES: CC(C)N(C(=O)c1cc(F)ccc1Oc1nncnc1N1CC2(CCN(C(=O)[C@H]3NCC[C@@H]3C)CC2)C1)C(C)C] |
| Example 65 | 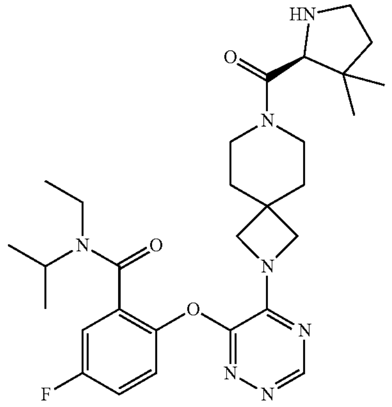 [SMILES: CCN(C(=O)c1cc(F)ccc1Oc1nncnc1N1CC2(CCN(C(=O)[C@H]3NCCC3(C)C)CC2)C1)C(C)C] |

-continued
| Compound Nos. | Structures |
| --- | --- |
| Example 66 | 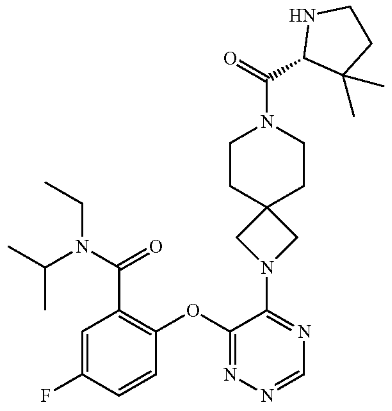 [SMILES: CCN(C(=O)c1cc(F)ccc1Oc1nncnc1N1CC2(CCN(C(=O)[C@@H]3NCCC3(C)C)CC2)C1)C(C)C] |
| Example 67 | 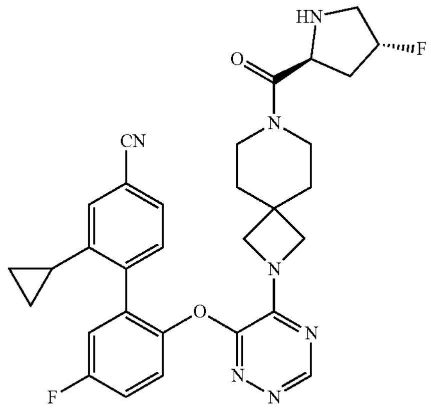 [SMILES: N#Cc1ccc(-c2cc(F)ccc2Oc2nncnc2N2CC3(CCN(C(=O)[C@@H]4C[C@@H](F)CN4)CC3)C2)c(C2CC2)c1] |
| Example 68 | 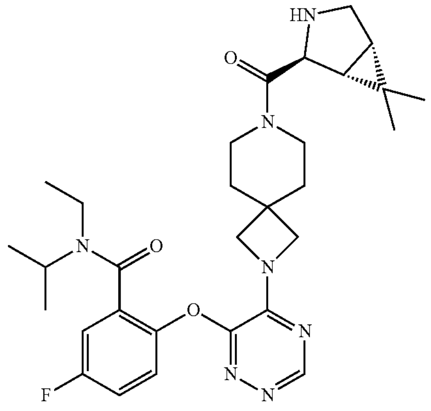 [SMILES: CCN(C(=O)c1cc(F)ccc1Oc1nncnc1N1CC2(CCN(C(=O)[C@H]3NC[C@H]4[C@@H]3C4(C)C)CC2)C1)C(C)C] |

-continued
| Compound Nos. | Structures |
| --- | --- |
| Example 69 | 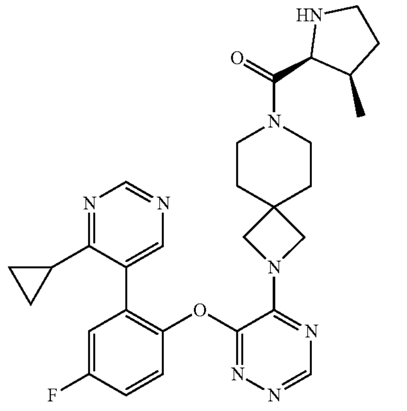 [SMILES: C[C@@H]1CCN[C@@H]1C(=O)N1CCC2(CC1)CN(c1ncnnc1Oc1ccc(F)cc1-c1cncnc1C1CC1)C2] |
| Example 70 | 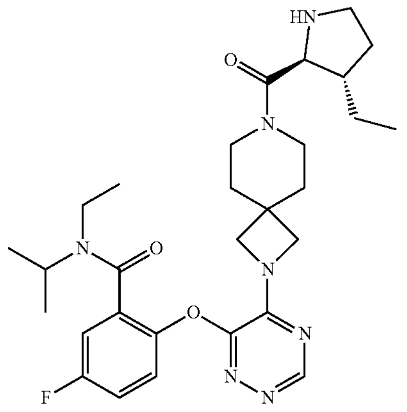 [SMILES: CC[C@H]1CCN[C@@H]1C(=O)N1CCC2(CC1)CN(c1ncnnc1Oc1ccc(F)cc1C(=O)N(CC)C(C)C)C2] |
| Example 71 | 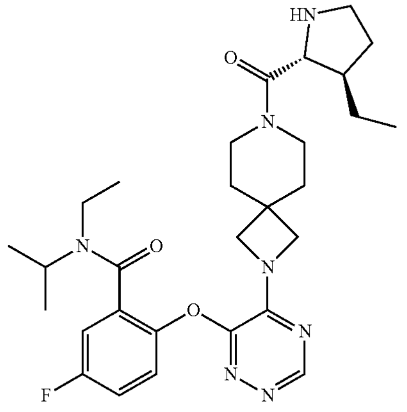 [SMILES: CC[C@@H]1CCN[C@H]1C(=O)N1CCC2(CC1)CN(c1ncnnc1Oc1ccc(F)cc1C(=O)N(CC)C(C)C)C2] |

-continued
| Compound Nos. | Structures |
| --- | --- |
| Example 72 | 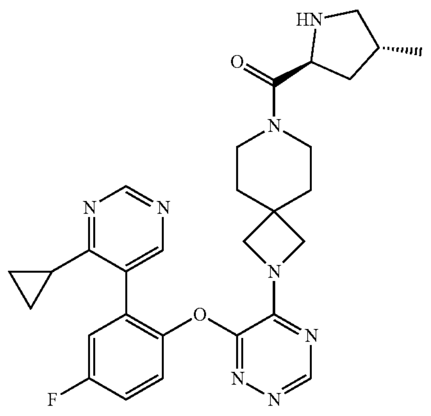 [SMILES: C[C@H]1CN[C@H](C(=O)N2CCC3(CC2)CN(c2ncnnc2Oc2ccc(F)cc2-c2cncnc2C2CC2)C3)C1] |
| Example 73 | 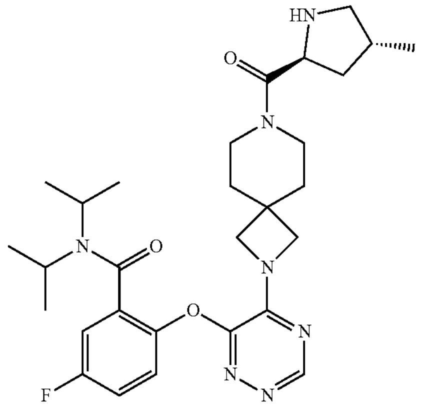 [SMILES: CC(C)N(C(=O)c1cc(F)ccc1Oc1nncnc1N1CC2(CCN(C(=O)[C@@H]3C[C@@H](C)CN3)CC2)C1)C(C)C] |
| Example 74 | 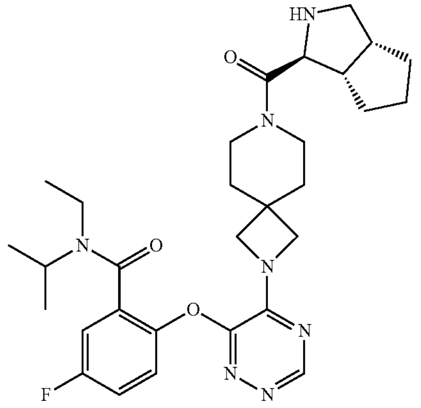 [SMILES: CCN(C(=O)c1cc(F)ccc1Oc1nncnc1N1CC2(CCN(C(=O)[C@H]3NC[C@@H]4CCC[C@@H]43)CC2)C1)C(C)C] |

-continued
| Compound Nos. | Structures |
| --- | --- |
| Example 75 | 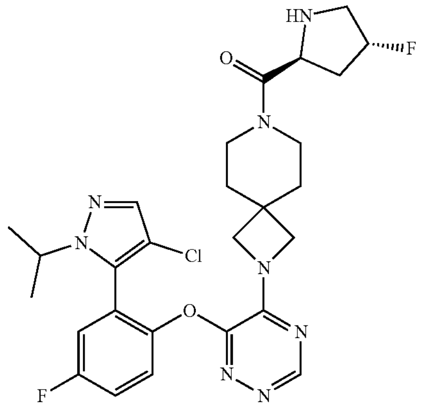 [SMILES: CC(C)n1ncc(Cl)c1-c1cc(F)ccc1Oc1nncnc1N1CC2(CCN(C(=O)[C@@H]3C[C@@H](F)CN3)CC2)C1] |
| Example 76 | 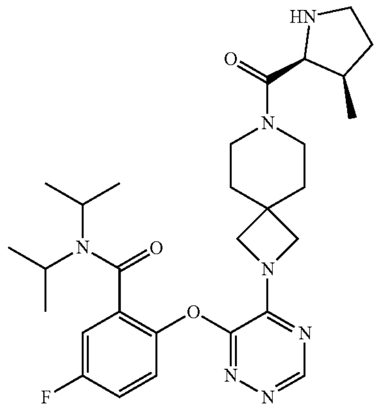 [SMILES: CC(C)N(C(=O)c1cc(F)ccc1Oc1nncnc1N1CC2(CCN(C(=O)[C@H]3NCC[C@H]3C)CC2)C1)C(C)C] |
| Example 77 | 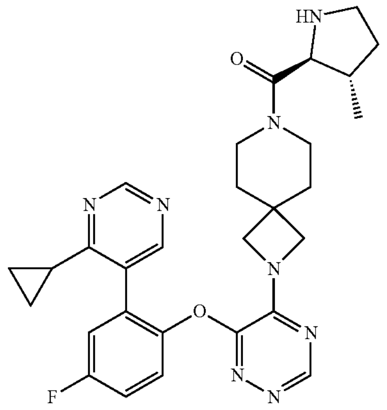 [SMILES: C[C@H]1CCN[C@@H]1C(=O)N1CCC2(CC1)CN(c1ncnnc1Oc1ccc(F)cc1-c1cncnc1C1CC1)C2] |

-continued
| Compound Nos. | Structures |
|---|---|
| Example 78 | 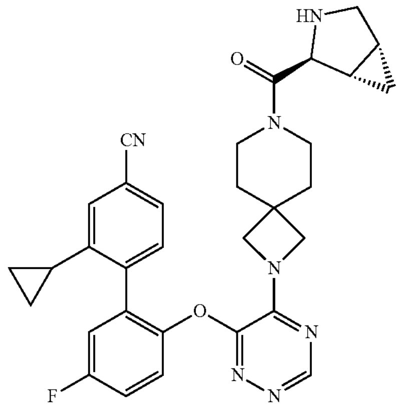 [SMILES: N#Cc1ccc(-c2cc(F)ccc2Oc2nncnc2N2CC3(CCN(C(=O)[C@H]4NC[C@@H]5C[C@@H]54)CC3)C2)c(C2CC2)c1] |
| Example 79 | 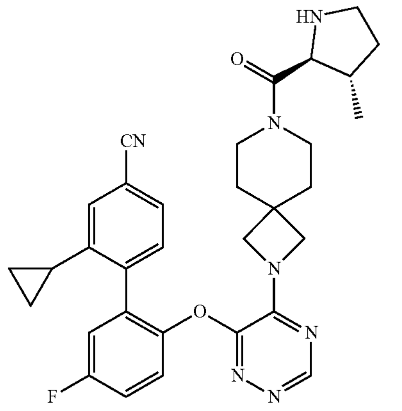 [SMILES: C[C@H]1CCN[C@@H]1C(=O)N1CCC2(CC1)CN(c1ncnnc1Oc1ccc(F)cc1-c1ccc(C#N)cc1C1CC1)C2] |
| Example 80 | 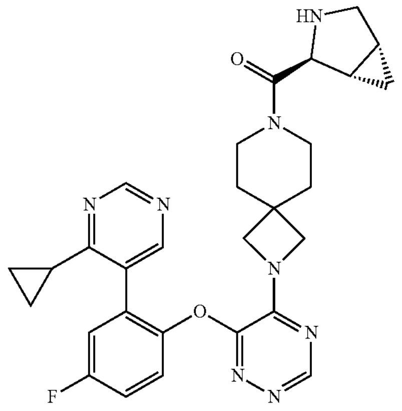 [SMILES: O=C([C@H]1NC[C@@H]2C[C@@H]21)N1CCC2(CC1)CN(c1ncnnc1Oc1ccc(F)cc1-c1cncnc1C1CC1)C2] |

-continued
| Compound Nos. | Structures |
|---|---|
| Example 81 | 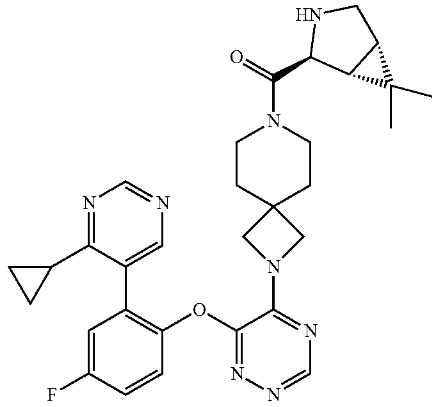 [SMILES: CC1(C)[C@@H]2[C@@H](C(=O)N3CCC4(CC3)CN(c3ncnnc3Oc3ccc(F)cc3-c3cncnc3C3CC3)C4)NC[C@@H]21] |
| Example 82 | 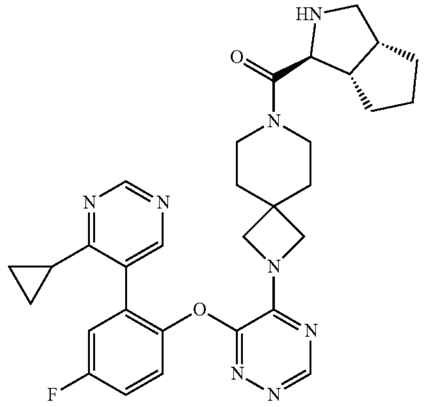 [SMILES: O=C([C@H]1NC[C@@H]2CCC[C@@H]21)N1CCC2(CC1)CN(c1ncnnc1Oc1ccc(F)cc1-c1cncnc1C1CC1)C2] |
| Example 83 | 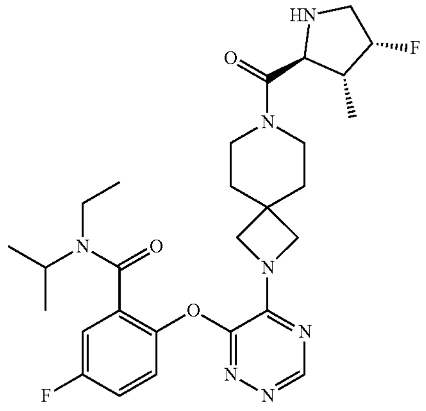 [SMILES: CCN(C(=O)c1cc(F)ccc1Oc1nncnc1N1CC2(CCN(C(=O)[C@H]3NC[C@H](F)[C@@H]3C)CC2)C1)C(C)C] |

-continued
| Compound Nos. | Structures |
| --- | --- |
| Example 84 | 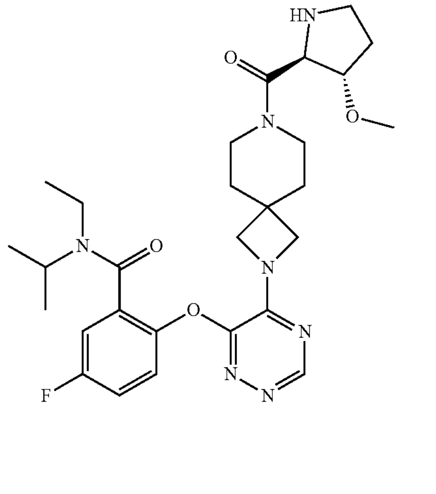 [SMILES: CCN(C(=O)c1cc(F)ccc1Oc1nncnc1N1CC2(CCN(C(=O)[C@H]3NCC[C@@H]3OC)CC2)C1)C(C)C] |
| Example 85 | 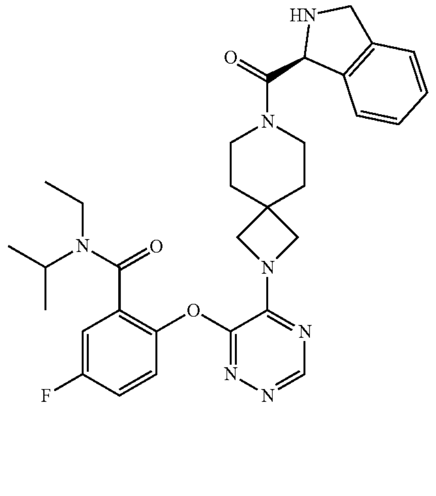 |
| Example 86 | 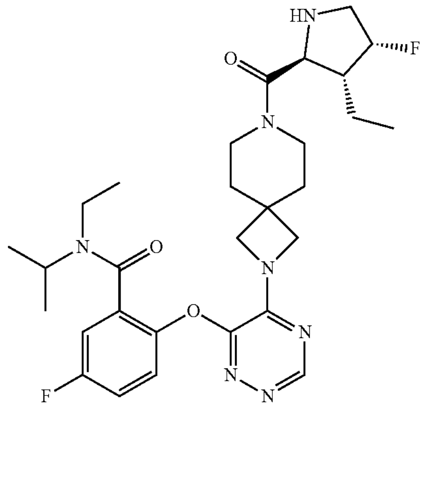 [SMILES: CC[C@@H]1[C@@H](C(=O)N2CCC3(CC2)CN(c2ncnnc2Oc2ccc(F)cc2C(=O)N(CC)C(C)C)C3)NC[C@@H]1F] |

-continued
| Compound Nos. | Structures |
| --- | --- |
| Example 87 | 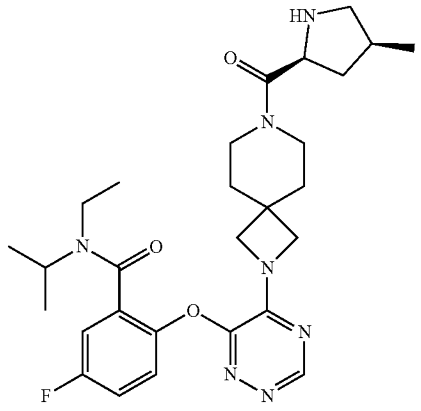 [SMILES: CCN(C(=O)c1cc(F)ccc1Oc1nncnc1N1CC2(CCN(C(=O)[C@@H]3C[C@H](C)CN3)CC2)C1)C(C)C] |
| Example 88 | 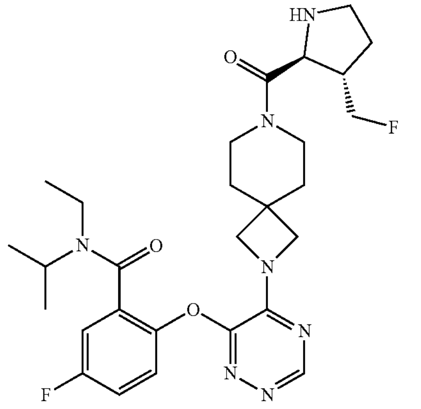 [SMILES: CCN(C(=O)c1cc(F)ccc1Oc1nncnc1N1CC2(CCN(C(=O)[C@H]3NCC[C@@H]3CF)CC2)C1)C(C)C] |
| Example 89 | 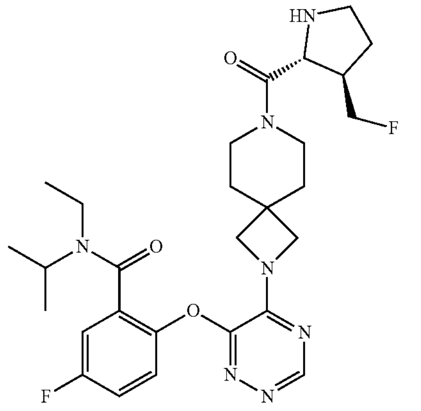 [SMILES: CCN(C(=O)c1cc(F)ccc1Oc1nncnc1N1CC2(CCN(C(=O)[C@@H]3NCC[C@H]3CF)CC2)C1)C(C)C] |

-continued
| Compound Nos. | Structures |
| --- | --- |
| Example 90 | 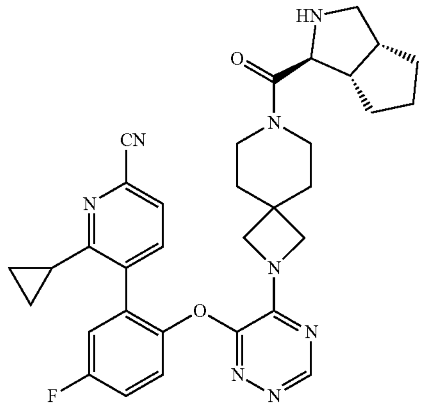 [SMILES: N#Cc1ccc(-c2cc(F)ccc2Oc2nncnc2N2CC3(CCN(C(=O)[C@H]4NC[C@@H]5CCC[C@@H]54)CC3)C2)c(C2CC2)n1] |
| Example 91 | 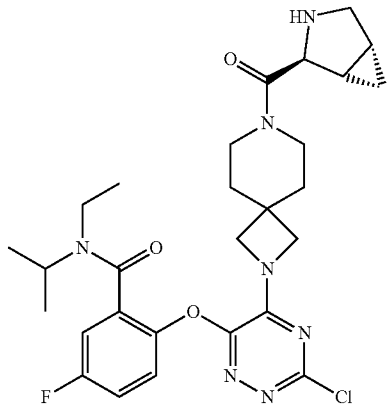 |
| Example 92 | 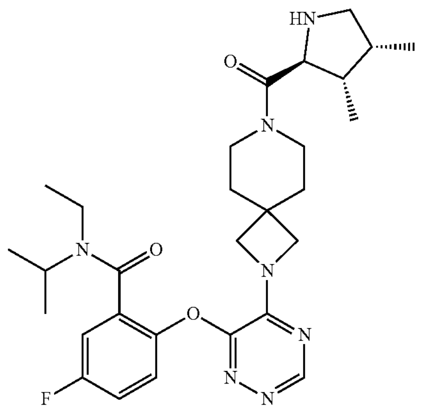 [SMILES: CCN(C(=O)c1cc(F)ccc1Oc1nncnc1N1CC2(CCN(C(=O)[C@H]3NC[C@H](C)[C@@H]3C)CC2)C1)C(C)C] |

-continued
| Compound Nos. | Structures |
|---|---|
| Example 93 | 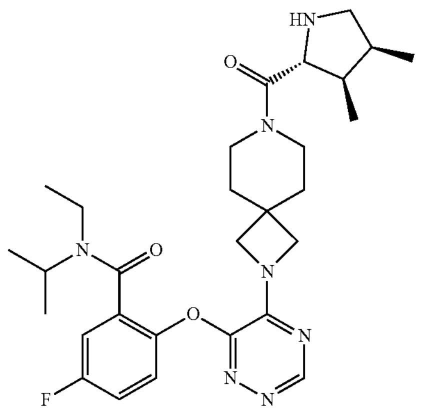 [SMILES: CCN(C(=O)c1cc(F)ccc1Oc1nncnc1N1CC2(CCN(C(=O)[C@@H]3NC[C@@H](C)[C@H]3C)CC2)C1)C(C)C] |
| Example 94 | 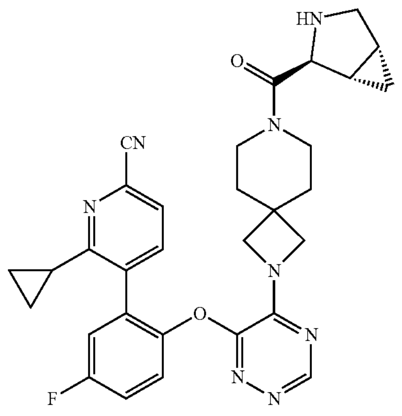 [SMILES: N#Cc1ccc(-c2cc(F)ccc2Oc2nncnc2N2CC3(CCN(C(=O)[C@H]4NC[C@@H]5C[C@@H]54)CC3)C2)c(C2CC2)n1] |
| Example 95 | 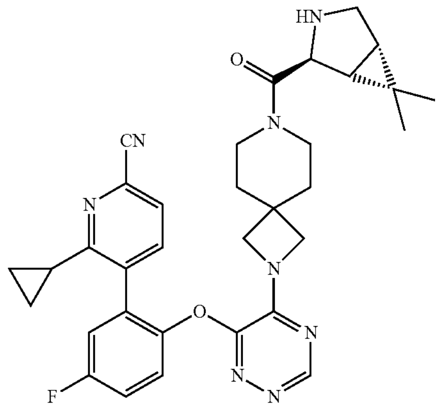 |

-continued
Compound Nos. Structures
Example 96
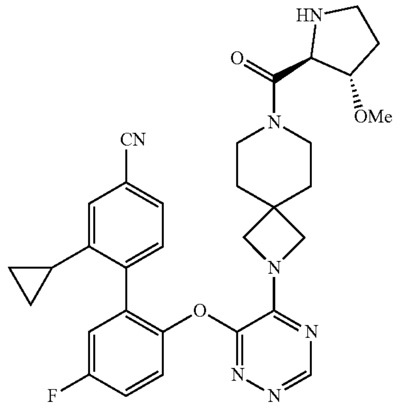 [SMILES: CO[C@H]1CCN[C@@H]1C(=O)N1CCC2(CC1)CN(c1ncnnc1Oc1ccc(F)cc1-c1ccc(C#N)cc1C1CC1)C2]
Example 97
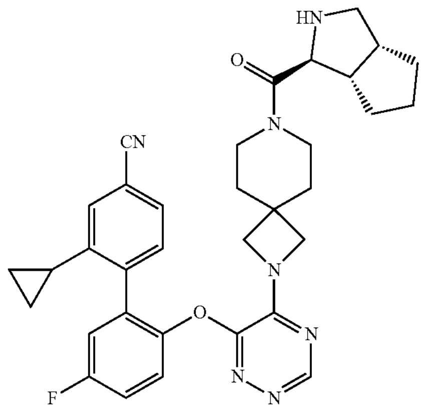
Example 98a
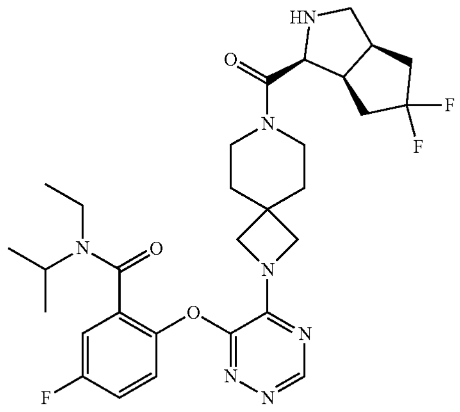 [SMILES: CCN(C(=O)c1cc(F)ccc1Oc1nncnc1N1CC2(CCN(C(=O)[C@H]3NC[C@H]4CC(F)(F)C[C@H]43)CC2)C1)C(C)C]

-continued
| Compound Nos. | Structures |
|---|---|
| Example 98b | 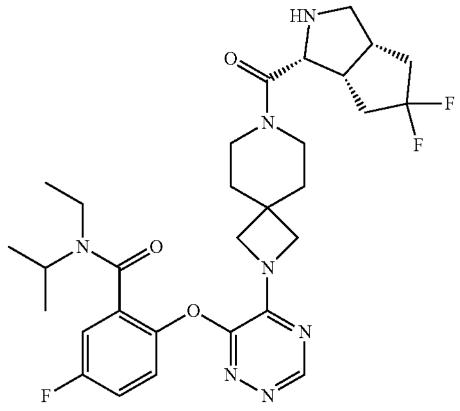 [SMILES: CCN(C(=O)c1cc(F)ccc1Oc1nncnc1N1CC2(CCN(C(=O)[C@@H]3NC[C@@H]4CC(F)(F)C[C@@H]43)CC2)C1)C(C)C] |
| Example 98c | 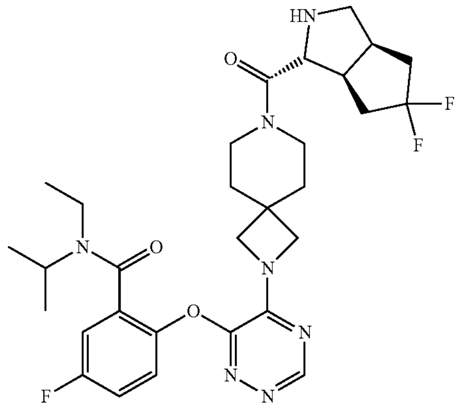 |
| Example 98d | 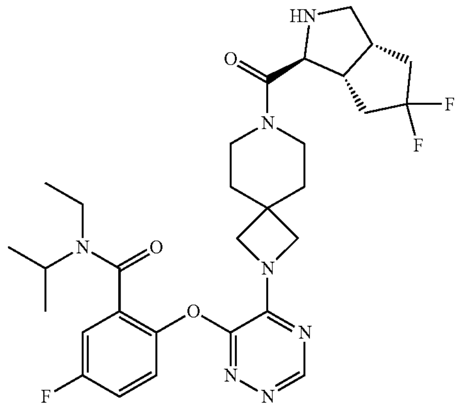 [SMILES: CCN(C(=O)c1cc(F)ccc1Oc1nncnc1N1CC2(CCN(C(=O)[C@H]3NC[C@@H]4CC(F)(F)C[C@@H]43)CC2)C1)C(C)C] |

-continued
| Compound Nos. | Structures |
|---|---|
| Example 99a | 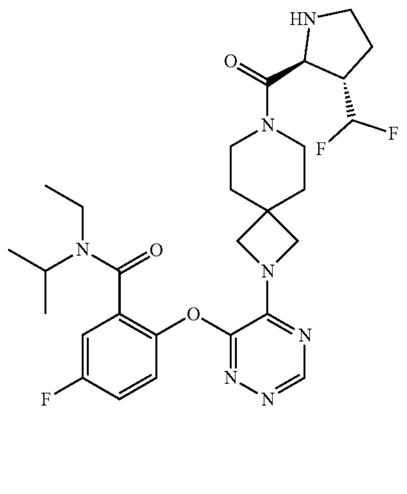 [SMILES: CCN(C(=O)c1cc(F)ccc1Oc1nncnc1N1CC2(CCN(C(=O)[C@H]3NCC[C@@H]3C(F)F)CC2)C1)C(C)C] |
| Example 99b | 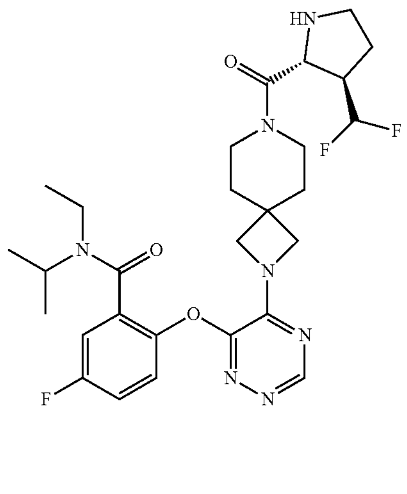 [SMILES: CCN(C(=O)c1cc(F)ccc1Oc1nncnc1N1CC2(CCN(C(=O)[C@@H]3NCC[C@H]3C(F)F)CC2)C1)C(C)C] |
| Example 100a | 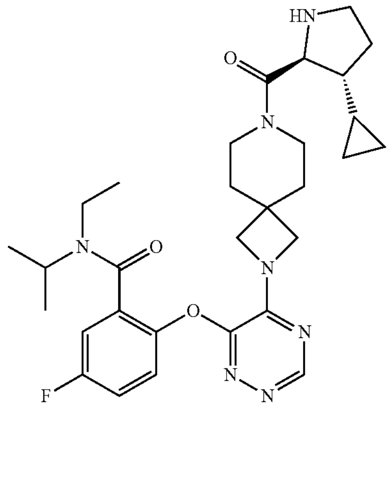 [SMILES: CCN(C(=O)c1cc(F)ccc1Oc1nncnc1N1CC2(CCN(C(=O)[C@H]3NCC[C@@H]3C3CC3)CC2)C1)C(C)C] |

-continued
| Compound Nos. | Structures |
|---|---|
| Example 100b | 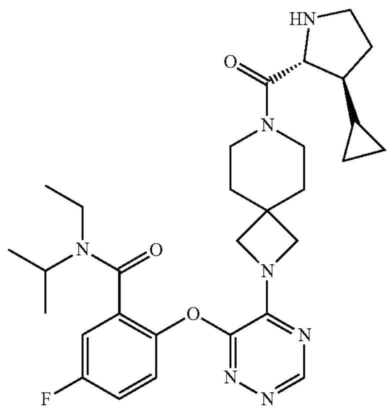 [SMILES: CCN(C(=O)c1cc(F)ccc1Oc1nncnc1N1CC2(CCN(C(=O)[C@@H]3NCC[C@H]3C3CC3)CC2)C1)C(C)C] |
| Example 101 | 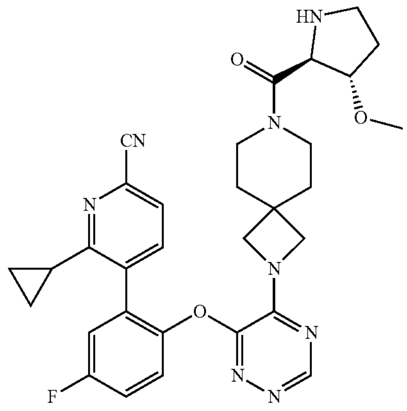 [SMILES: CO[C@H]1CCN[C@@H]1C(=O)N1CCC2(CC1)CN(c1ncnnc1Oc1ccc(F)cc1-c1ccc(C#N)nc1C1CC1)C2] |
| Example 102 | 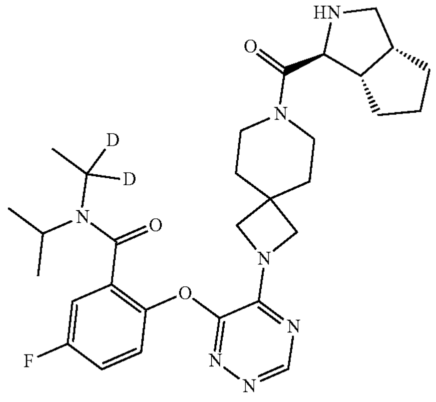 [SMILES: [2H]C([2H])(C)N(C(=O)c1cc(F)ccc1Oc1nncnc1N1CC2(CCN(C(=O)[C@H]3NC[C@@H]4CCC[C@@H]43)CC2)C1)C(C)C] |

-continued
| Compound Nos. | Structures |
| --- | --- |
| Example 103 | 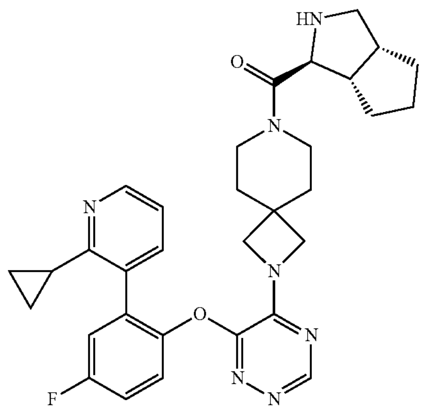 [SMILES: O=C([C@H]1NC[C@@H]2CCC[C@@H]21)N1CCC2(CC1)CN(c1ncnnc1Oc1ccc(F)cc1-c1cccnc1C1CC1)C2] |
| Example 104 | 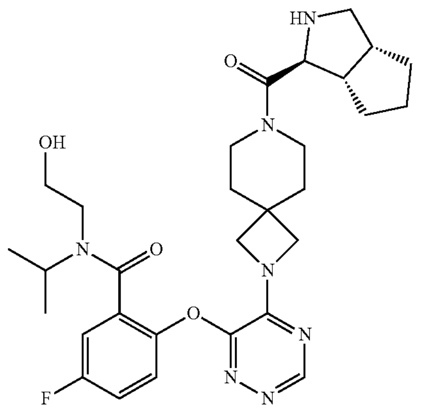 [SMILES: CC(C)N(CCO)C(=O)c1cc(F)ccc1Oc1nncnc1N1CC2(CCN(C(=O)[C@H]3NC[C@@H]4CCC[C@@H]43)CC2)C1] |
| Example 105 | 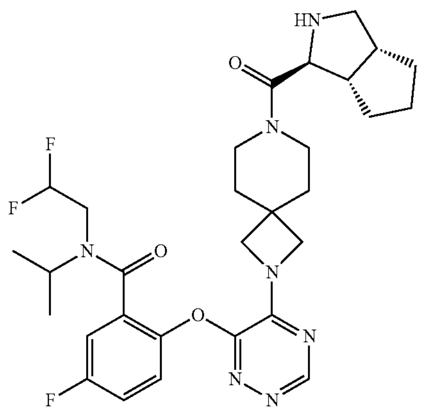 [SMILES: CC(C)N(CC(F)F)C(=O)c1cc(F)ccc1Oc1nncnc1N1CC2(CCN(C(=O)[C@H]3NC[C@@H]4CCC[C@@H]43)CC2)C1] |

-continued

| Compound Nos. | Structures |
| --- | --- |
| Example 106 | 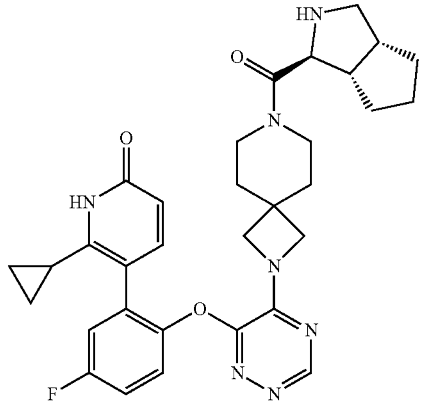 [SMILES: O=C([C@H]1NC[C@@H]2CCC[C@@H]21)N1CCC2(CC1)CN(c1ncnnc1Oc1ccc(F)cc1-c1ccc(=O)[nH]c1C1CC1)C2] |
| Example 107 | 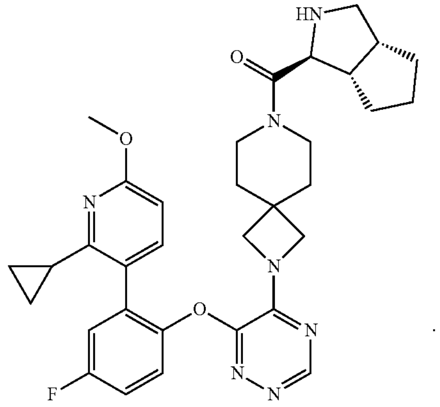 [SMILES: COc1ccc(-c2cc(F)ccc2Oc2nncnc2N2CC3(CCN(C(=O)[C@H]4NC[C@@H]5CCC[C@@H]54)CC3)C2)c(C2CC2)n1 ; "."] |

17. A pharmaceutical composition, comprising the compound of claim 1, or a stereoisomer, a racemate, a tautomer, a hydrate or a solvate, or pharmaceutically acceptable salt thereof, and optionally a pharmaceutically acceptable carrier.

18. A method of in vivo or in vitro inhibiting the interaction of menin with MLL and/or MLL fusion proteins, comprising contacting an effective amount of the compound of claim 1 or a pharmaceutically acceptable salt thereof with menin and MLL and/or MLL fusion proteins.

19. A method of treating cancer or diabetes, comprising administering to the subject in need thereof an effective amount of the compound of claim 1 or a stereoisomer, a racemate, a tautomer, a hydrate or a solvate, or pharmaceutically acceptable salt thereof.

20. A combination, comprising the compound of claim 1, or a stereoisomer, a racemate, a tautomer, a hydrate or a solvate, or pharmaceutically acceptable salt thereof, and at least one additional therapeutic agent.

21. The compound according to claim 2 or a stereoisomer, a racemate, a tautomer, a hydrate or a solvate, or pharmaceutically acceptable salt thereof, wherein $R_5$ is H.

22. The compound according to claim 5 or a stereoisomer, a racemate, a tautomer, a hydrate or a solvate, or pharmaceutically acceptable salt thereof, wherein Z is $CH_2$.

23. The compound according to claim 7 or a stereoisomer, a racemate, a tautomer, a hydrate or a solvate, or pharmaceutically acceptable salt thereof, wherein $R_1$ is

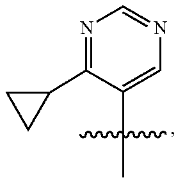,
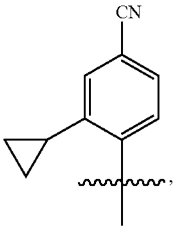, or
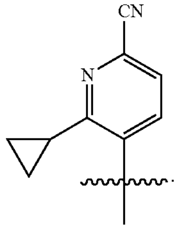.

24. The compound according to claim 7 or a stereoisomer, a racemate, a tautomer, a hydrate or a solvate, or pharmaceutically acceptable salt thereof, wherein $R_1$ is

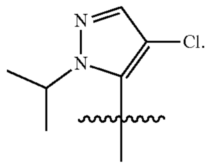 [SMILES: *c1c(Cl)cnn1C(C)C]

25. The compound according to claim 8 or a stereoisomer, a racemate, a tautomer, a hydrate or a solvate, or pharmaceutically acceptable salt thereof, wherein n is 0.

26. The compound according to claim 15 or a stereoisomer, a racemate, a tautomer, a hydrate or a solvate, or pharmaceutically acceptable salt thereof, wherein both p are 0, or both p are 1;

q is 0 or 2; and $R_{4a}$ is methyl.

27. The method of claim 19, wherein the cancer is hematological tumor or solid tumor.

28. The method of claim 27, wherein the hematological tumor is selected from leukemia, lymphomas, myelomas, myelodysplastic syndrome (MDS), and myeloproliferative neoplasms (MPN), and polycythemia vera.

29. The method of claim 28, wherein the leukemia is selected from acute leukemias, chronic leukemias, myeloid leukemias, myelogeneous leukemias, lymphoblastic leukemias, lymphocytic leukemias, acute myeloid leukemias (AML), chronic myeloid leukemias (CML), acute lymphoblastic leukemias (ALL), chronic lymphocytic leukemias (CLL), T cell prolymphocytic leukemias (T-PLL), Large granular lymphocytic leukemia, Hairy cell leukemia (HCL), mixed lineage leukemia (MLL), MLL-rearranged leukemias (MLLr leukemia), MLL-PTD leukemias, MLL amplified leukemias, MLL-positive leukemias, nucleophosmin (NPM)-mutated leukemia, MOZ acute leukemia, NUP98 acute leukemia, CALM acute leukemia, MLL-AF4 leukemia, MLL-AF6 leukemia, MLL-AF9 leukemia, MLL-AF10 leukemia, MLL-ENL leukemia and MLL-ELL leukemia.

30. The method of claim 27, wherein the solid tumor is selected from prostate cancer, lung cancer, breast cancer, pancreatic cancer, colon cancer, liver cancer, melanoma and glioblastoma.

31. The combination according to claim 20, wherein said additional therapeutic agent is an anti-neoplastic agent.

32. The combination according to claim 31, wherein the anti-neoplastic agent is a radiotherapeutic agent, a chemotherapeutic agent, an immunotherapeutic agent, or a targeted therapeutic agent.

* * * * *